US012577232B2

(12) United States Patent
Press et al.

(10) Patent No.: US 12,577,232 B2
(45) **Date of Patent: *Mar. 17, 2026**

(54) N-HETEROCYCLE SUBSTITUTED TRYPTAMINE DERIVATIVES AND METHODS OF USING

(71) Applicant: ENVERIC BIOSCIENCES CANADA INC., Calgary (CA)

(72) Inventors: David James Press, Calgary (CA); Glynnis Elizabeth Jensen, Calgary (CA); Kaveh Matinkhoo, Calgary (CA); Jessica Bik-Jing Lee, Calgary (CA); Jillian M. Hagel, Calgary (CA); Peter J. Facchini, Calgary (CA)

(73) Assignee: Enveric Biosciences Canada Inc., Calgary (CA)

(*) Notice: Subject to any disclaimer, the term of this patent is extended or adjusted under 35 U.S.C. 154(b) by 0 days.

This patent is subject to a terminal disclaimer.

(21) Appl. No.: 19/222,062

(22) Filed: May 29, 2025

(65) Prior Publication Data

US 2025/0289805 A1 Sep. 18, 2025

Related U.S. Application Data

(63) Continuation of application No. 18/752,072, filed on Jun. 24, 2024, now Pat. No. 12,338,231, which is a continuation of application No. PCT/CA2024/050312, filed on Mar. 15, 2024.

(51) Int. Cl.

*C07D 403/04* (2006.01)
*A61K 31/4045* (2006.01)
*A61K 31/496* (2006.01)
*A61K 31/5377* (2006.01)
*C07D 209/16* (2006.01)

(52) U.S. Cl.

CPC ........ *C07D 403/04* (2013.01); *A61K 31/4045* (2013.01); *A61K 31/496* (2013.01); *A61K 31/5377* (2013.01); *C07D 209/16* (2013.01)

(58) Field of Classification Search

CPC ................ C07D 403/04; C07D 209/16; A61K 31/4045; A61K 31/496; A61K 31/5377

See application file for complete search history.

(56) References Cited

FOREIGN PATENT DOCUMENTS

| | | | |
|---|---|---|---|
| WO | 94114771 | A1 | 7/1994 |
| WO | 2020176597 | A1 | 9/2020 |
| WO | 2022081631 | A1 | 9/2020 |
| WO | 2023173229 | A1 | 9/2023 |

OTHER PUBLICATIONS

STIC search, Registry compounds, p. 37, 38-40, 45-46, 2020 and 2021 (Year: 2021).*

(Continued)

*Primary Examiner* — Sarah Pihonak
*Assistant Examiner* — Padmaja S Rao
(74) *Attorney, Agent, or Firm* — Smart & Biggar LP; Michael Fenwick

(57) ABSTRACT

Disclosed are novel N-heterocycle-substituted tryptamine derivative compounds and pharmaceutical and recreational drug formulations containing the same. The pharmaceutical formulations may be used to treat brain neurological disorders.

29 Claims, 56 Drawing Sheets

X

MM868

(56) References Cited

OTHER PUBLICATIONS

Kim et al. Asian J. Org. Chem. 2020, 9:2103-2107.
Street et al. J. Med. Chem. 1995, 38:1799-1810.
Street et al. J. Med. Chem. 1993, 36:1529-1538.
Rene et al. Tetrahedron Letters, 2014, 55: 830-833.
Duan et al. Chem. Rev. 2024, 124:124-163.
ISR & Written Opinion_Dec. 13, 2024.
Daniel, J. et al., Mental Health Clin., 2017;7(1):24-28.
Grob, C. et al., Arch. Gen. Psychiatry, 2011, 68(1) 71-78.
Cathart-Harris, R.L. et al., Lancet Psychiatry, 2016, 3: 619-627.
Bodor, N. et al., 2001, J. Pharmacy and Pharmacology, 53: 889-894.
Vitale, A. et al., 2011, J. of Nucl. Med., 52(6), 970-977.
Inserra et al., 2020, Pharmacol. Rev. 73: 202.
Botti et al., 2021 Pharmaceutics 13:1114.
Gonzalez-Maeso et al., 2007, Neuron 53:439-452.
Finnin, B. and Morgan, T.M., 1999 J. Pharm. Sci, 88 (10), 955-958.
Halberstadt and Geyer, 2013, Psychopharmacol. 227:727.
Blair et al., 2000, J. Med. Chem. 43:4701-4710.
Ray, 2010, PLoS ONE 5:e9019.
Ross et al. ACS Pharmacol. Transl. Sci. 4: 553-562, 2021.
Simmler et al., 2013, British J. Pharmacol. 168: 458.
Roloff et al., 2015, PloS ONE 10:e0118536.
Kozell et al., 2023, Journal of Pharmacology and Experimental Therapeutics 385:62-75.
Bulling et al., 2009. Journal of Biological Chemistry 287:18524-18534.
Berg and Clarke, 2018, Int. J. Neuropsychopharmacol 21:962-977.
Zwartsen et al., 2017, Toxicology in Vitro 45:60-71.
Calder and Hasler, 2023, Neuropsychopharmacol. 48:104-112.
Raithatha et al., 2023, J. Med. Chem. 67:1024-1043.
Cameron et al., 2021, Nature 589:474-479.
Cheng and Bahar, 2019, Nature Structural and Molecular Biology 26:545-556.
Taciak et al. Pharmacol. Rep. 2018, 70:37-46.
McClure-Begley et al. Nat. Rev. Drug Discov. 2022, 21:463-473.
Cao et al., Science 2022, 375:403-411.
Islas and Scior, 2022, Molecules 27: 2977-2995.
Deliganis et al., 1990, Biochemical Pharmacol. 41: 1739-1744.
Gonda et al.. 2019, Expert Opinion on Drug Discovery 14: 81-89.
Tenenge et al., 2011, Cell Mol. Neurobiol. 31:635-643.
Donget al., 2021, Cell 184:2779-2792.
Romero et al. J. Psychiatr. Res 137: 273-282, 2021.
Singh et al., 2023, Cell 186:2160-2175.
Cussac et al., Europ. J. Pharmacol., 2008, 594 (1-3), 32-38.
Mestre et al., 2013, Expert Opin, Investig. Drugs 22:411-421.
Wang et al., 2023, ACS Chem. Neurosci. 14:977-987.
Goldberg et al., Psychiatric Res. 284:112749.
Levone et al., 2021, Neuropharmacol, 201:108843.
Moreau et al., 1992, Eur. Neurpsychopharmocol. 2:43-49.
Liu et al., 2018, Nature Protocols 13:1686-1698.
Sekssaoui et al., 2024, Neuropsychopharmacology doi: 10.1038/s41386-024-01794-6.
Kalir et al., 1963. J. Med. Chem. 6:716-719.
Wallach et al., 2023, Nature Comm. 14 https://doi.org/10.1038/s41467-023-44016-1.
Cummings et al., 2014, Lancet, 383:533-540.
Roberts, 2006, Curr. Opin. Invest. Drugs 7:653-660.
Haleem, Behay. Pharm. 2015, 26:45-58.
Hansch et al., Searching for Allosteric Effects via QSARs, Bioorganic & Medicinal Chemistry, vol. 9, 283-289, 2001 (Year: 2001).
Castro et al., Synthesis and Biological Activity of 342-(Dimethylamino)ethyl]-5-[(1,1-dioxo-5-methyl-1,2,5-thiadiazolidin-2-yl)methyl]-1H-indole and Analogues: Agonists for the 5-HT1D Receptor, Journal of Medicinal Chemistry, vol. 37, 3023-3032, 1994 (Year: 1994).
Chemical Catalog Compounds (from STN search results) (Year: 2019).

* cited by examiner

MM825

E

E

F

F

MM831

G

G H

H I

I MM832

J

J

K

K

L

L

MM833

M

M N

N

MM834

O

MM848

I

MM849

Q

Q

R

R

S

S

MM850

T

T

U

U

MM867

V

V W

W X

X

MM868

Y

Y

Z

Z

AA

AA

MM869

AB

AB AC

AC AD

AD MM880

AE

AE AF

AF AG

AG MM888

X

MM898

Y

AI

AI

AJ

AJ

MM923

AK

AK

AL

AL

AM

AM

MM925

AM

MM973

AC

AN

AN

MM975

AO

AO AP

AP MM982

AQ

AQ AR

AR MM983

W

AS

AS

MM992

AT

AT AU

AU AV

MM998

AV

AW

AW AX

AX AY

AY MM999

AX AZ

AZ MM1001

A

BA

BA

MM895

BA

MM896

BA

MM897

N-HETEROCYCLE SUBSTITUTED TRYPTAMINE DERIVATIVES AND METHODS OF USING

CROSS-REFERENCE TO RELATED APPLICATION

This application is a continuation of U.S. patent application Ser. No. 18/752,072, filed Jun. 24, 2024 and PCT Application No. PCT/CA2024/050312, filed Mar. 15, 2024 which are hereby incorporated by reference.

FIELD OF THE DISCLOSURE

The compositions and methods disclosed herein relate to a class of chemical compounds known as tryptamines. Furthermore, the compositions and methods disclosed herein relate in particular to N-heterocycle substituted tryptamine derivatives.

BACKGROUND OF THE DISCLOSURE

The following paragraphs are provided by way of background to the present disclosure. They are not however an admission that anything discussed therein is prior art or part of the knowledge of a person of skill in the art.

Tryptamines are a class of chemical compounds that share a common chemical structure (notably, a fused benzene and pyrrole ring, together known as an indole, and linked to the pyrrole ring, at the third carbon atom, a 2-aminoethyl group), and can be formulated as therapeutic drug compounds. For example, psilocybin has been evaluated as a drug for its clinical potential in the treatment of mental health conditions (Daniel, J. et al., Mental Health Clin., 2017; 7(1): 24-28), including to treat anxiety in terminal cancer patients (Grob, C. et al., Arch. Gen. Psychiatry, 2011, 68(1) 71-78) and to alleviate symptoms of treatment-resistant depression (Cathart-Harris, R. L. et al., Lancet Psychiatry, 2016, 3: 619-627). Other known drug compounds within the tryptamine class of compounds include, for example, melatonin, serotonin, bufotenin, dimethyltryptamine (DMT), and psilocin.

It is commonly understood that tryptamine-based drugs can produce their in vivo therapeutic effects by molecular interaction with macromolecules present in human cells, known as receptors. In this respect, in broad terms, specific receptors can be thought of as being located in a relatively fixed anatomical space (e.g., a specific brain tissue). Following administration of a drug, the drug moves through the body to the receptor to interact therewith, and then back out of the body. It is generally desirable that when a tryptamine-based drug is administered, the drug is specifically active at the desired anatomical location within a patient's body, such as, for example, in a specific brain tissue and/or at a specific receptor, a 5-hydroxytryptamine (5-HT) receptor, for example. Moreover, it is generally desirable that the specific molecular interaction between the drug and a receptor, such as a 5-HT receptor, is such that the drug-receptor molecular interaction results in appropriate modulation of the target receptor.

In many instances the observed pharmacological effect of tryptamine-based drugs is suboptimal. Thus, administration of the drug may fall short of the desired therapeutic effect (e.g., the successful treatment of a psychotic disorder) and/or undesirable side effects may be observed.

The underlying causes for these observed shortcomings in pharmacological effects may be manifold. For example, the administered drug additionally may interact with receptors other than the target receptor, and/or the specific molecular interaction between drug and target may not lead to the desired receptor modulation, and/or the concentration of the drug at the receptor may be suboptimal. In this respect, known tryptamine-based drugs can be said to frequently display suboptimal pharmacodynamic (PD) characteristics, i.e., suboptimal characteristics with respect to the pharmacological effect exerted by the drug on the body. Thus, for example, the intensity of the drug's effect, the concentration of the drug at the receptor, and the molecular interactions between the drug and receptor may not be as desired.

Furthermore, as is the case with many pharmaceutical compounds, tryptamine compounds, when administered, can penetrate multiple tissues by diffusion, resulting in broad bodily distribution of the drug compound (Bodor, N. et al., 2001, J. Pharmacy and Pharmacology, 53: 889-894). Thus, frequently a substantial proportion of the administered drug fails to reach the desired target receptor. This in turn may necessitate more frequent dosing of the drug. Such frequent dosing is less convenient to a patient, and, moreover, may negatively affect patient compliance with the prescribed drug therapy. In addition, general toxicity associated with drug formulations tends to be more problematic as a result of broad bodily distribution of the drug throughout the patient's body since undesirable side effects may manifest themselves as a result of interaction of the drug with healthy organs.

Furthermore, it is generally desirable that drug compounds exert a pharmacological effect for an appropriate period of time. However, tryptamine-based drugs when systemically administered to a patient can exhibit a high blood plasma clearance, typically on the order of minutes (Vitale, A. et al., 2011, J. of Nucl. Med., 52(6), 970-977). Thus, rapid drug clearance can also necessitate more frequent dosing of tryptamine-based drug formulations. In this respect, known tryptamine containing drug formulations can be said to frequently display suboptimal pharmacokinetic (PK) characteristics, i.e., suboptimal characteristics with respect to movement of the drug through the body to and from the desired anatomical location, including, for example, suboptimal drug absorption, distribution, metabolism, and excretion.

There exists therefore a need in the art for improved tryptamine compounds.

SUMMARY OF THE DISCLOSURE

The following paragraphs are intended to introduce the reader to the more detailed description, not to define or limit the claimed subject matter of the present disclosure.

In one aspect, the present disclosure relates to tryptamines and derivative compounds thereof.

In another aspect, the present disclosure relates to N-heterocycle substituted tryptamine derivative compounds.

Accordingly, in one aspect, the present disclosure provides, in at least one embodiment, in accordance with the teachings herein, a chemical compound having chemical formula (I):

(I)

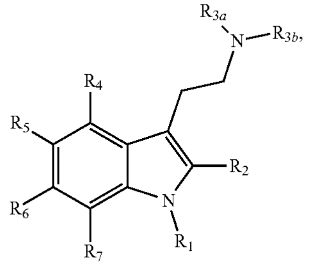

wherein at least one of $R_2$, $R_4$, $R_5$, $R_6$, and $R_7$ is an N-heterocycle substituent, wherein each of $R_2$, $R_4$, $R_5$, $R_6$, and $R_7$ which are not an N-heterocycle substituent are a hydrogen atom, a halogen atom, or a ketone group, wherein $R_1$ is alkyl or hydrogen, and wherein $R_{3a}$ and $R_{3b}$ are each independently a hydrogen atom, an alkyl group, an aryl group, or an alkyl-aryl group.

In at least one embodiment, in an aspect, the N-heterocycle substituent can be an N-linked heterocyclic ring.

In at least one embodiment, in an aspect, the N-heterocycle substituent can be a 3-10 membered N-linked heterocyclic ring.

In at least one embodiment, in an aspect, the N-heterocycle substituent can be a 3-10 membered saturated N-linked heterocyclic ring.

In at least one embodiment, in an aspect, the N-heterocycle substituent can be a 3-10 membered saturated N-linked heterocyclic ring further having a second heteroatom.

In at least one embodiment, in an aspect, one of $R_2$, $R_4$, $R_5$, $R_6$, and $R_7$ can be an N-heterocycle substituent.

In at least one embodiment, in an aspect, one of $R_2$, $R_4$, $R_5$, $R_6$, and $R_7$ can be an N-heterocycle substituent, and the other substituents $R_2$, $R_4$, $R_5$, $R_6$, and $R_7$ are hydrogen atoms.

In at least one embodiment, in an aspect, one of $R_2$, $R_4$, $R_5$, $R_6$, and $R_7$ can be an N-heterocycle substituent, one of $R_2$, $R_4$, $R_5$, $R_6$, and $R_7$ can be a halogen atom, and the other substituents $R_2$, $R_4$, $R_5$, $R_6$, and $R_7$ are hydrogen atoms.

In at least one embodiment, in an aspect, the N-heterocycle substituent can be a 3-10 membered saturated N-linked heterocyclic ring further having a second hetero-atom, wherein the second hetero-atom is an oxygen atom or a second optionally substituted nitrogen atom.

In at least one embodiment, in an aspect, the second optionally substituted nitrogen atom can be substituted with a ($C_1$-$C_6$)-alkyl group or an aryl group.

In at least one embodiment, in an aspect, the second optionally substituted nitrogen atom can be substituted with a methyl group ($-CH_3$).

In at least one embodiment, in an aspect, $R_1$ can be ($C_1$-$C_6$)-alkyl.

In at least one embodiment, in an aspect, $R_1$ can be ($C_1$-$C_3$)-alkyl.

In at least one embodiment, in an aspect, $R_1$ can be methyl ($-CH_3$).

In at least one embodiment, in an aspect, $R_1$ can be hydrogen.

In at least one embodiment, in an aspect, the ketone group can have the chemical formula (A):

(A)

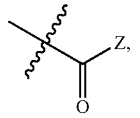

wherein Z is a ($C_1$-$C_6$)-alkyl.

In at least one embodiment, in an aspect, $R_2$ can be a ketone group having the chemical formula (A):

(A)

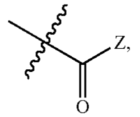

wherein Z is a ($C_1$-$C_6$)-alkyl, wherein Z optionally is methyl ($-CH_3$).

In at least one embodiment, in an aspect, the N-heterocycle substituent can have the chemical formula (II), (III), or (IV):

(II)

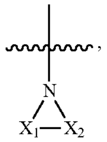

or (III)

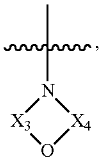

or (IV)

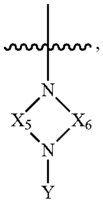

wherein in chemical formula (II), (III), and (IV), $X_1$, $X_2$, $X_3$, $X_4$, $X_5$, and $X_6$ are independently selected from a $C_1$ to $C_4$-alkylene, and wherein in formula (IV), Y is a hydrogen atom, an alkyl group, or an aryl group.

In at least one embodiment, in an aspect, in formula (II) $X_1$ and $X_2$ each can be methylene ($-CH_2-$).

In at least one embodiment, in an aspect, in formula (II) $X_1$ can be methylene ($-CH_2-$) and $X_2$ can be ethylene ($-CH_2-CH_2-$).

In at least one embodiment, in an aspect, in formula (II) $X_1$ and $X_2$ each can be ethylene ($-CH_2-CH_2-$).

In at least one embodiment, in an aspect, in formula (III) $X_3$ and $X_4$ each can be methylene ($-CH_2-$).

In at least one embodiment, in an aspect, in formula (III) $X_3$ can be methylene ($-CH_2-$) and $X_4$ can be ethylene ($-CH_2-CH_2-$).

In at least one embodiment, in an aspect, in formula (III) $X_3$ and $X_4$ each can be ethylene ($-CH_2-CH_2-$).

In at least one embodiment, in an aspect, in formula (IV) $X_5$ and $X_6$ each can be methylene ($—CH_2—$).

In at least one embodiment, in an aspect, in formula (IV) $X_5$ can be methylene ($—CH_2—$) and $X_6$ can be ethylene ($—CH_2—CH_2—$).

In at least one embodiment, in an aspect, in formula (IV) $X_5$ and $X_6$ each can be ethylene ($—CH_2—CH_2—$).

In at least one embodiment, in an aspect, $R_4$ can be an N-heterocycle substituent, $R_6$ can be a halogen atom, and $R_1$, $R_2$, $R_5$, and $R_7$ can each be a hydrogen atom.

In at least one embodiment, in an aspect, $R_4$ can be an N-linked heterocyclic ring, $R_6$ can be a halogen atom, and $R_1$, $R_2$, $R_5$, and $R_7$ can each be a hydrogen atom.

In at least one embodiment, in an aspect, $R_4$ can be an N-heterocycle substituent having formula (III), $R_6$ can be a halogen atom, and $R_1$, $R_2$, $R_5$, and $R_7$ can each be a hydrogen atom.

In at least one embodiment, in an aspect, $R_4$ can be an N-heterocycle substituent having formula (III), wherein $X_3$ and $X_4$ each can be methylene ($—CH_2—$), $R_6$ can be a halogen atom, and $R_1$, $R_2$, $R_5$, and $R_7$ can each be a hydrogen atom.

In at least one embodiment, in an aspect, $R_4$ can be an N-heterocycle substituent having formula (III), wherein one of $X_3$ and $X_4$ can be methylene ($—CH_2—$), one of $X_3$ and $X_4$ can be ethylene ($—CH_2—CH_2—$), $R_6$ can be a halogen atom, and $R_1$, $R_2$, $R_5$, and $R_7$ can each be a hydrogen atom.

In at least one embodiment, in an aspect, $R_4$ can be an N-heterocycle substituent having formula (III), wherein $X_3$ and $X_4$ each can be ethylene ($—CH_2—CH_2—$), $R_6$ can be a halogen atom, and $R_1$, $R_2$, $R_5$, and $R_7$ can each be a hydrogen atom.

In at least one embodiment, in an aspect, $R_4$ can be an N-heterocycle substituent having formula (III), wherein $X_3$ and $X_4$ each can be ethylene ($—CH_2—CH_2—$), $R_6$ can be a fluorine atom, and $R_1$, $R_2$, $R_5$, and $R_7$ can each be a hydrogen atom.

In at least one embodiment, in an aspect, $R_{3a}$ and $R_{3b}$ can each be a hydrogen atom.

In at least one embodiment, in an aspect, at least one of $R_{3a}$ and $R_{3b}$ can be a ($C_1$-$C_6$)-alkyl group.

In at least one embodiment, in an aspect, at least one of $R_{3a}$ and are $R_{3b}$ can be a ($C_1$-$C_3$)-alkyl group and the other of $R_{3a}$ and $R_{3b}$ can be a hydrogen atom.

In at least one embodiment, in an aspect, $R_{3a}$ and $R_{3b}$ can each be a ($C_1$-$C_6$)-alkyl group.

In at least one embodiment, in an aspect, $R_{3a}$ and $R_{3b}$ can each be a ($C_1$-$C_3$)-alkyl group.

In at least one embodiment, in an aspect, $R_{3a}$ and $R_{3b}$ can each be a methyl group ($—CH_3$).

In at least one embodiment, in an aspect, $R_4$ can be an N-heterocycle substituent having formula (III), wherein $X_3$ and $X_4$ each can be ethylene ($—CH_2—CH_2—$), $R_6$ can be a halogen atom, $R_1$, $R_2$, $R_5$, and $R_7$ can each be a hydrogen atom, and at least one of $R_{3a}$ and $R_{3b}$ can be a ($C_1$-$C_6$)-alkyl group, optionally a ($C_1$-$C_3$)-alkyl group, and optionally a methyl group ($—CH_3$).

In at least one embodiment, in an aspect, $R_4$ can be an N-heterocycle substituent having formula (III), wherein $X_3$ and $X_4$ each can be ethylene ($—CH_2—CH_2—$), $R_6$ can be a halogen atom, $R_1$, $R_2$, $R_5$, and $R_7$ can each be a hydrogen atom, and $R_{3a}$ and $R_{3b}$ can each be a ($C_1$-$C_6$)-alkyl group, optionally a ($C_1$-$C_3$)-alkyl group, and optionally a methyl group ($—CH_3$).

In at least one embodiment, in an aspect, $R_4$ can be an N-heterocycle substituent having formula (III), wherein $X_3$ and $X_4$ each can be ethylene ($—CH_2—CH_2—$), $R_6$ can be a halogen atom, $R_1$, $R_2$, $R_5$, and $R_7$ can each be a hydrogen atom, and $R_{3a}$ and $R_{3b}$ can each be a hydrogen atom.

In at least one embodiment, in an aspect, $R_4$ can be an N-heterocycle substituent having formula (III), wherein $X_3$ and $X_4$ each can be ethylene ($—CH_2—CH_2—$), $R_6$ can be a halogen atom, $R_1$, $R_2$, $R_5$, and $R_7$ can each be a hydrogen atom, and at least one of $R_{3a}$ and $R_{3b}$ can be a ($C_1$-$C_6$)-alkyl-aryl group, optionally, a $CH_2$-phenyl group.

In at least one embodiment, in an aspect, $R_4$ can be an N-heterocycle substituent, having formula (III), wherein $X_3$ and $X_4$ each can be ethylene ($—CH_2—CH_2—$), $R_6$ can be a halogen atom, $R_1$, $R_2$, $R_5$, and $R_7$ can each be a hydrogen atom, and at least one of $R_{3a}$ and are $R_{3b}$ can be a ($C_1$-$C_6$)-alkyl-aryl group, optionally a phenyl group, and the other of $R_{3a}$ and $R_{3b}$ can be a hydrogen atom.

In at least one embodiment, in an aspect, the compound having formula (I) can be selected from a compound having formula (V), (VI), (VII), (VIII), (IX), (X), (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), (XXIX), (XXX), (XXXI), (XXXII), and (XXXIII):

(V)

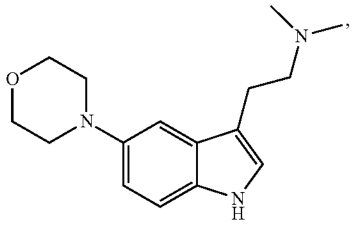

(VI)

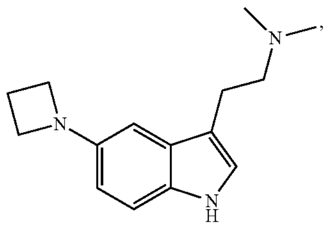

(VII)

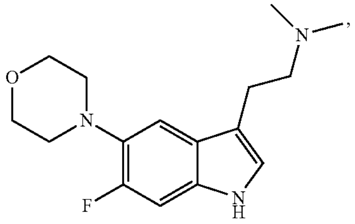

(VIII)

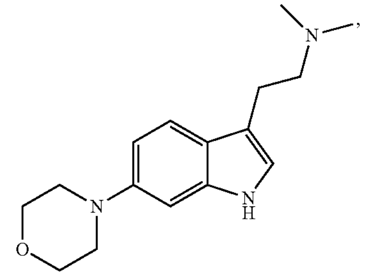

-continued
(IX)
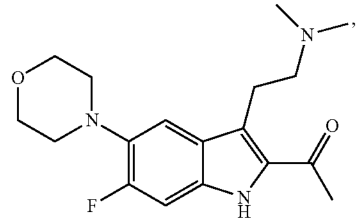
(X)
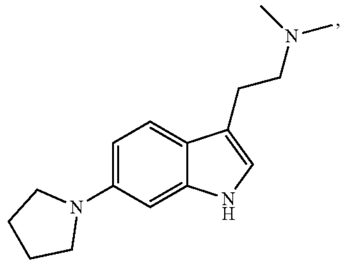
(XI)
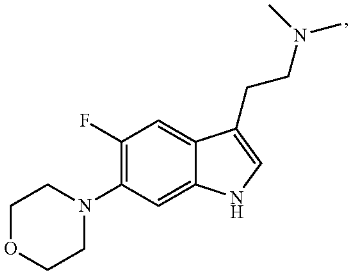
(XII)
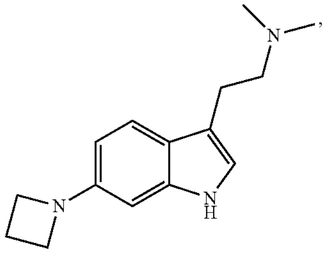
(XIII)
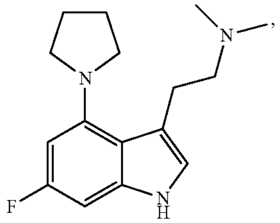
(XIV)
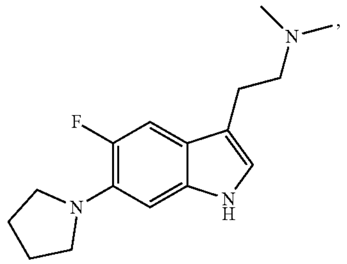
-continued
(XV)
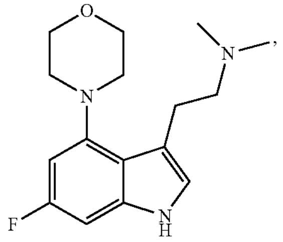
(XVI)
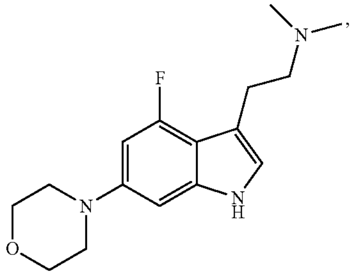
(XVII)
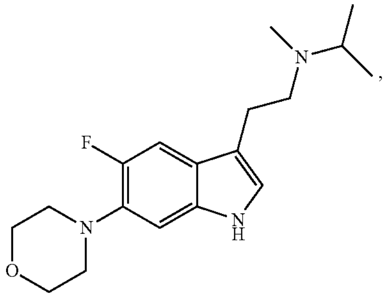
(XVIII)
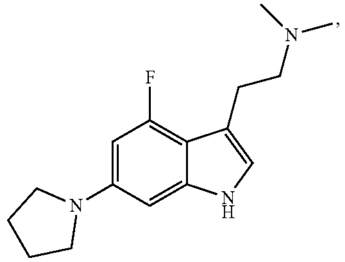
(XIX)
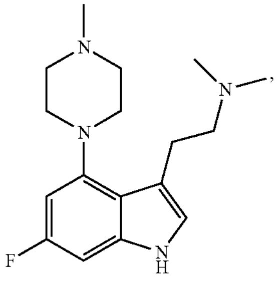

-continued
(XX)
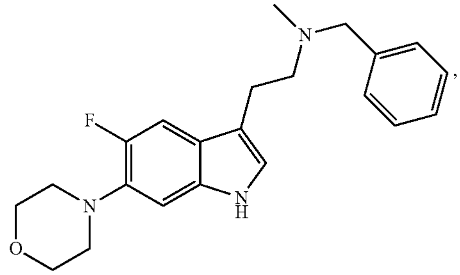
(XXI)
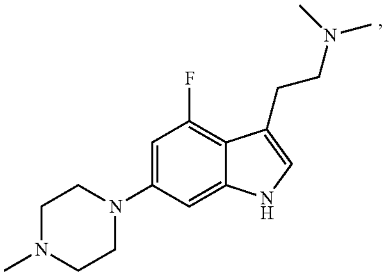
(XXII)
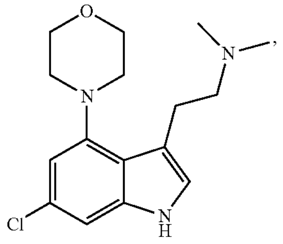
(XXIII)
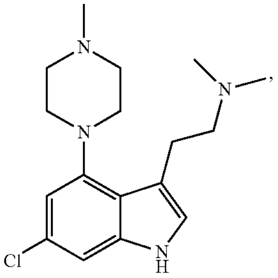
(XXIV)
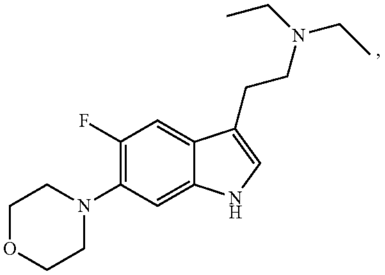
(XXV)
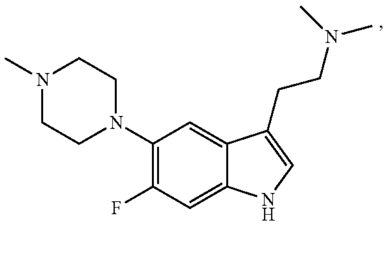
-continued
(XXVI)
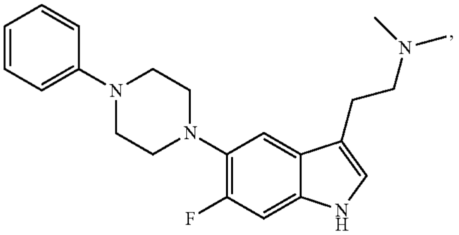
(XXVII)
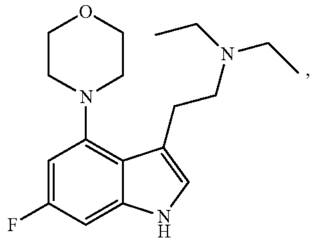
(XXVIII)
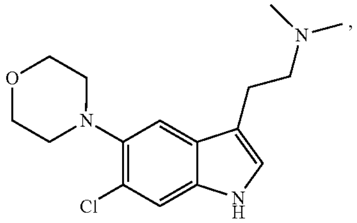
(XXIX)
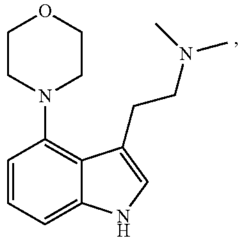
(XXX)
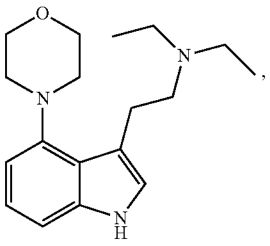
(XXXI)
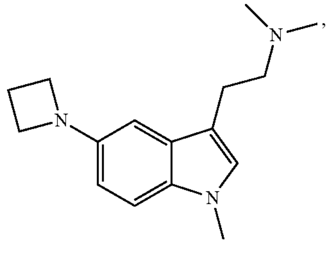

-continued (XXXII)

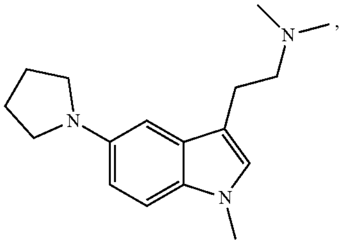

, and (XXXIII)

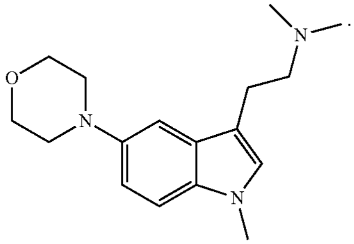

.

In another aspect, the present disclosure relates to pharmaceutical and recreational drug formulations comprising N-heterocycle substituted tryptamine derivative compounds. Accordingly, in one aspect, the present disclosure provides, in at least one embodiment, a pharmaceutical or recreational drug formulation comprising an effective amount of a chemical compound having a formula (I):

(I)

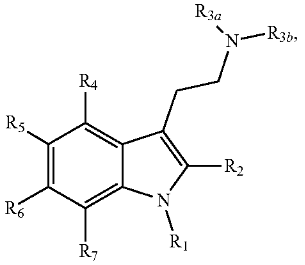

wherein at least one of $R_2$, $R_4$, $R_5$, $R_6$, and $R_7$ is an N-heterocycle substituent, wherein each of $R_2$, $R_4$, $R_5$, $R_6$, and $R_7$ which are not an N-heterocycle substituent are a hydrogen atom, a halogen atom, or a ketone group, wherein $R_1$ is alkyl or hydrogen, and wherein $R_{3a}$ and $R_{3b}$ are each independently a hydrogen atom, an alkyl group, an aryl group, or an alkyl-aryl group, together with a pharmaceutically acceptable excipient, diluent, or carrier.

In at least one embodiment, in an aspect, the compound having formula (I) can be a low or non-hallucinogenic compound.

In at least one embodiment, in an aspect, the compound having formula (I) can be a low or non-hallucinogenic compound causing a head-twitch response that is not statistically significantly greater than the head-twitch response caused by 5-bromo-dimethyltryptamine (5-Br-DMT) in a drug-induced animal behavior model.

In another aspect, the present disclosure relates to methods of treatment of brain neurological disorders. Accordingly, the present disclosure further provides, in one embodiment a method for treating a brain neurological disorder, the method comprising administering to a subject in need thereof a pharmaceutical formulation comprising a chemical compound having a formula (I):

(I)

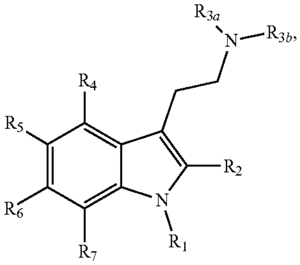

wherein at least one of $R_2$, $R_4$, $R_5$, $R_6$, and $R_7$ is an N-heterocycle substituent, wherein each of $R_2$, $R_4$, $R_5$, $R_6$, and $R_7$ which are not an N-heterocycle substituent are a hydrogen atom, a halogen atom, or a ketone group, wherein $R_1$ is alkyl or hydrogen, and wherein $R_{3a}$ and $R_{3b}$ are each independently a hydrogen atom, an alkyl group, an aryl group, or an alkyl-aryl group, wherein the pharmaceutical formulation is administered in an effective amount to treat the brain neurological disorder in the subject.

In at least one embodiment, in an aspect, upon administration the compound having formula (I) can interact with a receptor in the subject to thereby modulate the receptor and exert a pharmacological effect.

In at least one embodiment, in an aspect, the receptor can be a 5-$HT_{1A}$ receptor or a 5-$HT_{2A}$ receptor.

In at least one embodiment, in an aspect, the receptor can be a 5-$HT_{2A}$ receptor, and the compound can interact agonistically or antagonistically with the 5-$HT_{2A}$ receptor.

In at least one embodiment, in an aspect, upon administration the compound having formula (I) can interact with a transmembrane transport protein in the subject to thereby modulate the transmembrane transport protein and exert a pharmacological effect.

In at least one embodiment, in an aspect, the transmembrane transport protein can be a serotonin transporter (SERT) transmembrane transport protein.

In at least one embodiment, in an aspect, the disorder can be a 5-$HT_{1A}$ receptor-mediated disorder, or a 5-$HT_{2A}$ receptor-mediated disorder.

In at least one embodiment, in an aspect, the disorder can be a serotonin transporter (SERT)-mediated disorder.

In at least one embodiment, in an aspect, the pharmaceutical formulation can be a low or non-hallucinogenic pharmaceutical formulation.

In at least one embodiment, in an aspect, the pharmaceutical formulation can be a low or non-hallucinogenic pharmaceutical formulation, wherein the compound having formula (I) causes a head-twitch response that is not statistically significantly greater than the head-twitch response caused by 5-bromo-dimethyltryptamine (5-Br-DMT) in a drug-induced animal behavior model.

In at least one embodiment, in an aspect, a dose can be administered of from about 0.001 mg to about 5,000 mg.

In another aspect, the present disclosure provides, in at least one embodiment, a method for modulating (i) a receptor selected from be a 5-$HT_{1A}$ receptor or a 5-$HT_{2A}$ receptor; or (ii) a serotonin transporter (SERT) transmembrane transport protein, the method comprising contacting (i) the 5-$HT_{1A}$ receptor or 5-$HT_{2A}$ receptor; or (ii) the serotonin transporter (SERT) transmembrane transport protein with a chemical compound having a formula (I):

(I)

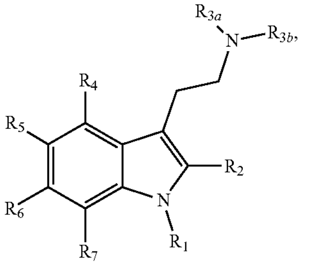

wherein at least one of $R_2$, $R_4$, $R_5$, $R_6$, and $R_7$ is an N-heterocycle substituent, wherein each of $R_2$, $R_4$, $R_5$, $R_6$, and $R_7$ which are not an N-heterocycle substituent are a hydrogen atom, a halogen atom, or a ketone group, wherein $R_1$ is alkyl or hydrogen, and wherein $R_{3a}$ and $R_{3b}$ are each independently a hydrogen atom, an alkyl group, an aryl group, or an alkyl-aryl group, under reaction conditions sufficient to modulate the (i) the 5-$HT_{1A}$ receptor or the 5-$HT_{2A}$ receptor; or (ii) the serotonin transporter (SERT) transmembrane transport protein.

In at least one embodiment, in an aspect, the reaction conditions can be in vitro reaction conditions.

In at least one embodiment, in an aspect, the reaction conditions can be in vivo reaction conditions.

In another aspect, the present disclosure relates to methods of making N-heterocycle substituted tryptamine derivative compounds. Accordingly, the present disclosure further provides, in one embodiment a method for making an N-heterocycle substituted tryptamine derivative compound having formula (I):

(I)

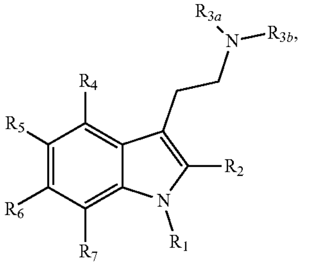

wherein at least one of $R_2$, $R_4$, $R_5$, $R_6$, and $R_7$ is an N-heterocycle substituent, wherein each of $R_2$, $R_4$, $R_5$, $R_6$, and $R_7$ which are not an N-heterocycle substituent are a hydrogen atom, a halogen atom, or a ketone group, wherein $R_1$ is alkyl or hydrogen, and wherein $R_{3a}$ and $R_{3b}$ are each independently a hydrogen atom, an alkyl group, an aryl group, or an alkyl-aryl group, wherein the method involves the performance of at least one chemical synthesis reaction selected from the reactions depicted in FIGS. 3A and 3B.

In at least one embodiment, in an aspect, the compound having chemical formula (I) can be a compound having formula (B):

(B)

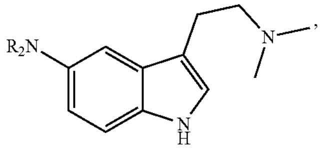

wherein

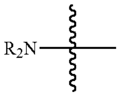 is 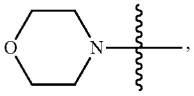, 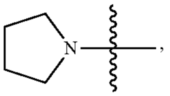, or 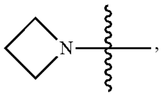, and the at least one chemical synthesis reaction can be a reaction selected from:

(d); (c) and (d); (b), (c), and (d); and (a), (b), (c), and (d) depicted in FIG. 3A.

In at least one embodiment, in an aspect, the compound having chemical formula (I) can be a compound having formula (C):

(C)

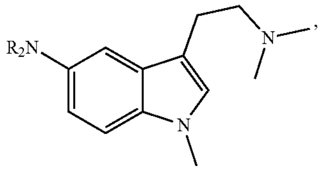

wherein

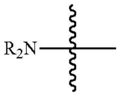 is 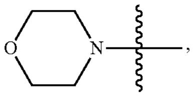, 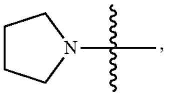, or 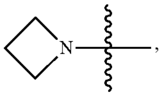, and the at least one chemical synthesis reaction can be a reaction selected from:

(f); (e) and (f); and (a), (e), and (f), depicted in FIG. 3A.

In at least one embodiment, in an aspect, the compound having chemical formula (I) can be a compound having formula (D):

(D)

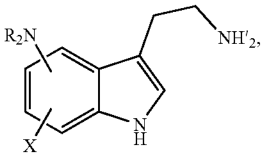

wherein X is Cl, F, or H, wherein

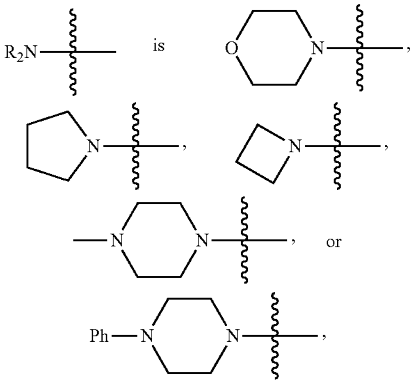

is … or and wherein

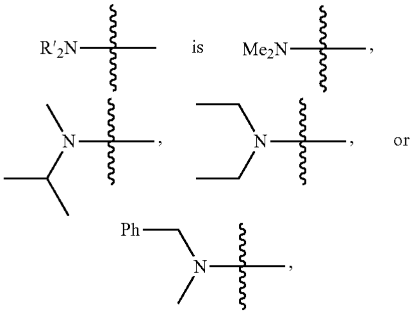

is … or and the at least one chemical synthesis reaction can be a reaction selected from:

(i) (c); (b) and (c); and (a), (b), and (c);

(ii) (k); (j) and (k); (b), (j), and (k); and (a), (b), (j), and (k);

(iii) (q); (p) and (q); (o), (p), and (q); and (a), (o), (p), and (q);

(iv) (g); (f) and (g); (e), (f), and (g); and (d), (e), (f), and (g);

(v) (i); (f) and (i); (e), (f), and (i); and (d), (e), (f), and (i); and (vi) (n); (m) and (n); (l), (m), and (n); and (d), (l), (m), and (n), depicted in FIG. 3B.

In at least one embodiment, in an aspect, the compound having chemical formula (I) can be a compound having formula (E):

(E)

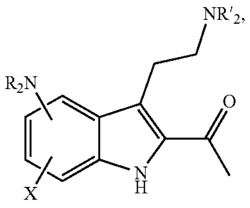

wherein X is Cl, F, or H, wherein

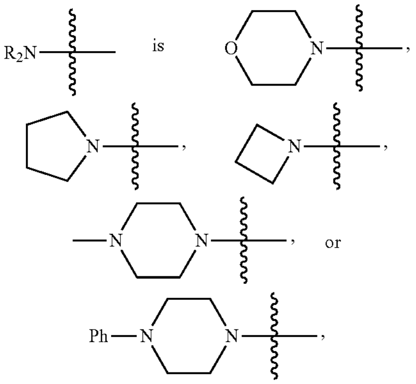

is … or and wherein

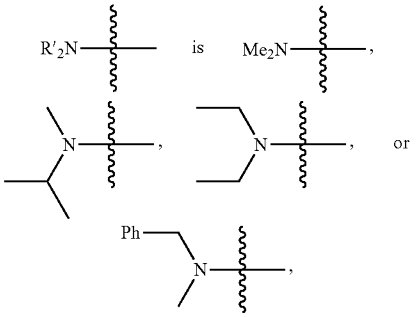

is … or and the at least one chemical synthesis reaction can be a reaction selected from:

(h); (g) and (h); (f), (g), and (h); (e), (f), (g), and (h); and (d), (e), (f), (g), and (h) depicted in FIG. 3B.

In another aspect, the present disclosure relates to uses of N-heterocycle substituted tryptamine derivative compounds. Accordingly, the present disclosure further provides, in at least one embodiment, a use of a chemical compound having a formula (I):

(I)

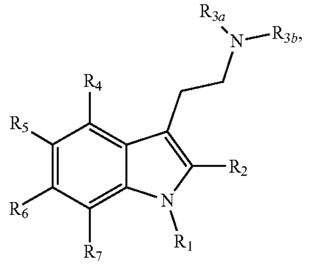

wherein at least one of $R_2$, $R_4$, $R_5$, $R_6$, and $R_7$ is an N-heterocycle substituent, wherein each of $R_2$, $R_4$, $R_5$, $R_6$, and $R_7$ which are not an N-heterocycle substituent are a hydrogen atom, a halogen atom or a ketone group, wherein $R_1$ is alkyl or hydrogen, and wherein $R_{3a}$ and $R_{3b}$ are each independently a hydrogen atom, an alkyl group, an aryl group, or an alkyl-aryl group, in the manufacture of a pharmaceutical or recreational drug formulation.

In at least one embodiment, the manufacture can comprise formulating the chemical compound with a pharmaceutically acceptable excipient, diluent, or carrier.

In another aspect the present disclosure provides, in at least one embodiment, a use of a chemical compound having a formula (I):

(I)

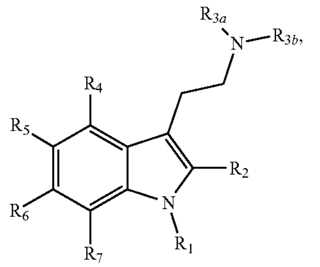

wherein at least one of $R_2$, $R_4$, $R_5$, $R_6$, and $R_7$ is an N-heterocycle substituent, wherein each of $R_2$, $R_4$, $R_5$, $R_6$, and $R_7$ which are not an N-heterocycle substituent are a hydrogen atom, a halogen atom or a ketone group, wherein $R_1$ is alkyl or hydrogen, and wherein $R_{3a}$ and $R_{3b}$ are each independently a hydrogen atom, an alkyl group, an aryl group, or an alkyl-aryl group, together with a pharmaceutically acceptable diluent, carrier, or excipient as a pharmaceutical or recreational drug formulation.

In at least one embodiment, in aspect, the pharmaceutical drug can be a drug for the treatment of a brain neurological disorder.

Other features and advantages will become apparent from the following detailed description. It should be understood, however, that the detailed description, while indicating preferred implementations of the disclosure, are given by way of illustration only, since various changes and modifications within the spirit and scope of the disclosure will become apparent to those of skill in the art from the detailed description.

BRIEF DESCRIPTION OF THE DRAWINGS

The disclosure is in the hereinafter provided paragraphs described, by way of example, in relation to the attached figures. The figures provided herein are provided for a better understanding of the example embodiments and to show more clearly how the various embodiments may be carried into effect. The figures are not intended to limit the present disclosure.

Figure 1:
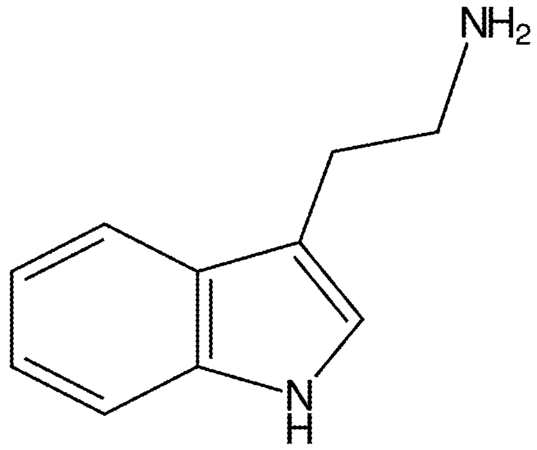
FIG. 1 depicts the chemical structure of tryptamine.

The figures together with the following detailed description make apparent to those skilled in the art how the disclosure may be implemented in practice.

DETAILED DESCRIPTION

Various compositions, systems or processes will be described below to provide an example of an embodiment of each claimed subject matter. No embodiment described below limits any claimed subject matter and any claimed subject matter may cover processes, compositions or systems that differ from those described below. The claimed subject matter is not limited to compositions, processes or systems having all of the features of any one composition, system or process described below or to features common to multiple or all of the compositions, systems or processes described below. It is possible that a composition, system, or process described below is not an embodiment of any claimed subject matter. Any subject matter disclosed in a composition, system or process described below that is not claimed in this document may be the subject matter of another protective instrument, for example, a continuing patent application, and the applicant(s), inventor(s) or owner(s) do not intend to abandon, disclaim or dedicate to the public any such subject matter by its disclosure in this document.

As used herein and in the claims, the singular forms, such "a", "an" and "the" include the plural reference and vice versa unless the context clearly indicates otherwise. Throughout this specification, unless otherwise indicated, "comprise," "comprises" and "comprising" are used inclusively rather than exclusively, so that a stated integer or group of integers may include one or more other non-stated integers or groups of integers.

When ranges are used herein for physical properties, such as molecular weight, or chemical properties, such as chemical formulae, all combinations and sub-combinations of ranges and specific embodiments therein are intended to be included. Other than in the operating examples, or where otherwise indicated, all numbers expressing quantities of ingredients or reaction conditions used herein should be understood as modified in all instances by the term "about." The term "about" when referring to a number or a numerical range means that the number or numerical range referred to is an approximation within experimental variability (or within statistical experimental error), and thus the number or numerical range may vary between 1% and 15% of the stated number or numerical range, as will be readily recognized by context. Furthermore, any range of values described herein is intended to specifically include the limiting values of the range, and any intermediate value or sub-range within the given range, and all such intermediate values and sub-ranges are individually and specifically disclosed (e.g., a range of 1 to 5 includes 1, 1.5, 2, 2.75, 3, 3.90, 4, and 5). Similarly, other terms of degree such as "substantially" and "approximately" as used herein mean a reasonable amount of deviation of the modified term such that the end result is not significantly changed. These terms of degree should be construed as including a deviation of the modified term if this deviation would not negate the meaning of the term it modifies.

Unless otherwise defined, scientific and technical terms used in connection with the formulations described herein shall have the meanings that are commonly understood by those of ordinary skill in the art. The terminology used herein is for the purpose of describing particular embodiments only, and is not intended to limit the scope of the present invention, which is defined solely by the claims.

All publications, patents and patent applications are herein incorporated by reference in their entirety to the same extent as if each individual publication, patent, or patent application was specifically and individually indicated to be incorporated by reference in its entirety.

Terms and Definitions

The term "tryptamine", as used herein, refers to a chemical compound having the structure set forth in FIG. 1.

Figure 2:
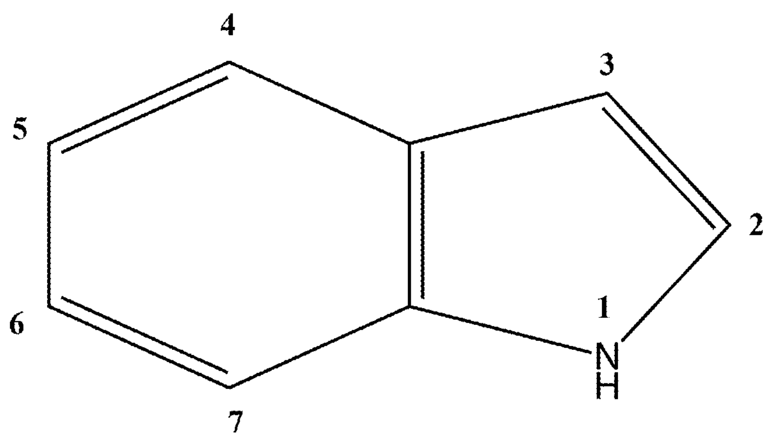
FIG. 2 depicts a certain prototype structure of tryptamine and tryptamine derivative compounds, namely an indole. Certain carbon and nitrogen atoms may be referred to herein by reference to their position within the indole structure, i.e., $N_1$, $C_2$, $C_3$ etc. The pertinent atom numbering is shown.

The term "indole prototype structure", as used herein, refers to the chemical structure shown in FIG. 2. It is noted that specific carbon atoms and a nitrogen atom in the indole prototype structure are numbered. Reference may be made to these carbon and nitrogen numbers herein, for example $C_2$, $C_4$, $N_1$, and so forth. Furthermore, reference may be made to chemical groups attached to the indole prototype structure in accordance with the same numbering, for example, $R_4$ and $R_6$ reference chemical groups attached to the $C_4$ and $C_6$ atom, respectively. In addition, $R_{3a}$ and $R_{3b}$, in this respect, reference chemical groups extending from the ethyl-amino group extending in turn from the $C_3$ atom of the prototype indole structure.

The term "tryptamine derivative", as used herein, refers to compounds that can be derivatized from tryptamine, wherein such compounds include an indole prototype structure and a $C_3$ ethylamine or ethylamine derivative group having the formula (F):

(F)

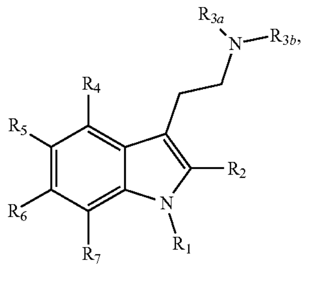

wherein at least one of $R_1$, $R_2$, $R_3$, $R_4$, $R_5$, $R_6$, or $R_7$, is a substituent (any atom or group other than a hydrogen atom) comprising, in particular, a N-heterocycle moiety or derivative thereto, and wherein $R_{3a}$ and $R_{3b}$ are each independently a hydrogen atom, an alkyl group, an aryl group, or an alkyl-aryl group. Thus, tryptamine derivative compounds include compounds containing, for example, a substituent at $C_2$, $C_4$, $C_5$, $C_6$, and $C_7$, as defined. Additional other atoms, such as $N_1$, may also be substituted.

The terms "N-heterocycle moiety or derivative thereof", "N-heterocycle substituent", and "N-heterocycle", as used herein, refer to a saturated or partially saturated cyclic or aromatic cyclic group in which one or more (for example, one or two) ring atoms are hetero atoms, selected from N, O, and S, provided however that, at least one hetero atom is N, the remaining ring atoms being C. Included are for example ($C_3$-$C_{20}$), ($C_3$-$C_{10}$), and ($C_3$-$C_6$) cyclic groups, comprising a hetero atom, at least one of which is N. It is noted that the N-hetero atom can be bonded to another moiety, for example, to a tryptamine moiety, including, for example, to the $C_4$, $C_5$, $C_6$, and C atoms of the tryptamine moiety. In instances where the N-hetero atom is bonded to another moiety the heterocycle can be said to be N-linked to the other moiety. Example N-heterocycle substituents include substituents having the chemical formula (II), (III), or (IV):

(II)

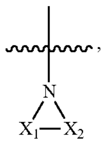

, or (III)

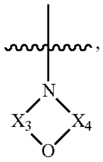

, or (IV)

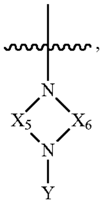

, wherein in chemical formula (II), (III), and (IV), $X_1$, $X_2$, $X_3$, $X_4$, $X_5$, and $X_6$ are independently selected from a $C_1$ to $C_6$-alkylene, and wherein in formula (IV), Y is a hydrogen atom, an alkyl group, or an aryl group.

The terms "halogen", "halogenated" and "halo-", as used herein, refer to the class of chemical elements consisting of fluorine (F), chlorine (Cl), bromine (Br), and iodine (I). Accordingly, halogenated compounds can refer to "fluorinated", "chlorinated", "brominated", or "iodinated" compounds.

The term "alkyl group", as used herein, refers to a straight and/or branched chain, saturated alkyl radical containing from one to "p" carbon atoms ("$C_1$-$C_p$-alkyl"; for example, p can be an integer between 2 and 20, for example, 3, 6, 10 or 20) and includes, depending on the identity of "p", methyl, ethyl, propyl, isopropyl, n-butyl, s-butyl, isobutyl, t-butyl, 2,2-dimethylbutyl, n-pentyl, 2-methylpentyl, 3-methylpentyl, 4-methylpentyl, n-hexyl, and the like, where the variable p is an integer representing the largest number of carbon atoms in the alkyl radical. Alkyl groups further include hydrocarbon groups arranged in a chain having the chemical formula $-C_nH_{2n+1}$, including, without limitation, methyl groups ($-CH_3$), ethyl groups ($-C_2H_5$), propyl groups ($-C_3H_7$), butyl groups ($-C_4H_9$) and pentyl groups ($-C_5H_{11}$).

The term "alkylene", as used herein, refers to a divalent group derived from an alkane by removal of two hydrogen atoms from the same carbon atom. Examples of alkylenes include, without limitation, methylene ($—CH_2—$), ethylene ($—C_2H_4—$), propylene ($—C_3H_6—$), and butylene ($—C_4H_8—$).

The term "aryl group", as used herein, refers to a hydrocarbon group arranged in an aromatic ring and can, for example, be a $C_6$-$C_{14}$-aryl, a $C_6$-$C_{10}$-aryl. Aryl groups further include phenyl, naphthyl, tetrahydronaphthyl, phenanthrenyl, biphenylenyl, indanyl, tolyl, xylyl, or indenyl groups, and the like.

The term "alkyl-aryl", as used herein, refers to an alkylene group substituted with an aryl group.

The terms "ketone" or "ketone group", as used herein, refer to a molecule containing at least two atoms of carbon, a first carbon atom double bonded to an oxygen atom, and the first carbon further bonded to a second carbon atom, the molecule having the chemical formula:

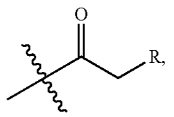

wherein R is any entity or plurality of entities which taken together allow the carbon atom bonded to R to achieve its ordinary valency. Thus, for example, R may represent 3 hydrogen atoms, or R may represent 2 hydrogen atoms and an alkyl group, including a straight chain alkyl group (e.g., methyl, ethyl, propyl, butyl etc.) or a branched chain alkyl group, or R may represent, for example, 3 halogen atoms, 2 halogen atoms and a hydrogen atom, or one halogen atom and 2 hydrogen atoms. It is to be understood that a ketone through its first carbon atom may be chemically bonded to another entity.

The term "receptor", as used herein, refers to a protein present on the surface of a cell, or in a cell not associated with a cellular surface (e.g., a soluble receptor) capable of mediating signaling to and/or from the cell, or within the cell and thereby affect cellular physiology. Receptors may be classified in classes, such as the G-protein coupled receptors ("GPCRs"), families, such as 5-HT receptors, and sub-families such as $5\text{-}HT_{1A}$ receptors, $5\text{-}HT_{2A}$ receptors, and $5\text{-}HT_{2B}$ receptors, and so on. In this respect, "signaling" refers to a response in the form of a series of chemical reactions which can occur when a molecule, including, for example, the fused heterocyclic mescaline derivatives disclosed herein, interacts with a receptor. Signaling generally proceeds across a cellular membrane and/or within a cell, to reach a target molecule or chemical reaction, and results in a modulation in cellular physiology. Thus, signaling can be thought of as a transduction process by which a molecule interacting with a receptor can modulate cellular physiology, and, furthermore, signaling can be a process by which molecules inside a cell can be modulated by molecules outside a cell. Signaling and interactions between molecules and receptors, including for example, affinity, binding efficiency, and kinetics, can be evaluated through a variety of assays, including, for example, assays known as receptor binding assays (for example, radioligand binding assays, such as e.g., [$^3$H]ketanserin assays may be used to evaluate receptor $5\text{-}HT_{2A}$ receptor activity), competition assays, and saturation binding assays, and the like.

The term "G-protein coupled receptor" or "GPCR", as used herein, refers to a class of evolutionarily related transmembrane receptors capable of interacting with a class of proteins known as G-proteins (guanine nucleotide binding proteins). GPCRs can mediate cellular responses to external stimuli (Weis and Kobilka, 2018, Annual Review of Biochemistry 87: 897-919) and can be activated by interacting with a ligand, including neurotransmitters, such as serotonin or dopamine, for example, which, can then initiate an interaction of the receptor with a G-protein and can elicit dissociation of the G-protein into $\alpha$ and $\beta\gamma$ subunits. In turn, these $\alpha$ and $\beta\gamma$ subunits can mediate further downstream signaling. GPCRs can also activate other signaling pathways, for example, through arrestin proteins and kinases. Certain ligands can preferentially activate a subset of all GPCR signaling pathways. Signaling pathways downstream of a GPCR can mediate therapeutic efficacy, or can cause drug adverse effects (Bock and Bermudez, 2021, FEBS Journal 288: 2513-2528).

The term "5-HT receptor", as used herein, refers to a family of GPCR receptors found in the central and peripheral nervous system and include sub-families, such as, $5\text{-}HT_{1A}$ receptors, $5\text{-}HT_{2A}$ receptors, and $5\text{-}HT_2$B receptors. 5-HT receptors can mediate signaling through specific G-proteins, including notably $G\alpha_i$, $G\alpha_{q/11}$, and $G\alpha_s$ and can be involved in the control of multiple physiological processes including cognition, mood, and modulation of sleep-wake cycles, for example (McCorvy and Roth, 2015, Pharmacology and Therapeutics 150: 129-142). 5-HT receptors can further mediate signaling through arrestin as well as G-protein independent signaling pathways. 5-HT-receptors are implicated in multiple brain neurological disorders including migraine headaches, and neuropsychiatric disorders, such as schizophrenia and depression, for example.

The term "$5\text{-}HT_{1A}$ receptor" (also referred to as "$HT_{1A}$" or "HTR1A"), as used herein, refers to a sub-family of a family of receptors for the neurotransmitter and peripheral signal mediator serotonin. $5\text{-}HT_{1A}$ receptors can mediate a plurality of central and peripheral physiologic functions of serotonin. Ligand activity at $5\text{-}HT_{1A}$ is generally not associated with hallucination, although many hallucinogenic compounds are known to modulate $5\text{-}HT_{1A}$ receptors to impart physiological responses (Inserra et al., 2020, Pharmacol. Rev. 73: 202). $5\text{-}HT_{1A}$ receptors are implicated in various brain neurological disorders, including depression and anxiety, schizophrenia, and Parkinson's disease (Behav. Pharm. 2015, 26:45-58).

The term "$5\text{-}HT_{2A}$ receptor" (also referred to as "HT2A" or "HTR2A"), as used herein, refers to a sub-family of a family of receptors for the neurotransmitter and peripheral signal mediator serotonin. $5\text{-}HT_{2A}$ receptors can mediate a plurality of central and peripheral physiologic functions of serotonin. Central nervous system effects can include mediation of hallucinogenic effects of hallucinogenic compounds. $5\text{-}HT_{2A}$ receptors are implicated in various brain neurological disorders (Nat. Rev. Drug Discov. 2022, 21:463-473; Science 2022, 375:403-411).

The term "SERT", as used herein, refers to a transmembrane transport protein also known as "serotonin transporter" which is involved in neuronal serotonin transport, notably from the synaptic cleft back to the presynaptic neuron, thereby terminating the action of serotonin. SERT is implicated in various brain neurological disorders, including anxiety and depression (Pharmacol. Rep. 2018, 70:37-46).

The term "modulating receptors", as used herein, refers to the ability of a compound disclosed herein to alter the function of receptors. A receptor modulator may activate the activity of a receptor or inhibit the activity of a receptor depending on the concentration of the compound exposed to the receptor. Such activation or inhibition may be contingent on the occurrence of a specific event, such as activation of a signal transduction pathway, and/or maybe manifest only in particular cell types. The term “modulating receptors,” also refers to altering the function of a receptor by increasing or decreasing the probability that a complex forms between a receptor and a natural binding partner to form a multimer. A receptor modulator may increase the probability that such a complex forms between the receptor and the natural binding partner, may increase or decrease the probability that a complex forms between the receptor and the natural binding partner depending on the concentration of the compound exposed to the receptor, and or may decrease the probability that a complex forms between the receptor and the natural binding partner. It is further noted that the fused heterocyclic mescaline derivatives of the present disclosure may alter the function of a receptor by acting as an agonist, inverse agonist, or antagonist of the receptor, and that fused heterocyclic mescaline derivatives according to the present disclosure may alter the function of a receptor by directly interacting therewith or binding thereto, or by indirectly interacting therewith through one or more other molecular entities. In general, the receptor may be any receptor, including any receptor set forth herein, such as, a 5-$HT_{1A}$ or 5-$HT_{2A}$ receptor, for example. Accordingly, it will be clear, that in order to refer to modulating specific receptors, terms such as “modulating 5-$HT_{1A}$ receptors” or “modulating 5-$HT_{2A}$ receptors”, and so forth, may be used herein.

The term “receptor-mediated disorder”, as used herein, refers to a disorder that is characterized by abnormal receptor activity. A receptor-mediated disorder may be completely or partially mediated by modulating a receptor. In particular, a receptor-mediated disorder is one in which modulation of the receptor results in some effect on an underlying disorder e.g., administration of a receptor modulator results in some improvement in at least some of the subjects being treated. In general, the receptor may be any receptor, including any receptor set forth herein, such as a 5-$HT_{1A}$ or 5-$HT_{2A}$, receptor, for example. Accordingly, it will be clear, that in order to refer to specific receptor-mediated disorders, terms such as “5-$HT_{1A}$ receptor-mediated disorder”, “5-$HT_{2A}$ receptor-mediated disorder”, and so forth, may be used.

The term “transmembrane transport protein-mediated disorder”, as used herein, refers to a disorder that is characterized by abnormal transmembrane transport protein activity. A transmembrane transport protein-mediated disorder may be completely or partially mediated by modulating a transmembrane transport protein. In particular, a transmembrane transport protein-mediated disorder is one in which modulation of the transmembrane transport protein results in some effect on an underlying disorder e.g., administration of a transmembrane transport protein modulator results in some improvement in at least some of the subjects being treated. In general, the transmembrane transport protein may be any transmembrane transport protein, including any transmembrane transport protein set forth herein, such as the serotonin transporter (SERT) transmembrane transport protein, for example. Accordingly, it will be clear, that in order to refer to specific transmembrane transport protein-mediated disorders, terms such as “SERT-mediated disorder”, may be used.

The term “pharmaceutical formulation”, as used herein, refers to a preparation in a form which allows an active ingredient, including a psychoactive ingredient, contained therein to provide effective treatment, and which does not contain any other ingredients which cause excessive toxicity, an allergic response, irritation, or other adverse response commensurate with a reasonable risk/benefit ratio. The pharmaceutical formulation may contain other pharmaceutical ingredients such as excipients, carriers, diluents, or auxiliary agents.

The term “recreational drug formulation”, as used herein, refers to a preparation in a form which allows a psychoactive ingredient contained therein to be effective for administration as a recreational drug, and which does not contain any other ingredients which cause excessive toxicity, an allergic response, irritation, or other adverse response commensurate with a reasonable risk/benefit ratio. The recreational drug formulation may contain other ingredients such as excipients, carriers, diluents, or auxiliary agents.

The term “effective for administration as a recreational drug”, as used herein, refers to a preparation in a form which allows a subject to voluntarily induce a psychoactive effect for non-medical purposes upon administration, generally in the form of self-administration. The effect may include an altered state of consciousness, satisfaction, pleasure, euphoria, perceptual distortion, or hallucination.

The term “effective amount”, as used herein, refers to an amount of an active agent, pharmaceutical formulation, or recreational drug formulation, sufficient to induce a desired biological or therapeutic effect, including a prophylactic effect, and further including a psychoactive effect. Such effect can include an effect with respect to the signs, symptoms or causes of a disorder, or disease or any other desired alteration of a biological system. The effective amount can vary depending, for example, on the health condition, injury stage, disorder stage, or disease stage, weight, or sex of a subject being treated, timing of the administration, manner of the administration, age of the subject, and the like, all of which can be determined by those of skill in the art.

The terms “treating” and “treatment”, and the like, as used herein, are intended to mean obtaining a desirable physiological, pharmacological, or biological effect, and includes prophylactic and therapeutic treatment. The effect may result in the inhibition, attenuation, amelioration, or reversal of a sign, symptom or cause of a disorder, or disease, attributable to the disorder, or disease, which includes mental and psychiatric diseases and disorders. Clinical evidence of the prevention or treatment may vary with the disorder, or disease, the subject, and the selected treatment.

The term “pharmaceutically acceptable”, as used herein, refers to materials, including excipients, carriers, diluents, or auxiliary agents, that are compatible with other materials in a pharmaceutical or recreational drug formulation and within the scope of reasonable medical judgement suitable for use in contact with a subject without excessive toxicity, allergic response, irritation, or other adverse response commensurate with a reasonable risk/benefit ratio.

The term “low or non-hallucinogenic”, as used herein in connection with a chemical compound, or a pharmaceutical formulation containing the same, refers to a subject having been administered the compound in an effective amount of the compound, experiencing limited or no hallucinogenic effects. The potential for a drug compound to cause a hallucinogenic effect can be assayed, for example, using an animal behavior model, including, a rodent head-twitch response (HTR) model, such as described, for example, by Halberstadt and Geyer, 2013, Psychopharmacol. 227:727, and Gonzalez-Maeso et al., 2007, Neuron 53:439-452. Low or non-hallucinogenic drug compounds can include compounds which cause a limited head-twitch response (HTR) in a drug-induced animal behavior model, preferably, that is not statistically significantly greater than the head-twitch response caused by a known non-hallucinogenic derivative of a hallucinogenic compound, for example, the non-hallucinogenic tryptamine derivative compounds: 5-bromo-dimethyltryptamine (5-Br-DMT) and 6-fluoro-diethyltryptamine; (6-F-DET), or non-hallucinogenic ibogaine derivative compounds, for example, tabernanthalog (TBG), as can be determined, for example, by ordinary one-way analysis of variance (ANOVA) wherein the mean HTR for each compound can be compared to the mean HTR of, for example, 5-Br-DMT, 6-F-DET, or TBG, as a control, using Dunnett's Multiple Comparison Test, wherein each p-value can be adjusted to account for multiple comparisons, and wherein family-wise alpha threshold and confidence levels are: 0.05 (95% confidence level).

The terms "substantially pure" and "isolated", as may be used interchangeably herein, describe a compound, e.g., an N-heterocycle-substituted tryptamine derivative, which has been separated from components that naturally or synthetically accompany it. Typically, a compound is substantially pure when at least 60%, more preferably at least 75%, more preferably at least 90%, 95%, 96%, 97%, or 98%, and most preferably at least 99% of the total material (by volume, by wet or dry weight, or by mole percent or mole fraction) in a sample is the compound of interest. Purity can be measured by any appropriate method, e.g., by chromatography, gel electrophoresis or HPLC analysis.

General Implementation

As hereinbefore mentioned, the present disclosure relates to tryptamine derivatives. In particular, the present disclosure provides novel substituted tryptamine derivatives, and in particular, relates to N-heterocycle substituted tryptamine derivatives. In general, the herein provided compositions exhibit functional properties which deviate from the functional properties of tryptamine. Thus, for example, the N-heterocycle-substituted tryptamine derivatives can exhibit pharmacological properties which deviate from tryptamine. Furthermore, the N-heterocycle-substituted tryptamine derivatives may exhibit physico-chemical properties which differ from tryptamine. Thus, for example, N-heterocycle substituted tryptamine derivatives may exhibit superior solubility in a solvent, for example, an aqueous solvent. Furthermore, the N-heterocycle-substituted tryptamine derivatives may exhibit pharmacokinetics or pharmacodynamics which are different from a non-substituted compound. Furthermore, upon administration to a subject, the subject may, surprisingly, experience limited or no hallucinogenic side-effects. The N-heterocycle-substituted tryptamine derivatives in this respect are useful in the formulation of pharmaceutical and recreational drug formulations.

In what follows selected embodiments are described with reference to the drawings.

Accordingly, in one aspect, the present disclosure provides derivatives of a compound known as tryptamine of which the chemical structure is shown in FIG. 1. The derivatives herein provided are, N-heterocycle-substituted tryptamine derivatives, and in particular tryptamine derivatives wherein at least one of the $C_2$, $C_4$, $C_5$, $C_6$, and $C_7$ atom of the tryptamine moiety is chemically bonded to an N-heterocycle substituent.

Thus, in one aspect, the present disclosure provides, in accordance with the teachings herein, in at least one embodiment, a compound having chemical formula (I):

(I)

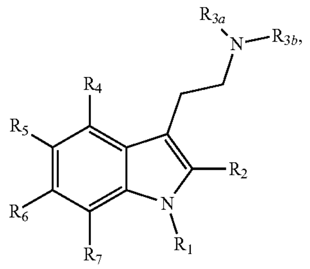

wherein at least one of $R_2$, $R_4$, $R_5$, $R_6$, and $R_7$ is an N-heterocycle substituent, wherein each of $R_2$, $R_4$, $R_5$, $R_6$, and $R_7$ which are not an N-heterocycle substituent are a hydrogen atom, a halogen atom, or a ketone group, wherein $R_1$ is alkyl or hydrogen, and wherein $R_{3a}$ and $R_{3b}$ are each independently a hydrogen atom, an alkyl group, an aryl group, or an alkyl-aryl group.

Thus, referring to the chemical compound having the formula (I), in an aspect hereof, at least one of $R_2$, $R_4$, $R_5$, $R_6$, and $R_7$ is an N-heterocycle substituent, i.e., an N-heterocycle moiety or derivative thereof which is bonded to the $C_2$, $C_4$, $C_5$, $C_6$, or $C_7$ atom of the tryptamine compound. In some embodiments, the at least one N-heterocycle substituent can be bonded to the tryptamine compound through the nitrogen atom of the N-heterocycle substituent, and thus, the N-heterocycle substituent can be an N-linked heterocyclic ring. In some embodiments, a plurality of the $C_2$, $C_4$, $C_5$, $C_6$, or $C_7$ carbon atoms, for example, two or three of $C_2$, $C_4$, $C_5$, $C_6$, or $C_7$ carbon atoms can be bonded to an N-heterocycle substituent.

Continuing to refer to the compound having chemical formula (I), in some embodiments, the N-heterocycle substituent can be a 3-10 membered N-heterocyclic ring, for example, a 3-membered, a 4-membered, a 5-membered, or 6-membered heterocyclic ring. The N-heterocyclic ring can be a saturated ring, or a partially saturated ring, including an aromatic ring, such as an imidazole, a pyrrole, a pyrazole, a thiozole, or an oxazole, for example.

Continuing to refer to the compound having chemical formula (I), in some embodiments, the N-heterocyclic ring can include be a 3-10 membered N-heterocyclic ring, including at least one additional hetero atom, including, for example, an oxygen atom (see e.g., formula (III) below), or a second nitrogen atom (see e.g., formula (IV) below).

Continuing to refer to the compound having chemical formula (I), in some embodiments, the N-heterocycle substituent can have the chemical formula (II), (III), or (IV):

(II)

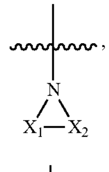

or (III)

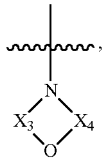

or

-continued (IV)

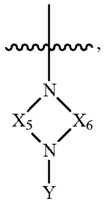

wherein in chemical formula (II), (III), and (IV), $X_1$, $X_2$, $X_3$, $X_4$, $X_5$, and $X_6$ are independently selected from a $C_1$ to $C_4$-alkylene, and wherein in formula (IV), Y is a hydrogen atom, an alkyl group, or an aryl group. Thus, for example, referring to formula (II), $X_1$ and $X_2$ each can be methylene ($—CH_2—$), or $X_1$ can be methylene ($—CH_2—$) and $X_2$ can be ethylene ($—CH_2—CH_2—$), or $X_1$ and $X_2$ each can be ethylene ($—CH_2—CH_2—$). Furthermore, referring to chemical formula (III), $X_3$ and $X_4$ each can be methylene ($—CH_2—$), or $X_3$ can be methylene ($—CH_2—$) and $X_4$ can be ethylene ($—CH_2—CH_2—$), or $X_3$ and $X_4$ each can be ethylene ($—CH_2—CH_2—$). Furthermore, referring to chemical formula (IV), $X_5$ and $X_6$ each can be methylene ($—CH_2—$), or $X_5$ can be methylene ($—CH_2—$) and $X_6$ can be ethylene ($—CH_2—CH_2—$), or $X_5$ and $X_6$ each can be ethylene ($—CH_2—CH_2—$). Continuing to refer to chemical formula (IV), in some embodiments, Y can be H, a ($C_1$-$C_6$) alkyl group, including for example, a methyl group ($—CH_3$) or ethyl group ($—CH_2—CH_3$), or an aryl group, including, for example, a phenyl group.

Continuing to refer to the compound having chemical formula (I), each of $R_2$, $R_4$, $R_5$, $R_6$, and $R_7$ which are not an N-heterocycle substituent can be a hydrogen atom, a halogen atom (F, Cl, Br, I), or a ketone group. The ketone group can have the chemical formula (A):

(A)

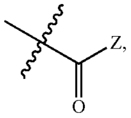

wherein Z can be ($C_1$-$C_6$)-alkyl, optionally methyl ($—CH_3$). In some embodiments, each of $R_2$, $R_4$, $R_5$, $R_6$, and $R_7$ which are not an N-heterocycle substituent can be a hydrogen atom. In some embodiments, at least one of $R_2$, $R_4$, $R_5$, $R_6$, and $R_7$ which are not an N-heterocycle substituent can be a halogen atom (F, Cl, Br, I), and the remaining $R_2$, $R_4$, $R_5$, $R_6$, and $R_7$ can be hydrogen atom.

In one example embodiment, $R_4$ can be an N-heterocycle substituent, for example, an N-heterocycle substituent, having formula (III), wherein, for example, $X_3$ and $X_4$ each can be methylene ($—CH_2—$), or one of $X_3$ and $X_4$ can be methylene ($—CH_2—$) and one of $X_3$ and $X_4$ can be ethylene ($—CH_2—CH_2—$), or $X_3$ and $X_4$ each can be ethylene ($—CH_2—CH_2—$), $R_6$ can be a halogen atom, for example, a fluorine or a chorine atom, and $R_1$, $R_2$, $R_5$, and $R_7$ can each be a hydrogen atom.

Continuing to refer to the compound having chemical formula (I), in some embodiments, in an aspect, $R_1$ can be ($C_1$-$C_6$)-alkyl, ($C_1$-$C_3$)-alkyl, methyl ($—CH_3$), or hydrogen.

Referring further to the compound having chemical formula (I), $R_{3a}$ and $R_{3b}$ can be independently a hydrogen atom or a ($C_1$-$C_{20}$)-alkyl group, an aryl group, for example a phenyl group, or an alkyl-aryl group, for example, $CH_2$-phenyl. In another embodiment, $R_{3a}$ and $R_{3b}$ can independently be a hydrogen atom or a ($C_1$-$C_{10}$)-alkyl group, an aryl group, for example, a phenyl group, or an alkyl-aryl group, for example, $CH_2$-phenyl. In another embodiment, $R_{3a}$ and $R_{3b}$ can independently be a hydrogen atom or a ($C_1$-$C_6$)-alkyl group, an aryl group, for example a phenyl group, or an alkyl-aryl group, for example, $CH_2$-phenyl. In another embodiment, $R_{3a}$ and $R_{3b}$ can independently be a hydrogen atom, a methyl group, an ethyl group, or a propyl group, or an aryl group, for example, a phenyl group, or an alkyl-aryl group, for example, $CH_2$-phenyl.

In a further example embodiment, in accordance herewith, the compound having formula (I) can be a compound having formula (V):

(V)

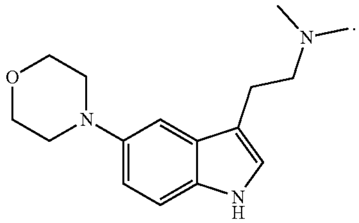

In a further example embodiment, in accordance herewith, the compound having formula (I) can be a compound having formula (VI):

(VI)

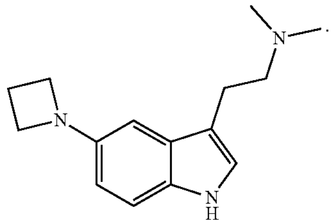

In a further example embodiment, in accordance herewith, the compound having formula (I) can be a compound having formula (VII):

(VII)

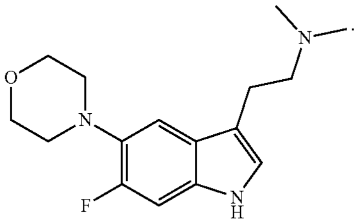

In a further example embodiment, in accordance herewith, the compound having formula (I) can be a compound having formula (VIII):

(VIII)

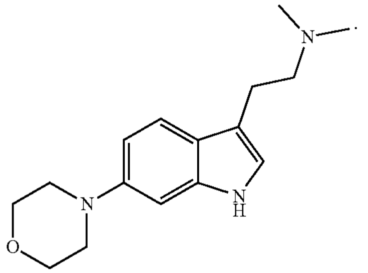

In a further example embodiment, in accordance herewith, the compound having formula (I) can be a compound having formula (IX):

(IX)

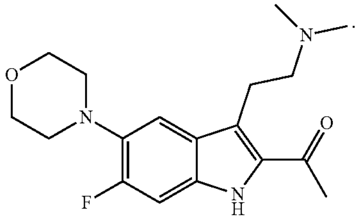

In a further example embodiment, in accordance herewith, the compound having formula (I) can be a compound having formula (X):

(X)

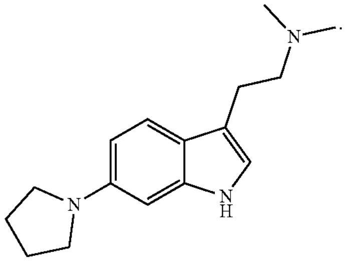

In a further example embodiment, in accordance herewith, the compound having formula (I) can be a compound having formula (XI):

(XI)

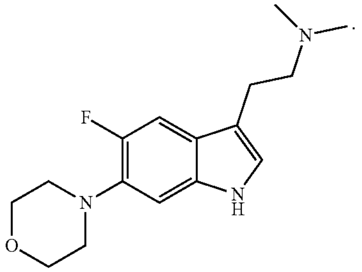

In a further example embodiment, in accordance herewith, the compound having formula (I) can be a compound having formula (XII):

(XII)

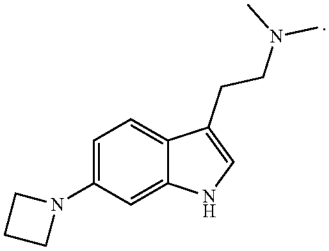

In a further example embodiment, in accordance herewith, the compound having formula (I) can be a compound having formula (XIII):

(XIII)

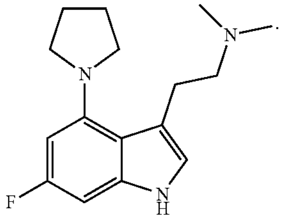

In a further example embodiment, in accordance herewith, the compound having formula (I) can be a compound having formula (XIV):

(XIV)

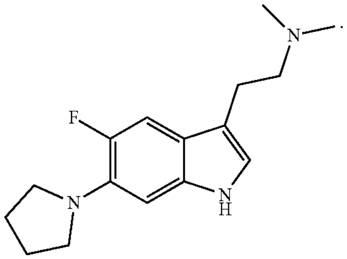

In a further example embodiment, in accordance herewith, the compound having formula (I) can be a compound having formula (XV):

(XV)

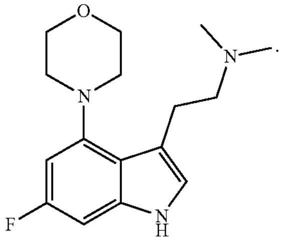

In a further example embodiment, in accordance herewith, the compound having formula (I) can be a compound having formula (XVI):

(XVI)

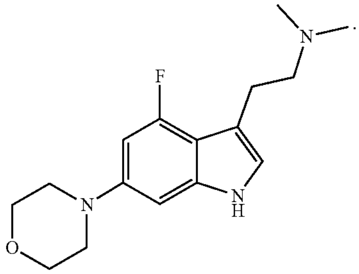

In a further example embodiment, in accordance herewith, the compound having formula (I) can be a compound having formula (XVII):

(XVII)

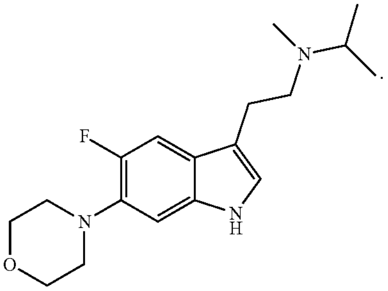

In a further example embodiment, in accordance herewith, the compound having formula (I) can be a compound having formula (XVIII):

(XVIII)

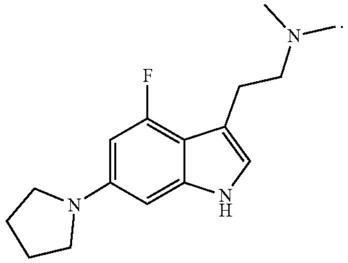

In a further example embodiment, in accordance herewith, the compound having formula (I) can be a compound having formula (XIX):

(XIX)

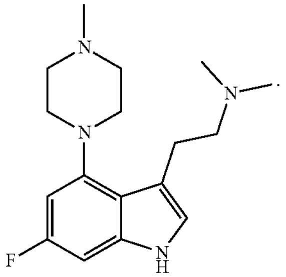

In a further example embodiment, in accordance herewith, the compound having formula (I) can be a compound having formula (XX):

(XX)

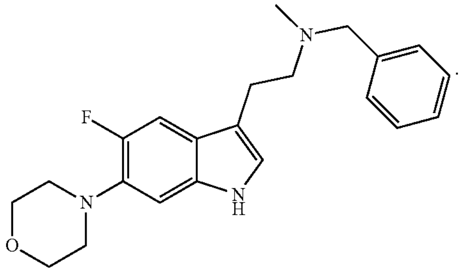

In a further example embodiment, in accordance herewith, the compound having formula (I) can be a compound having formula (XXI):

(XXI)

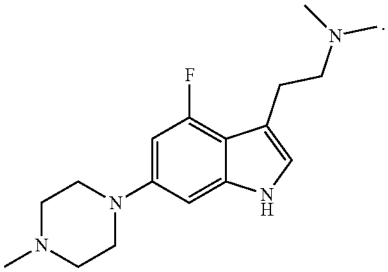

In a further example embodiment, in accordance herewith, the compound having formula (I) can be a compound having formula (XXII):

(XXII)

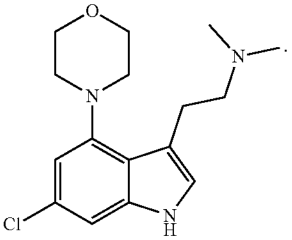

In a further example embodiment, in accordance herewith, the compound having formula (I) can be a compound having formula (XXIII):

(XXIII)

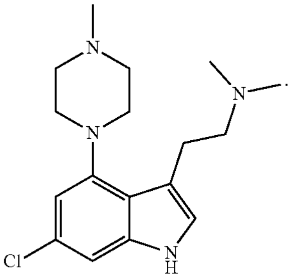

In a further example embodiment, in accordance herewith, the compound having formula (I) can be a compound having formula (XXIV):

(XXIV)

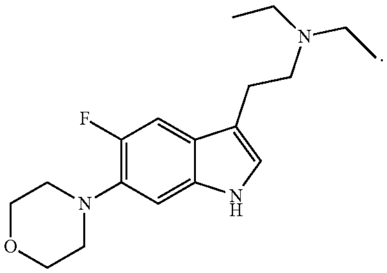

In a further example embodiment, in accordance herewith, the compound having formula (I) can be a compound having formula (XXV):

(XXV)

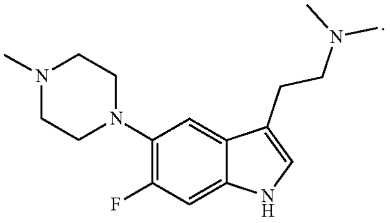

In a further example embodiment, in accordance herewith, the compound having formula (I) can be a compound having formula (XXVI):

(XXVI)

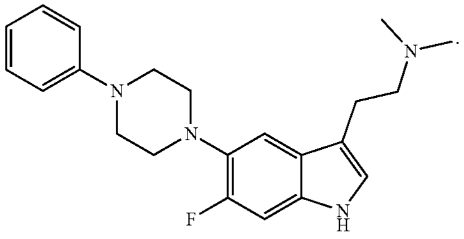

In a further example embodiment, in accordance herewith, the compound having formula (I) can be a compound having formula (XXVII):

(XXVII)

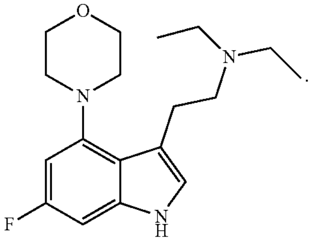

In a further example embodiment, in accordance herewith, the compound having formula (I) can be a compound having formula (XXVIII):

(XXVIII)

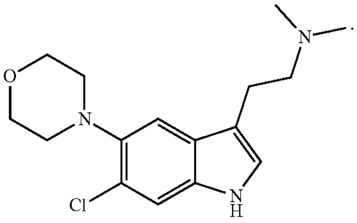

In a further example embodiment, in accordance herewith, the compound having formula (I) can be a compound having formula (XXIX):

(XXIX)

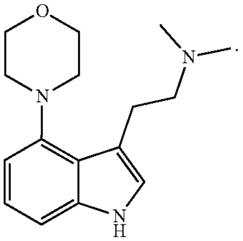

In a further example embodiment, in accordance herewith, the compound having formula (I) can be a compound having formula (XXX):

(XXX)

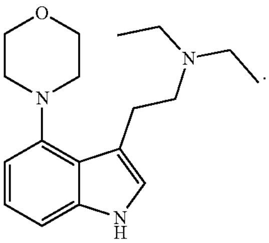

In a further example embodiment, in accordance herewith, the compound having formula (I) can be a compound having formula (XXXI):

(XXXI)

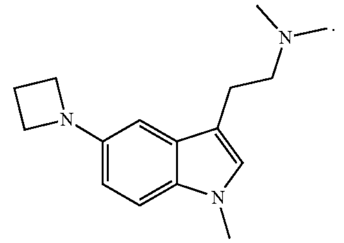

In a further example embodiment, in accordance herewith, the compound having formula (I) can be a compound having formula (XXXII):

(XXXII)

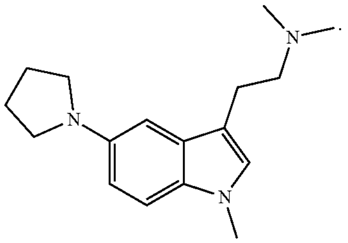

In a further example embodiment, in accordance herewith, the compound having formula (I) can be a compound having formula (XXXIII):

(XXXIII)

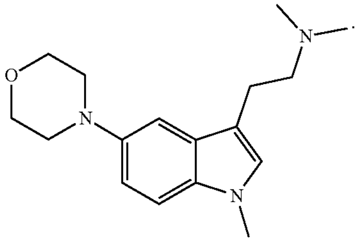

Thus, to briefly recap, the present disclosure provides N-heterocycle-substituted tryptamine derivatives. The disclosure provides, in particular, a chemical compound having a formula (I):

(I)

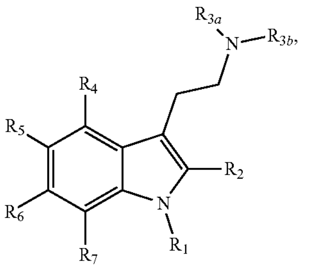

wherein at least one of $R_2$, $R_4$, $R_5$, $R_6$, and $R_7$ is an N-heterocycle substituent, wherein each of $R_2$, $R_4$, $R_5$, $R_6$, and $R_7$ which are not an N-heterocycle substituent are a hydrogen atom, a halogen atom, or a ketone group, wherein $R_1$ is alkyl or hydrogen, and wherein $R_{3a}$ and $R_{3b}$ are each independently a hydrogen atom, an alkyl group, an aryl group, or an alkyl-aryl group.

The foregoing includes compounds wherein the N-heterocycle substituent has the chemical formula (II), (III), or (IV):

(II)

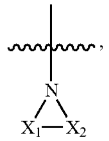

, or (III)

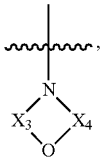

, or (IV)

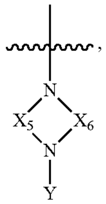

, wherein in chemical formula (II), (III), and (IV), $X_1$, $X_2$, $X_3$, $X_4$, $X_5$, and $X_6$ are independently selected from a $C_1$-alkylene ($—CH_2—$), $C_2$-alkylene ($—CH_2—CH_2—$), $C_3$-alkylene ($—CH_2—CH_2—CH_2—$), and $C_4$-alkylene ($—CH_2—CH_2—CH_2—CH_2—$), and wherein in formula (IV), Y is a hydrogen atom, an alkyl group, including a ($C_1$-$C_6$)-alkyl group, ($C_1$-$C_3$)-alkyl group, propyl group ($—CH_2CH_2CH_3$), ethyl group ($—CH_2CH_3$) or methyl group ($—CH_3$), or an aryl group, including a phenyl group.

The foregoing also includes compounds wherein one of $R_2$, $R_4$, $R_5$, $R_6$, and $R_7$ is an N-heterocycle substituent and the remaining of $R_2$, $R_4$, $R_5$, $R_6$, and $R_7$ are a hydrogen atom, as well as compounds wherein one of $R_2$, $R_4$, $R_5$, $R_6$, and $R_7$ is an N-heterocycle substituent, and one of $R_2$, $R_4$, $R_5$, $R_6$, and $R_7$ is a halogen atom (F, Cl, Br, I), and the remaining of $R_2$, $R_4$, $R_5$, $R_6$, and $R_7$ are hydrogen atoms.

In some embodiments, $R_{3a}$ and $R_{3b}$ are independently a hydrogen atom or a ($C_1$-$C_{20}$)-alkyl group, an aryl group, for example a phenyl group, or an alkyl-aryl group, for example, ($C_1$-$C_{20}$)-alkyl aryl group, for example, a $CH_2$-phenyl group. In another embodiment, $R_{3a}$ and $R_{3b}$ are independently a hydrogen atom or a ($C_1$-$C_{10}$)-alkyl group, an aryl group, for example a phenyl group or an alkyl-aryl group, for example, ($C_1$-$C_{10}$)-alkyl aryl group, for example, a $CH_2$-phenyl group. In another embodiment, $R_{3a}$ and $R_{3b}$ are independently a hydrogen atom or a ($C_1$-$C_6$)-alkyl group, an aryl group, for example, a phenyl group, or an alkyl-aryl group, for example, ($C_1$-$C_6$)-alkyl aryl group, for example, a $CH_2$-phenyl group. In another embodiment, $R_{3a}$ and $R_{3b}$ are independently a hydrogen atom, a methyl group, an ethyl group, or a propyl group, an aryl group, for example, a phenyl group, or an alkyl-aryl group, for example, a $CH_2$-phenyl group.

The N-heterocycle-substituted tryptamine derivatives of the present disclosure may be used to prepare a pharmaceutical or recreational drug formulation. Thus, in one embodiment, the present disclosure further provides in another aspect, pharmaceutical and recreational drug formulations comprising N-heterocycle-substituted tryptamine derivatives. Accordingly, in one aspect, the present disclosure provides in a further embodiment a pharmaceutical or recreational drug formulation comprising a chemical compound having a formula (I):

(I)

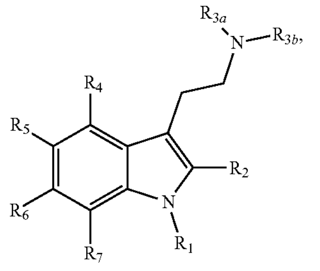

wherein at least one of $R_2$, $R_4$, $R_5$, $R_6$, and $R_7$ is an N-heterocycle substituent, wherein each of $R_2$, $R_4$, $R_5$, $R_6$, and $R_7$ which are not an N-heterocycle substituent are a hydrogen atom, a halogen atom, or a ketone group, wherein $R_1$ is alkyl or hydrogen, and wherein $R_{3a}$ and $R_{3b}$ are each independently a hydrogen atom, an alkyl group, an aryl group, or an alkyl-aryl group.

The pharmaceutical or recreational drug formulations may be prepared as liquids, tablets, capsules, microcapsules, nanocapsules, trans-dermal patches, gels, foams, oils, aerosols, nanoparticulates, powders, creams, emulsions, micellar systems, films, sprays, ovules, infusions, teas, decoctions, suppositories, etc. and include a pharmaceutically acceptable salt or solvate of the N-heterocycle-substituted tryptamine derivative compound together with an excipient. The term "excipient" as used herein means any ingredient other than the chemical compound of the disclosure. In order to prepare a pharmaceutical drug formulation in accordance herewith, the N-heterocycle-substituted tryptamine derivative compounds are generally initially prepared and obtained in a substantially pure form, most preferably, at least in a 98%, 99% or 99.9% pure form, and thereafter formulated with a pharmaceutically acceptable excipient. As will readily be appreciated by those of skill in art, the selection of excipient may depend on factors such as the particular mode of administration, the effect of the excipient on solubility of the chemical compounds of the present disclosure and methods for their preparation will be readily apparent to those skilled in the art. Such compositions and methods for their preparation may be found, for example, in "Remington's Pharmaceutical Sciences", 22nd Edition (Pharmaceutical Press and Philadelphia College of Pharmacy at the University of the Sciences, 2012).

The dose when using the compounds of the present disclosure can vary within wide limits, and as is customary and is known to those of skill in the art, the dose can be tailored to the individual conditions in each individual case. The dose depends, for example, on the nature and severity of the illness to be treated, on the condition of the patient, on the compound employed or on whether an acute or chronic disease state is treated, or prophylaxis is conducted, on the mode of delivery of the compound, or on whether further active compounds are administered in addition to the compounds of the present disclosure. Representative doses of the present invention include, but are not limited to, about 0.001 mg to about 5000 mg, about 0.001 mg to about 2500 mg, about 0.001 mg to about 1000 mg, about 0.001 mg to about 500 mg, about 0.001 mg to about 250 mg, about 0.001 mg to about 100 mg, about 0.001 mg to about 50 mg, and about 0.001 mg to about 25 mg. Representative doses of the present disclosure include, but are not limited to, about 0.0001 to about 1,000 mg, about 10 to about 160 mg, about 10 mg, about 20 mg, about 40 mg, about 80 mg or about 160 mg. Multiple doses may be administered during the day, especially when relatively large amounts are deemed to be needed, for example 2, 3 or 4, doses. Depending on the subject and as deemed appropriate from the patient's physician or care giver it may be necessary to deviate upward or downward from the doses described herein.

The pharmaceutical and drug formulations comprising the N-heterocycle-substituted tryptamine derivative compounds of the present disclosure may be administered orally. Oral administration may involve swallowing, so that the compound enters the gastrointestinal tract, or buccal or sublingual administration may be employed by which the compound enters the blood stream directly from the mouth. Formulations suitable for oral administration include both solid and liquid formulations.

Solid formulations include tablets, capsules (containing particulates, liquids, microcapsules, or powders), lozenges (including liquid-filled lozenges), chews, multi- and nano-particulates, gels, solid solutions, liposomal preparations, microencapsulated preparations, creams, films, ovules, suppositories, and sprays.

Liquid formulations include suspensions, solutions, syrups, and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose.

Tablets may also contain diluents, such as lactose (monohydrate, spray-dried monohydrate, anhydrous and the like), mannitol, xylitol, dextrose, sucrose, sorbitol, microcrystalline cellulose, starch, and dibasic calcium phosphate dihydrate.

Tablets may also optionally comprise surface active agents, such as sodium lauryl sulfate and polysorbate 80. When present, surface active agents may comprise from 0.2% (w/w) to 5% (w/w) of the tablet.

Tablets may further contain lubricants such as magnesium stearate, calcium stearate, zinc stearate, sodium stearyl fumarate, and mixtures of magnesium stearate with sodium lauryl sulphate. Lubricants generally comprise from 0.25% (w/w) to 10% (w/w), from 0.5% (w/w) to 3% (w/w) of the tablet.

In addition to the N-heterocycle-substituted tryptamine derivative compounds, tablets may contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from 1% (w/w) to 25% (w/w) or from 5% (w/w) to 20% (w/w) of the dosage form.

Other possible auxiliary ingredients include anti-oxidants, colourants, flavouring agents, preservatives, and taste-masking agents.

For tablet dosage forms, depending on the desired effective amount of the chemical compound, the chemical compound of the present disclosure may make up from 1% (w/w) to 80% (w/w) of the dosage form, more typically from 5% (w/w) to 60% (w/w) of the dosage form.

Exemplary tablets contain up to about 80% (w/w) of the chemical compound, from about 10% (w/w) to about 90% (w/w) binder, from about 0% (w/w) to about 85% (w/w) diluent, from about 2% (w/w) to about 10% (w/w) disintegrant, and from about 0.25% (w/w) to about 10% (w/w) lubricant.

The formulation of tablets is discussed in "Pharmaceutical Dosage Forms: Tablets", Vol. 1-Vol. 3, by CRC Press (2008).

The pharmaceutical and recreational drug formulations comprising the N-heterocycle-substituted tryptamine derivative compound of the present disclosure may also be administered directly into the blood stream, into muscle, or into an internal organ. Thus, the pharmaceutical and recreational drug formulations can be administered parenterally (for example, by subcutaneous, intravenous, intraarterial, intrathecal, intraventricular, intracranial, intramuscular, or intraperitoneal injection). Parenteral formulations are typically aqueous solutions which may contain excipients such as salts, carbohydrates, and buffering agents (in one embodiment, to a pH of 3 to 9), but, for some applications, they may be more suitably formulated as a sterile non-aqueous solution or as a dried form to be used in conjunction with a suitable vehicle such as sterile water.

Formulations comprising the N-heterocycle-substituted tryptamine derivative compound of the present disclosure for parenteral administration may be formulated to be immediate and/or modified release. Modified release formulations include delayed-, sustained-, pulsed-, controlled-, targeted and programmed release. Thus, the chemical compounds of the disclosure may be formulated as a solid, semi-solid, or thixotropic liquid for administration as an implanted depot providing modified release of the active compound. Examples of such formulations include drug-coated stents and poly(dl-lactic-coglycolic)acid (PGLA) microspheres.

The pharmaceutical or recreational drug formulations of the present disclosure also may be administered topically to the skin or mucosa, i.e., dermally or transdermally. Example pharmaceutical and recreational drug formulations for this purpose include gels, hydrogels, lotions, solutions, creams, ointments, dusting powders, cosmetics, oils, eye drops, dressings, foams, films, skin patches, wafers, implants, sponges, fibres, bandages and microemulsions. Liposomes may also be used. Example carriers include alcohol, water, mineral oil, liquid petrolatum, white petrolatum, glycerin, polyethylene glycol and propylene glycol. Penetration enhancers may be incorporate (see: for example, Finnin, B. and Morgan, T. M., 1999 J. Pharm. Sci, 88 (10), 955-958).

Other means of topical administration include delivery by electroporation, iontophoresis, phonophoresis, sonophoresis and microneedle or needle-free (e.g., Powderject™, Bioject™, etc.) injection.

Pharmaceutical and recreational drug formulations for inhalation or insufflation include solutions and suspensions in pharmaceutically acceptable, aqueous, or organic solvents, or mixtures thereof, and powders. The liquid or solid pharmaceutical compositions can contain suitable pharmaceutically acceptable excipients. In some embodiments, the pharmaceutical compositions are administered by the oral or nasal respiratory route for local or systemic effect. Pharmaceutical compositions in pharmaceutically acceptable solvents can be nebulized by use of inert gases. Nebulized solutions can be inhaled directly from the nebulizing device, or the nebulizing device can be attached to a face mask tent, or intermittent positive pressure breathing machine. Solution, suspension, or powder pharmaceutical compositions can be administered, e.g., orally, or nasally, from devices that deliver the formulation in an appropriate manner.

It is noted that in some embodiments, the chemical compounds in the pharmaceutical formulation may act as pro-drugs. Pro-drugs represent a modality to control drug bioavailability, control timing of drug release, and/or reduce negative side-effects. Similarly, formulation and delivery considerations can achieve these outcomes. Thus, optimization of all three variables together (prodrug moiety, formulation, delivery system) can be an effective strategy in drug development. Examples of 'targeting systems' designed to specifically reach cells within the brain, obtained by simultaneously leveraging pro-drug, nanoparticle. And nasal administration strategies are described, for example by Botti et al., 2021 Pharmaceutics 13:1114).

In further embodiments, in which the N-heterocycle-substituted tryptamine derivative compounds of present disclosure are used as a recreational drug, the compounds may be included in compositions such as a food or food product, a beverage, a food seasoning, a personal care product, such as a cosmetic, perfume or bath oil, or oils (both for topical administration as massage oil, or to be burned or aerosolized). The chemical compounds of the present disclosure may also be included in a "vape" product, which may also include other drugs, such as nicotine, and flavorings.

Thus, it will be clear that the N-heterocycle-substituted tryptamine derivative compounds may be used as a pharmaceutical or recreational drug. Accordingly, in another aspect the present disclosure provides, in at least one embodiment, a use of a chemical compound having a formula (I):

(I)

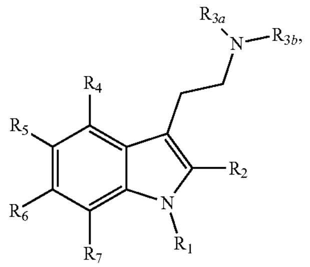

wherein at least one of $R_2$, $R_4$, $R_5$, $R_6$, and $R_7$ is an N-heterocycle substituent, wherein each of $R_2$, $R_4$, $R_5$, $R_6$, and $R_7$ which are not an N-heterocycle substituent are a hydrogen atom, a halogen atom, or a ketone group, wherein $R_1$ is alkyl or hydrogen, and wherein $R_{3a}$ and $R_{3b}$ are each independently a hydrogen atom, an alkyl group, an aryl group, or an alkyl-aryl group, as a pharmaceutical or recreational drug The pharmaceutical formulations comprising the chemical compounds of the present disclosure may be used to treat a subject, and to treat a brain neurological disorder in a subject. Accordingly, the present disclosure includes in a further embodiment, a method for treating a brain neurological disorder, the method comprising administering to a subject in need thereof a pharmaceutical formulation comprising a chemical compound having a formula (I):

(I)

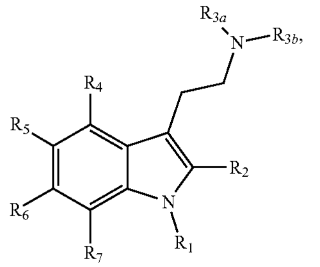

wherein at least one of $R_2$, $R_4$, $R_5$, $R_6$, and $R_7$ is an N-heterocycle substituent, wherein each of $R_2$, $R_4$, $R_5$, $R_6$, and $R_7$ which are not an N-heterocycle substituent are a hydrogen atom, a halogen atom, or a ketone group, wherein $R_1$ is alkyl or hydrogen, and wherein $R_{3a}$ and $R_{3b}$ are each independently a hydrogen atom, an alkyl group, an aryl group, or an alkyl-aryl group, wherein the pharmaceutical formulation is administered in an effective amount to treat the brain neurological disorder.

Brain neurological disorders include psychiatric disorders that may be treated include, for example, neurodevelopmental disorders such as intellectual disability, global development delay, communication disorders, autism spectrum disorder, and attention-deficit hyperactivity disorder (ADHD); bipolar and related disorders, such as mania, and depressive episodes; anxiety disorder, such as generalized anxiety disorder (GAD), agoraphobia, social anxiety disorder, specific phobias (natural events, medical, animal, situational, for example), panic disorder, and separation anxiety disorder; stress disorders, such as acute stress disorder, adjustment disorders, post-traumatic stress disorder (PTSD), and reactive attachment disorder; dissociative disorders, such as dissociative amnesia, dissociative identity disorder, and depersonalization/derealization disorder; somatoform disorders, such as somatic symptom disorders, illness anxiety disorder, conversion disorder, and factitious disorder; eating disorders, such as anorexia nervosa, bulimia nervosa, rumination disorder, pica, and binge-eating disorder; sleep disorders, such as narcolepsy, insomnia disorder, hypersomnolence, breathing-related sleep disorders, parasomnias, and restless legs syndrome; disruptive disorders, such as kleptomania, pyromania, intermittent explosive disorder, conduct disorder, and oppositional defiant disorder; depressive disorders, such as disruptive mood dysregulation disorder, major depressive disorder (MDD), persistent depressive disorder (dysthymia), premenstrual dysphoric disorder, substance/medication-induced depressive disorder, postpartum depression, and depressive disorder caused by another medical condition, for example, psychiatric and existential distress within life-threatening cancer situations (ACS Pharmacol. Transl. Sci. 4: 553-562; J. Psychiatr. Res 137: 273-282); substance-related disorders, such as alcohol-related disorders, *cannabis* related disorders, inhalant-use related disorders, stimulant use disorders, and tobacco use disorders; neurocognitive disorders, such as delirium; schizophrenia; compulsive disorders, such as obsessive compulsive disorders (OCD), body dysmorphic disorder, hoarding disorder, trichotillomania disorder, excoriation disorder, substance/medication induced obsessive-compulsive disorder, and obsessive-compulsive disorder related to another medical condition; and personality disorders, such as anti-social personality disorder, avoidant personality disorder, borderline personality disorder, dependent personality disorder, histrionic personality disorder, narcissistic personality disorder, obsessive-compulsive personality disorder, paranoid personality disorder, schizoid personality disorder, and schizotypal personality disorder. Brain neurological disorders further include headache disorders, including migraines, including, for example, aural migraine, non-aural migraine, menstrual migraine, chronic migraine, vestibular migraine, abdominal migraine, hemiplegic migraine, and other headache disorders.

In one embodiment, the subject may experience no hallucinogenic side effect, or a low hallucinogenic side effect, upon having been administered a pharmaceutical composition comprising an effective amount of a compound of the present disclosure. Thus, for example, the subject can experience a hallucinogenic effect no larger that the hallucinogenic side effect being experienced when administered with the same dose of a known non-hallucinogenic derivative of a hallucinogenic compound, including, for example, the non-hallucinogenic tryptamine derivative compounds: 5-bromo-dimethyltryptamine (5-Br-DMT) (Dong et al., 2021, Cell 184:2779-2792; Dong et al., 2022, WO2022081631A1) and 6-fluoro-diethyltryptamine (6-F-DET) (Kalir et al., 1963, J. Med. Chem. 6:716-719; Blair et al., 2000, J. Med. Chem. 43:4701-4710), or non-hallucinogenic ibogaine derivative compounds, for example, tabernanthalog (TBG) (Cameron et al., 2021, Nature 589:474-479).

In one embodiment, the compound having formula (I) can be a low or non-hallucinogenic compound, causing a head-twitch response that is not statistically significantly greater than the head-twitch response caused by 5-bromo-dimethyltryptamine (5-Br-DMT) in a drug-induced animal behavior model.

In an aspect, the compounds of the present disclosure may be used to be contacted with a receptor to thereby modulate the receptor. Such contacting includes bringing a compound of the present disclosure and receptor together under in vitro conditions, for example, by introducing the compounds in a sample containing a receptor, for example, a sample containing purified receptors, or a sample containing cells comprising receptors. In vitro conditions further include the conditions described in Example 11 hereof. Contacting further includes bringing a compound of the present disclosure and receptor together under in vivo conditions. Such in vivo conditions include the administration to an animal or human subject, for example, of a pharmaceutically effective amount of the compound of the present disclosure, when the compound is formulated together with a pharmaceutically active carrier, diluent, or excipient, as hereinbefore described, to thereby treat the subject. Upon having contacted the receptor, the compound may activate the receptor or inhibit the receptor.

In an aspect receptors with which the compounds of the present disclosure may be contacted include, for example, the 5-$HT_{1A}$ receptor or the 5-$HT_{2A}$ receptor.

Thus, in a further aspect, the condition that may be treated in accordance herewith can be any receptor mediated disorder, including, for example, a 5-$HT_{1A}$ receptor-mediated disorder or a 5-$HT_{2A}$ receptor-mediated disorder. Such disorders include, but are not limited to schizophrenia, psychotic disorder, attention deficit hyperactivity disorder, autism, and bipolar disorder.

In some embodiments, upon having contacted a receptor the compound may modulate the receptor. However, at the same time other receptors may not be modulated. e.g., a compound may activate or inhibit a first receptor, e.g., a 5-$HT_{2A}$ receptor, however the compound may at the same time not modulate a second receptor, e.g., a 5-$HT_{1A}$ receptor.

In at least one embodiment, in an aspect, upon administration the compound having formula (I) can interact with a transmembrane transport protein in the subject to thereby modulate the transmembrane transport protein and exert a pharmacological effect.

In one embodiment, in an aspect, upon administration the compounds of the present disclosure can interact with a transmembrane transport protein in the subject to thereby modulate the transmembrane transport protein and exert a pharmacological effect. Such contacting includes bringing a compound of the present disclosure and transmembrane protein together under in vitro conditions, for example, by introducing the compounds in a sample containing a transmembrane transport protein, for example, a sample containing a purified transmembrane transport protein, or a sample containing cells comprising a transmembrane transport protein. Contacting further includes bringing a compound of the present disclosure and a transmembrane transport protein together under in vivo conditions. Such in vivo conditions include the administration to an animal or human subject, for example, of a pharmaceutically effective amount of the compound of the present disclosure, when the compound is formulated together with a pharmaceutically active carrier, diluent, or excipient, as hereinbefore described, to thereby treat the subject.

In one embodiment, in an aspect, the transmembrane transport protein can be a serotonin transporter (SERT) transmembrane transport protein.

Turning now to methods of making the N-heterocycle-substituted tryptamine derivative compounds of the present disclosure, it is initially noted, by way of general comment that the N-heterocycle-substituted tryptamine derivative compounds of the present disclosure may be prepared in any suitable manner, including by any organic chemical synthesis methods, biosynthetic methods, or a combination thereof.

Figure 3A:
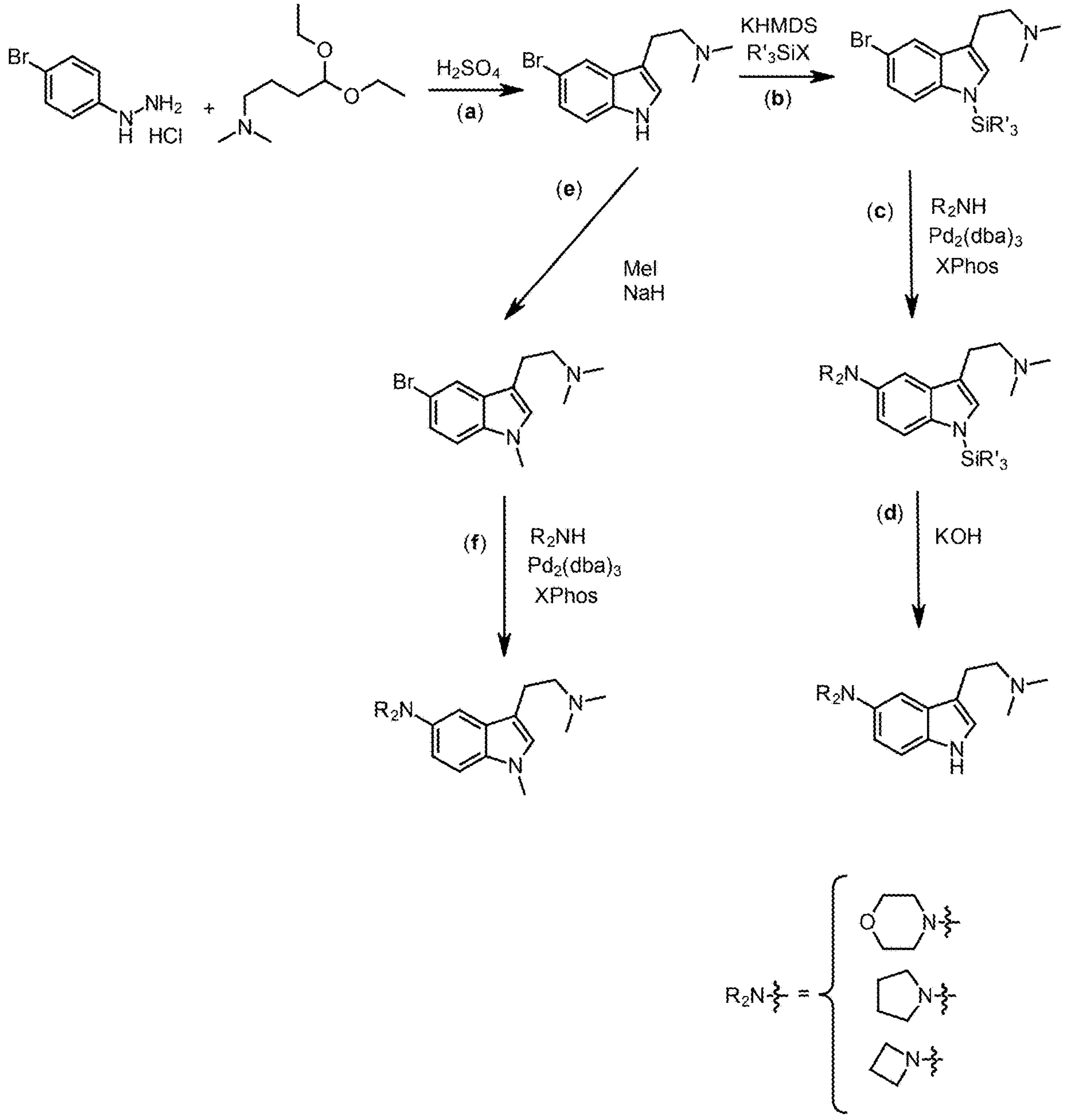
FIGS. 3A and 3B show example synthesis pathways and chemical reactions comprising such pathways for certain example mescaline compounds of the present disclosure. Individual chemical reactions are denoted as (a), (b), (c), (d), (e), and (f) in FIG. 3A; and (a), (b), (c), (d), (e), (f), (g), (h), (i), (j), (k), (l), (m), (n), (o), (p), and (q) in FIG. 3B.
Figure 3B:
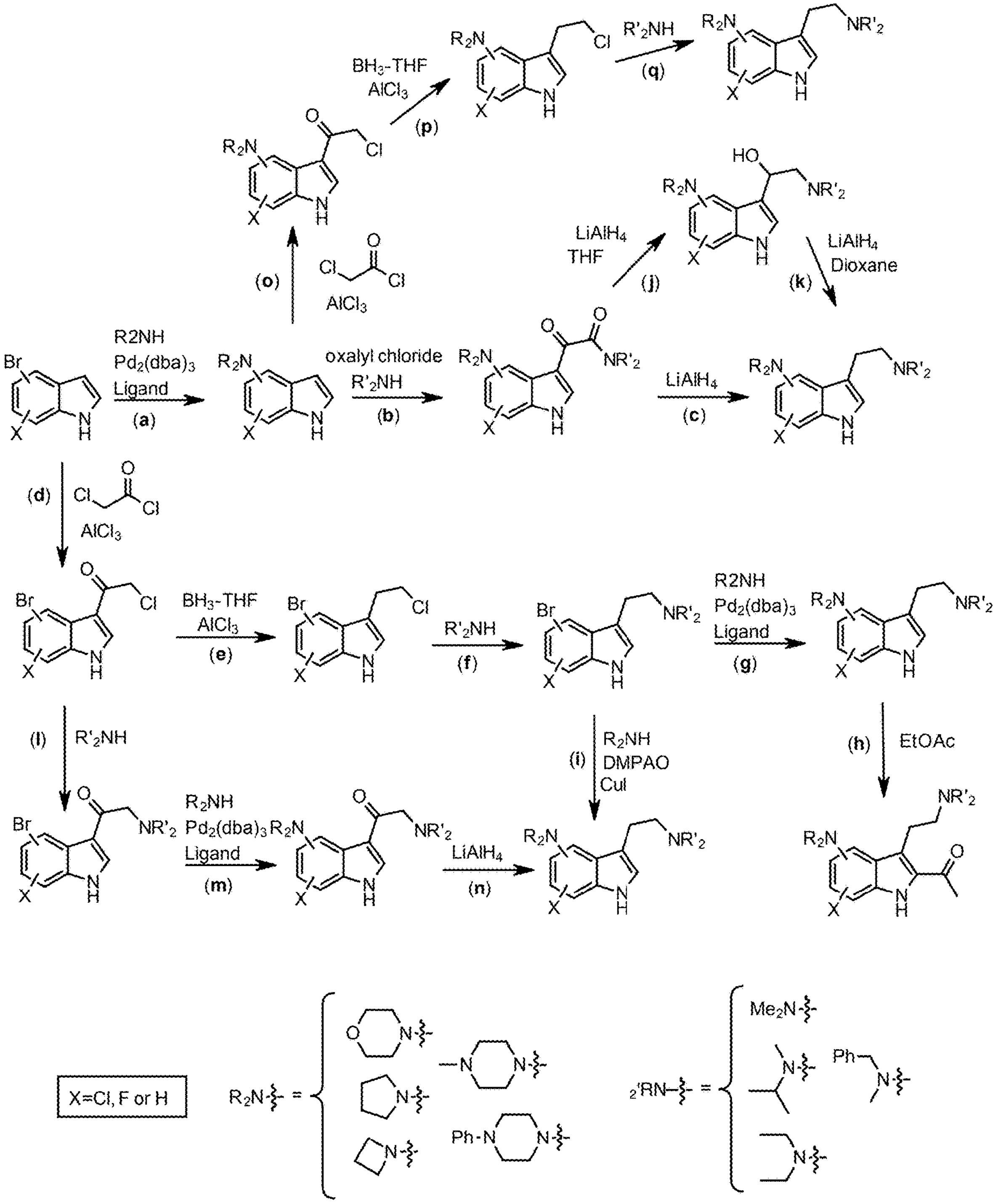

Examples of suitable chemical reactions that may be performed in accordance herewith are depicted in FIGS. 3A and 3B, and are further additionally detailed hereinafter in the Example section, and further depicted in FIGS. 4A-4D, 5A-5B, 6A-6C, 7A-7D, 8A-8D, 9A-9C, 10A-10C, 11, 12A-12D, 13A-13C, 14A-14D, 15A-15D, 16A-16D, 17A-17D, 18, 19A-19B, 20A-20C, 21A-21D, 22, 23A-23B, 24A-24C, 25A-25C, 26A-26B, 27A-27D, 28A-28D, 29A-29B, 30A-30B, 31, and 32.

In accordance with the foregoing, in an aspect, included herein, in accordance with at least one embodiment, is a method of making an N-heterocycle substituted tryptamine derivative compound having formula (I):

(I)

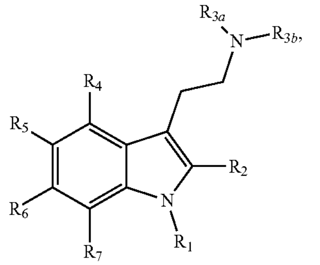

wherein at least one of $R_2$, $R_4$, $R_5$, $R_6$, and $R_7$ is an N-heterocycle substituent, wherein each of $R_2$, $R_4$, $R_5$, $R_6$, and $R_7$ which are not an N-heterocycle substituent are a hydrogen atom, a halogen atom, or a ketone group, wherein $R_1$ is alkyl or hydrogen, and wherein $R_{3a}$ and $R_{3b}$ are each independently a hydrogen atom, an alkyl group, an aryl group, or an alkyl-aryl group, wherein in the method involves the performance of at least one chemical synthesis reaction selected from the reactions depicted in FIGS. 3A, and 3B.

Thus, referring to FIG. 3A, the compound having chemical formula (I) can be a compound having formula (B):

(B)

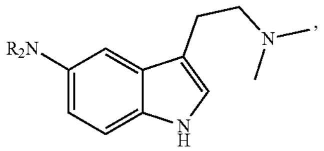

wherein

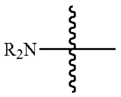

is

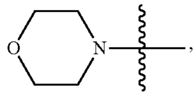

,

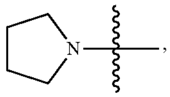

, or

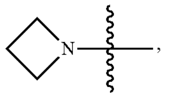

, and the at least one chemical synthesis reaction can be a reaction selected from (d); (c) and (d); (b), (c), and (d); and (a), (b), (c), and (d) depicted in FIG. 3A.

Referring further to FIG. 3A, the compound having chemical formula (I) can be a compound having formula (C):

(C)

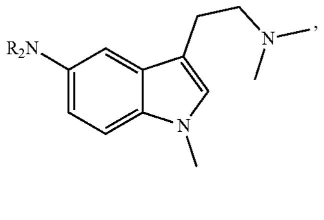

wherein

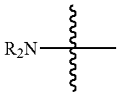

is

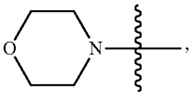,

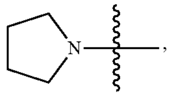, or

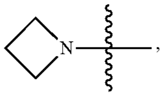, and the at least one chemical synthesis reaction can be a reaction selected from (f); (e) and (f); and (a), (e), and (f), depicted in FIG. 3A.

Referring further to FIG. 3B, the compound having chemical formula (I) can be a compound having formula (D):

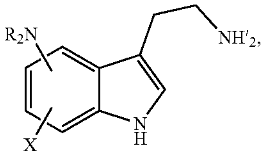

(D)

wherein X is Cl, F, or H,
wherein

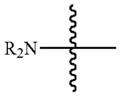

is

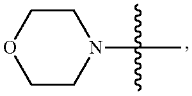,

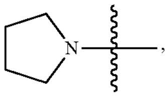,

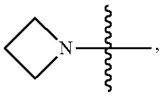,

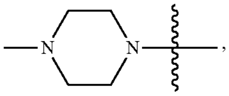, or

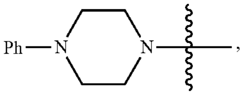, and wherein

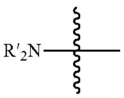

is

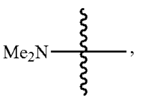,

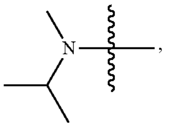,

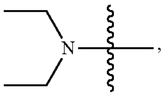, or

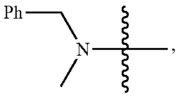, and the at least one chemical synthesis reaction can be a reaction selected from:

(i) (c); (b) and (c); and (a), (b), and (c);
(ii) (k); (j) and (k); (b), (j), and (k); and (a), (b), (j), and (k);
(iii) (q); (p) and (q); (o), (p), and (q); and (a), (o), (p), and (q);
(iv) (g); (f) and (g); (e), (f), and (g); and (d), (e), (f), and (g);
(v) (i); (f) and (i); (e), (f), and (i); and (d), (e), (f), and (i); and
(vi) (n); (m) and (n); (l), (m), and (n); and (d), (l), (m), and (n), depicted in FIG. 3B.

Referring further to FIG. 3B, the compound having chemical formula (I) can be a compound having formula (E):

(E)

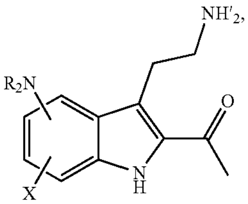

wherein X is Cl, F, or H,
wherein

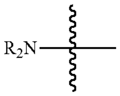

is

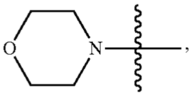,

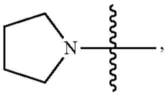,

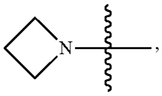,

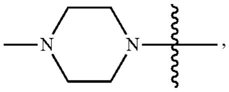, or

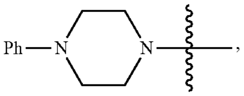, and wherein

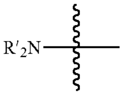

is

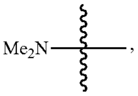,

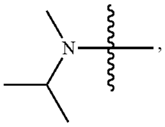,

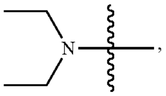, or

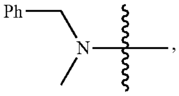, and the at least one chemical synthesis reaction can be a reaction selected from (h); (g) and (h); (f), (g), and (h); (e), (f), (g), and (h); and (d), (e), (f), (g), and (h) depicted in FIG. 3B.

In general, as is known to those of skill in the art, in order to perform chemical synthetic reactions selected reactants are reacted under reaction conditions suitable for the reactants to chemically react with each other and form a product, i.e., the N-heterocycle-substituted tryptamine derivative compounds of the present disclosure. Such suitable reactions conditions may be selected, adjusted, and optimized as known by those of skill in the art. The reactions may be conducted in any suitable reaction vessel (e.g., a tube, bottle). Suitable solvents that may be used are polar solvents such as, for example, dichloromethane, dimethylformamide, dichloroethane, toluene, and so called participating solvents such as acetonitrile and diethyl ether. Suitable temperatures may range from, for example, e.g., from about −78° C. to about 60° C. Furthermore, catalysts, also known as promoters, may be included in the reaction such as iodonium dicollidine perchlorate (IDCP), any silver or mercury salts, trimethylsilyl trifluoromethanesulfonate (TMS-triflate, TMSOTf), or trifluoronmethanesulfonic acid (triflic acid, TfOH), N-iodosuccinimide, methyl triflate. Furthermore, reaction times may be varied. As will readily be appreciated by those of skill in the art, the reaction conditions may be optimized, for example, by preparing several reactant preparations and reacting these in separate reaction vessels under different reaction conditions, for example, different temperatures, using different solvents etc., evaluating the obtained N-heterocycle-substituted tryptamine derivative compounds product, adjusting reaction conditions, and selecting a desired reaction condition.

In some embodiments, the chemical compounds referred to herein, including, without limitation, the N-heterocycle-substituted tryptamine derivatives having chemical formulas (V), (VI), (VII), (VIII), (IX), (X), (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), (XXIX), (XXX), (XXXI), (XXXII), and (XXXIII), may be isolated in pure or substantially pure form. Thus, the compounds referred to herein may be, for example, at least 90%, 95%, 96%, 97%, or 98%, or at least 99% pure.

It will now be clear from the foregoing that novel N-heterocycle-substituted tryptamine derivatives are disclosed herein, the N-heterocycle-substituted tryptamine derivatives may be formulated for use as a pharmaceutical drug or recreational drug. Example embodiments and implementations of the present disclosure are further illustrated by the following examples.

EXAMPLES

Figure 4A:
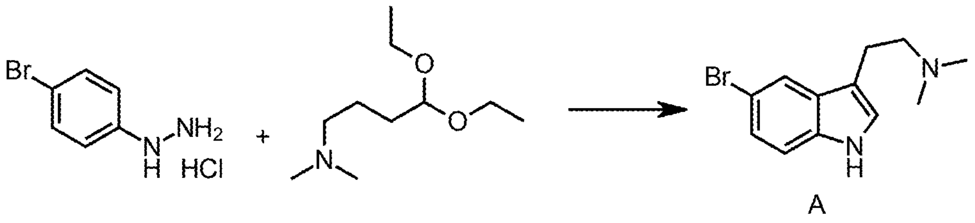
FIGS. 4A, 4B, 4C, and 4D depict example reactions in an example chemical synthesis pathway for the synthesis of a certain example compound according to the present disclosure.

Example 1—Synthesis and Analysis of a First N-Heterocycle Substituted Tryptamine Derivative Referring to FIG. 4A, a mixture of 4-bromophenylhydrazine hydrochloride (2.40 g, 10.5 mmol), 4% aqueous $H_2SO_4$ (63.1 mL), 4,4-diethoxy-N,N-dimethyl-1-butanamine (2.89 mL, 12.6 mmol) was heated to 105° C. in a reaction vial. After 2 hours, the mixture was monitored by LCMS and the desired product, intermediate A, had formed as the major species. The reaction mixture was quenched with saturated aqueous $NaHCO_3$ to increase the pH of the mixture to 10. The resulting aqueous layer was extracted with DCM, all organic layers were combined, washed with brine, dried ($Na_2SO_4$), filtered and concentrated to leave a lightly brown solid. The material, intermediate A (2.70 g, 96%) was used in the next step without further purification. LRMS-HESI: calculated for $C_{12}H_{16}BrN_2$ $(M+H)^+$ 267.05 m/z, observed 267.11 m/z. $^1H$ NMR (400 MHz, $CDCl_3$) δ 8.09, 7.75-7.70 (m, 1H), 7.29-7.17 (m, 2H), 7.02 (dd, J=2.3, 1.1 Hz, 1H), 2.93-2.84 (m, 2H), 2.65-2.57 (m, 2H), 2.33 (s, 6H). (FIG. 4A, see: further also chemical reaction (a) in FIG. 3A).

Figure 4B:
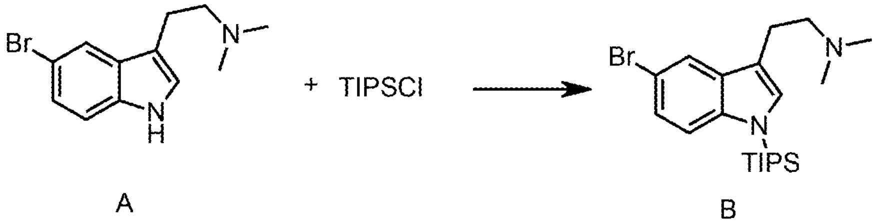

Referring next to FIG. 4B, a solution of intermediate A (1.50 g, 5.61 mmol) in dry THE (33.1 mL) was cooled to −78° C. under argon. Added to this in a dropwise manner was 1 M KHMDS (6.18 mL, 6.18 mmol) in THF. After stirring at −78° C. for 1 h, a solution of TIPSCl (1.32 mL, 6.18 mmol) in THE (6.28 mL) was added. Once addition was complete, the reaction was warmed to room temperature and stirring was continued for 2 hours. At this point, half sat aqueous $NaHCO_3$ was added to the reaction mixture. The resulting aqueous phase was extracted with EtOAc. All organic layers were combined, washed with brine, dried over $Na_2SO_4$, filtered and concentrated in vacuo. The crude material was purified on silica gel (gradient 0 to 20% MeOH in DCM to afford intermediate B (1.97 g, 83%) as a thick brown oil. LRMS-HESI: calculated for $C_{21}H_{36}BrN_2Si$ $(M+H)^+$ 423.18 m/z, observed 423.26 m/z. (FIG. 4B, see: further also chemical reaction (b) in FIG. 3A).

Figure 4C:
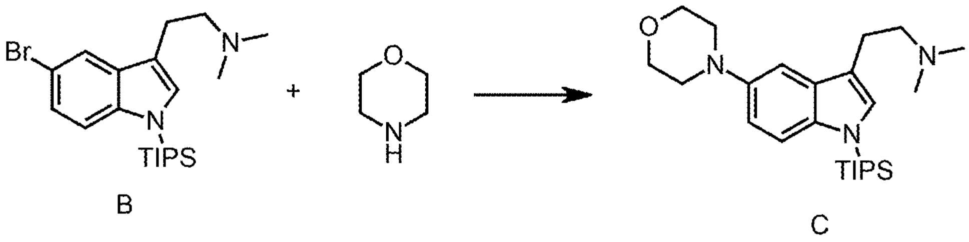

Referring next to FIG. 4C, intermediate B (200 mg, 472 μmol) was dissolved in toluene (7.08 mL) followed by the addition of $Pd_2(dba)_3$ (22.3 mg, 23.6 μmol), argon was bubbled through the reaction mixture for a few minutes prior to the addition of potassium tert-butoxide (108 mg, 944 μmol), XPhos (23.7 mg, 47.2 μmol) and morpholine (45.9 μL, 519 μmol). A pressure rated reaction vial was capped and the temperature of the mixture was brought to 110° C. After reacting overnight, LCMS indicated that the desired product, intermediate C, was the major component of the reaction mixture. The reaction was filtered through a pad of celite and the celite was washed with EtOAc and the filtrate was concentrated under reduced pressure. The resulting crude material was purified via column chromatography using 0 to 20% MeOH (with 10% NH4OH) in DCM on silica gel to afford intermediate C (85.0 mg, 42%). LRMS-HESI: calculated for $C_{25}H_{44}N_3OSi$ $(M+H)^+$ 430.32 m/z, observed 430.39 m/z. (FIG. 4C, see: further also chemical reaction (c) in FIG. 3A).

Figure 4D:
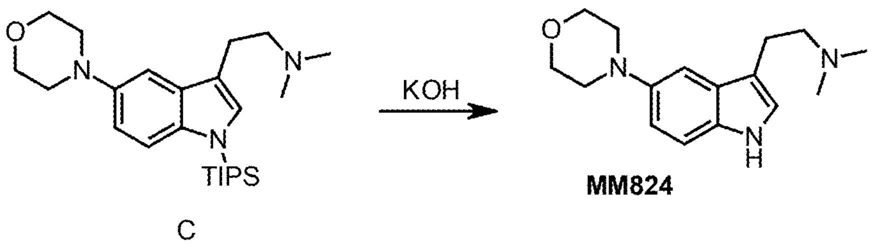

Referring next to FIG. 4D, intermediate C (85.0 mg, 198 μmol), sodium hydroxide solution (1.0 M, 9.00 mL, 9.00 mmol) and MeOH (5.00 mL) were added to a reaction vial. The resulting mixture was heated to 55° C. and left to react for 3 hours. At this point the mixture was cooled back down to room temperature. Once cool, water and EtOAc were added, and the aqueous phase was extracted with EtOAc. All the organic layers were combined, washed with water, dried ($Na_2SO_4$), filtered and concentrated. This material was purified via column chromatography using 0 to 20% MeOH (with 10% NH4OH) in DCM on silica gel to afford MM824 (39.0 mg, 72%) beige solid as product. LRMS-HESI: calculated for $C_{16}H_{24}N_3O$ $(M+H)^+$ 274.19 m/z, observed 274.15 m/z. $^1H$ NMR (600 MHz, $CDCl_3$) δ 8.36 (s, 1H), 7.24 (d, J=8.8 Hz, 1H), 7.10 (d, J=2.3 Hz, 1H), 6.96 (d, J=2.2 Hz, 1H), 6.94 (dd, J=8.8, 2.3 Hz, 1H), 3.94-3.89 (m, 4H), 3.16-3.10 (m, 4H), 2.96-2.90 (m, 2H), 2.68-2.62 (m, 2H), 2.36 (s, 6H). (FIG. 4D, see: further also chemical reaction (d) in FIG. 3A).

It is noted that MM824 corresponds with chemical compound (V):

(V)

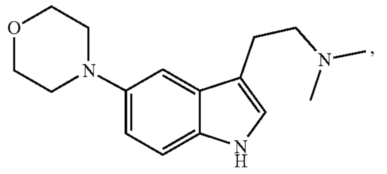

set forth herein.

5-HT Receptor Radioligand Competition Assay.

Competition assays at the 5-$HT_{2A}$ receptor were performed as described in Example 11, except compound with formula V was used in place of compound with formula (XV). Resulting $K_i$ data for controls and test compounds in 5-$HT_{2A}$ receptor binding assays, including data acquired for compound with formula V, are summarized in Table 2. Compound with formula V (designated 'V' in Table 2) exhibited a $K_i$ value of 15 μM at the 5-$HT_{2A}$ receptor. This $K_i$ value was less than those of negative controls (i.e., $K_i$<1000 μM) and hence suggested binding by compound with formula V at this receptor.

Neuroplastogenicity Assays.

Assays to reveal potential of drugs to enhance neurite outgrowth in human model (NT2) neurons were conducted as described in Example 11, except that compound with formula V was used in place of compound with formula (XV). Results of visual inspection are summarized in Table 4, where (1) (+) designates strong evidence of enhanced neurite outgrowth in drug-treated NT2 cells compared to vehicle-treated cells, and (2) (−) designates weak or no evidence of enhanced neurite outgrowth in drug-treated NT2 cells compared to vehicle-treated cells. Similar to the effects imparted by positive controls and compound with formula (XV) (FIG. 37A), human model (NT2) neurons incubated with 1 μM or 10 μM compound (V) grew larger in size and displayed greater overall neurite outgrowth compared with vehicle-treated (0.1% DMSO) human model neurons. These observations are summarized as a (+) designation in Table 4.

Mouse Head Twitch Response (HTR) Assay to Assess Hallucinogenic Potential.

Figure 38A:
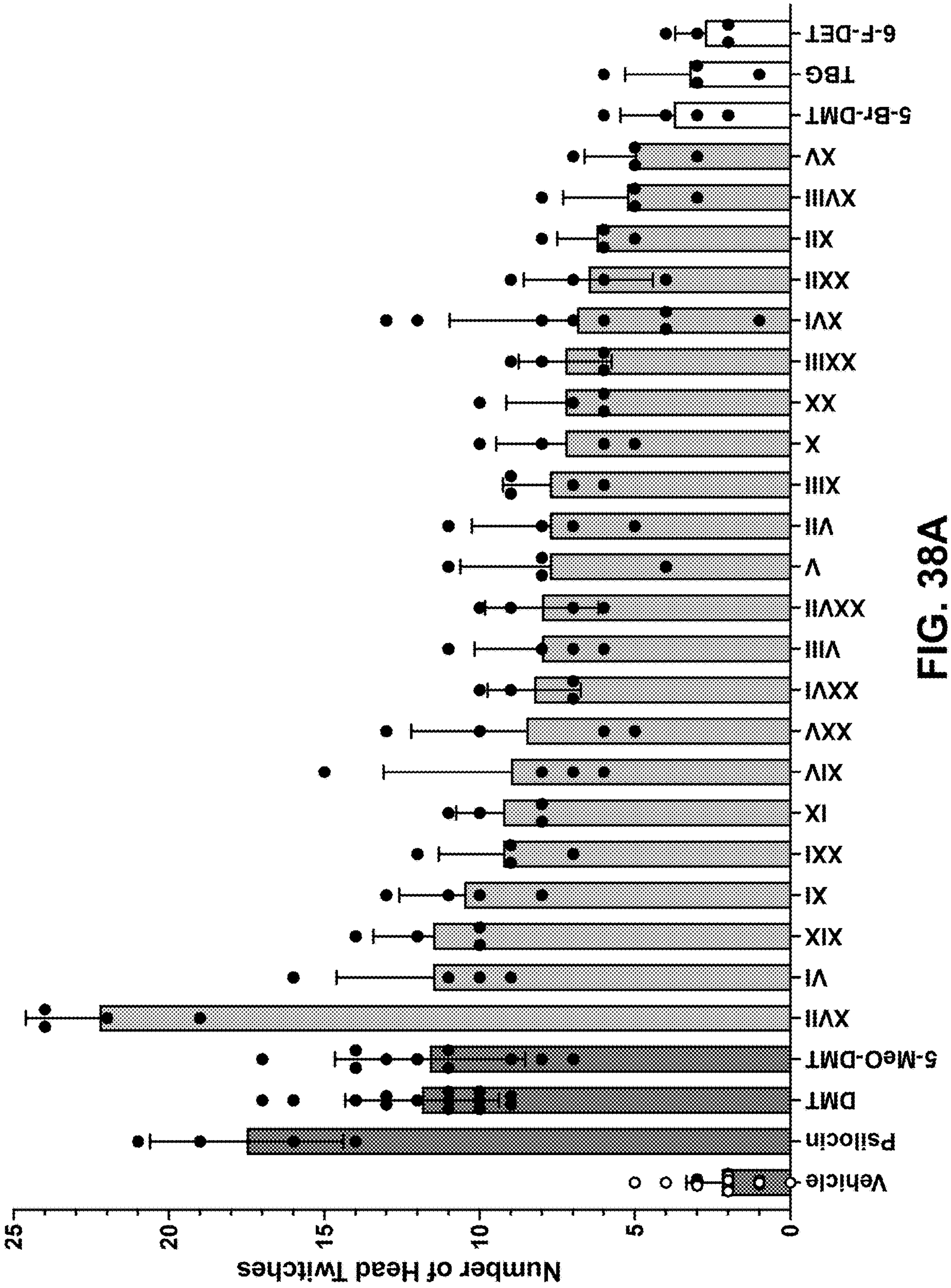
FIGS. 38A and 38B depict graphs representing certain experimental results, notably graphs obtained in the performance of experimental assays, notably Head Twitch Response (HTR) assays, to evaluate the pharmaceutical efficacy of example compounds having chemical formula (V); (VI); (VII); (VIII); (IX); (X); (XI); (XII); (XIII); (XIV); (XV); (XVII); (XIX): (XXI); (XXII); (XXIII): (XXV); (XXVI); and (XXVII) (FIG. 38A); and (XII); (XV); (XVII); and (XVIII) (FIG. 38B), notably a bar graph, representing assay results to screen for hallucinogenic potential of the noted example compounds, wherein drugs were administered to $C_{57}$BL/6 mice (n=4) at 3 mg/kg (i.p.) to observe Head Twitch Response (HTR) for the 0-15 min interval, wherein psilocin, dimethyltryptamine (DMT) and 5-methoxy-dimethyltryptamine (5-MeO-DMT) (hatched bars) are established hallucinogens and served as positive controls, and wherein known (or putative) non-hallucinogens 5-bromo-dimethyltryptamined (5-Br-DMT), tabernanthalog (TBG), and 6-fluoro-diethyltryptamine (6-F-DET) served as negative controls (white bars) (FIG. 38A); and a graph representing an assay to evaluate dose dependence of the as assayed compounds on HTR for the 0-15 min interval, wherein C57BL/6 mice (n=4) were dosed with a single administration of each drug at 0.5, 2, 4, 7, and 10 mg/kg (i.p.) (FIG. 38B).

Head Twitch Response (HTR) assays were conducted as described in Example 11, except that compound with formula V was used in place of compound with formula (XV). FIG. 38A shows HTR assay results for all drugs administered at 3 mg/kg (preliminary screening). Results show high hallucinogenic potential (mean HTR≥10) for positive controls (hatched bars; psilocin, DMT, 5-MeO-DMT). In contrast, low/no hallucinogenic potential (mean HTR≤5) is observed for negative controls (white bars; 5-Br-DMT, TBG, 6-F-DET). Mean HTR between 10 and 5 signifies reduced hallucinogenic potential relative to positive controls. Compound (V) has a mean HTR of 7.8, suggesting reduced hallucinogenic potential relative to positive controls.

Figure 5A:
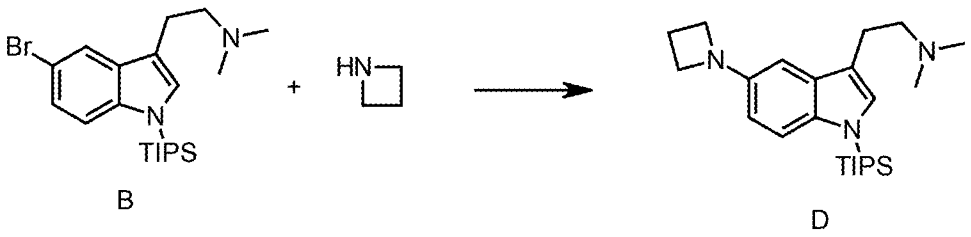
FIGS. 5A and 5B depict further example reactions in another example chemical synthesis pathway for the synthesis of another example compound according to the present disclosure.

Example 2—Synthesis and Analysis of a Second N-Heterocycle Substituted Tryptamine Derivative Referring to FIG. 5A, intermediate B (100 mg, 236 μmol), prepared as described in Example 1, was dissolved in toluene (3.5 mL) followed by the addition of $Pd_2(dba)_3$ (13.4 mg, 14.2 μmol), argon was bubbled through the reaction mixture for a few minutes prior to the addition of potassium tert-butoxide (54.1 mg, 472 μmol), XPhos (11.8 mg, 23.6 μmol) and azetidine (18.4 μL, 260 μmol). A pressure rated reaction vial was capped and the temperature of the mixture was brought to 110° C. After reacting overnight, LCMS indicated that the desired product, intermediate D, was the major component of the reaction mixture. The reaction was filtered through a pad of celite and the celite was washed with EtOAc and the filtrate was concentrated under reduced pressure. The resulting crude material was purified via column chromatography using 0 to 20% MeOH (with 10% NH4OH) in DCM on silica gel to afford intermediate D (42.0 mg, 45%). LRMS-HESI: calculated for $C_{24}H_{42}N_3Si$ (M+H)+400.31 m/z, observed 400.37 m/z. (FIG. 5A, see: further also chemical reaction (c) in FIG. 3A).

Figure 5B:
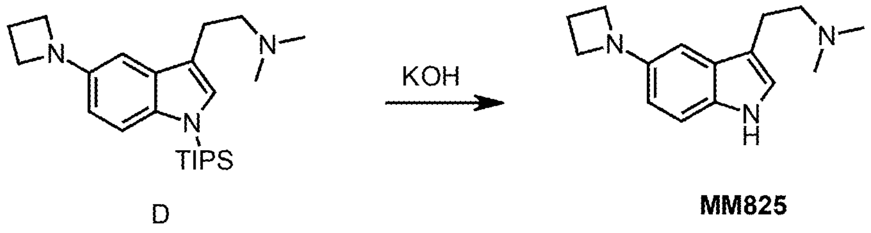

Referring next to FIG. 5B, intermediate D (42.0 mg, 105 μmol), sodium hydroxide solution (1.0 M, 9.00 mL, 9.00 mmol) and MeOH (5.00 mL) were added to a reaction vial. The resulting mixture was heated to 55° C. and left to react for 3 hours. At this point the mixture was cooled back down to room temperature. Once cool, water and EtOAc were added, and the aqueous phase was extracted with EtOAc. All the organic layers were combined, washed with water, dried ($Na_2SO_4$), filtered and concentrated. This material was purified via column chromatography using 0 to 20% MeOH (with 10% NH4OH) in DCM on silica gel to afford MM825 (12.0 mg, 47%) beige solid as product. LRMS-HESI: calculated for $C_{15}H_{22}N_3$ $(M+H)^+$ 244.18 m/z, observed 244.15 m/z. $^1H$ NMR (400 MHz, $CDCl_3$) δ 7.24-7.15 (m, 1H), 6.95 (d, J=2.4 Hz, 1H), 6.62 (d, J=2.2 Hz, 1H), 3.87 (t, J=7.1 Hz, 4H), 2.92-2.86 (m, 2H), 2.69-2.58 (m, 2H), 2.40-2.31 (m, 8H). (FIG. 5B, see: further also chemical reaction (d) in FIG. 3A).

It is noted that MM825 corresponds with chemical compound (VI):

(VI)

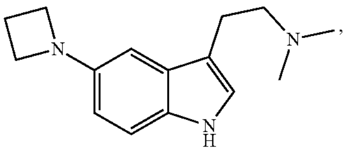

set forth herein.

5-HT Receptor Radioligand Competition Assay.

Competition assays at the 5-$HT_{2A}$ receptor were performed as described in Example 11, except compound with formula (VI) was used in place of compound with formula (XV). Resulting $K_i$ data for controls and test compounds in 5-$HT_{2A}$ receptor binding assays, including data acquired for compound with formula (VI), are summarized in Table 2. Compound with formula (VI) (designated 'VI' in Table 2) exhibited a $K_i$ value of 12 μM at the 5-$HT_{2A}$ receptor. This $K_i$ value was less than those of negative controls (i.e., $K_i$<1000 μM) and hence suggested binding by compound with formula (VI) at this receptor.

Neuroplastogenicity Assays.

Assays to reveal potential of drugs to enhance neurite outgrowth in human model (NT2) neurons were conducted as described in Example 11, except that compound with formula (VI) was used in place of compound with formula (XV). Results of visual inspection are summarized in Table 4, where (1) (+) designates strong evidence of enhanced neurite outgrowth in drug-treated NT2 cells compared to vehicle-treated cells, and (2) (−) designates weak or no evidence of enhanced neurite outgrowth in drug-treated NT2 cells compared to vehicle-treated cells. Similar to the effects imparted by positive controls and compound with formula (XV) (FIG. 37A), human model (NT2) neurons incubated with 1 μM or 10 μM compound (VI) grew larger in size and displayed greater overall neurite outgrowth compared with vehicle-treated (0.1% DMSO) human model neurons. These observations are summarized as a (+) designation in Table 4.

Mouse Head Twitch Response (HTR) Assay to Assess Hallucinogenic Potential.

Head Twitch Response (HTR) assays were conducted as described in Example 11, except that compound with formula (VI) was used in place of compound with formula (XV). FIG. 38A shows HTR assay results for all drugs administered at 3 mg/kg (preliminary screening). Results show high hallucinogenic potential (mean HTR≥10) for positive controls (hatched bars; psilocin, DMT, 5-MeO-DMT). In contrast, low/no hallucinogenic potential (mean HTR≤5) is observed for negative controls (white bars; 5-Br-DMT, TBG, 6-F-DET). Mean HTR between 10 and 5 signifies reduced hallucinogenic potential relative to positive controls. Compound (VI) has a mean HTR of 11.5, suggesting high hallucinogenic potential similar to positive controls.

Figure 6A:
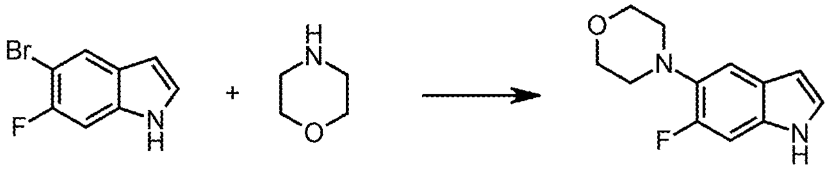
FIGS. 6A, 6B, and 6C depict further example reactions in an example chemical synthesis pathway for the synthesis of a certain example compound according to the present disclosure.

Example 3—Synthesis and Analysis of a Third N-Heterocycle Substituted Tryptamine Derivative Referring to FIG. 6A, in an oven-dried vial under nitrogen atmosphere was dissolved 5-bromo-6-fluoro-1H-indole (557 mg, 2.55 mmol), $Pd_2(dba)_3$ (24.1 mg, 25.5 μmol), and DavePHOS (24.1 mg, 61.2 μmol) in dry THE (3.19 mL). To this stirring solution was added 1 M LiHMDS solution in THE (5.61 mL, 5.61 mmol) and argon sparged morpholine (451 μL, 5.10 mmol). The reaction mixture was heated to 60° C. for 20 hrs. After this time, the mixture was cooled to room temperature and poured into a separatory funnel containing DCM (15 mL) and water (15 mL). The aqueous layer was extracted with DCM (2×15 mL), all organic layers were combined, washed with brine, dried ($MgSO_4$), filtered and concentrated to leave a brown solid. This was adsorbed to silica and purified by FC (12 g silica, 0% to 10% MeOH in DCM) to obtain the desired product, intermediate E (387 mg, 69%) as a tan solid. LRMS-HESI: calculated for $C_{12}H_{14}N_2O$ $(M+H)^+$ 221.11 m/z, observed 221.10 m/z. (FIG. 6A, see: further also chemical reaction (a) in FIG. 3B).

Figure 6B:
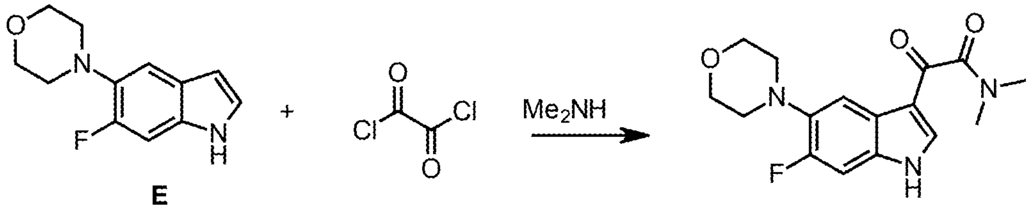

Referring next to FIG. 6B, to an ice-cold solution of oxalyl chloride (148 μL, 1.74 mmol) in dry THE (3.91 mL), under nitrogen atmosphere, was added a solution of intermediate E (255 mg, 1.16 mmol) in dry THE (3.91 mL) dropwise. The reaction mixture was allowed to warm to room temperature and stirred for 3 hrs. After cooling to 0° C., 2 M dimethylamine in THE (4.63 mL, 9.26 mmol) was added, and the reaction mixture allowed to stir for a further 18 hours. The reaction was quenched with 15 mL water and poured into a separatory funnel containing ethyl acetate (15 mL). The aqueous layer was extracted with ethyl acetate (2×15 mL), all organic layers were combined, washed with brine, dried ($MgSO_4$) and concentrated to provide the crude product as a brown solid. This was adsorbed to silica and purified by FC (12 g silica, 50% to 100% EtOAc in hexanes) to provide the desired product, intermediate F (205 mg, 55%), as a white solid. (FIG. 6B, see: further also chemical reaction (b) in FIG. 3B).

Figure 6C:
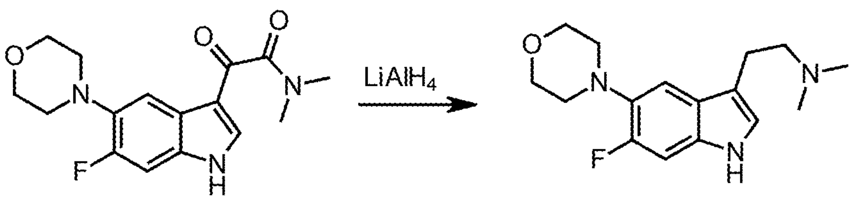

Referring next to FIG. 6C, to a solution of 2.0 M (THF) lithium aluminum hydride (939 μL, 1.88 mmol) in 2 mL of THF was added the glyoxyl amide, intermediate F (120 mg, 376 μmol), dissolved in 2 mL of THF. The mixture was heated to 60° C. At 2 hours, 4 hours and 22 hours the reaction was monitored by LCMS. While the desired product had formed, conversion was split between that and the beta-hydroxy congener. The reaction was stopped via a Fieser quench and the crude material was isolated as a white solid. The crude material was adsorbed to silica and the mixture was purified was by FC (12 g silica, 0% to 20% MeOH in DCM) to provide MM831 (36.0 mg, 33%) as a white solid. LRMS-HESI: calculated for $C_{16}H_{23}FN_3O$ $(M+H)^+$ 292.18 m/z, observed 292.18 m/z. $^1H$ NMR (300 MHz, $CDCl_3$) δ 8.04 (s, 1H), 7.13 (d, J=8.2 Hz, 1H), 7.04 (d, J=12.4 Hz, 1H), 6.97-6.96 (m, 1H), 3.93-3.90 (m, 4H), 3.09-3.06 (m, 4H), 2.93-2.88 (m, 2H), 2.66-2.61 (m, 2H), 2.36 (s, 6H). (FIG. 6B, see: further also chemical reaction (c) in FIG. 3B).

It is noted that MM831 corresponds with chemical compound (VII):

(VII)

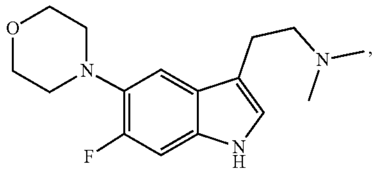

set forth herein.

5-HT Receptor Radioligand Competition Assay.

Competition assays at the $5\text{-}HT_{2A}$ receptor were performed as described in Example 11, except compound with formula (VII) was used in place of compound with formula (XV). Resulting $K_i$ data for controls and test compounds in $5\text{-}HT_{2A}$ receptor binding assays, including data acquired for compound with formula (VII), are summarized in Table 2. Compound with formula (VII) (designated 'VII' in Table 2) exhibited a $K_i$ value of 63.9 μM at the $5\text{-}HT_{2A}$ receptor. This $K_i$ value was less than those of negative controls (i.e., $K_i$<1000 μM) and hence suggested binding by compound with formula (VII) at this receptor.

Neuroplastogenicity Assays.

Assays to reveal potential of drugs to enhance neurite outgrowth in human model (NT2) neurons were conducted as described in Example 11, except that compound with formula (VII) was used in place of compound with formula (XV). Results of visual inspection are summarized in Table 4, where (1) (+) designates strong evidence of enhanced neurite outgrowth in drug-treated NT2 cells compared to vehicle-treated cells, and (2) (−) designates weak or no evidence of enhanced neurite outgrowth in drug-treated NT2 cells compared to vehicle-treated cells. Similar to the effects imparted by positive controls and compound with formula (XV) (FIG. 37A), human model (NT2) neurons incubated with 1 μM or 10 μM compound (VII) grew larger in size and displayed greater overall neurite outgrowth compared with vehicle-treated (0.1% DMSO) human model neurons. These observations are summarized as a (+) designation in Table 4.

Mouse Head Twitch Response (HTR) Assay to Assess Hallucinogenic Potential.

Head Twitch Response (HTR) assays were conducted as described in Example 11, except that compound with formula (VII) was used in place of compound with formula (XV). FIG. 38A shows HTR assay results for all drugs administered at 3 mg/kg (preliminary screening). Results show high hallucinogenic potential (mean HTR≥10) for positive controls (hatched bars; psilocin, DMT, 5-MeO-DMT). In contrast, low/no hallucinogenic potential (mean HTR≤5) is observed for negative controls (white bars; 5-Br-DMT, TBG, 6-F-DET). Mean HTR between 10 and 5 signifies reduced hallucinogenic potential relative to positive controls. Compound (VII) has a mean HTR of 7.75, suggesting reduced hallucinogenic potential compared to positive controls.

Figure 7A:
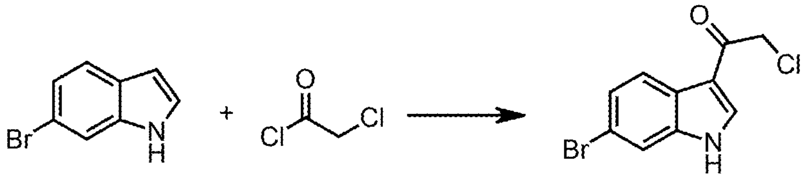
FIGS. 7A, 7B, 7C, and 7D depict further example reactions in an example chemical synthesis pathway for the synthesis of a certain example compound according to the present disclosure.

Example 4—Synthesis and Analysis of a Fourth N-Heterocycle Substituted Tryptamine Derivative Referring to FIG. 7A, to a stirring solution of aluminum chloride (756 mg, 5.61 mmol) and 6-bromoindole (1000 mg, 5.10 mmol) in dry DCM (35.0 mL) under nitrogen atmosphere at 0° C. was added chloroacetyl chloride (456 μL, 5.61 mmol) in dry DCM (15.0 mL) dropwise, and the resulting mixture stirred for 1 hour. After this time the reaction mixture was quenched by pouring over ice-water (50 mL), agitating thoroughly, and filtering the resulting precipitate. After allowing the tan solid to dry under vacuum, the solid was suspended in ethyl acetate and poured into a separatory funnel containing 75 mL of saturated sodium bicarbonate and 50 mL ethyl acetate. The resulting aqueous layer was extracted with ethyl acetate (3×50 mL). All organic layers were combined, washed with water and brine, dried ($MgSO_4$) filtered and concentrated to leave intermediate G (371 mg, 31%) as a tan coloured solid. No purification was performed. LRMS-HESI: calculated for $C_{10}H_8BrClNO$ $(M+H)^+$ 271.94 m/z, observed 271.92 m/z. $^1H$ NMR (300 MHz, $CDCl_3$) δ 12.24 (s, 1H), 8.47 (d, J=3.1 Hz, 1H), 8.10 (d, J=8.5 Hz, 1H), 7.72 (d, J=1.8 Hz, 1H), 7.38 (dd, J=8.5, 1.8 Hz, 1H), 4.91 (s, 2H). (FIG. 7A, see: further also chemical reaction (d) in FIG. 3B).

Figure 7B:
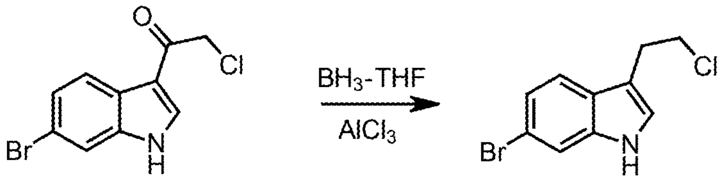

Referring next to FIG. 7B, to a suspension of aluminum chloride (545 mg, 4.08 mmol) in dry DCM (4 mL) at 0° C. under nitrogen atmosphere was added 1M borane-THF complex in THF (8.17 mL, 8.17 mmol), and the resulting solution stirred for 10 minutes. A suspension of intermediate G (371 mg, 1.36 mmol) in dry DCM (2.6 mL) was added, and the resulting mixture was stirred at 0° C. for 3 hrs. After this time the reaction was quenched via the addition of water (4.5 mL) and 1 M HCl (500 μL). The biphasic mixture was poured into a separatory funnel containing water (50 mL) and ethyl acetate (30 mL), and the aqueous phase was extracted (3×30 mL ethyl acetate). The combined organic extracts were washed with brine (30 mL), dried over anhydrous magnesium sulphate, and concentrated under reduced pressure to yield the product, intermediate H (284 mg, 81%) as a colourless oil. This was used in the next step without further purification. LRMS-HESI: calculated for $C_{10}H_{10}BrClN$ $(M+H)^+$ 257.97 m/z, observed 257.97 m/z. (FIG. 7B, see: further also chemical reaction (e) in FIG. 3B).

Figure 7C:
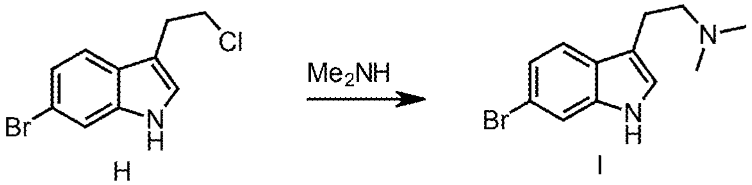

Referring next to FIG. 7C, to a stirring solution of intermediate H (285 mg, 1.10 mmol) in DMF (22.0 mL) under nitrogen atmosphere was added potassium carbonate (457 mg, 3.31 mmol) and potassium bromide (394 mg, 3.31 mmol). After stirring at room temperature for 10 minutes, 2.0 M dimethylamine in THF (4.41 mL, 8.82 mmol) was added and the reaction mixture heated to 55° C. for 20 h. At this point the reaction mixture was poured into a separatory funnel containing water (100 mL) and brine (10 mL). The aqueous phase was extracted with ethyl acetate (4×50 mL), and the combined organic extracts washed with water (5×50 mL), brine (50 mL), dried over anhydrous magnesium sulphate and concentrated under reduced pressure. Purification by FC (12 g silica, 0% to 10% MeOH in DCM) provided intermediate I (130 mg, 44%) as a brown oil. LRMS-HESI: calculated for $C_{12}H_{16}BrN_2$ $(M+H)^+$ 267.05 m/z, observed 267.03 m/z. (FIG. 7C, see: further also chemical reaction (f) in FIG. 3B).

Figure 7D:
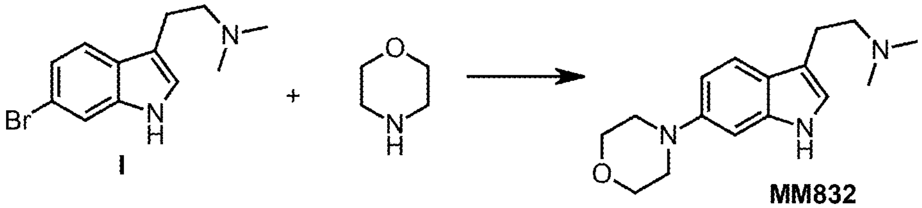

Referring next to FIG. 7D, in a flame-dried vial under nitrogen atmosphere was dissolved intermediate I (56.0 mg, 210 μmol), $Pd_2(dba)_3$ (1.98 mg, 2.10 μmol), and DavePHOS (1.98 mg, 5.03 μmol) in dry THE (262 μL). To this stirring solution was added 1 M LiHMDS in THE (461 μL, 461 μmol) and morpholine (40.7 μL, 461 μmol). The reaction mixture was heated to 60° C. for 20 hrs. After cooling to room temperature, the reaction mixture was diluted with ethyl acetate and poured into a separatory funnel containing water (30 mL) and ethyl acetate (15 mL). The aqueous phase was extracted with ethyl acetate (3×15 mL), and the combined organic extracts washed with brine (20 mL), dried over anhydrous magnesium sulphate, and concentrated under reduced pressure. Purification by FC (4 g silica 0% to 20% MeOH in DCM) provided the product, MM832 (11.3 mg, 20%) as a colourless oil. LRMS-HESI: calculated for $C_{16}H_{24}N_3O$ $(M+H)^+$ 274.19 m/z, observed 274.17 m/z. $^1H$ NMR (300 MHz, $CDCl_3$) δ 7.99 (s, 1H), 7.52 (dt, J=8.6, 0.7 Hz, 1H), 6.95-6.81 (m, 3H), 3.95-3.87 (m, 4H), 3.20-3.12 (m, 4H), 2.98-2.87 (m, 2H), 2.70-2.60 (m, 2H), 2.36 (s, 6H). (FIG. 7D, see: further also chemical reaction (g) in FIG. 3B).

It is noted that MM832 corresponds with chemical compound (VIII):

(VIII)

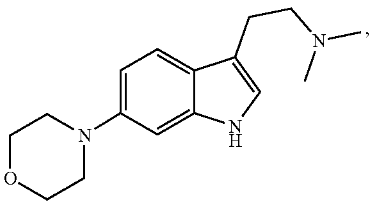

set forth herein.

5-HT Receptor Radioligand Competition Assay.

Competition assays at the $5\text{-}HT_{2A}$ receptor were performed as described in Example 11, except compound with formula (VIII) was used in place of compound with formula (XV). Resulting $K_i$ data for controls and test compounds in $5\text{-}HT_{2A}$ receptor binding assays, including data acquired for compound with formula (VIII), are summarized in Table 2. Compound with formula (VIII) (designated 'VIII' in Table 2) exhibited a $K_i$ value of 10.9 μM at the $5\text{-}HT_{2A}$ receptor. This $K_i$ value was less than those of negative controls (i.e., $K_i$<1000 μM) and hence suggested binding by compound with formula (VIII) at this receptor.

Neuroplastogenicity Assays.

Assays to reveal potential of drugs to enhance neurite outgrowth in human model (NT2) neurons were conducted as described in Example 11, except that compound with formula (VIII) was used in place of compound with formula (XV). Results of visual inspection are summarized in Table 4, where (1) (+) designates strong evidence of enhanced neurite outgrowth in drug-treated NT2 cells compared to vehicle-treated cells, and (2) (−) designates weak or no evidence of enhanced neurite outgrowth in drug-treated NT2 cells compared to vehicle-treated cells. Unlike the effects imparted by positive controls and compound with formula (XV) (FIG. 37A), human model (NT2) neurons incubated with 1 μM or 10 μM compound (VIII) did not grow larger in size or display greater overall neurite outgrowth compared with vehicle-treated (0.1% DMSO) human model neurons. These observations are summarized as a (−) designation in Table 4.

Mouse Head Twitch Response (HTR) Assay to Assess Hallucinogenic Potential.

Head Twitch Response (HTR) assays were conducted as described in Example 11, except that compound with formula (VIII) was used in place of compound with formula (XV). FIG. 38A shows HTR assay results for all drugs administered at 3 mg/kg (preliminary screening). Results show high hallucinogenic potential (mean HTR≥10) for positive controls (hatched bars; psilocin, DMT, 5-MeO-DMT). In contrast, low/no hallucinogenic potential (mean HTR≤5) is observed for negative controls (white bars; 5-Br-DMT, TBG, 6-F-DET). Mean HTR between 10 and 5 signifies reduced hallucinogenic potential relative to positive controls. Compound (VIII) has a mean HTR of 8.0, suggesting reduced hallucinogenic potential compared to positive controls.

Figure 8A:
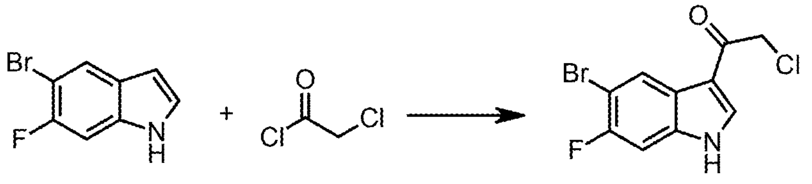
FIGS. 8A, 8B, 8C, and 8D depict further example reactions in an example chemical synthesis pathway for the synthesis of a certain example compound according to the present disclosure.

Example 5—Synthesis and Analysis of a Fifth N-Heterocycle Substituted Tryptamine Derivative Referring to FIG. 8A, to a stirring solution of aluminum chloride (692 mg, 5.14 mmol) in dry DCM (11.7 mL), under nitrogen atmosphere, was added chloroacetyl chloride (417 μL, 5.14 mmol) in dry DCM (11.7 mL), and the resulting mixture was stirred for 30 minutes. A solution of 5-bromo-6-fluoro-1H-indole (1000 mg, 4.67 mmol) in dry DCM (23.4 mL) was added dropwise, and the reaction mixture stirred for 2 hrs. After this time the reaction mixture was quenched by pouring over ice-water (50 mL). After agitating, the resulting precipitate was collected by filtration. After allowing the tan solid to dry under vacuum, it was suspended in ethyl acetate and poured into a separatory funnel containing 75 mL of saturated sodium bicarbonate and 50 mL ethyl acetate. The resulting aqueous layer was extracted with ethyl acetate (2×50 mL). All organic layers were combined, washed with water and brine, dried ($MgSO_4$), filtered and concentrated to leave intermediate J (825 mg, 71%) as an off-white coloured solid. The material was used in the next step without further purification. LRMS-HESI: calculated for $C_{10}H_7BrClFNO$ $(M+H)^+$ 289.94 m/z, observed 289.87 m/z. $^1H$ NMR (400 MHz, DMSO) δ 12.37 (s, 1H), 8.52 (s, 1H), 8.37 (d, J=7.1 Hz, 1H), 7.55 (d, J=9.3 Hz, 1H), 4.91 (s, 2H). (FIG. 8A, see: further also chemical reaction (d) in FIG. 3B).

Figure 8B:
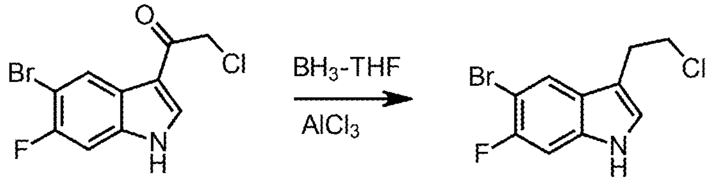

Referring next to FIG. 8B, to a suspension of aluminum chloride (942 mg, 7.06 mmol) in dry DCM (25 mL) at 0° C., under nitrogen atmosphere, was added 1M borane-THF complex in THF (14.1 mL, 14.1 mmol), and the resulting solution stirred for 10 minutes. A suspension of intermediate J (684 mg, 2.35 mmol) in dry DCM (22 mL) was added, and the resulting mixture was stirred at 0° C. for 3 h. After this time the reaction was quenched via the addition of water (9 mL) and 1 M HCl (1 mL). The biphasic mixture was poured into a separatory funnel containing water (50 mL) and ethyl acetate (30 mL), and the aqueous phase was extracted (3×30 mL ethyl acetate). The combined organic extracts were washed with brine (30 mL), dried over anhydrous magnesium sulphate, and concentrated under reduced pressure to yield the product, intermediate K (523 mg, 80%) as a colourless oil. This was used in the next step without further purification. LRMS-HESI: calculated for $C_{10}H_9BrClFN$ $(M+H)^+$ 277.96 m/z, observed 277.90 m/z. (FIG. 8B, see: further also chemical reaction (e) in FIG. 3B).

Figure 8C:
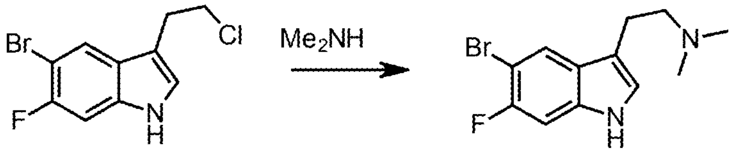

Referring next to FIG. 8C, to a stirring solution of intermediate K (523 mg, 1.89 mmol) in DMF (38 mL), under nitrogen atmosphere, was added potassium carbonate (784 mg, 5.67 mmol) and potassium bromide (675 mg, 5.67 mmol). After stirring at room temperature for 10 minutes, 2.0 M dimethylamine in THE (9.46 mL, 18.9 mmol) was added and the reaction mixture heated to 55° C. for 20 h. At this point the reaction mixture was poured into a separatory funnel containing water (100 mL) and brine (10 mL). The aqueous phase was extracted with ethyl acetate (4×50 mL), and the combined organic extracts washed with water (5×50 mL), brine (50 mL), dried over anhydrous magnesium sulphate and concentrated under reduced pressure. Purification by FC (12 g silica, 0% to 10% MeOH in DCM) provided intermediate L (322 mg, 60%) as a brown solid. LRMS-HESI: calculated for $C_{12}H_{15}BrFN_2$ $(M+H)^+$ 285.04 m/z, observed 285.01 m/z. (FIG. 8C, see: further also chemical reaction (f) in FIG. 3B).

Figure 8D:
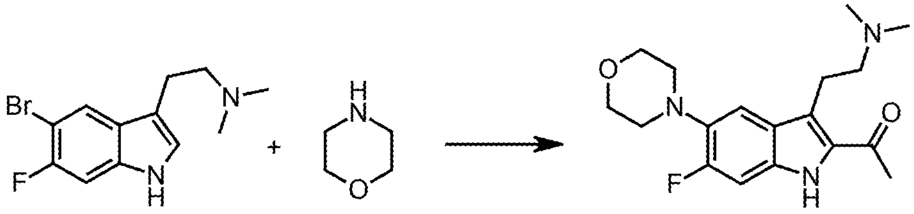

Referring next to FIG. 8D, in a flame-dried vial under nitrogen atmosphere was dissolved intermediate L (127 mg, 445 μmol), $Pd_2(dba)_3$ (4.2 mg, 4.5 μmol), and DavePHOS (4.2 mg, 11 μmol) in dry THE (557 μL). To this stirring solution was added 1 M LiHMDS in THE (980 μL, 980 μmol) and morpholine (87 μL, 980 μmol). The reaction mixture was heated to 60° C. for 3 hrs. After cooling to room temperature, the reaction mixture was diluted with ethyl acetate and poured into a separatory funnel containing water (30 mL) and ethyl acetate (15 mL). The aqueous phase was extracted with ethyl acetate (3×15 mL), and the combined organic extracts washed with brine (20 mL), dried over anhydrous magnesium sulphate, and concentrated under reduced pressure. Purification by FC (4 g silica 0% to 20% MeOH in ethyl acetate) provided the product, MM833 (10.1 mg, 7%), as a colourless solid. NOTE: This product probably arose from acylation by ethyl acetate during purification. LRMS-HESI: calculated for $C_{18}H_{25}FN_3O_2$ $(M+H)^+$ 334.19 m/z, observed 334.22 m/z. $^1H$ NMR (300 MHz, $CDCl_3$) δ 8.19 (d, J=13.1 Hz, 1H), 7.22 (s, 1H), 7.05 (d, J=8.2 Hz, 1H), 3.98-3.88 (m, 4H), 3.17-3.07 (m, 4H), 2.95-2.84 (m, 2H), 2.70 (dd, J=8.8, 6.6 Hz, 2H), 2.60 (s, 3H), 2.41 (s, 6H). (FIG. 8D, see: further also chemical reaction (g) and (h) in FIG. 3B).

It is noted that MM833 corresponds with chemical compound (IX):

(IX)

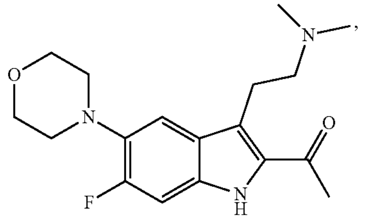

set forth herein.

5-HT Receptor Radioligand Competition Assay.

Competition assays at the $5\text{-}HT_{2A}$ receptor were performed as described in Example 11, except compound with formula (IX) was used in place of compound with formula (XV). Resulting $K_i$ data for controls and test compounds in $5\text{-}HT_{2A}$ receptor binding assays, including data acquired for compound with formula (IX), are summarized in Table 2. Compound with formula (IX) (designated 'IX' in Table 2) exhibited a $K_i$ value of 14.2 μM at the $5\text{-}HT_{2A}$ receptor. This $K_i$ value was less than those of negative controls (i.e., $K_i$<1000 μM) and hence suggested binding by compound with formula IX at this receptor.

Neuroplastogenicity Assays.

Assays to reveal potential of drugs to enhance neurite outgrowth in human model (NT2) neurons were conducted as described in Example 11, except that compound with formula (IX) was used in place of compound with formula (XV). Results of visual inspection are summarized in Table 4, where (1) (+) designates strong evidence of enhanced neurite outgrowth in drug-treated NT2 cells compared to vehicle-treated cells, and (2) (−) designates weak or no evidence of enhanced neurite outgrowth in drug-treated NT2 cells compared to vehicle-treated cells. Unlike the effects imparted by positive controls and compound with formula (XV) (FIG. 37A), human model (NT2) neurons incubated with 1 μM or 10 μM compound (IX) did not grow larger in size or display greater overall neurite outgrowth compared with vehicle-treated (0.1% DMSO) human model neurons. These observations are summarized as a (−) designation in Table 4.

Mouse Head Twitch Response (HTR) Assay to Assess Hallucinogenic Potential.

Head Twitch Response (HTR) assays were conducted as described in Example 11, except that compound with formula (IX) was used in place of compound with formula (XV). FIG. 38A shows HTR assay results for all drugs administered at 3 mg/kg (preliminary screening). Results show high hallucinogenic potential (mean HTR≥10) for positive controls (hatched bars; psilocin, DMT, 5-MeO-DMT). In contrast, low/no hallucinogenic potential (mean HTR≤5) is observed for negative controls (white bars; 5-Br-DMT, TBG, 6-F-DET). Mean HTR between 10 and 5 signifies reduced hallucinogenic potential relative to positive controls. Compound (IX) has a mean HTR of 9.25, suggesting marginally reduced hallucinogenic potential compared to positive controls.

Figure 9A:
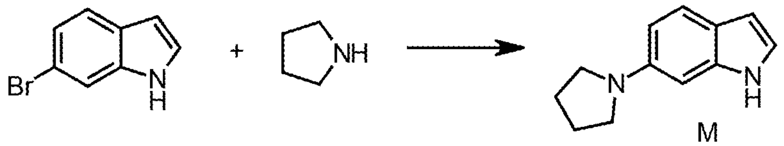
FIGS. 9A, 9B, and 9C depict further example reactions in an example chemical synthesis pathway for the synthesis of a certain example compound according to the present disclosure.

Example 6—Synthesis and Analysis of a Sixth N-Heterocycle Substituted Tryptamine Derivative Referring to FIG. 9A, in a flame-dried vial under nitrogen atmosphere was dissolved 6-bromoindole (500 mg, 2.55 mmol), $Pd_2(dba)_3$ (24.1 mg, 25.5 μmol), and DavePHOS (24.1 mg, 61.2 μmol) in dry THE (3.19 mL). To this stirring solution was added 1 M LiHMDS in THE (5.61 mL, 5.61 mmol) and pyrrolidine (430 μL, 5.10 mmol). The reaction mixture was sparged with argon for 30 minutes then heated to 60° C. for 20 hrs. At this point the mixture was cooled to room temperature and the reaction mixture was transferred to a separatory funnel containing 1:1 water/brine (50 mL) and DCM (30 mL). The aqueous layer was extracted (DCM, 3×50 mL), the resulting organic extracts were combined, washed with brine (50 mL), dried over anhydrous magnesium sulphate, and concentrated under reduced pressure to yield the crude as a brown solid. This was adsorbed to silica and purification was carried out by FC (24 g silica, 0-100% DCM in hexanes) providing intermediate M (319 mg, 67%) as a white powder. LRMS-HESI: calculated for $C_{12}H_{15}N_2$ $(M+H)^+$ 187.92 m/z, observed 187.12 m/z. (FIG. 9A, see: further also chemical reaction (a) in FIG. 3B).

Figure 9B:
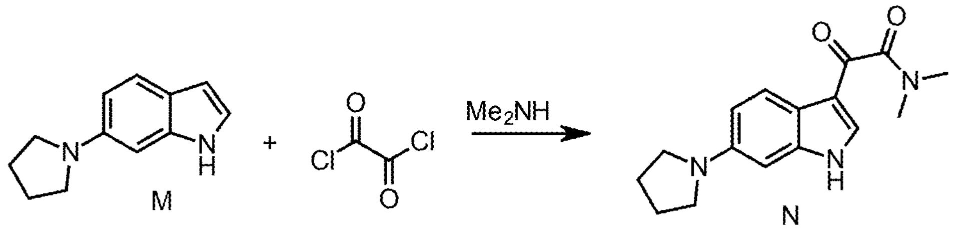

Referring next to FIG. 9B, to an ice-cold solution of oxalyl chloride (213 μL, 2.50 mmol) in dry THE (5.55 mL), under nitrogen atmosphere, was added a solution of intermediate M (310 mg, 1.66 mmol) in dry THE (5.55 mL) in a dropwise manner. The reaction mixture was allowed to warm to room temperature and stirred for 2 h. After cooling to 0° C., 2 M dimethylamine in THE (6.66 mL, 13.3 mmol) was added, and the reaction mixture allowed to stir for a further 18 hours. At this point the reaction mixture was poured into a separatory funnel containing DCM (15 mL) and a 1:1 water/brine solution (30 mL). The aqueous phase was extracted with DCM (3×15 mL), and the combined organic extracts were washed with brine (10 mL), dried over anhydrous magnesium sulphate, and concentrated under reduced pressure to give a light tan solid. This was purified by FC (24 g silica, 0% to 10% MeOH in DCM) to provide the product, intermediate N (185 mg, 39%) as a white solid. LRMS-HESI: calculated for $C_{16}H_{20}N_3O_2$ $(M+H)^+$ 286.16 m/z, observed 286.13 m/z. (FIG. 9B, see: further also chemical reaction (b) in FIG. 3B).

Figure 9C:
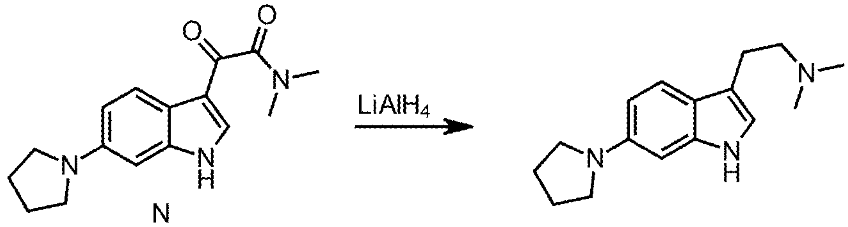

Referring next to FIG. 9C, a flame-dried flask, under nitrogen atmosphere, was charged with 2 M lithium aluminum hydride in THE (1.62 mL, 3.24 mmol) and cooled to 0° C. To the reaction vessel was added a solution of intermediate N (185 mg, 648 μmol) in dry THE (6.00 mL), and the mixture was heated to reflux for 2.5 hrs and left to react. After cooling to room temperature, the reaction mixture was worked up according to the Fieser method. The resulting crude material was purified by FC (12 g silica, 0% to 20% MeOH in DCM) to provide the product, MM834 (46.5 mg, 28%) as a white solid. LRMS-HESI: calculated for $C_{16}H_{24}N_3$ $(M+H)^+$ 258.20 m/z, observed 258.21 m/z. $^1H$ NMR (300 MHz, $CDCl_3$) δ 7.79 (s, 1H), 7.46 (d, J=8.6 Hz, 1H), 6.79 (dd, J=2.2, 1.1 Hz, 1H), 6.59 (dd, J=8.6, 2.1 Hz, 1H), 6.48 (d, J=2.1 Hz, 1H), 3.40-3.25 (m, 4H), 2.98-2.87 (m, 2H), 2.70-2.60 (m, 2H), 2.36 (s, 6H), 2.09-1.98 (m, 4H). (FIG. 9C, see: further also chemical reaction (c) in FIG. 3B).

It is noted that MM834 corresponds with chemical compound (X):

(X)

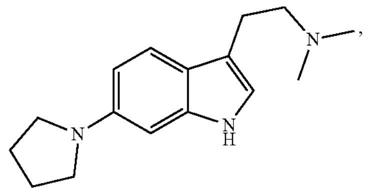

set forth herein.

5-HT Receptor Radioligand Competition Assay.

Competition assays at the $5\text{-}HT_{2A}$ receptor were performed as described in Example 11, except compound with formula (X) was used in place of compound with formula (XV). Resulting $K_i$ data for controls and test compounds in $5\text{-}HT_{2A}$ receptor binding assays, including data acquired for compound with formula (X), are summarized in Table 2. Compound with formula (X) (designated 'X' in Table 2) exhibited a $K_i$ value of 7.8 μM at the $5\text{-}HT_{2A}$ receptor. This $K_i$ value was less than those of negative controls (i.e., $K_i$<1000 μM) and hence suggested binding by compound with formula (X) at this receptor.

Neuroplastogenicity Assays.

Assays to reveal potential of drugs to enhance neurite outgrowth in human model (NT2) neurons were conducted as described in Example 11, except that compound with formula (X) was used in place of compound with formula (XV). Results of visual inspection are summarized in Table 4, where (1) (+) designates strong evidence of enhanced neurite outgrowth in drug-treated NT2 cells compared to vehicle-treated cells, and (2) (−) designates weak or no evidence of enhanced neurite outgrowth in drug-treated NT2 cells compared to vehicle-treated cells. Similar to the effects imparted by positive controls and compound with formula (XV) (FIG. 37A), human model (NT2) neurons incubated with 1 μM or 10 μM compound (X) grew larger in size and displayed greater overall neurite outgrowth compared with vehicle-treated (0.1% DMSO) human model neurons. These observations are summarized as a (+) designation in Table 4.

Mouse Head Twitch Response (HTR) Assay to Assess Hallucinogenic Potential.

Head Twitch Response (HTR) assays were conducted as described in Example 11, except that compound with formula (X) was used in place of compound with formula (XV). FIG. 38A shows HTR assay results for all drugs administered at 3 mg/kg (preliminary screening). Results show high hallucinogenic potential (mean HTR≥10) for positive controls (hatched bars; psilocin, DMT, 5-MeO-DMT). In contrast, low/no hallucinogenic potential (mean HTR≤5) is observed for negative controls (white bars; 5-Br-DMT, TBG, 6-F-DET). Mean HTR between 10 and 5 signifies reduced hallucinogenic potential relative to positive controls. Compound (X) has a mean HTR of 7.25, suggesting reduced hallucinogenic potential compared to positive controls.

Figure 10A:
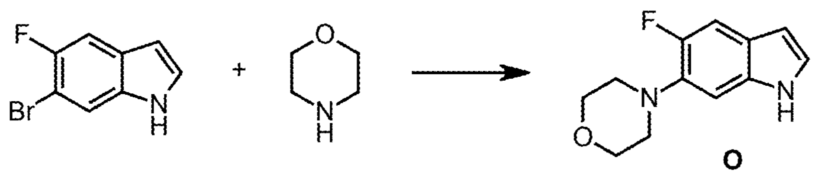
FIGS. 10A, 10B, and 10C depict further example reactions in an example chemical synthesis pathway for the synthesis of a certain example compound according to the present disclosure.

Example 7—Synthesis and Analysis of a Seventh N-Heterocycle Substituted Tryptamine Derivative Referring to FIG. 10A, in a flame-dried vial, under nitrogen atmosphere, was dissolved 6-bromo-5-fluoroindole (500 mg, 2.34 mmol), $Pd_2(dba)_3$ (22.1 mg, 23.4 μmol), and DavePhos (22.1 mg, 56.1 μmol) in THE (2.92 mL). To it was added 1 M LiHMDS in THE (5.14 mL, 5.14 mmol) and morpholine (413 μL, 4.67 mmol) while stirring, and the resulting mixture was degassed with nitrogen. The vial was sealed and the reaction mixture was stirred at 60° C. for 20 hrs. Once cooled to room temperature, the reaction mixture was transferred to a separatory funnel containing 1:1 water/brine (25 mL) and DCM (25 mL). The layers were separated, and the aq. layer was extracted with DCM (×3). The combined organic extracts were washed with brine, dried over anhydrous $Na_2SO_4$, filtered and concentrated. The crude residue was purified by FC on silica gel (solid loading, 25 g, DCM) to afford the semi-pure intermediate O (390 mg, 76%) as a brown solid, which was used in the next step without further purification. LRMS-HESI: calculated for $C_{12}H_{14}FN_2O$ $(M+H)^+$ 221.11 m/z, observed 221.13 m/z. (FIG. 10A, see: further also chemical reaction (a) in FIG. 3B).

Figure 10B:
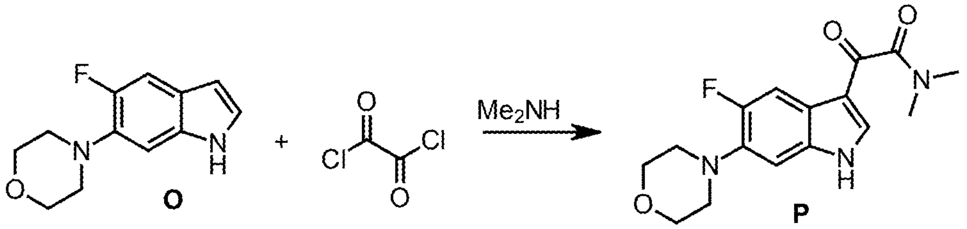

Referring next to FIG. 10B, to a solution of oxalyl chloride (227 μL, 2.66 mmol) in THE (5.95 mL) at 0° C. under nitrogen was added a solution of intermediate O (390 mg, 1.77 mmol) in THE (5.95 mL) in a dropwise manner. The reaction mixture was stirred at 0° C. for 1 h, then warmed to room temperature and stirred for a further 1 h, at which point LCMS was performed to confirm conversion to the acyl chloride intermediate (confirmed by quenching an aliquot of the intermediate with methanol). At this point 2 M dimethylamine in THE (4.43 mL, 8.85 mmol) was added, and the reaction was then stirred at room temperature for 18 h. After pouring the reaction mixture into a separatory funnel containing water (15 mL) and DCM (30 mL), the aqueous phase was extracted with DCM (×3). The combined organic extracts were washed with brine, dried over anhydrous sodium sulfate, and concentrated under reduced pressure. The crude intermediate P (565 mg) (brown foamy solid) was used in the next step without further purification. LRMS-HESI: calculated for $C_{16}H_{18}FN_3O_3$ $(M+H)^+$ 320.14 m/z, observed 320.14 m/z. (FIG. 10B, see: further also chemical reaction (b) in FIG. 3B).

Figure 10C:
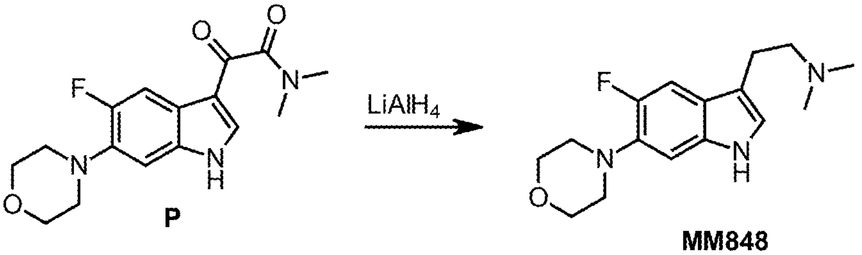

Referring next to FIG. 10C, a solution of intermediate P (565 mg, 1.77 mmol) in THE (16.1 mL) at 0° C., under nitrogen was added 2 M lithium aluminum hydride (4.42 mL, 8.85 mmol) in a dropwise manner. The reaction mixture was then heated to 60° C. (RBF with condenser) and left to react for 90 minutes. After confirming conversion by LCMS, the reaction was cooled to 0° C., diluted with ether (10 mL), and quenched through slow successive addition of water (V (μL)=mg of LAH), 15% NaOH (V (μL)=mg of LAH) and water (V (μL)=3×mg of LAH). The slurry was warmed to room temperature and stirred for 10 minutes. Anhydrous magnesium sulphate was added, and the slurry stirred for a further 10 minutes, filtered, and the filter cake rinsed with THE (30 mL). The filtrate was concentrated under reduced pressure to yield a crude colourless oil that was purified by FC on silica gel (solid loading, 25 g silica, (10% $NH_4OH$ in methanol)/DCM 0:100 to 20:80) to afford MM848 (113 mg, 20%) as a white solid. LRMS-HESI: calculated for $C_{16}H_{23}FN_3O$ $(M+H)^+$ 292.18 m/z, observed 292.19 m/z. $^1H$ NMR (400 MHz, $CDCl_3$) δ 7.22 (s, 1H), 6.97 (s, 1H), 6.90 (d, J=7.1 Hz, 1H), 3.94-3.88 (m, 4H), 3.09-3.05 (m, 4H), 2.88-2.83 (m, 2H), 2.62-2.57 (m, 2H), 2.33 (s, 6H). (FIG. 10C, see: further also chemical reaction (c) in FIG. 3B).

It is noted that MM848 corresponds with chemical compound (XI):

(XI)

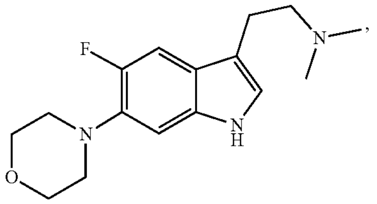

set forth herein.

5-HT Receptor Radioligand Competition Assay.

Competition assays at the $5\text{-HT}_{2A}$ receptor were performed as described in Example 11, except compound with formula (XI) was used in place of compound with formula (XV). Resulting $K_i$ data for controls and test compounds in $5\text{-HT}_{2A}$ receptor binding assays, including data acquired for compound with formula (XI), are summarized in Table 2. Compound with formula (XI) (designated 'XI' in Table 2) exhibited a $K_i$ value of 0.71 μM at the $5\text{-HT}_{2A}$ receptor. This $K_i$ value was less than those of negative controls (i.e., $K_i$<1000 μM) and hence suggested binding by compound with formula (XI) at this receptor.

Neuroplastogenicity Assays.

Assays to reveal potential of drugs to enhance neurite outgrowth in human model (NT2) neurons were conducted as described in Example 11, except that compound with formula (XI) was used in place of compound with formula (XV). Results of visual inspection are summarized in Table 4, where (1) (+) designates strong evidence of enhanced neurite outgrowth in drug-treated NT2 cells compared to vehicle-treated cells, and (2) (−) designates weak or no evidence of enhanced neurite outgrowth in drug-treated NT2 cells compared to vehicle-treated cells. Unlike the effects imparted by positive controls and compound with formula (XV) (FIG. 37A), human model (NT2) neurons incubated with 1 μM or 10 μM compound (XI) did not grow larger in size or display greater overall neurite outgrowth compared with vehicle-treated (0.1% DMSO) human model neurons. These observations are summarized as a (−) designation in Table 4.

Mouse Head Twitch Response (HTR) Assay to Assess Hallucinogenic Potential.

Head Twitch Response (HTR) assays were conducted as described in Example 11, except that compound with formula (XI) was used in place of compound with formula (XV). FIG. 3 38A shows HTR assay results for all drugs administered at 3 mg/kg (preliminary screening). Results show high hallucinogenic potential (mean HTR≥10) for positive controls (hatched bars; psilocin, DMT, 5-MeO-DMT). In contrast, low/no hallucinogenic potential (mean HTR≤5) is observed for negative controls (white bars; 5-Br-DMT, TBG, 6-F-DET). Mean HTR between 10 and 5 signifies reduced hallucinogenic potential relative to positive controls. Compound (XI) has a mean HTR of 10.5, suggesting high hallucinogenic potential similar to positive controls.

Figure 11:
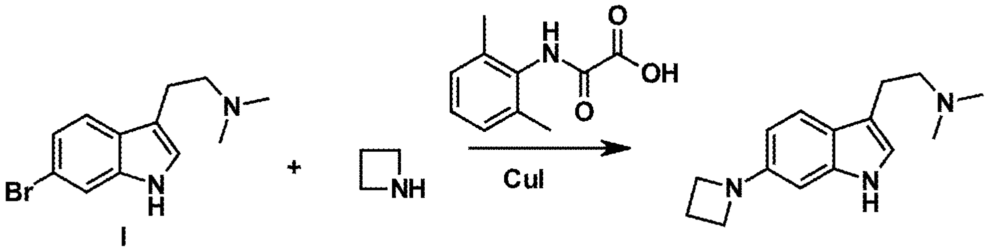
FIG. 11 depicts a further example reaction in another example chemical synthesis pathway for the synthesis of another example compound according to the present disclosure.

Example 8—Synthesis and Analysis of an Eighth N-Heterocycle Substituted Tryptamine Derivative Referring to FIG. 11, an oven-dried two-necked flask was charged with intermediate I (145 mg, 543 μmol), prepared as described in Example 4, copper(i) iodide (13.7 mg, 68.4 μmol), 2,6-dimethylanilino(oxo)acetic acid (24.4 mg, 123 μmol), and potassium phosphate tribasic (270 mg, 1.25 mmol). The flask was evacuated and backfilled with argon this was followed by addition of an argon sparged solution of azetidine (70.9 μL, 999 μmol) in n-butanol (760 μL). The reaction mixture was stirred at 110° C. for 1 h. After this time the mixture was cooled to room temperature and water was added followed by extraction with DCM. The combined organic layers were dried over $MgSO_4$, filtered and concentrated. The resulting crude material was purified by flash chromatography (4 g silica, 0%-20% MeOH in DCM) to provide MM849 (67 mg, 51%) as a white solid. LRMS-HESI: calculated for $C_{15}H_{22}N_3$ $(M+H)^+$ 244.18 m/z, observed 244.21 m/z. $^1H$ NMR (400 MHz, $CDCl_3$) δ 7.97 (s, 1H), 7.43 (dt, J=8.4, 0.7 Hz, 1H), 6.81 (dd, J=2.2, 1.0 Hz, 1H), 6.40 (dd, J=8.4, 2.0 Hz, 1H), 6.38-6.33 (m, 1H), 3.86 (t, J=7.1 Hz, 4H), 2.98-2.84 (m, 2H), 2.72-2.61 (m, 2H), 2.42-2.30 (m, 8H). $^{13}C$ NMR (101 MHz, $CDCl_3$) δ 149.34, 137.57, 120.29, 119.23, 119.07, 114.08, 106.50, 93.11, 60.39, 53.16, 45.42, 23.78, 17.14. (FIG. 11, see: further also chemical reaction (i) in FIG. 3B).

It is noted that MM849 corresponds with chemical compound (XII):

(XII)

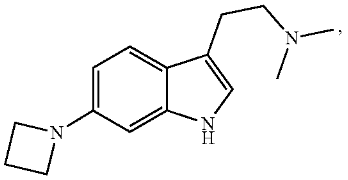

set forth herein.

5-HT Receptor Radioligand Competition Assays.

Competition assays at the $5\text{-}HT_{1A}$ receptor were performed as described in Example 11, except compound with formula (XII) was used in place of compound with formula (XV). Resulting $K_i$ data for controls and test compounds in $5\text{-}HT_{1A}$ receptor binding assays, including data acquired for compound with formula (XII), are summarized in Table 1. Compound with formula (XII) (designated 'XII' in Table 1) exhibited a $K_i$ value of 20.8 μM at the $5\text{-}HT_{1A}$ receptor. This $K_i$ value was less than those of negative controls (i.e., $K_i$<1000 μM) and hence suggested binding by compound with formula (XII) at this receptor. Competition assays at the $5\text{-}HT_{2A}$ receptor were performed as described in Example 11, except compound with formula (XII) was used in place of compound with formula (XV). Resulting $K_i$ data for controls and test compounds in $5\text{-}HT_{2A}$ receptor binding assays, including data acquired for compound with formula (XII), are summarized in Table 2. Compound with formula (XII) (designated 'XII' in Table 2) exhibited a $K_i$ value of 23.7 μM at the $5\text{-}HT_{2A}$ receptor. This $K_i$ value was less than those of negative controls (i.e., $K_i$<1000 μM) and hence suggested binding by compound with formula (XII) at this receptor.

5-HT Transporter (SERT) Radioligand Competition Assay.

Binding assays at SERT were performed as described in Example 11, except compound with formula (XII) was used in place of compound with formula (XV). Resulting $K_i$ data for controls and test compounds in SERT binding assays, including data acquired for compound with formula (XII), are summarized in Table 3. Compound with formula (XII) (designated 'XII' in Table 3) exhibited a $K_i$ value of 1.68 μM at SERT. This $K_i$ value was less than those of negative controls (i.e., $K_i$<1000 μM) and hence suggested binding by compound with formula (XII) at this transporter.

Neuroplastogenicity Assays.

Assays to reveal potential of drugs to enhance neurite outgrowth in human model (NT2) neurons were conducted as described in Example 11, except that compound with formula (XII) was used in place of compound with formula (XV). Results of visual inspection are summarized in Table 4, where (1) (+) designates strong evidence of enhanced neurite outgrowth in drug-treated NT2 cells compared to vehicle-treated cells, and (2) (−) designates weak or no evidence of enhanced neurite outgrowth in drug-treated NT2 cells compared to vehicle-treated cells. Similar to the effects imparted by positive controls and compound with formula (XV) (FIG. 37A), human model (NT2) neurons incubated with 1 μM or 10 μM compound (XII) grew larger in size and displayed greater overall neurite outgrowth compared with vehicle-treated (0.1% DMSO) human model neurons. These observations are summarized as a (+) designation in Table 4.

Mouse Head Twitch Response (HTR) Assay to Assess Hallucinogenic Potential.

Figure 38B:
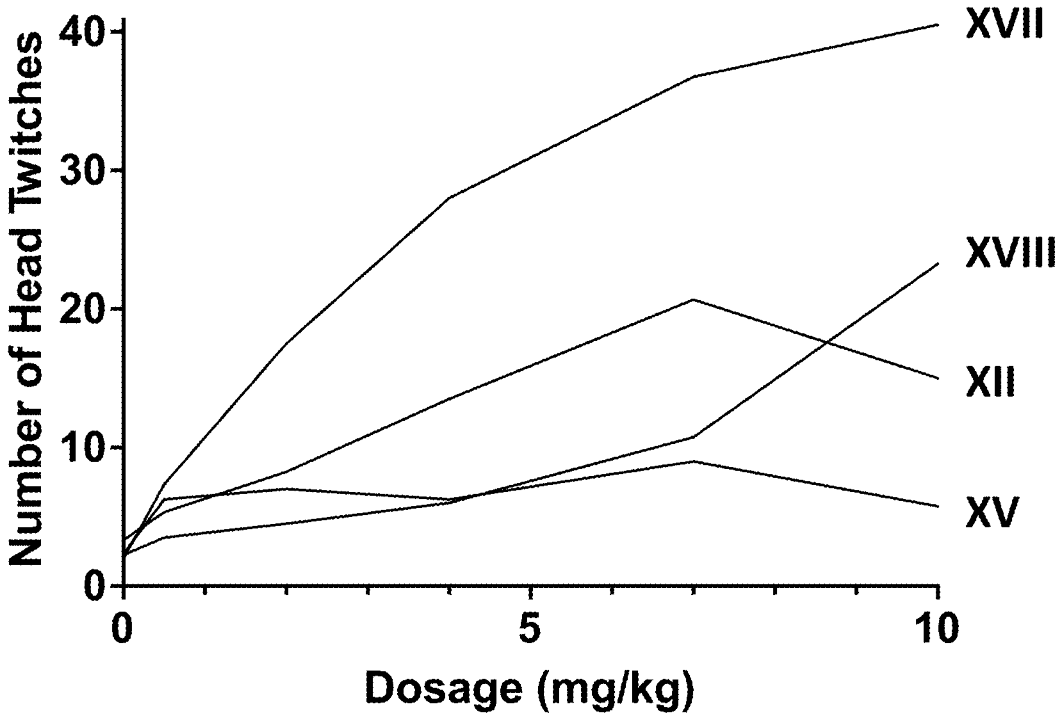

Head Twitch Response (HTR) assays were conducted as described in Example 11, except that compound with formula (XII) was used in place of compound with formula (XV). FIG. 38A shows HTR assay results for all drugs administered at 3 mg/kg (preliminary screening). Results show high hallucinogenic potential (mean HTR≥10) for positive controls (hatched bars; psilocin, DMT, 5-MeO-DMT). In contrast, low/no hallucinogenic potential (mean HTR≤5) is observed for negative controls (white bars; 5-Br-DMT, TBG, 6-F-DET). Mean HTR between 10 and 5 signifies reduced hallucinogenic potential relative to positive controls. Compound (XII) has a mean HTR of 6.25, suggesting reduced hallucinogenic potential relative to positive controls. FIG. 38B. shows HTR assay results for selected drugs administered at increasing doses (0.5-10 mg/kg). Results reveal that HTR for compound (XII) increases to ~20 HTR at 7 mg/kg dose, but then decreases to ~12 HTR at maximum dosage (10 mg/kg). These results suggest mild hallucinogenic potential as dosage increases to 7 mg/kg, but further point to reduced potential past 7 mg/kg dosage.

Mouse Plasma Pharmacokinetics (PK) Survey.

A pharmacokinetics (PK) survey was performed as described in Example 11, except that compound with formula (XII) was used in place of compound with formula (XV). Calculated parameters for compound with formula (XII) and other drugs are listed in Table 5. Systemic exposure ($AUC_{t0\text{-}tlast}$) was determined to be 39.7±3.0 hr*ng/mL for cohorts administered 4 mg/kg Compound (XII), whereas those administered 10 mg/kg exhibited a mean exposure of 145.4±5.3 hr*ng/mL. Further, $C_{max}$ was determined to be 92.8±17.2 ng/mL and 302.3±33.7 ng/mL for cohorts administered 4 and 10 mg/kg Compound (XII), respectively.

Figure 12A:
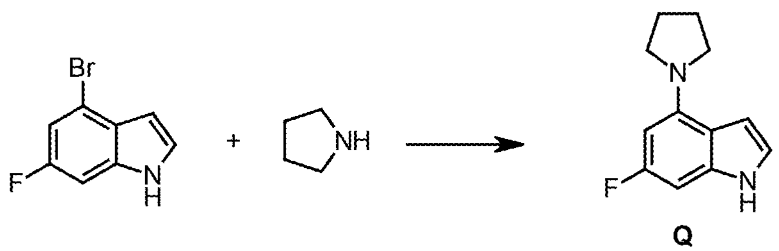
FIGS. 12A, 12B, 12C, and 12D depict further example reactions in an example chemical synthesis pathway for the synthesis of a certain example compound according to the present disclosure.

Example 9—Synthesis and Analysis of a Ninth N-Heterocycle Substituted Tryptamine Derivative Referring to FIG. 12A, in an oven-dried vial, under nitrogen atmosphere, was dissolved 4-bromo-6-fluoro-1H-indole (569 mg, 2.55 mmol), $Pd_2(dba)_3$ (24.1 mg, 25.5 μmol), and DavePHOS (24.1 mg, 61.2 μmol) in dry THE (3.19 mL). To this stirring solution was added 1 M LiHMDS in THE (5.61 mL, 5.61 mmol) and pyrrolidine (473 μL, 5.61 mmol). The reaction mixture was heated to 60° C. for 2 hours. At this point the mixture was cooled to room temperature and poured into a separatory funnel containing DCM (15 mL) and water (15 mL). The aqueous layer was extracted with DCM (2×15 mL), all organic layers were combined, washed with brine, dried ($MgSO_4$), filtered and concentrated to leave a brown solid. This was adsorbed to silica and purified by FC (12 g silica, DCM to DCM:MeOH 9:1) to obtain the desired product, intermediate Q (334 mg, 64%) as a tan solid. LRMS-HESI: calculated for $C_{12}H_{14}FN_2$ $(M+H)^+$ 205.11 m/z, observed 205.11 m/z. (FIG. 12A, see: further also chemical reaction (a) in FIG. 3B).

Figure 12B:
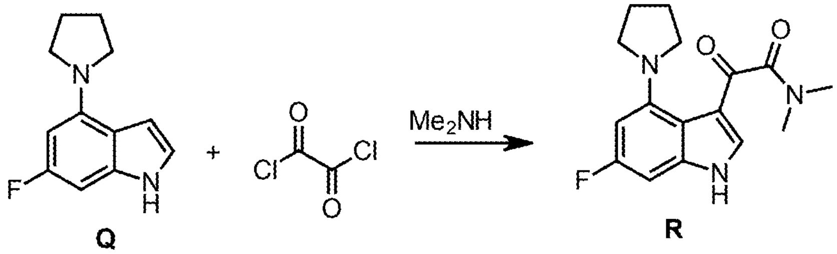

Referring next to FIG. 12B, to an ice-cold solution of oxalyl chloride (180 μL, 2.11 mmol) in dry THE (4.74 mL), under nitrogen atmosphere, was added a solution of intermediate Q (287 mg, 1.41 mmol) in dry THE (4.74 mL) in a dropwise manner. The reaction mixture was allowed to warm to room temperature and stirred for 3 h. After cooling to 0° C., 2 M dimethylamine in THE (5.62 mL, 11.2 mmol) was added, and the reaction mixture allowed to stir for a further 18 hours. The reaction was quenched with 15 mL water and poured into a separatory funnel containing DCM (15 mL). The aqueous layer was extracted with DCM (2×15 mL), all organic layers were combined, washed with brine, dried ($MgSO_4$) and concentrated to provide the crude product as a brown solid. This was adsorbed to silica and purified by FC (12 g silica, 30% to 80% EtOAc in Hex) to provide the desired product, intermediate R (375 mg, 88%), as a red solid. LRMS-HESI: calculated for $C_{16}H_{19}FN_3O_2$ $(M+H)^+$ 304.15 m/z, observed 304.13 m/z. (FIG. 12B, see: further also chemical reaction (b) in FIG. 3B).

Figure 12C:
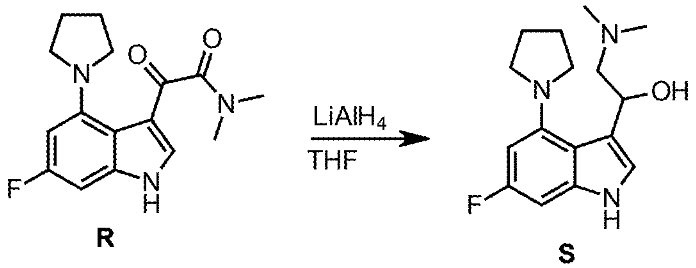

Referring next to FIG. 12C, the glyoxyl amide, intermediate R (315 mg, 1.04 mmol), was dissolved in dry THE (10.4 mL) and cooled to 0° C. Added to this was a 2 M solution of lithium aluminum hydride (2.60 mL, 5.19 mmol) in THE and the mixture was warmed to 60° C. IPC was performed at 1 hour, the mixture contained only the beta-hydroxy tryptamine and the mixture was left overnight at 60° C. In the morning the mixture was again assessed by LCMS and it was clear that the reaction had stalled at the beta-hydroxy tryptamine. Fieser workup was performed and intermediate S (260 mg, 86%) was isolated as a yellow solid. LRMS-HESI: calculated for $C_{16}H_{23}FN_3O$ $(M+H)^+$ 292.18 m/z, observed 292.17 m/z. (FIG. 12C, see: further also chemical reaction (j) in FIG. 3B).

Figure 12D:
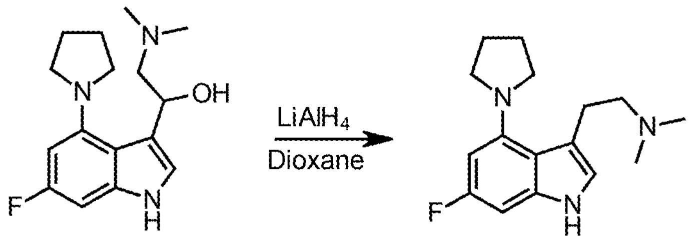

Referring next to FIG. 12D, the beta-hydroxy tryptamine, intermediate S (80.0 mg, 275 μmol), was dissolved in dry dioxane (2.75 mL) and cooled to 0° C. Added to this was a 2 M solution of lithium aluminum hydride (549 μL, 1.10 mmol) in THE and the mixture was warmed to 105° C. The mixture was left to react at this temperature overnight. In the morning the mixture was assessed by LCMS and the desired product had formed as the only major component of the reaction mixture. Fieser workup was performed and the material was isolated. Purification by flash column chromatography (4 g silica, DCM to DCM:MeOH 9:1) provided purified MM850 (58.0 mg, 77%) as a light grey solid. LRMS-HESI: calculated for $C_{16}H_{23}FN_3$ $(M+H)^+$ 276.19 m/z, observed 276.22 m/z. $^1H$ NMR (400 MHz, $CDCl_3$) δ 11.61 (s 1H), 7.04-7.03 (m, 1H), 6.72-6.70 (m, 1H), 5.90 (d, J=13.8 Hz, 1H), 3.61-3.57 (m, 4H), 3.00-2.97 (m, 2H), 2.64-2.61 (m, 2H), 2.41 (s, 6H), 2.02-1.99 (m, 4H). (FIG. 12D, see: further also chemical reaction (k) in FIG. 3B)

It is noted that MM850 corresponds with chemical compound (XIII):

(XIII)

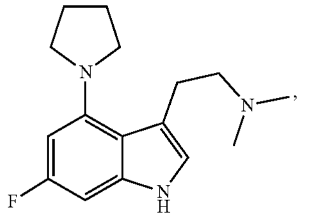

set forth herein.

5-HT Receptor Radioligand Competition Assay.

Competition assays at the $5\text{-}HT_{2A}$ receptor were performed as described in Example 11, except compound with formula (XIII) was used in place of compound with formula (XV). Resulting $K_i$ data for controls and test compounds in $5\text{-}HT_{2A}$ receptor binding assays, including data acquired for compound with formula (XIII), are summarized in Table 2. Compound with formula (XIII) (designated 'XIII' in Table 2) exhibited a $K_i$ value of 2.96 μM at the $5\text{-}HT_{2A}$ receptor. This $K_i$ value was less than those of negative controls (i.e., $K_i$<1000 μM) and hence suggested binding by compound with formula (XIII) at this receptor.

Neuroplastogenicity Assays.

Assays to reveal potential of drugs to enhance neurite outgrowth in human model (NT2) neurons were conducted as described in Example 11, except that compound with formula (XIII) was used in place of compound with formula (XV). Results of visual inspection are summarized in Table 4, where (1) (+) designates strong evidence of enhanced neurite outgrowth in drug-treated NT2 cells compared to vehicle-treated cells, and (2) (–) designates weak or no evidence of enhanced neurite outgrowth in drug-treated NT2 cells compared to vehicle-treated cells. Similar to the effects imparted by positive controls and compound with formula (XV) (FIG. 37A), human model (NT2) neurons incubated with 1 μM or 10 μM compound (XIII) grew larger in size and displayed greater overall neurite outgrowth compared with vehicle-treated (0.1% DMSO) human model neurons. These observations are summarized as a (+) designation in Table 4.

Mouse Head Twitch Response (HTR) Assay to Assess Hallucinogenic Potential.

Head Twitch Response (HTR) assays were conducted as described in Example 11, except that compound with formula (XIII) was used in place of compound with formula (XV). FIG. 38A shows HTR assay results for all drugs administered at 3 mg/kg (preliminary screening). Results show high hallucinogenic potential (mean HTR≥10) for positive controls (hatched bars; psilocin, DMT, 5-MeO-DMT). In contrast, low/no hallucinogenic potential (mean HTR≤5) is observed for negative controls (white bars; 5-Br-DMT, TBG, 6-F-DET). Mean HTR between 10 and 5 signifies reduced hallucinogenic potential relative to positive controls. Compound (XIII) has a mean HTR of 7.75, suggesting reduced hallucinogenic potential relative to positive controls.

Figure 13A:
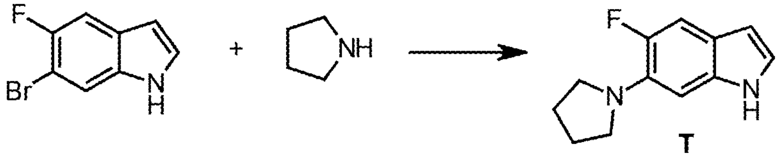
FIGS. 13A, 13B, and 13C depict further example reactions in an example chemical synthesis pathway for the synthesis of a certain example compound according to the present disclosure.

Example 10—Synthesis and Analysis of a Tenth N-Heterocycle Substituted Tryptamine Derivative Referring to FIG. 13A, in an oven-dried vial under nitrogen atmosphere was dissolved 6-bromo-5-fluoroindole (282 mg, 1.25 mmol), $Pd_2(dba)_3$ (11.8 mg, 12.5 μmol), and BINAP (12.0 mg, 18.8 μmol) in dry THE (1.56 mL). To this stirring solution was added LiHMDS (2.75 mL, 2.75 mmol) and argon sparged pyrrolidine (232 μL, 2.75 mmol). The reaction mixture was heated to 60° C. for 20 hrs. The mixture was cooled to room temperature and poured into a separatory funnel containing DCM (15 mL) and water (15 mL). The aqueous layer was extracted with DCM (2×15 mL), all organic layers were combined, washed with brine, dried ($MgSO_4$), filtered and concentrated to leave a brown solid. This was adsorbed to silica and purified by FC (12 g silica, DCM to DCM:MeOH 9:1) to obtain the desired product, intermediate T (40.0 mg, 16%) as a red solid. LRMS-HESI: calculated for $C_{12}H_{14}FN_2$ $(M+H)^+$ 205.11 m/z, observed 205.14 m/z. (FIG. 13A, see: further also chemical reaction (a) in FIG. 3B).

Figure 13B:
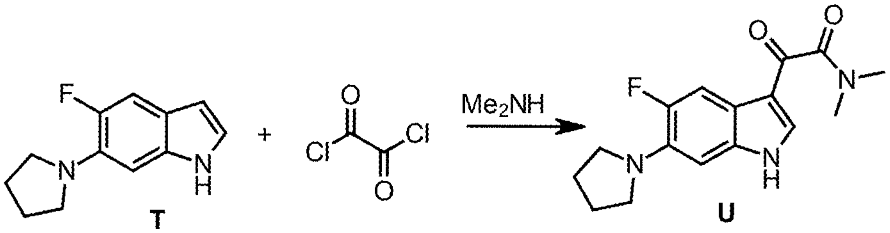

Referring next to FIG. 13B, to an ice-cold solution of oxalyl chloride (50 μL, 0.59 mmol) in dry THE (1.32 mL), under nitrogen atmosphere, was added a solution of intermediate T (80 mg, 0.39 mmol) in dry THE (1.32 mL) in a dropwise manner. The reaction mixture was allowed to warm to room temperature and stirred for 3 h. After cooling to 0° C., 2 M dimethylamine in THE (1.57 mL, 3.13 mmol) was added, and the reaction mixture allowed to stir for a further 18 hours. The reaction was quenched with 15 mL water and poured into a separatory funnel containing DCM (15 mL). The aqueous layer was extracted with DCM (2×15 mL), all organic layers were combined, washed with brine, dried ($MgSO_4$) and concentrated to provide the crude product as a brown solid. This was adsorbed to silica and purified by FC (12 g silica, 30% to 80% EtOAc in Hex) to provide the desired product, intermediate U (110 mg, 93%), as a red solid. LRMS-HESI: calculated for $C_{16}H_{19}FN_3O_2$ $(M+H)^+$ 304.15 m/z, observed 304.13 m/z. (FIG. 13B, see: further also chemical reaction (b) in FIG. 3B).

Figure 13C:
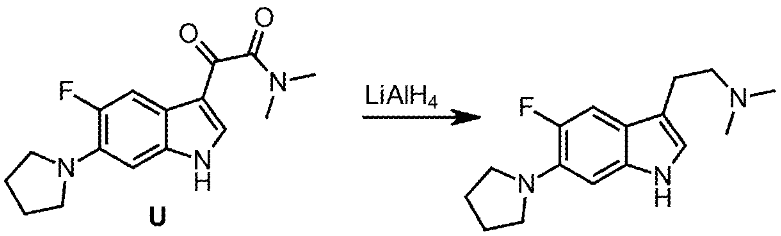

Referring next to FIG. 13C, a solution of the glyoxyl amide, intermediate U (110 mg, 363 μmol), in THE (3.66 mL) was cooled to 0° C. and 2.0 M lithium aluminum hydride (907 μL, 1.81 mmol) was added. The mixture was warmed to 60° C. and left to react overnight. In the morning it was determined that full reduction had occurred. Fieser work-up was performed and the crude material was isolated as a light brown solid. This was subjected to purification by column chromatography (4 g silica, DCM to 9:1 DCM:MeOH) and the MM867 (35.0 mg, 35%) was obtained as a light grey solid. LRMS-HESI: calculated for $C_{16}H_{23}FN_3$ $(M+H)^+$ 276.19 m/z, observed 276.21 m/z. $^1H$ NMR (400 MHz, $CDCl_3$) δ 7.88 (s, 1H), 7.18 (d, J=13.6 Hz, 1H)), 6.86-6.85 (m, 1H), 6.65 (d, J=7.4 Hz, 1H), 3.33-3.30 (m, 4H), 2.90-2.86 (m, 2H), 2.68-2.64 (m, 2H), 2.37 (s, 6H), 1.99-1.95 (m, 4H). (FIG. 13C, see: further also chemical reaction (c) in FIG. 3B).

It is noted that MM867 corresponds with chemical compound (XIV):

(XIV)

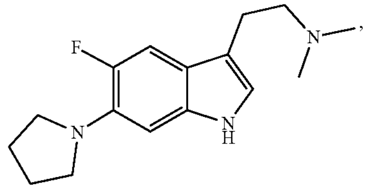

set forth herein.

5-HT Receptor Radioligand Competition Assay.

Competition assays at the $5\text{-}HT_{2A}$ receptor were performed as described in Example 11, except compound with formula (XIV) was used in place of compound with formula (XV). Resulting $K_i$ data for controls and test compounds in $5\text{-}HT_{2A}$ receptor binding assays, including data acquired for compound with formula (XIV), are summarized in Table 2. Compound with formula (XIV) (designated 'XIV' in Table 2) exhibited a $K_i$ value of 3.1 μM at the $5\text{-}HT_{2A}$ receptor. This $K_i$ value was less than those of negative controls (i.e., $K_i$<1000 μM) and hence suggested binding by compound with formula (XIV) at this receptor.

Neuroplastogenicity Assays.

Assays to reveal potential of drugs to enhance neurite outgrowth in human model (NT2) neurons were conducted as described in Example 11, except that compound with formula (XIV) was used in place of compound with formula (XV). Results of visual inspection are summarized in Table 4, where (1) (+) designates strong evidence of enhanced neurite outgrowth in drug-treated NT2 cells compared to vehicle-treated cells, and (2) (−) designates weak or no evidence of enhanced neurite outgrowth in drug-treated NT2 cells compared to vehicle-treated cells. Similar to the effects imparted by positive controls and compound with formula (XV) (FIG. 37A), human model (NT2) neurons incubated with 1 μM or 10 μM compound (XIV) grew larger in size and displayed greater overall neurite outgrowth compared with vehicle-treated (0.1% DMSO) human model neurons. These observations are summarized as a (+) designation in Table 4.

Mouse Head Twitch Response (HTR) Assay to Assess Hallucinogenic Potential.

Head Twitch Response (HTR) assays were conducted as described in Example 11, except that compound with formula (XIV) was used in place of compound with formula (XV). FIG. 38A shows HTR assay results for all drugs administered at 3 mg/kg (preliminary screening). Results show high hallucinogenic potential (mean HTR≥10) for positive controls (hatched bars; psilocin, DMT, 5-MeO-DMT). In contrast, low/no hallucinogenic potential (mean HTR≤5) is observed for negative controls (white bars; 5-Br-DMT, TBG, 6-F-DET). Mean HTR between 10 and 5 signifies reduced hallucinogenic potential relative to positive controls. Compound (XIV) has a mean HTR of 9.0, suggesting somewhat reduced hallucinogenic potential relative to positive controls.

Figure 14A:
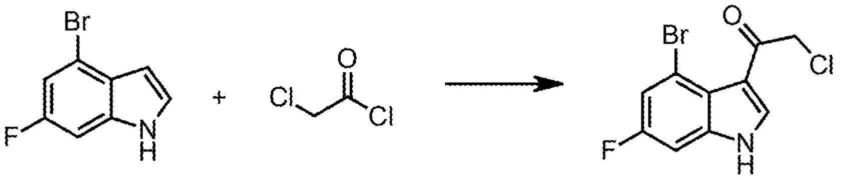
FIGS. 14A, 14B, 14C, and 14D depict further example reactions in an example chemical synthesis pathway for the synthesis of a certain example compound according to the present disclosure.

Example 11—Synthesis and Analysis of an Eleventh N-Heterocycle Substituted Tryptamine Derivative Referring to FIG. 14A, to a stirring solution of aluminum chloride (1.36 g, 10.1 mmol) in DCM (22.4 mL) under nitrogen atmosphere was added chloroacetyl chloride (820 μL, 10.1 mmol) in DCM (22.4 mL) and stirred for 30 min. At this juncture, a solution of 4-bromo-6-fluoro-1H-indole (1.50 g, 6.73 mmol) in DCM (44.9 mL) was added dropwise via addition funnel, and the resulting mixture stirred for 20 hrs. The reaction mixture was quenched by pouring over ice-water (200 mL), agitating thoroughly, filtering the resulting precipitate (sintered glass), and washing with saturated sodium bicarbonate and water. Upon drying, intermediate V (936 mg, 48%) was collected as a beige solid. The material was used without further purification in the next step. LRMS-HESI: calculated for $C_{10}H_7BrClFNO$ $(M+H)^+$ 289.94 m/z, observed 289.98 m/z. (FIG. 14A, see: further also chemical reaction (d) in FIG. 3B).

Figure 14B:
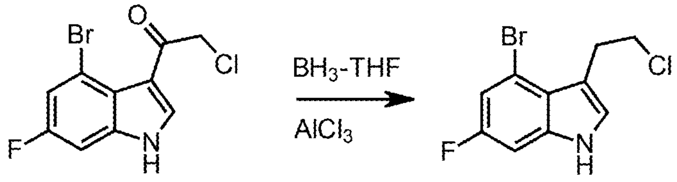

Referring next to FIG. 14B, to a suspension of aluminum chloride (1.29 g, 9.71 mmol) in dry DCM (28.2 mL) at 0° C. under nitrogen atmosphere was added 1 M borane-THF complex in THE (19.4 mL, 19.4 mmol), and the resulting solution was stirred for 10 minutes. A suspension of intermediate V (940 mg, 3.24 mmol) in dry DCM (18.8 mL) was added, and the resulting mixture was stirred at 0° C. for 3 hrs. The reaction mixture, at 0° C., was quenched through addition of water (20 mL) and 1 M HCl (20 mL). The biphasic mixture was poured into a separatory funnel containing water and DCM. The layers were separated and the aqueous phase was extracted with DCM (×3). The combined organic layers were washed with brine, dried over anhydrous sodium sulfate, and concentrated under reduced pressure to yield the crude product, intermediate W, which was used in the next step without further purification. (FIG. 14B, see: further also chemical reaction (e) in FIG. 3B).

Figure 14C:
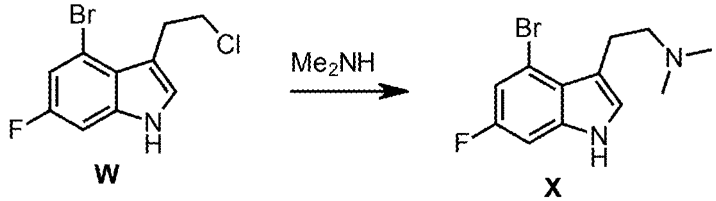

Referring next to FIG. 14C, to a solution of intermediate W (791 mg, 2.86 mmol) in dry ACN (14.9 mL) were added potassium bromide (1.02 g, 8.58 mmol) and potassium carbonate (791 mg, 5.72 mmol) followed by 2 M dimethylamine in THE (12.9 mL, 25.7 mmol). The resulting mixture was stirred at 70° C. for 18 hrs. The solids were filtered and washed with DCM, the solvent was removed under reduced pressure, and the remaining residue was purified by FC (25 g silica—0% to 20% MeOH in DCM) to provide intermediate X (526 mg, 64%) as a beige solid. LRMS-HESI calculated for $C_{12}H_{15}BrFN_2$ $(M+H)^+$ 285.04 m/z, observed 285.07 m/z. (FIG. 14C, see: further also chemical reaction (f) in FIG. 3B).

Figure 14D:
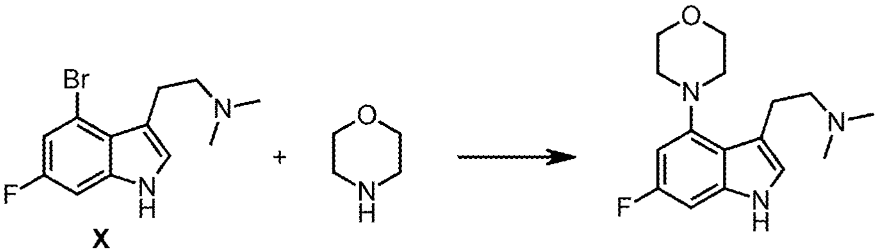

Referring next to FIG. 14D, in an oven-dried vial under nitrogen atmosphere was dissolved intermediate X (55.0 mg, 193 μmol), $Pd_2(dba)_3$ (18.2 mg, 19.3 μmol), and DavePHOS (18.2 mg, 46.3 μmol) in dry THE (400 μL). To this stirring solution was added 1 M LiHMDS in THE (424 μL, 424 μmol) and morpholine (100 μL, 1.13 mmol). The reaction mixture was heated to 60° C. for 1.5 hours. At which point IPC was run via LCMS and the reaction was determined to be complete. The mixture was cooled to room temperature and poured into a separatory funnel containing ethyl acetate (15 mL) and water (15 mL). The aqueous layer was extracted with ethyl acetate (2×15 mL), all organic layers were combined, washed with brine, dried ($MgSO_4$), filtered and concentrated to leave a brown solid. This was adsorbed to silica and purified by FC (4 g silica, 0% to 20% MeOH in DCM) to obtain the MM868 (32.0 mg, 57%) as a light brown solid. LRMS-HESI: calculated for $C_{16}H_{23}FN_3O$ $(M+H)^+$292.18 m/z, observed 292.18 m/z. $^1H$ NMR (400 MHz, $CDCl_3$) δ 8.19 (s, 1H), 6.97-6.96 (m, 1H), 6.76 (dd, J=8.8 Hz, 2.1 Hz, 1H), 6.56 (dd, J=11.5 Hz, 2.2 Hz), 3.94-3.92 (m, 4H), 3.14-3.10 (m, 2H), 3.05-3.03 (m, 4H), 2.77-2.73 (m, 2H), 2.39 (s, 6H). (FIG. 14D, see: further also chemical reaction (g) in FIG. 3B).

It is noted that MM868 corresponds with chemical compound (XV):

(XV)

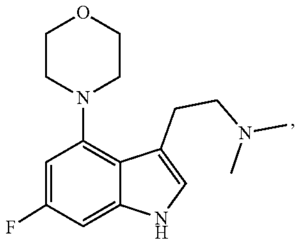

set forth herein.

5-HT Receptor Radioligand Competition Assays.

Figure 33A:
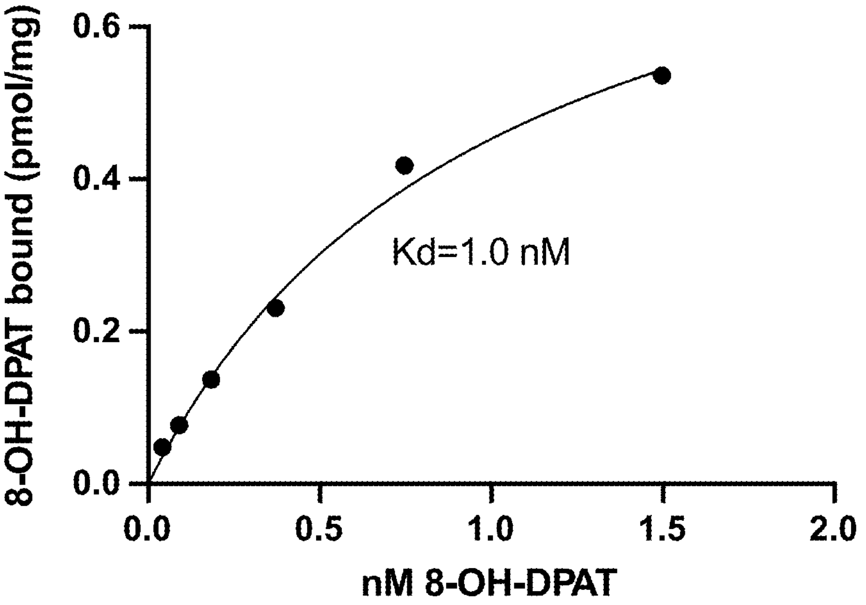
FIGS. 33A, 33B, 33C, 33D, 33E, 33F, 33G, and 33H depict various graphs representing certain experimental results, notably graphs obtained in the performance of experimental assays to evaluate the pharmaceutical efficacy of an example compound having chemical formula (XV), notably a radiolabelled ligand competition assay at the 5-$HT_{1A}$ receptor using radiolabeled 8-hydroxy-DPAT [propyl-2,3-ring-1,2,3-$^3$H](binding curve) (FIG. 33A); a 5-$HT_{1A}$ receptor competition assay using DMSO (negative control) (FIG. 33B); a 5-$HT_{1A}$ receptor competition assay using tryptophan (negative control) (FIG. 33C); a 5-$HT_{1A}$ receptor competition assay using serotonin (positive control) (FIG. 33D); a 5-$HT_{1A}$ receptor competition assay using fluoxetine (positive control) (FIG. 33E); a 5-$HT_{1A}$ receptor competition assay using vortioxetine (positive control) (FIG. 33F); a 5-$HT_{1A}$ receptor competition assay using MDMA (positive control) (FIG. 33G); and a 5-$HT_{1A}$ receptor competition assay using the compound with formula (XV) ("XV") (FIG. 33H).
Figure 33B:
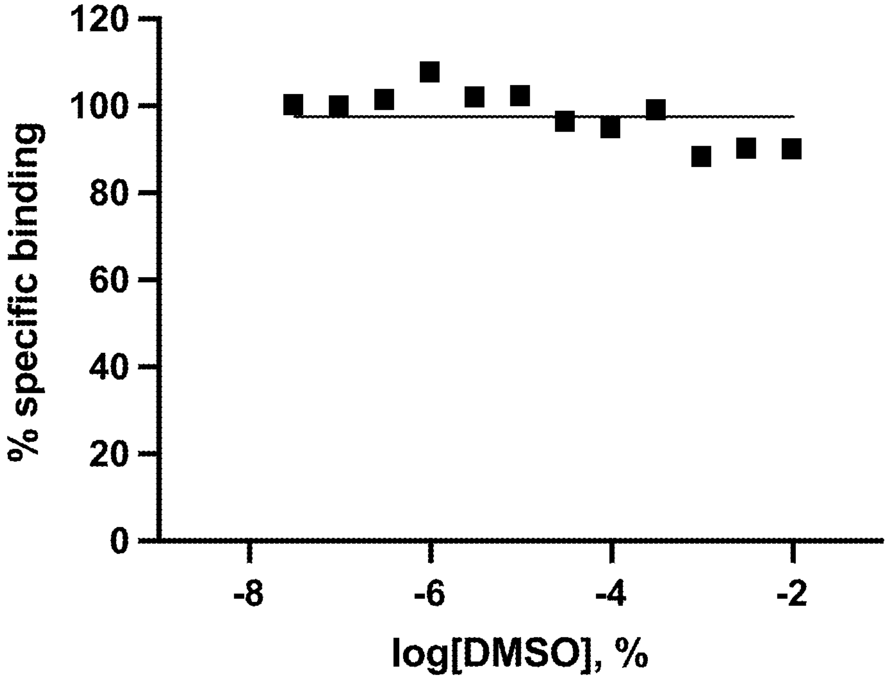
Figure 33C:
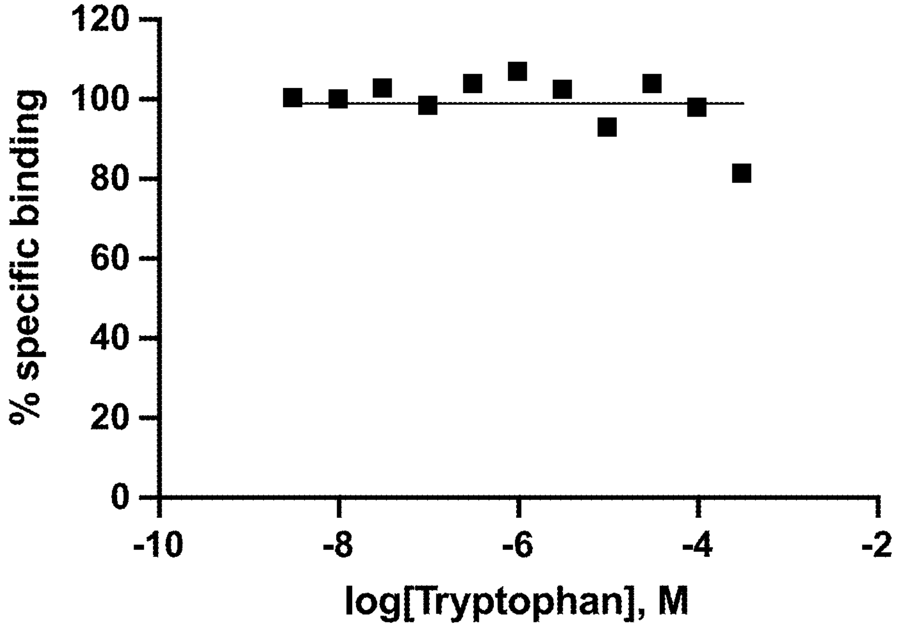
Figure 33D:
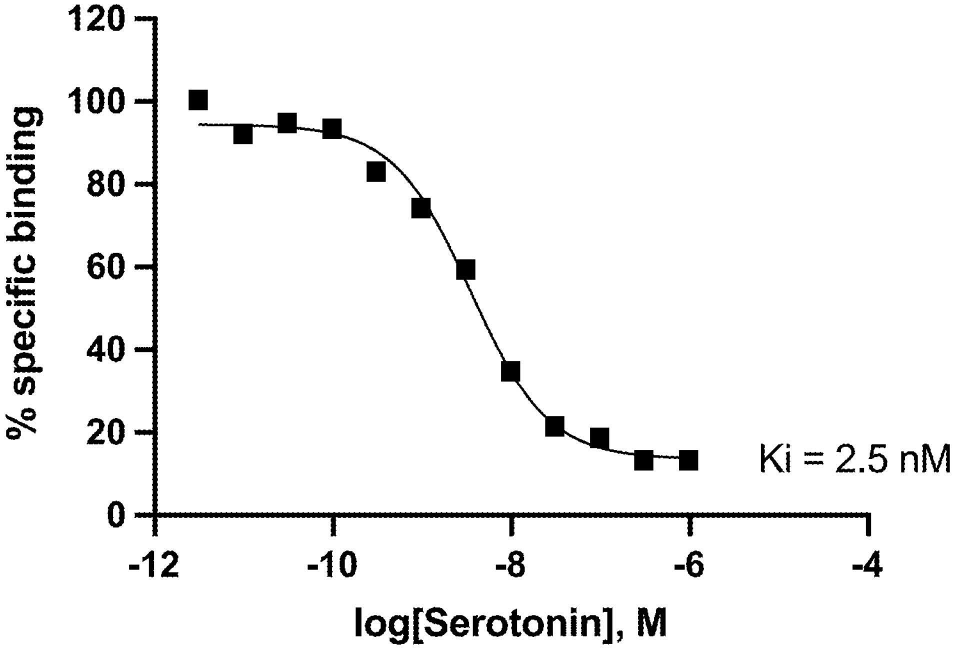
Figure 33E:
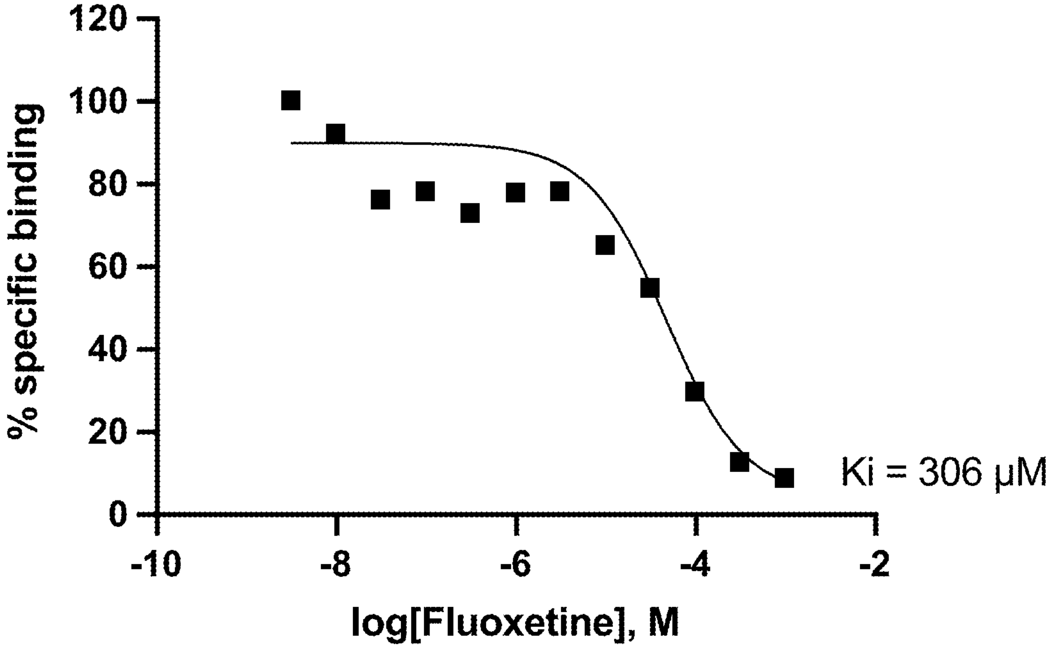
Figure 33F:
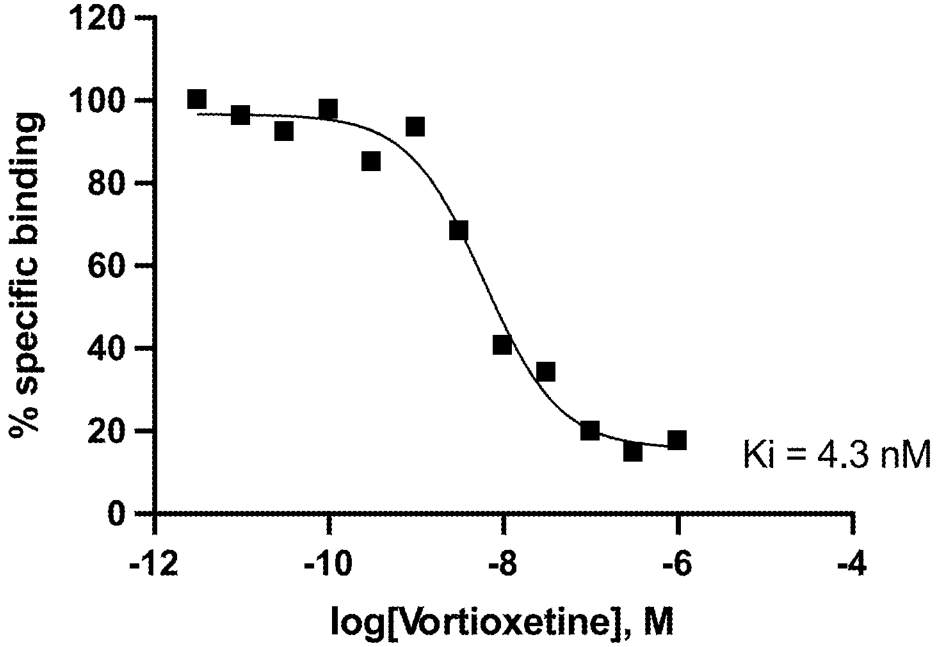
Figure 33G:
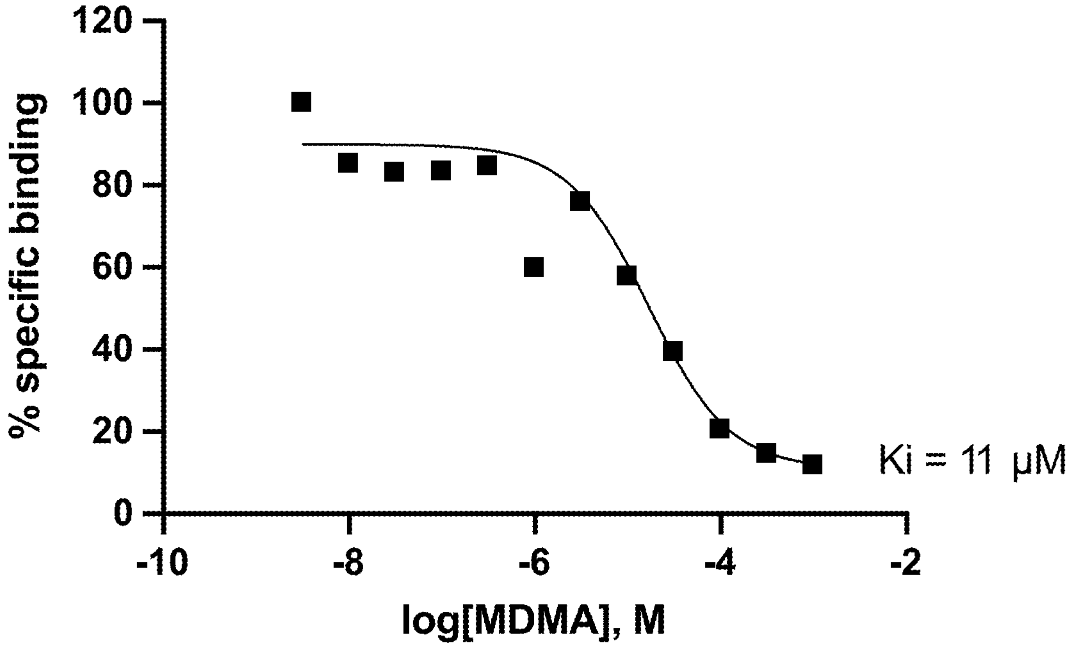
Figure 33H:
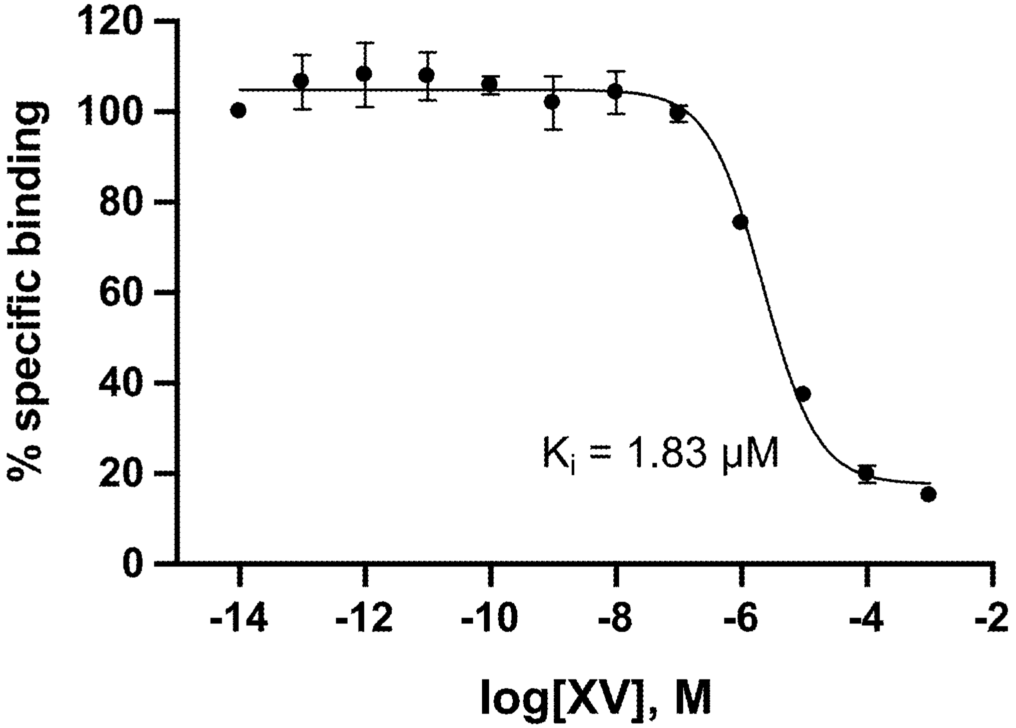

$5\text{-}HT_{1A}$ receptor. Competition assays were performed as follows: SPA beads (RPNQ0011), radiolabeled 8-hydroxy-DPAT [propyl-2,3-ring-1,2,3-$^3H$](labelled 7-(dipropylamino)-5,6,7,8-tetrahydronaphthalen-1-ol; NET929250UC), membranes containing $5\text{-}HT_{1A}$ (6110501400UA), and isoplate-96 microplate (6005040) were from Perkin Elmer (perkinelmer.com). Radioactive binding assays were carried out using a scintillation proximity assay (SPA; Maguire et al., 2012, Methods in Molecular Biology 897:31-77). For saturation binding assays, mixtures of 10 μg of membrane containing $HT_{1A}$ receptor was pre-coupled to 1 mg of SPA beads at room temperature in a tube rotator for 1 h in binding buffer [50 mM Tris-HCl pH 7.4, 10 mM magnesium sulfate, 0.5 mM EDTA, 3.7% (v/v) glycerol, 1 mM ascorbic acid, 10 μM pargyline HCl]. After pre-coupling, the beads and membrane were aliquoted in an isoplate-96 microplate with increasing amounts of 8-hydroxy-DPAT [propyl-2,3-ring-1,2,3-$^3H$](0.1525 nM to 5 nM) and incubated for two hours at room temperature in the dark with shaking. After incubation, the samples were read on a MicroBeta 2 Microplate Counter (perkinelmer.com). Non-specific binding was carried out in the presence of 100 μM of metergoline (M3668-500MG, Sigma-Aldrich). Equilibrium binding constant for 8-hydroxy-DPAT ($K_D$) was determined from a saturation binding curve using one-site saturation binding analysis from GraphPad PRISM software (Version 9.2.0). Test compound was dissolved to 100 mM in dimethylsulfoxide (DMSO), and dilutions were carried out in assay buffer. Competition binding assays were performed using 0.5 nM hot 8-hydroxy-DPAT and different concentrations of DMSO (up to 1%), tryptophan (3 nM to 1 mM), or unlabelled test compounds (3 nM to 1 mM) similar to the saturation binding assay. $K_i$ values were calculated from the competition displacement data using the competitive binding analysis from GraphPad PRISM software. Serotonin was used as a positive control, as it is the natural, endogenous ligand for all serotonergic receptors. Fluoxetine and vortioxetine were included as positive controls as they are widely prescribed pharmaceuticals with established binding to the $5\text{-HT}_{1A}$ receptor (Owens et al., 1997, Journal of Pharmacology and Experimental Therapeutics 283:1305-1322; Celada et al., 2013, CNS Drugs 27:703-716). MDMA was used as a positive control since it is a psychotropic drug with therapeutic potential and a moderate binder of the $5\text{-HT}_{1A}$ receptor (Simmler et al., 2013, British J. Pharmacol. 168: 458). Conversely, blank preparations lacking any drug (simply termed 'DMSO' samples) were used as negative controls, in addition to those containing tryptophan which is not known to bind the $5\text{-HT}_{1A}$ receptor. FIG. 33A illustrates the binding curve used to determine the $K_D$ of 8-hydroxy-DPAT. FIGS. 33B and 33C illustrate binding curves of negative controls DMSO and tryptophan. As seen in FIGS. 33B and 33C, data precluded $K_i$ determination (i.e., $K_i$>1000 μM) which indicated no binding for these negative controls. Sigmoidal binding curves illustrated in FIGS. 33D, 33E, 33F, and 33G reveal data permitting $K_i$ determinations for the positive controls: serotonin, fluoxetine, vortioxetine and MDMA respectively. These data reveal $5\text{-HT}_{1A}$ receptor binding for these positive controls (i.e., $K_i$<1000 μM) at indicated ligand concentrations. Similarly, data in FIG. 33H indicates binding to the $5\text{-HT}_{1A}$ receptor of the compound with formula (XV). Resulting $K_i$ data for controls and test compounds in $5\text{-HT}_{1A}$ receptor binding assays is summarized in Table 1.

$5\text{-HT}_{2A}$ receptor.

Figure 34A:
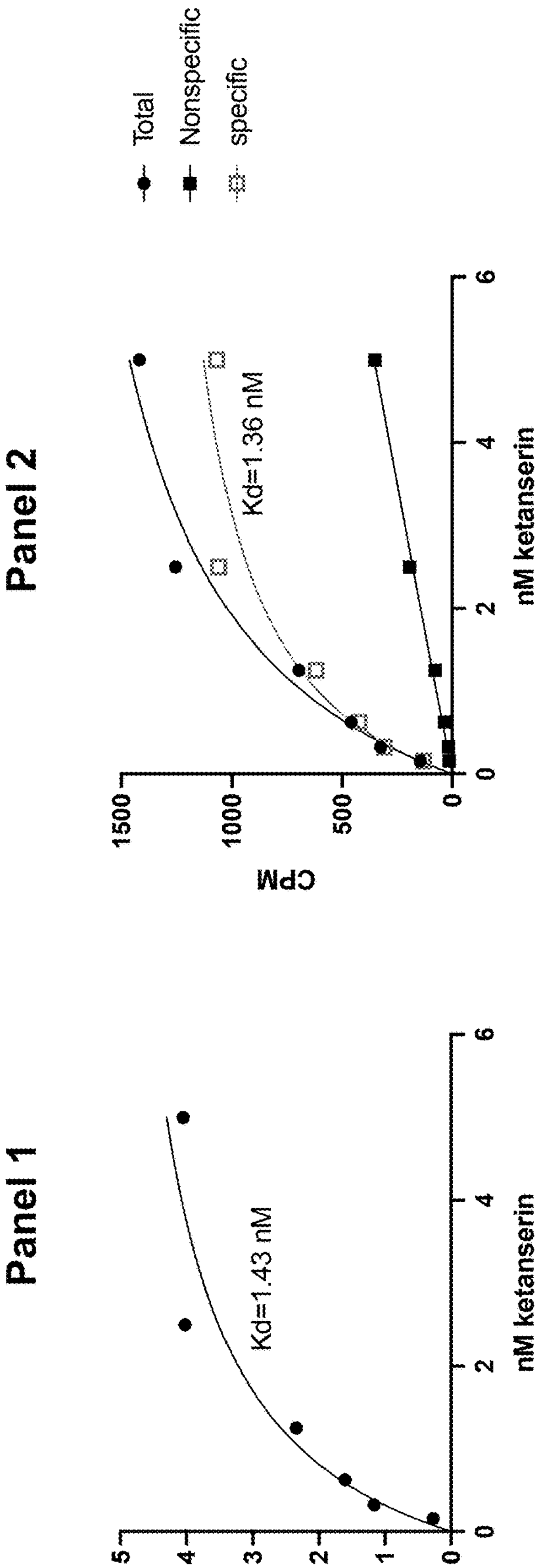
FIGS. 34A, 34B, 34C, 34D, and 34E depict various graphs representing certain experimental results, notably graphs obtained in the performance of experimental assays to evaluate the pharmaceutical efficacy of an example compound having chemical formula (XV), notably a radiolabelled ligand competition assay at the 5-$HT_{2A}$ receptor using radiolabeled [$^3$H-ketanserin](binding curves) (FIG. 34A); a 5-$HT_{2A}$ receptor competition assay using psilocin (positive control) (FIG. 34B); a 5-$HT_{2A}$ receptor competition assay using tryptophan (negative control) (FIG. 34C); a 5-$HT_{2A}$ receptor competition assay using MDMA (positive control) (FIG. 34D), and; a 5-$HT_{2A}$ receptor competition assay using the compound with formula (XV) (FIG. 34E).
Figure 34B:
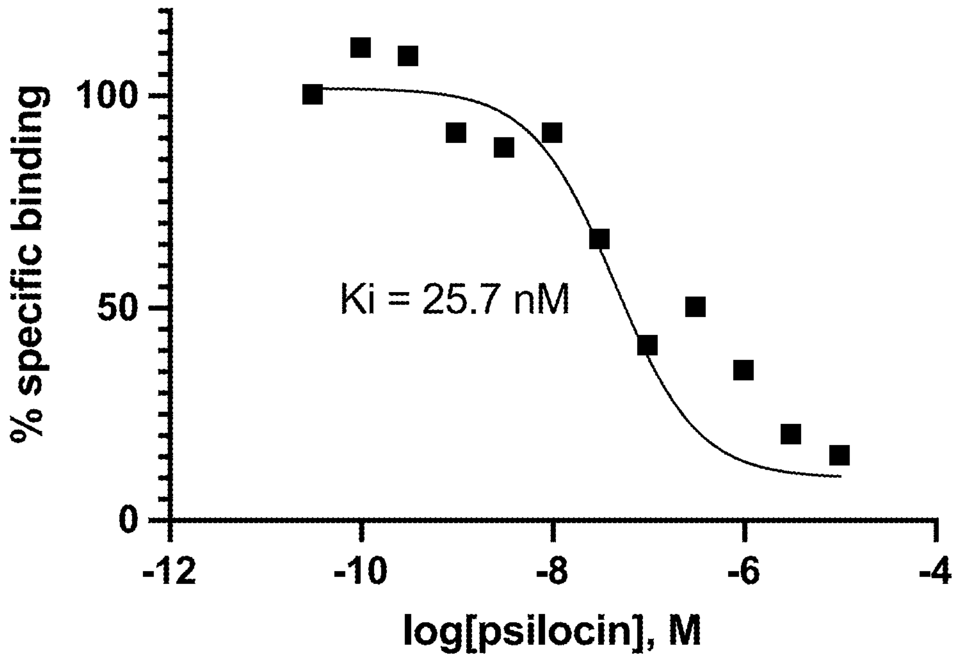
Figure 34C:
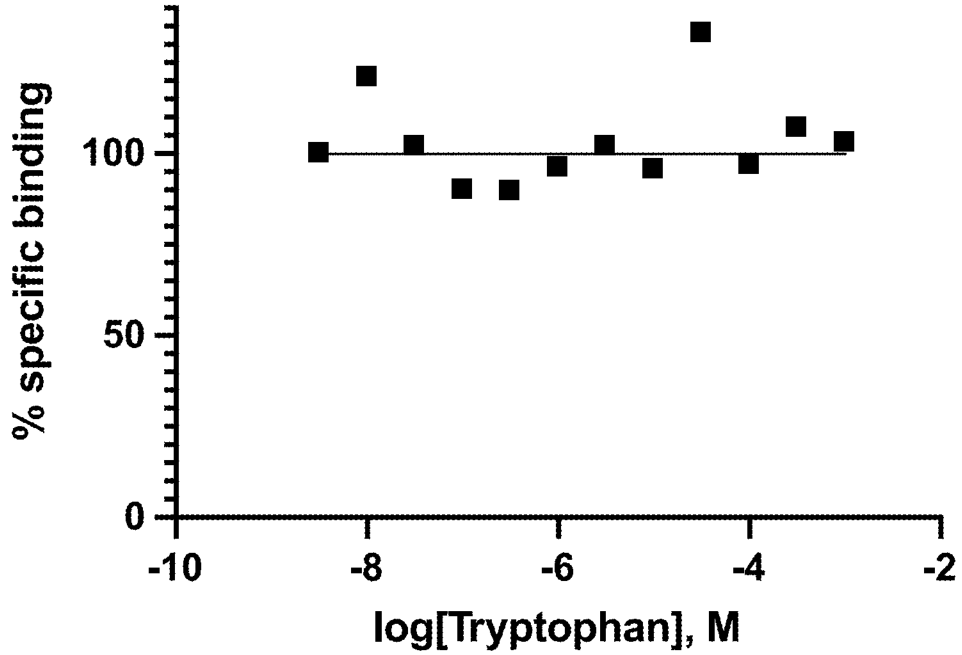
Figure 34D:
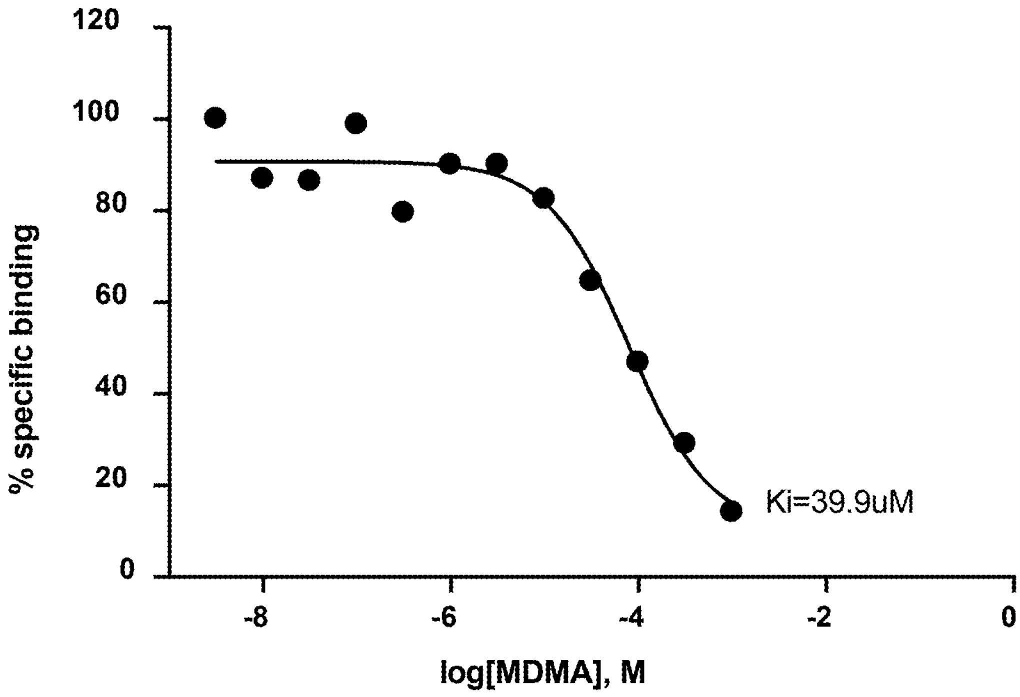
Figure 34E:
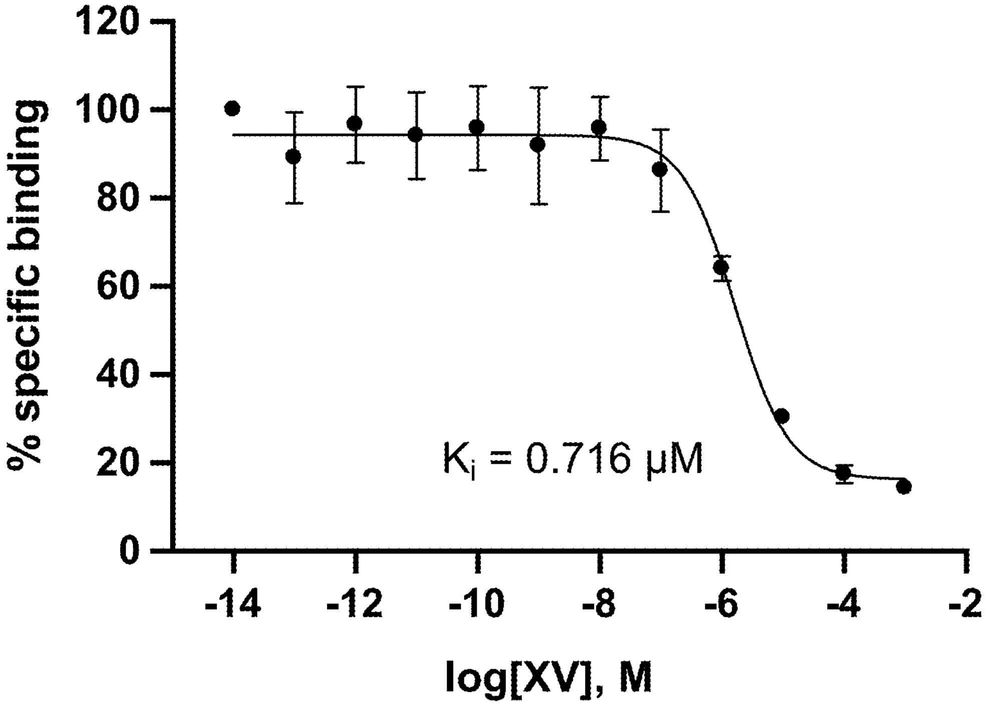

Competition assays were performed as for $5\text{-HT}_{1A}$ assays with the following differences. SPA beads (RPNQ0010), [$^3$H]ketanserin (NET1233025UC), and membranes containing $5\text{-HT}_{2A}$ (ES-313-M400UA) were from PerkinElmer. After pre-coupling, the beads and membrane were aliquoted in an isoplate-96 microplate with increasing amounts of [$^3$H]ketanserin (0.1525 nM to 5 nM). Determination of non-specific binding was carried out in the presence of 20 mM of spiperone (S7395-250MG, Sigma-Aldrich). Equilibrium binding constant for ketanserin ($K_d$) was determined from saturation binding curves using the 'one-site saturation binding analysis' method in GraphPad PRISM software (Version 9.2.0). Competition binding assays were performed using fixed (1 nM) [$^3$H]ketanserin and different concentrations of unlabeled test compounds (3 nM to 1 mM) similar to the saturation binding assay. FIG. 34A illustrates data in support of overall $K_D$ determination for ketanserin (Panel 1), in addition to the $K_D$ owed to specific binding (Panel 2). FIG. 34B illustrates data obtained for psilocin and supports binding at the $5\text{-HT}_{2A}$ receptor. Psilocin is a well-established binder at the $5\text{-HT}_{2A}$ receptor and thus served as a positive control (Ray, 2010, PLoS ONE 5:e9019). FIG. 34C illustrates data obtained for tryptophan and supports a lack of binding at the $5\text{-HT}_{2A}$ receptor (i.e., $K_i$>1000 μM). Notably, tryptophan has no known activity at the $5\text{-HT}_{2A}$ receptor and thus served as a negative control. FIG. 34D reveals data for MDMA and the resulting $K_i$ value (i.e., <1000 μM) reveals binding at the $5\text{-HT}_{2A}$ receptor at the indicated concentrations. MDMA was used as a positive control owing to its established moderate $5\text{-HT}_{2A}$ receptor binding activity (Simmler et al., 2013, British J. Pharmacol. 168: 458). Data in FIG. 34E indicates binding to the $5\text{-HT}_{2A}$ receptor of the compound with formula (XV). Resulting $K_i$ data for controls and test compounds in the $5\text{-HT}_{2A}$ receptor binding assay are summarized in Table 2.

TABLE 1

Data summary for the $5\text{-HT}_{1A}$ receptor radioligand competition assay.

| Molecule | $5\text{-HT}_{1A}$, $K_i$ (μM) |
|---|---|
| DMSO | >1000 |
| tryptophan | >1000 |
| serotonin | 0.0025 |
| fluoxetine | 0.306 |
| vortioxetine | 0.0043 |
| MDMA | 11 |
| (XV) | 1.83 |
| (XII) | 20.8 |
| (XVIII) | 18.1 |

Abbreviations: DMSO, dimethylsulfoxide; MDMA, 3,4-methylenedioxymethamphetamine.

TABLE 2

Data summary for the $5\text{-HT}_{2A}$ receptor radioligand competition assay.

| Molecule | $5\text{-HT}_{2A}$, $K_i$ (μM) |
|---|---|
| DMSO | >1000 |
| tryptophan | >1000 |
| psilocin | 0.0257 |
| MDMA | 39.9 |
| DMT | 1.03 |
| 5-MeO-DMT | 0.18 |
| 5-Br-DMT | 0.36 |
| 6-F-DET | 0.35 |
| TBG | 0.80 |
| (XV) | 0.72 |
| (XII) | 23.7 |
| (XVIII) | 6.13 |
| (V) | 15 |
| (VI) | 12 |
| (VII) | 63.9 |
| (VIII | 10.9 |
| (IX) | 14.2 |
| (X) | 7.8 |
| (XI) | 0.71 |
| (XIII) | 2.96 |
| (XIV) | 3.06 |
| (XVI) | 6.19 |
| (XVII) | 8.34 |
| (XX) | 25.6 |
| (XXIII) | 12.5 |
| (XXVII) | 5.38 |

Abbreviations: DMSO, dimethylsulfoxide; DMT, dimethyltryptamine; 5-MeO-DMT, 5-methoxy-dimethyltryptamine; 5-Br-DMT, 5-bromo-dimethyltryptamine; 6-F-DET, 6-fluoro-diethyltryptamine; MDMA, 3,4-methylenedioxymethamphetamine; TBG, tabernanthalog. It is noted that 5-Br-DMT (Dong et al., 2021, *Cell* 184:2779-2792; Dong et al., 2022, WO2022081631A1), 6-F-DET (Kalir et al., 1963, *J. Med. Chem.* 6:716-719; Blair et al., 2000), and TBG (Cameron et al., 2021, *Nature* 589:474-479) are considered to be non-hallucinogenic.

5-HT Transporter (SERT) Radioligand Competition Assay.

Figure 35A:
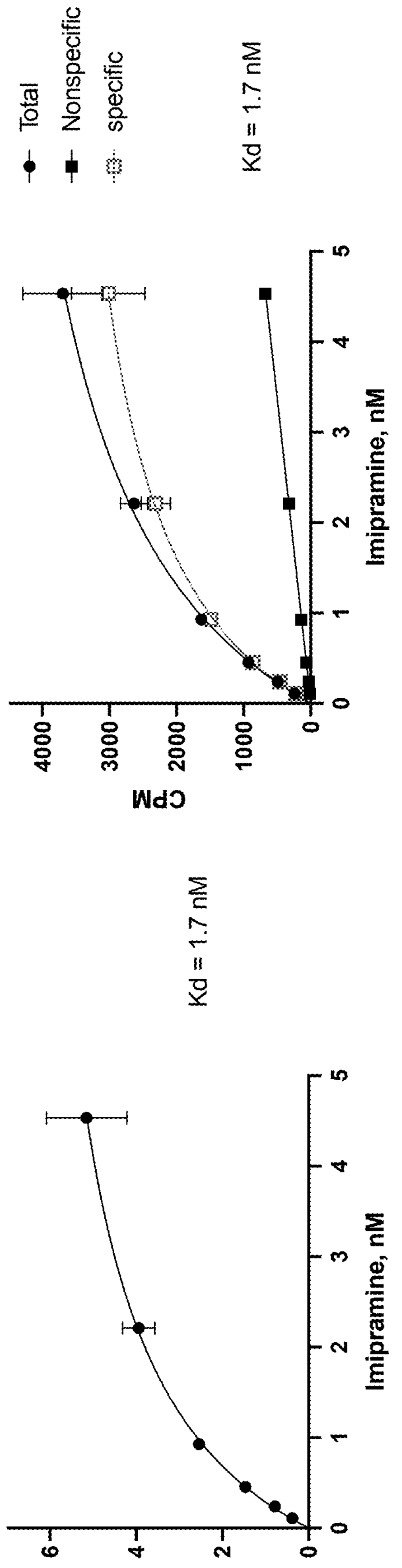
FIGS. 35A, 35B, 35C, 35D, 35E, 35F, 35G, 35H, and 35I depict various graphs representing certain experimental results, notably graphs obtained in the performance of experimental assays to evaluate the pharmaceutical efficacy of an example compound having chemical formula (XV), notably a serotonin transporter (SERT) assay, using imipramine binding for overall $K_D$ determination and specific binding results for imipramine (binding curves) (FIG. 35A); a SERT competition assay using serotonin (positive control) (FIG. 35B); a SERT competition assay using DMSO (negative control) (FIG. 35C); a SERT competition assay using tryptophan (negative control) (FIG. 35D); a SERT competition assay using 2C-B (positive control) (FIG. 35E); a SERT competition assay using MDMA (positive control) (FIG. 35F); a SERT competition assay using fluoxetine (positive control) (FIG. 35G) a SERT competition assay using vortioxetine (positive control) (FIG. 35H); and a SERT competition assay using the compound with formula (XV) (FIG. 35I).
Figure 35B:
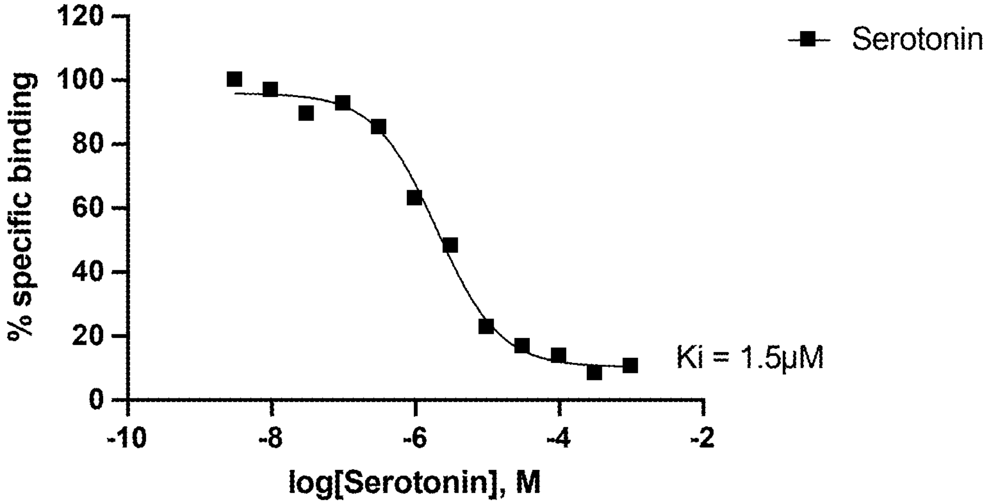
Figure 35C:
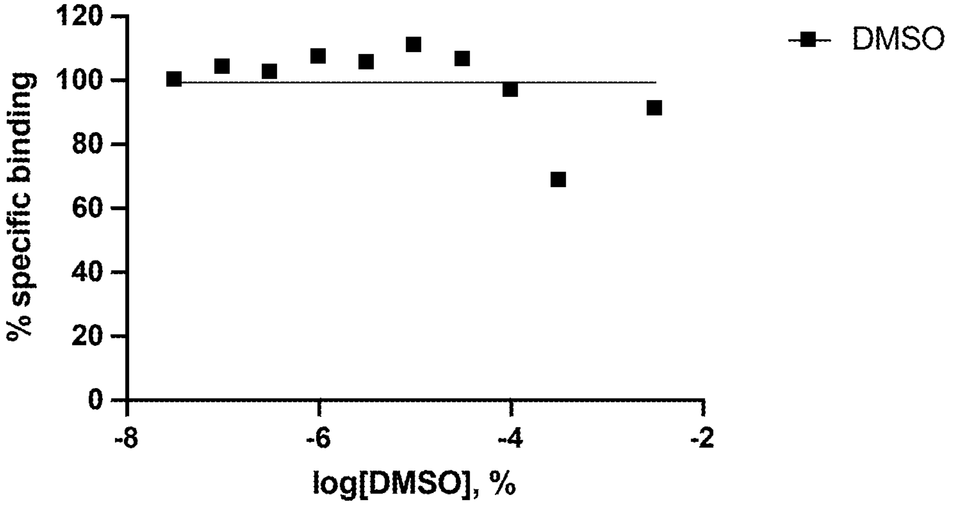
Figure 35D:
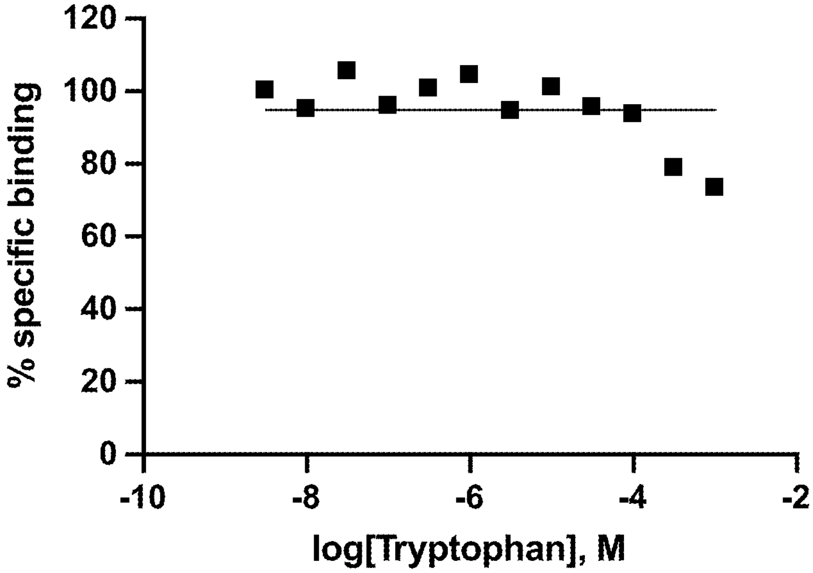
Figure 35E:
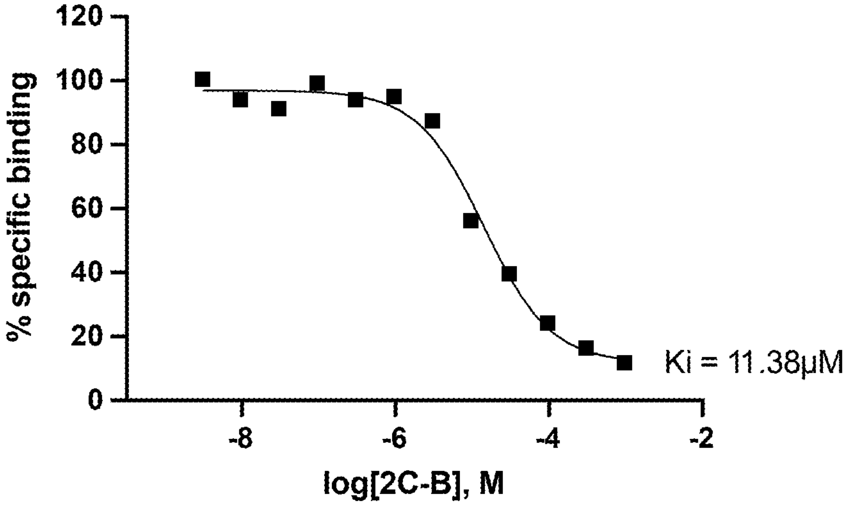
Figure 35F:
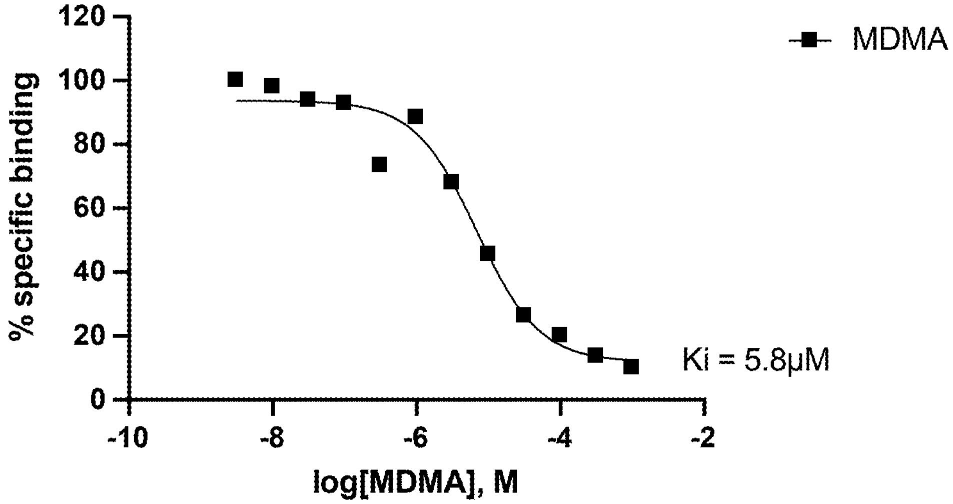
Figure 35G:
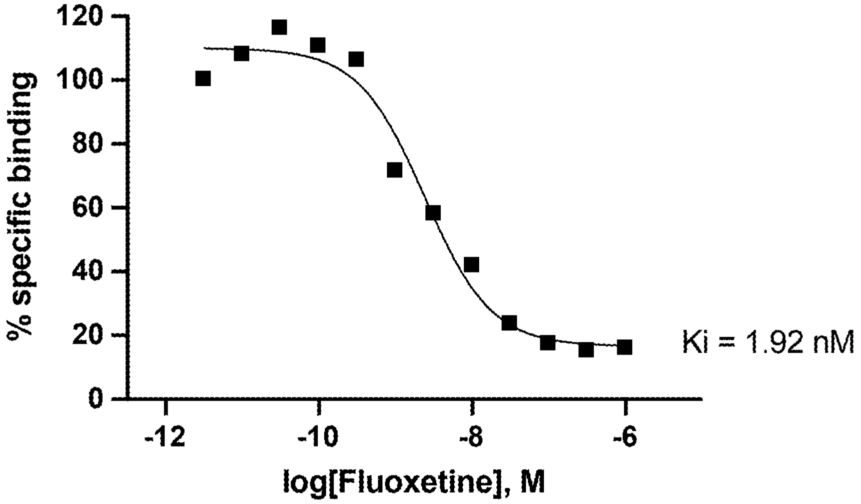
Figure 35H:
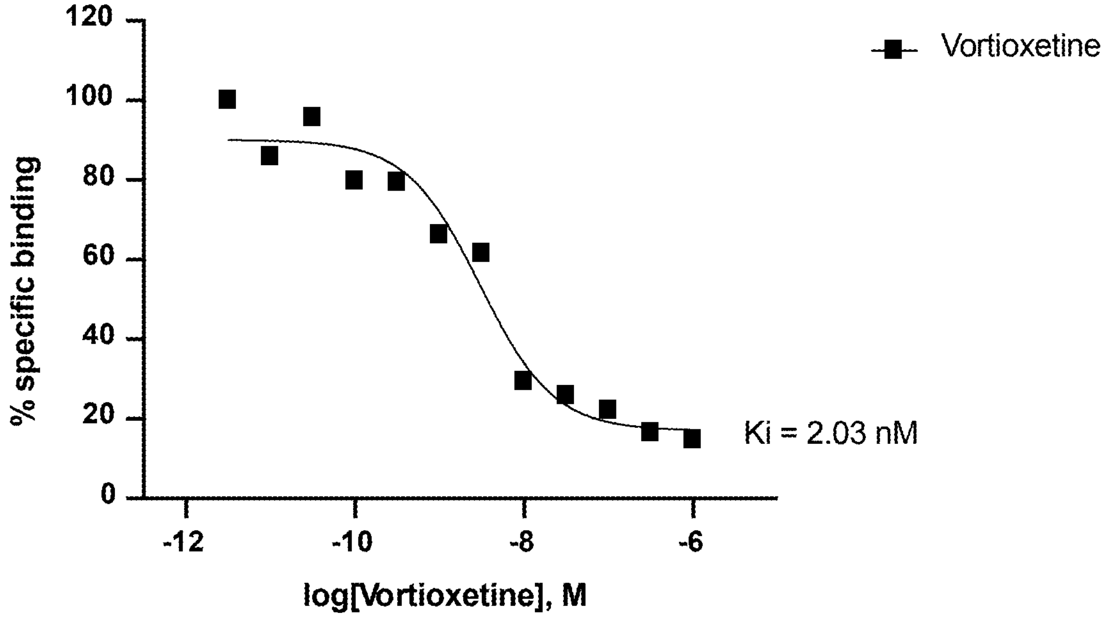
Figure 35I:
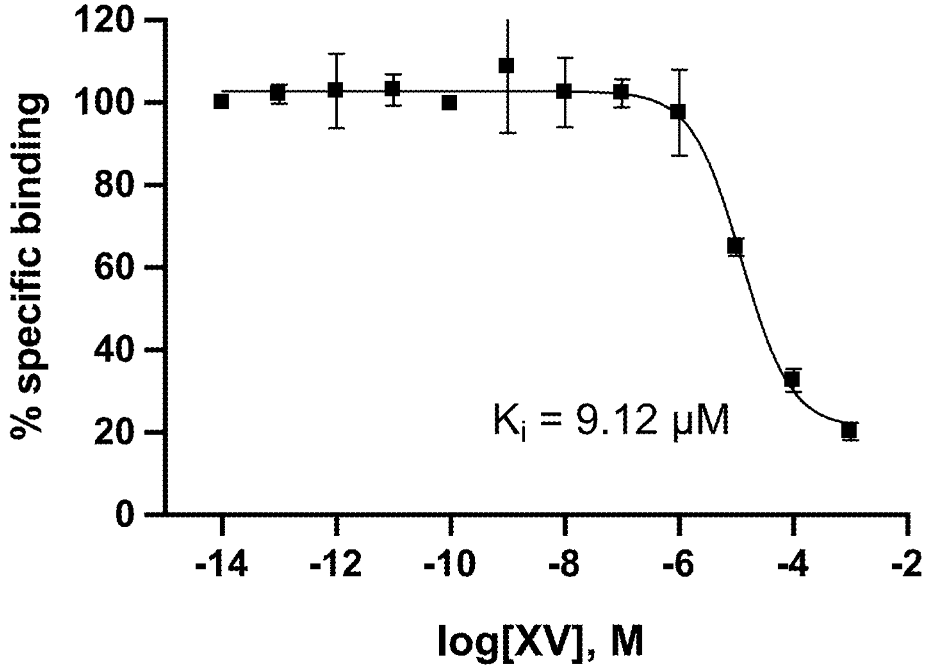

The serotonin transporter (SERT) regulates neurotransmission through the reuptake of serotonin from extra-neuronal regions such as synapses, and its function is closely linked to mental health and neurological homeostasis. SERT is a membrane-localized protein with several binding sites, including one for the cognate substrate serotonin (primary substrate binding site) and an additional allosteric binding site generally targeted by ligands acting as antidepressants, anxiolytics, or other drugs used in the treatment of neuropathologies (Cheng and Bahar, 2019, Nature Structural and Molecular Biology 26:545-556). Ligands acting as allosteric modulators of SERT include SSRIs (selective serotonin reuptake inhibitors) which diminish the ability of SERT to transport serotonin, in effect increasing serotonin presence in synapses. However, other non-SSRI pharmaceuticals such as vortioxetine, which bind tightly to SERT, also act as reuptake inhibitors (Gonda et al., 2019, Expert Opinion on Drug Discovery 14: 81-89). In essence, an ability to bind SERT is viewed as a marker of drug candidate potential, and thus SERT binding assays have become routine screening procedures in the field of drug discovery. Psychotropics such as substituted tryptamines (Kozell et al., 2023, Journal of Pharmacology and Experimental Therapeutics 385:62-75), ibogaine (Singh et al., 2023, Cell 186:2160-2175), and MDMA (Islas and Scior, 2022, Molecules 27: 2977-2995) are known to bind SERT and modulate serotonin reuptake. A commonly applied SERT binding assay involves competition binding assays employing radiolabelled ligands. To assay binding potential of test compounds, the following procedure was adapted from Bulling et al., (2009, Journal of Biological Chemistry 287:18524-18534). SPA beads (RPNQ0011), imipramine hydrochloride [benzene ring—$^3$H(N)](NET576250UC), membranes containing human serotonin transporter (RBHSTM400UA), and isoplate-96 microplate (6005040) were all purchased from PerkinElmer. Radioactive binding assays were carried out using the Scintillation Proximity Assay (SPA). For saturation binding assay, mixtures of 9 μg of membrane containing human SERT was pre-coupled to 1 mg of SPA beads at room temperature in a tube rotator for 1 hour in binding buffer (50 mM Tris-HCl pH7.4, 120 mM NaCl, 5 mM KCl, 1 mM ascorbic acid, 10 μM pargyline HCl). After pre-coupling, the beads and membrane were aliquoted in an isoplate-96 microplate with increasing amounts of imipramine hydrochloride [benzene ring—$^3$H(N)](0.1525 nM to 5 nM) and incubated for two hours at room temperature in the dark with shaking. After incubation, the samples are read on a MicroBeta 2 Microplate Counter. Non-specific binding was carried out in the presence of 200 μM of clomipramine hydrochloride (C7291-1G, Sigma). Equilibrium binding constant for imipramine ($K_D$) was determined from saturation binding curve using one-site saturation binding analysis from GraphPad PRISM software (Version 9.2.0). All test compounds were dissolved to 100 mM in DMSO and dilutions were carried out in assay buffer. Competition binding assays were performed using 1 nM imipramine and different concentrations of vehicle, or 'DMSO' (up to 1% DMSO, which is the highest used in competition experiments), tryptophan (3 nM to 1 mM), or unlabelled test compounds (3 nM to 1 mM) similar to the saturation binding assay. $K_i$ values were calculated from the competition displacement data using the competitive binding analysis from GraphPad PRISM software. Serotonin is the cognate ligand for SERT and was thus used as a positive control. Tryptophan has no known ability to bind SERT and was thus included as a negative control. Vehicle (DMSO) without drug was used as a negative control. MDMA and 2C-B are known to bind SERT (Zwartsen et al., 2017, Toxicology in Vitro 45:60-71) and were used as positive controls. Fluoxetine and vortioxetine are commonly prescribed mental health drugs known to tightly bind SERT and were used as positive controls. FIG. 35A illustrates overall $K_D$ determination and specific binding results for imipramine. FIGS. 35B and 35C illustrate binding curves for serotonin and vehicle (DMSO), which reveal binding and no binding, respectively. The binding curve for the negative control tryptophan (FIG. 35D) reveals no binding to SERT, and no $K_i$ determination was possible (i.e., $K_i$>1000 μM). The binding curves of FIGS. 35E and 35F demonstrate that the respective ligands 2C-B, and MDMA each bind SERT to varying degrees (i.e., $K_i$<1000 μM). The binding curves of FIGS. 35G and 35H demonstrate very tight interaction of drugs fluoxetine and vortioxetine to SERT, respectively. The binding curve of FIG. 35I demonstrates that compound with formula (XV) binds SERT. The $K_i$ values of all controls, calibrators, and test compounds are summarized in Table 3.

TABLE 3

Data summary for SERT radioligand binding competition assays.

| Molecule | SERT, $K_i$ (μM) |
|---|---|
| DMSO | >1000 |
| tryptophan | >1000 |
| serotonin | 1.5 |
| 2C-B | 11.38 |
| MDMA | 5.8 |
| fluoxetine | 0.00192 |
| vortioxetine | 0.00203 |
| DMT | 2.58 |
| (XV) | 9.13 |
| (XII) | 1.68 |
| (XVIII) | 39.2 |

Functional Cell-Based Assays for Determining 5-$HT_{2a}$ Receptor Engagement.

A variety of 5-$HT_{2A}$ receptor engagement modes have been correlated with positive outcomes in the treatment of neurological disorders. While agonism is associated with a host of favourable effects, antagonizing the 5-$HT_{2A}$ receptor is also an attractive pharmacological approach. For example, antagonism is known to alleviate both dyskinesisa and psychosis in Parkinson's Disorder and holds promise for other psychiatric diseases (Mestre et al., 2013, Expert Opin. Investig. Drugs 22:411-421). Similarly positive outcomes are noted for inverse agonists (Cummings et al., 2014, Lancet, 383:533-540; Roberts, 2006, Curr. Opin. Invest. Drugs 7:653-660). It is well-established that drugs acting at a single receptor subtype can simultaneously act as agonists, antagonists, or inverse agonists depending on which receptor-coupled response is activated (Berg and Clarke, 2018, Int. J. Neuropsychopharmacol 21:962-977). Herein, functional, cell-based assays were conducted to determine (1) agonist potency and efficacy of drugs at the 5-$HT_{2A}$ receptor (agonist mode), and (2) antagonist potency at the 5-$HT_{2A}$ receptor (antagonist mode).

Figure 36A:
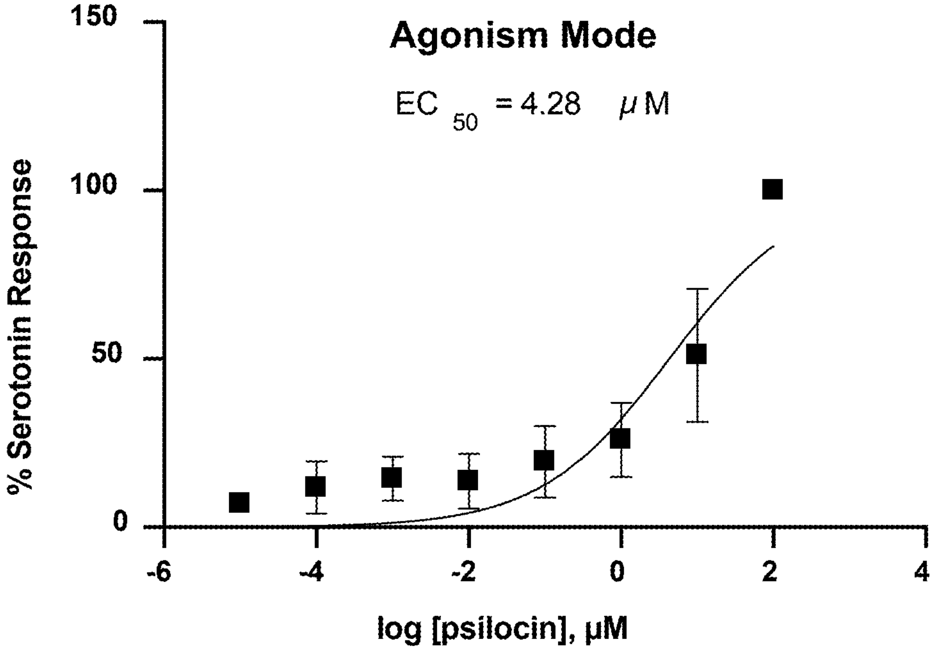
FIGS. 36A, 36B, 36C, 36D, 36E, and 36F depict various graphs representing certain experimental results, notably graphs obtained in the performance of experimental assays to evaluate the pharmaceutical efficacy of an example compound having chemical formula (XV), notably a 5-$HT_{2A}$ functional (cellular) assay to assess: agonist potency and intrinsic efficacy of psilocin at the 5-$HT_{2A}$ receptor (FIG. 36A); agonist potency and intrinsic efficacy DMT at the 5-$HT_{2A}$ receptor (FIG. 36B); agonist potency and intrinsic efficacy compound (XV) at the 5-$HT_{2A}$ receptor (FIG. 36C); antagonist potency and abilities to dampen serotonin efficacy of psilocin at the 5-$HT_{2A}$ receptor (FIG. 36D); antagonist potency and abilities to dampen serotonin efficacy of DMT at the 5-$HT_{2A}$ receptor (FIG. 36E); and antagonist potency and abilities to dampen serotonin efficacy of compound (XV) at the 5-$HT_{2A}$ receptor (FIG. 36F).
Figure 36B:
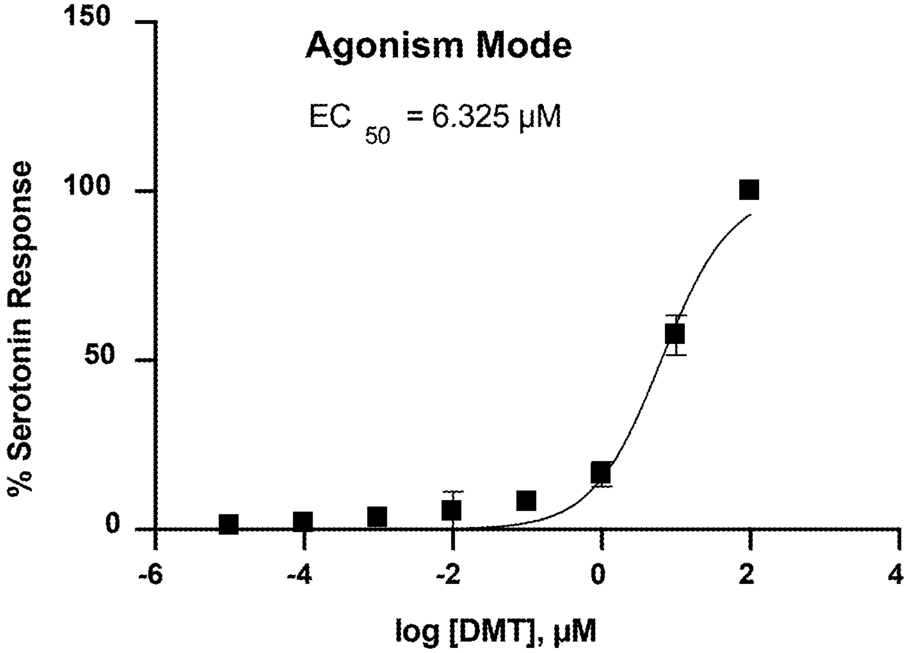
Figure 36C:
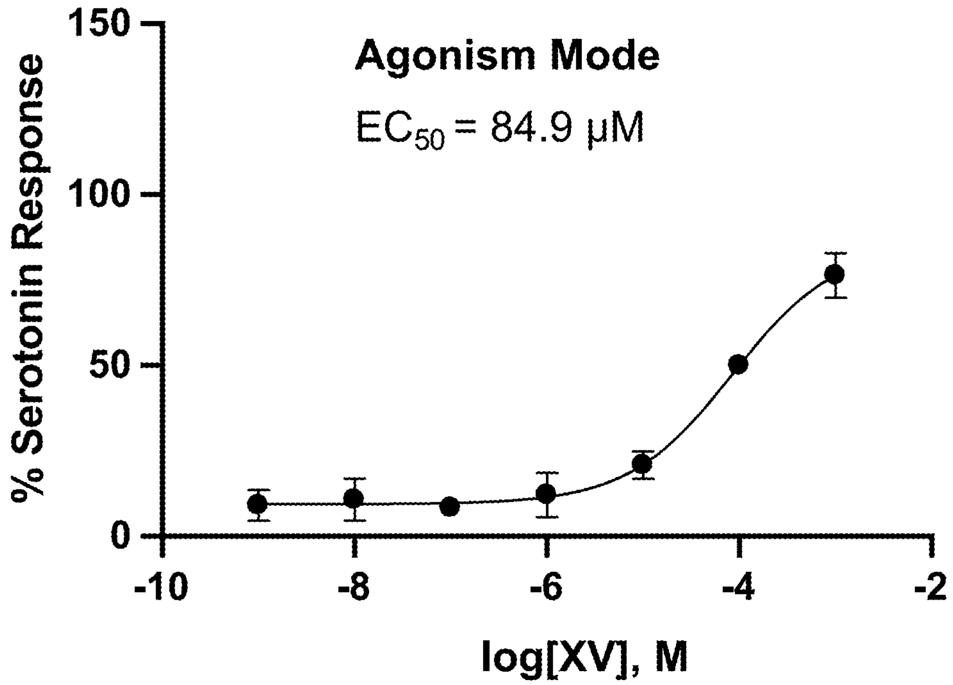

Agonism Mode:

The Chinese hamster ovary (CHO)-derived cell line, CHO-K1/5-$HT_{2A}$ (GenScript, genscript.com) stably transformed to express 5-$HT_{2A}$ serotonin receptor, was used to evaluate specific agonist-mediated stimulation of 5-$HT_{2A}$ signal transduction. Stimulation of 5-$HT_{2A}$ coupled to the Gq family proteins leads to activation of the phospholipase C (PLC) pathway, ultimately resulting in the accumulation of cytosolic calcium (Cussac et al., Europ. J. Pharmacol., 2008, 594 (1-3), 32-38). Hence, 5-$HT_{2A}$ activation was assessed quantitatively by measuring increased cytosolic free calcium levels using the Fluo-8 Calcium Flux Assay Kit (Abcam, abcam.com). All cells were grown and maintained as a monolayer in Ham's F12 nutrient mix supplemented with 10% fetal bovine serum (FBS) and 400 μg/mL geneticin (G418) all from ThermoFisher Scientific and used according to the manufacturer's instructions. Cells were cultured and incubated at 37° C. in a humidified oxygen atmosphere with 5% $CO_2$. To evaluate the activation of $5\text{-HT}_{2A}$ signal transduction, cells were first seeded in tissue culture-treated, black-walled, clear-bottom 96-well plates (Thermo Scientific) at a density of 40,000 cells/well in 100 pl Ham's F12 nutrient mix supplemented with 2% FBS. Cells were cultured for 24 h in a humidified incubator at 37° C. and 5% $CO_2$. Cells were then loaded with Fluo-8 calcium indicator dye for 1 h at 37° C. and an additional 30 min at room temperature as per the manufacturer's protocol. After incubation cells were stimulated with test compounds, prepared in titration beginning at 1 mM and dissolved in serum-free medium. Kinetic increases in intracellular calcium levels were measured immediately after addition of test compounds every 6.4 s for a total of 3 min using the FlexStation 3 multimode microplate reader and SoftMax Pro 7.1 analysis software (Molecular Devices, moleculardevices.com). Maximum fluorescence reading (excitation, 485 nm; emission, 530 nm) minus baseline reading from each well was normalized relative to the endogenous ligand, serotonin to determine percent stimulation for each test compound. $EC_{50}$ values were calculated from the normalized data from GraphPad PRISM software. Psilocin and DMT were used as positive controls for this assay, as both drugs are known to engage as agonists at the 5-HT2x receptor (Wallach et al., 2023, Nature Comm. 14 doi.org/10.1038/s41467-023-44016-1. Data in FIGS. 36A and 36B. reveal agonism at the $5\text{-HT}_{2A}$ receptor for positive controls psilocin and DMT, respectively. Similarly, data in FIG. 36C reveals agonism at the $5\text{-HT}_{2A}$ receptor for compound with formula (XV).

Figure 36D:
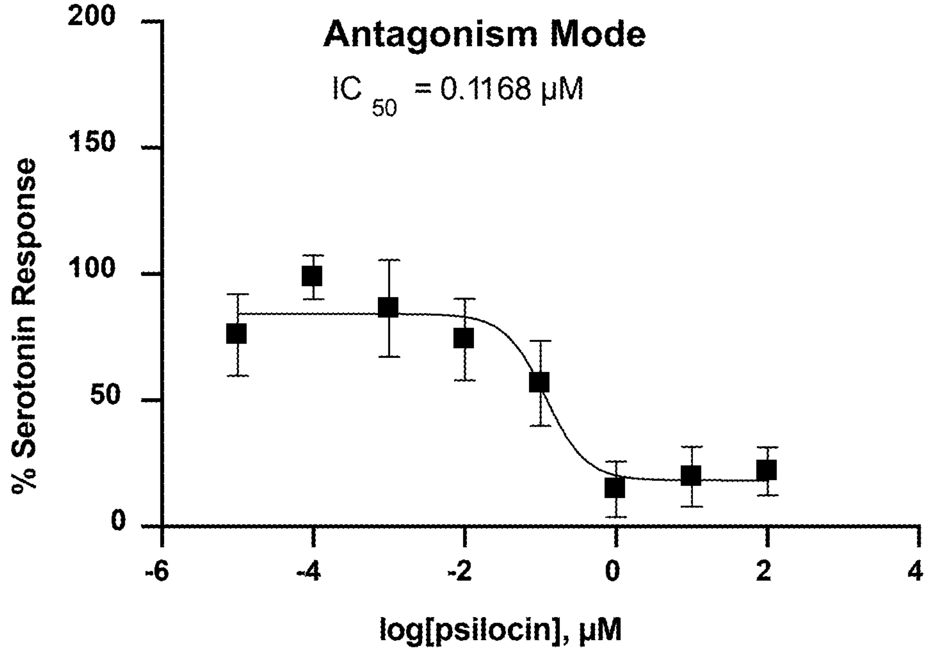
Figure 36E:
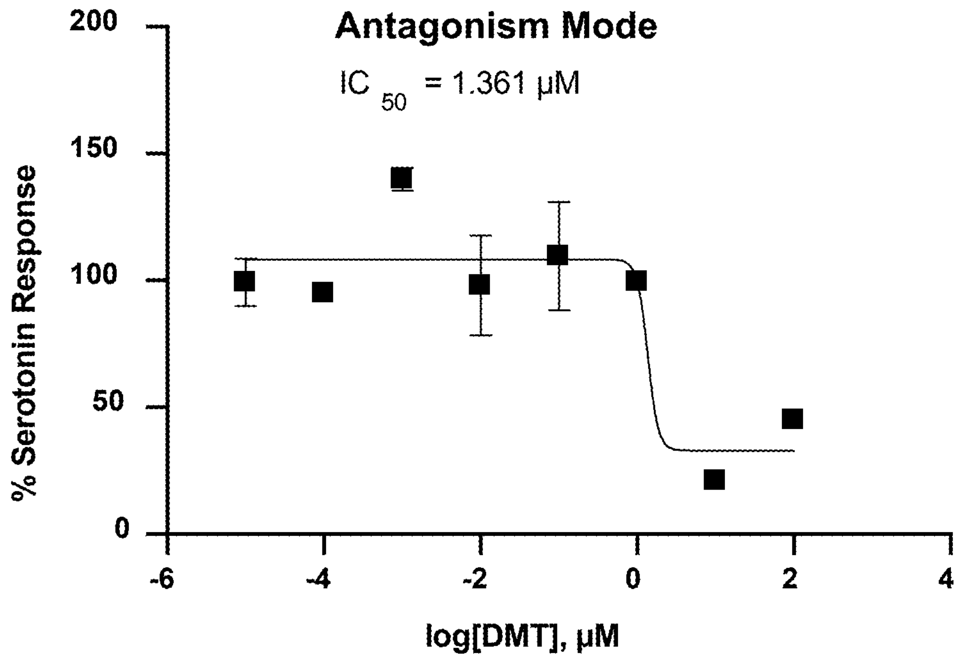
Figure 36F:
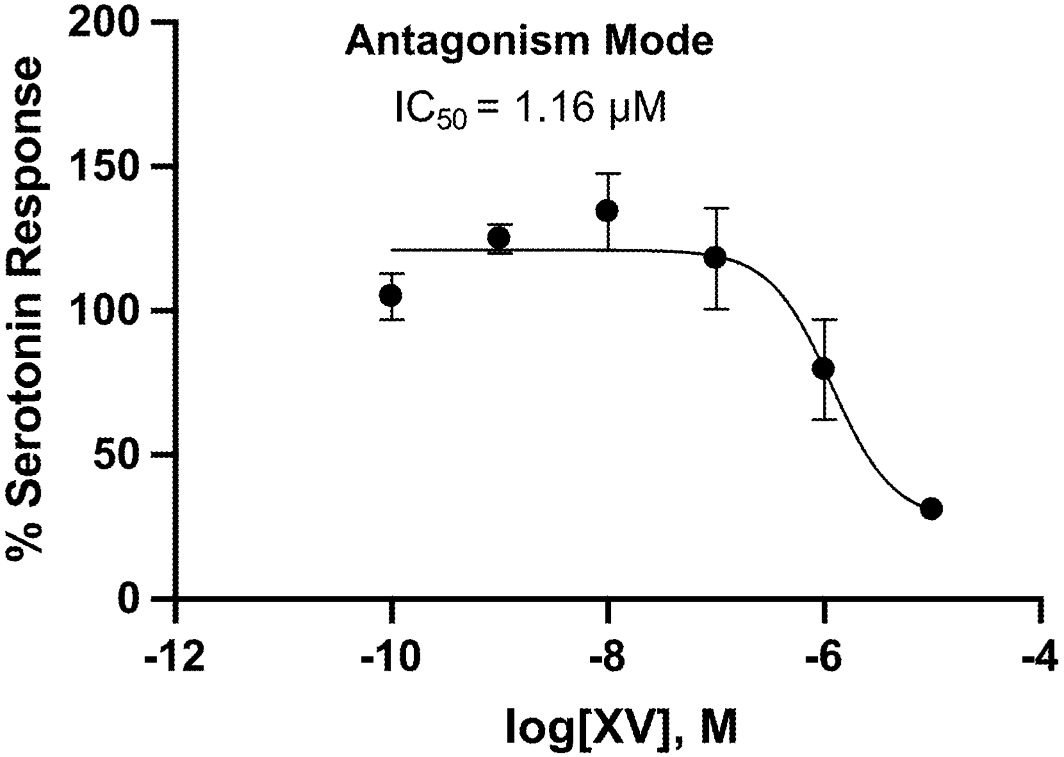

Antagonism Mode:

The Chinese hamster ovary (CHO)-derived cell line CHO-K1/$5\text{-HT}_{2A}$ (GenScript, genscript.com), stably transformed to express the $5\text{-HT}_{2A}$ serotonin receptor, was used to evaluate inhibition of serotonin-mediated $5\text{-HT}_{2A}$ signal transduction through antagonist activity of test ligands. Stimulation of $5\text{-HT}_{2A}$ coupled to the Gq family proteins leads to activation of the phospholipase C (PLC) pathway, ultimately resulting in the accumulation of cytosolic calcium (Cussac et al., Europ. J. Pharmacol., 2008, 594 (1-3), 32-38). Hence, $5\text{-HT}_{2A}$ activation (and similarly, inhibition) was assessed quantitatively by measuring increased cytosolic free calcium levels using the Fluo-8 Calcium Flux Assay Kit (Abcam, abcam.com). All cells were grown and maintained as a monolayer in Ham's F12 nutrient mix supplemented with 10% fetal bovine serum (FBS) and 400 μg/mL geneticin (G418) all from ThermoFisher Scientific and used according to the manufacturer's instructions. Cells were cultured and incubated at 37° C. in a humidified oxygen atmosphere with 5% $CO_2$. To evaluate the degree of $5\text{-HT}_{2A}$ signal transduction, cells were first seeded in tissue culture-treated, black-walled, clear-bottom 96-well plates (Thermo Scientific) at a density of 40,000 cells/well in 100 μl Ham's F12 nutrient mix supplemented with 2% FBS. Cells were cultured for 24 h in a humidified incubator at 37° C. and 5% $CO_2$. Cells were then loaded with Fluo-8 calcium indicator dye for 1 h at 37° C. and an additional 30 min at room temperature as per the manufacturer's protocol. After incubation cells were treated with serotonin+test compound. The test compounds were prepared in titration beginning at 100 μM and dissolved in serum-free medium with 100 nM serotonin (held constant). Kinetic increases in intracellular calcium levels were measured immediately after addition of ligands every 6.4 s for a total of 3 min using the FlexStation 3 multimode microplate reader and SoftMax Pro 7.1 analysis software (Molecular Devices, moleculardevices.com). Maximum fluorescence reading (excitation, 485 nm; emission, 530 nm) minus baseline reading from each well was normalized relative to the endogenous ligand (100 nM serotonin) to determine percent stimulation for each replicate. $IC_{50}$ values were calculated from the normalized data from GraphPad PRISM software. DMT was used as a positive control for this assay, as it is known to engage as an antagonist at the $5\text{-HT}_{2A}$ receptor (Deliganis et al., 1990, Biochemical Pharmacol. 41: 1739-1744). Psilocin was included in the assay for comparison purposes owing to its structural similarity to DMT. Data in FIGS. 36D and 36E reveal antagonism at the $5\text{-HT}_{2A}$ receptor for the comparison molecule psilocin and the positive control DMT, respectively. Similarly, data in FIG. 36F reveals antagonism at the $5\text{-HT}_{2A}$ receptor for compound with formula (XV).

Neuroplastogenicity Assays.

Classic psychedelics such as psilocybin and DMT show potential to treat anxiety and depression, and it has been theorized that such long-term improvements arise because these drugs rapidly and lastingly stimulate neuroplasticity (Calder and Hasler, 2023, Neuropsychopharmacol. 48:104-112). Thus, it was of interest to determine the potential of new compounds as neuroplastogens. Herein, we assess the capacity of various compounds to enhance neurite outgrowth in human model (NT2) neurons.

Human Model Neurons.

The acquisition and deployment of NT2 model neurons in neurite outgrowth assays has been demonstrated previously (Tenenge et al., 2011, Cell Mol. Neurobiol. 31:635-643; Roloff et al., 2015, PloS ONE 10:e0118536). Human NT2/D1 precursor cells were purchased from the American Type Culture Collection (ATCC, Manassas, VA, USA). Neuronal differentiation was carried out as previously described (Roloff et al., 2015, PloS ONE 10:e0118536) with minor modifications. Firstly, NT2/D1 cells were seeded in T-25 suspension culture flasks (REF #690190, Greiner bio-one, Germany). Each flask contains a minimum of $5\times10^6$ cells in 10 ml of DMEM/F12 supplemented with 10% fetal bovine serum (FBS), 1% penicillin and streptomycin and 10 μM retinoic acid (RA) medium to start neuronal differentiation. The cells were cultured for 3 days in free floating medium. At the end of the incubation cells were trypsinized and collected by centrifugation, mechanically dispersed, and counted. Counted cells were seeded along Poly D-Lysine (PDL) coated cover slips (12 mm; diameter round, Fisher Scientific; GG-12-PDL) containing a minimum of $0.1\times10^5$ cells in culture medium without RA. The next day culture medium was replaced with RA medium containing 2% of FBS. These cells cultured for 5 days and two days later, RA medium was changed.

Neurite Outgrowth Assay.

After cells had successfully attached and established along coverslips, the RA medium was replaced with new medium containing 2% FBS and one of the following: (1) test compound (1 or 10 μM), (2) RhoK (ROCK) inhibitor Y-27632 (1 μM) as a positive control (Dihydrochloride; Sigma-Aldrich) (Roloff et al., 2015, PloS ONE 10:e0118536); (3) DMT (1 or 10 μM) as a positive control (Calder and Hasler, 2023, Neuropsychopharmacol. 48:104-112), or (4) vehicle (0.1% DMSO) as a negative control. These cells were incubated for 48 hours under standard conditions (370C, 5% $CO_2$). The cells cultured along coverslips were collected after 48 hours of treatment. The coverslips washed with calcium chloride and magnesium chloride-free phosphate buffered saline (PBS) pH 7.4 (Gibco, #70011-044) and fixed in paraformaldehyde (PFA) 4% in PBS (#J61899, thermoscientific) for 15 min at room temperature (RT) and washed three times with 0.01% of Triton-X100 in PBS (PBST) to remove remaining PFA and to permeabilize the cells. Non-specific binding sites were blocked with 5% of Bovine Serum Albumin (BSA) solution (#9048-46-8, Millipore) in PBST for 60 minutes at RT. Rabbit monoclonal antibody β-III-tubulin (1:5,000, ab52623, Abcam) was applied overnight (O/N) at 4° C. Next day cells are washed three times in PBST, neurons were incubated with secondary antibody Donkey anti-rabbit IgG (H+L) Alexa Fluor™ Plus488 (1:5000 #A32790, Invitrogen) for 1 hour at RT. These coverslips were mounted on Gluoromount-G™, with 4'6-diamidino-2'henylindoldihydrochloride (DAPI) (#E141818, Invitrogen). The immunofluorescence images were analyzed using an Olympus VS110 slide scanner microscope.

Image and Statistical Analyses.

B-III-Tubulin immunofluorescence was quantified using ImageJ. Briefly, Corrected Total Cell Fluorescence (CTCF) was acquired for at least ~8-10 representative cells, where CTCF=Integrated Density−[Area of selected cell*Mean Fluorescence of background]. The CTCF values, referred to herein as 'signal intensities', were used to calculate overall means±SD for each treatment. One-Way ANOVA was used to compare treatments. Further, the mean of each treatment was compared with the mean of the control treatment (RA-differentiated cells treated with vehicle, 0.1% DMSO) using Dunnett's multiple comparison procedure. Results are reported with an α threshold of 0.05 (Cl 95%), with adjusted p-values indicated as follows: * p=0.05-0.01;  p=0.01-0.001; * p=0.001-0.0001; **** p<0.0001.

Figure 37A:
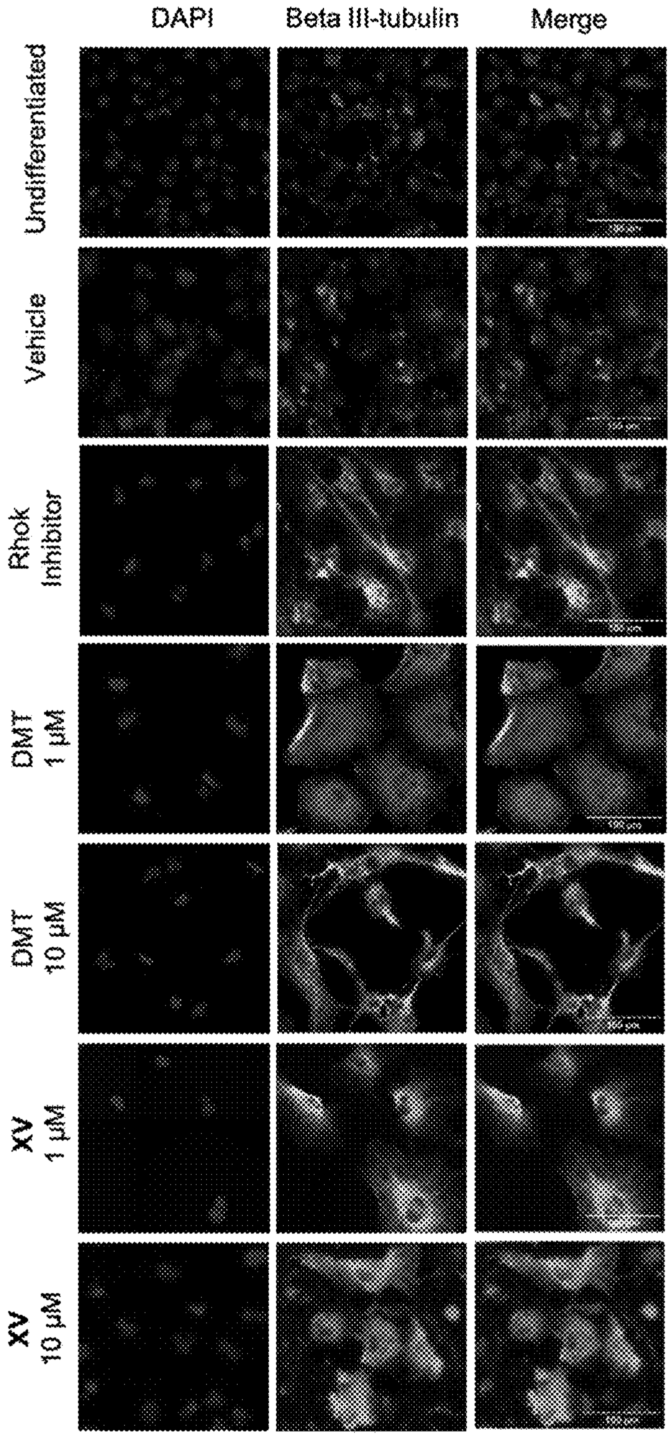
FIGS. 37A and 37B depict microscopical images (FIG. 37A) and a graph (FIG. 37B) obtained in the performance of experimental assays, notably a neuropathogenicity assays, to evaluate the pharmaceutical efficacy of an example compound having chemical formula (XV), notably microscopic images of neuronal cells treated with vehicle (0.1% DMSO), RhoK Inhibitor, DMT, or Compound (XV) (1 or 10 μM) for 48 h, wherein immunostaining was performed with beta-III-tubulin, wherein nuclei were visualized using DAPI as a counterstain, wherein NT2 precursor cells remained undifferentiated (marked 'Undifferentiated' in FIG. 37A) until application of retinoic acid (RA), and wherein scaling in all cases is identical (scale bar indicates 100 micrometers) (FIG. 37A); and notably a bar graph to quantify neuropathogenicity induced by compound (XV), wherein UD refers undifferentiated progenitor cells, wherein all other bars refer to differentiated neuronal cells (i.e., those treated with retinoic acid), wherein 'RhoK inhibitor' is an inhibitor of Rho kinase, which is a regulator of morphological neuroplasticity, wherein RhoK inhibitor and N,N-dimethyltryptamine (DMT) serve as positive controls, wherein the relative level of neuroplasticity was determined for Compound (XV) at 1 and 10 μM, wherein the results are reported with an α threshold of 0.05 (Cl 95%), with adjusted p-values indicated as follows: * p=0.05-0.01;  p=0.01-0.001; * p=0.001-0.0001; ** p<0.0001 (FIG. 37**B).
Figure 37B:
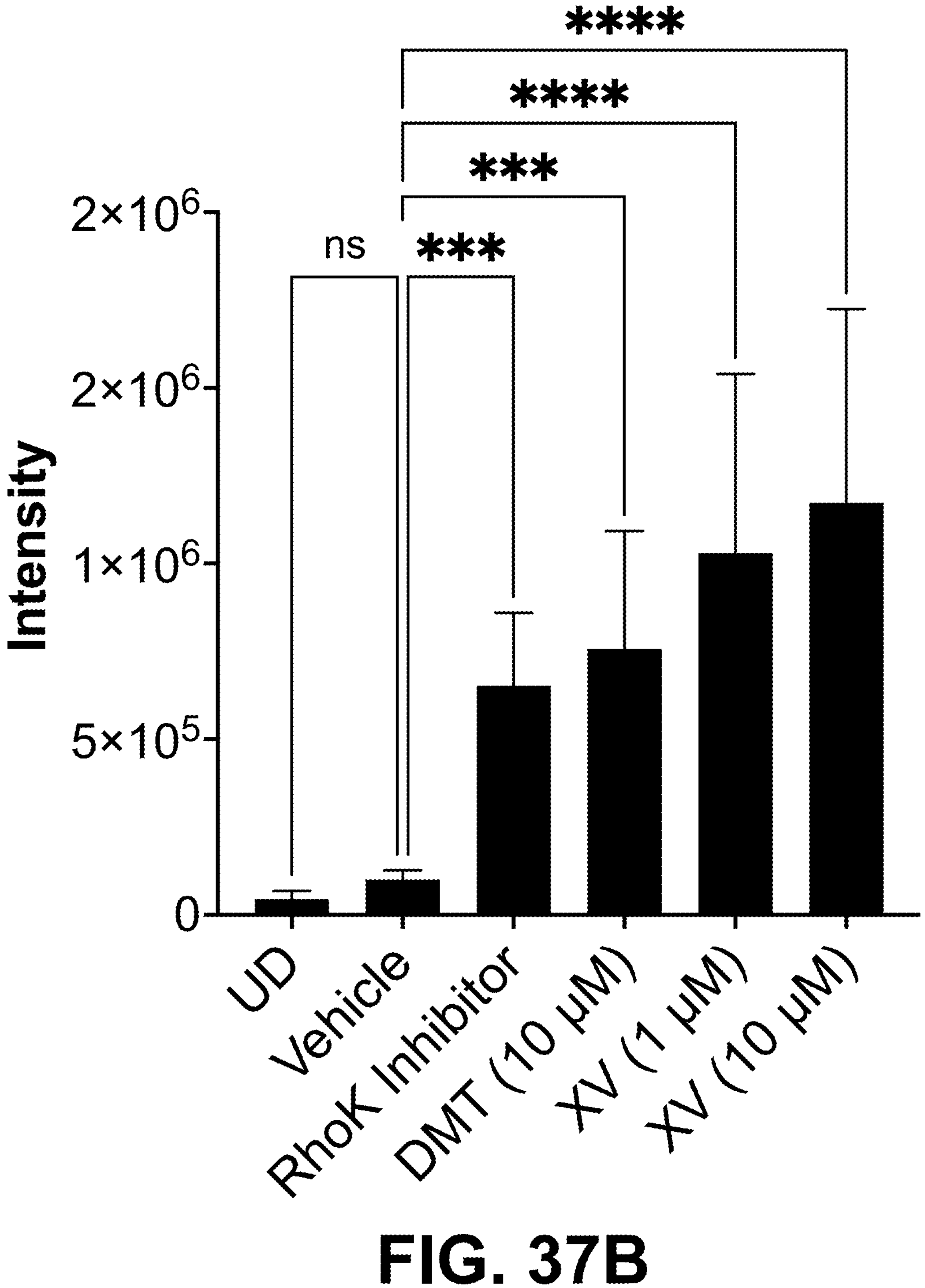

The results of this study confirmed the neuroplastogenic effects of compound with formula (XV). Human model (NT2) neurons incubated with 1 μM or 10 μM compound (XV) grew larger in size and displayed greater overall neurite outgrowth compared with vehicle-treated (0.1% DMSO) human model neurons (FIG. 37A). Visual inspection of images confirmed an increase in neurite length for compound (XV)-treated cells compared to those of negative controls. Further visual inspection suggested that the enhanced neurite outgrowth observed in compound (XV)-treated cells was mirrored in positive control treatments (i.e., NT2 neurons exposed to RhoK inhibitor and DMT). Results of visual inspection are summarized in Table 4, where (1) (+) designates strong evidence of enhanced neurite outgrowth in drug-treated NT2 cells compared to vehicle-treated cells, and (2) (−) designates weak or no evidence of enhanced neurite outgrowth in drug-treated NT2 cells compared to vehicle-treated cells. Results were quantitatively confirmed by comparing CTCF values (signal intensities), revealing a statistically significant increase of β-III-tubulin immunofluorescence in compound (XV)-treated cells (p<0.0001 for both 1 μM and 10 μM) compared with those of vehicle-treated (0.1% DMSO) cells (FIG. 37B).

TABLE 4

Summary of neuroplastogenicity assays.

| Molecule | Evidence of neurite outgrowth: Yes (+) or No (−) |
|---|---|
| RhoK | + |
| DMT | + |
| 5-MeO-DMT | + |
| TBG | + |
| 5-Br-DMT | + |
| 6-F-DET | + |
| (XV) | + |
| (XII) | + |
| (XVIII) | + |

TABLE 4-continued

Summary of neuroplastogenicity assays.

| Molecule | Evidence of neurite outgrowth: Yes (+) or No (−) |
|---|---|
| (V) | + |
| (VI) | + |
| (VII) | + |
| (VIII) | − |
| (IX) | − |
| (X) | + |
| (XI) | − |
| (XIII) | + |
| (XIV) | + |
| (XVII) | + |
| (XX) | + |
| (XXIII) | + |
| (XXV) | − |
| (XXVII) | − |

For each treatment, visual inspection of micrographs was conducted as described, allowing assignment of one of two designations: (1) a positive (+) designation indicating strong evidence of enhanced neurite outgrowth in drug-treated NT2 cells compared to vehicle-treated cells, or (2) a negative (−) designation indicating weak or no evidence of enhanced neurite outgrowth in drug-treated NT2 cells compared to vehicle-treated cells.

Mouse Head Twitch Response (HTR) Assay to Assess Hallucinogenic Potential.

Head Twitch Response (HTR) is widely utilized as a behavioral proxy in rodents for human hallucinogenic effects and can reliably differentiate between hallucinogenic and non-hallucinogenic 5-$HT_{2A}$ receptor agonists (Halberstadt and Geyer, 2013, Psychopharmacol. 227:727; Gonzalez-Maeso et al., 2007, Neuron 53:439-452). All experiments were approved by the University of Calgary Animal Care and Use Committee in accordance with Canadian Council on Animal Care guidelines. $C_{57}$BL/6-Elite mixed sex mice were obtained from Charles River (8 weeks old). Until the first experiment, mice were group-housed, then single-housed on a 12:12 h light/dark schedule (lights on at 07:00 hours) with ad libitum access to food and water. Before any behavioral screening, mice were handled and exposed to the testing chamber for at least 5 min each day for three successive days and habituated to the experimental room 1 h before testing. The testing chamber was cleaned with a 70% ethanol solution between experiments to eliminate odor from other mice. Drug compounds (100 mM in DMSO) were diluted in sterile excipient (10% EtOH/15% PEG400 in ddH2O) to 3 mg/kg (preliminary screening) or 0.5, 2, 4, 7, and 10 mg/kg (dose-curve analysis) and administered using intraperitoneal (i.p.) drug injections. Mice were video monitored using infrared light and camera in a plexiglass testing chamber (25.5×12.5×12.5 cm [L×W×H], with 5 cm of fresh bedding) to record HTRs and returned to their home cage. Behavioral analysis was conducted by an individual blinded to subject treatment group using Behavioral Observation Research Interactive Software (BORIS, version 7, DOI: 10.1111/2041-210X.12584). HTR was analyzed during the 0-to-15-minute window following drug administration. Psilocin, dimethyltryptamine (DMT) and 5-methoxy-dimethyltryptamine (5-MeO-DMT) are established hallucinogens and served as positive controls. Negative controls were as follows: 5-Br-DMT (5-bromodimethyltryptamine) is a predicted non-hallucinogen based on mice model data (Dong et al., 2021, Cell 184:2779-2792), TBG (tabernanthalog) is a purported non-hallucinogen with therapeutic potential (Cameron et al., 2021, Nature 589:474-479), and 6-F-DET (6-fluoro-diethyltryptamine) is an established non-hallucinogen in humans (Blair et al., 2000, J. Med. Chem. 43:4701-4710). FIG. 38A shows HTR assay results for all drugs administered at 3 mg/kg (preliminary screening). Results show high hallucinogenic potential (mean HTR≥10) for positive controls (hatched bars; psilocin, DMT, 5-MeO-DMT). In contrast, low/no hallucinogenic potential (mean HTR≤5) is observed for negative controls (white bars; 5-Br-DMT, TBG, 6-F-DET). Mean HTR between 10 and 5 signifies reduced hallucinogenic potential relative to positive controls. Compound (XV) has an HTR of 5.0±0.82 (mean±SE), suggesting low/no hallucinogenic potential comparable to negative controls. Furthermore, the HTRs observed for each of compounds (XXI), (IX), (XXI), (IX), (XIV), (XXV) (XXVI), (Vill), (XXVII), (V), (VII), (XXVII), (V), (VII), (XIII), (X), (XX), (XXIII), (XVI), (XXII), (XII), (XVIII), and (XV) is not statistically significantly higher than the HTR response for 5-Br-DMT (Ordinary one-way ANOVA. Mean of each compound compared to the mean of 5-Br-DMT as a control, using Dunnett's Multiple Comparison Test. Each p-value is adjusted to account for multiple comparisons. Family-wise alpha threshold and confidence level: 0.05 (95% confidence level)). FIG. 38B shows HTR assay results for selected drugs administered at increasing doses (0.5-10 mg/kg). Results reveal that HTR for compound (XV) remains low over increasing dosage, suggesting low/no hallucinogenic potential as dosages increase.

Mouse Marble Burying (MB) Assay to Assess Anxiolytic Potential.

Marble burying behavior is used to measure the level of anxiety in a rodent when it encounters unfamiliar objects (Deacon, 2006, Nature Protocols 1:122-124). This assay is routinely applied to the study of chronically stressed mice, where drug candidates are evaluated for an ability to diminish stress-induced, anxiety-like behaviours (e.g., Wang et al., ACS Chem. Neurosci. 14:977-987). Positive results in this assay may be interpreted as an indication of therapeutic (anxiolytic) potential in the treatment of various psychiatric disorders. Herein, we applied the marble burying model to investigate whether selected drugs could alleviate anxiety behaviour in stressed mice. Psilocin, whether administered pure or in prodrug form (psilocybin), has established anxiolytic properties (Goldberg et al., Psychiatric Res. 284: 112749) and thus served as a positive control in this assay.

Mice.

All animal protocols were approved by the University of Calgary Animal Care and Use Committee. $C_{57}$BL/6-Elite mixed sex mice were obtained from Charles River Laboratories (Toronto, Canada) at 8-9 weeks old. Mice were maintained on a 12:12 h light/dark schedule (lights on at 07:00 hours) with ad libitum access to food and water and group-housed until 2 days prior to the start of the mild chronic stress paradigm, then mice were single-housed. All subjects were randomly assigned to different experimental conditions used in this study and analysis was completed by an investigator blinded to experimental group. Before any behavioral manipulation, mice were handled for 5-10 min each day for at least three successive days and habituated to the experimental room 1 h before all testing.

Mild Chronic Stress Paradigm.

Prior to behavioral testing, mice were exposed to vehicle (1% ethanol) or corticosterone (25 ug/mL in 1% ethanol) in their drinking water for 7 days (refreshed once). For the final 5 days, mice were also exposed to restraint stress using 50 mL conical tubes (Eppendorf) for 30 mins/day in their home cage.

Drug Administration.

24 hrs after the 7-day stress paradigm, mice were weighed and drugs were administered via i.p. injection. Mice were treated with vehicle (1% DMSO in excipient consisting of filter sterilized ethanol:PEG400:water [10:15:75]) or drug (dissolved in DMSO to 100 mM and diluted in excipient to 3 mg/kg for psilocin or 10 mg/kg for Compound (XV) and remained in their home cage. As psilocin is hallucinogenic at 3 mg/kg, this dose was selected for the study. Conversely, the hallucinogenic potential of compound (XV) is negligible at 3 mg/kg and thus a higher amount (10 mg/kg) was selected for this initial study. 24 hrs and 7 days after drug administration, mice underwent marble burying tests to evaluate anxiety-related behaviors.

Marble Burying.

In the week prior to initial experimentation, mice were exposed to the plexiglass testing chamber (25.5×12.5×12.5 cm [L×W×H]) without marbles for 10 mins to reduce impact of cage novelty. On the testing days, 10 glass marbles (approx. 15 mm in diameter) were evenly spaced on 5 cm of wood-chip bedding (lightly tamped down to make a flat and even surface). Each mouse was placed in the tested chamber and allowed to explore for 30 mins and returned to their home cage. Bedding was changed and marbles were cleaned with 70% ethanol solution between experiments to eliminate odor from other mice. The number of marbles buried to ⅔rds their depth was measured. Fully buried marbles were counted as 1 and partially (at least ⅔rds) buried marbles were counted as 0.5.

Statistical Analysis.

One-Way ANOVA was used to compare mice cohorts. Additionally, the mean of each test cohort was compared with the mean of the control cohort (Vehicle+Stress) using Dunnett's multiple comparison procedure. Results are reported with an $\alpha$ threshold of 0.05 (Cl 95%), with adjusted p-values indicated as follows: * p=0.05-0.01; ** p=0.01-0.001.

Results.

Figure 39:
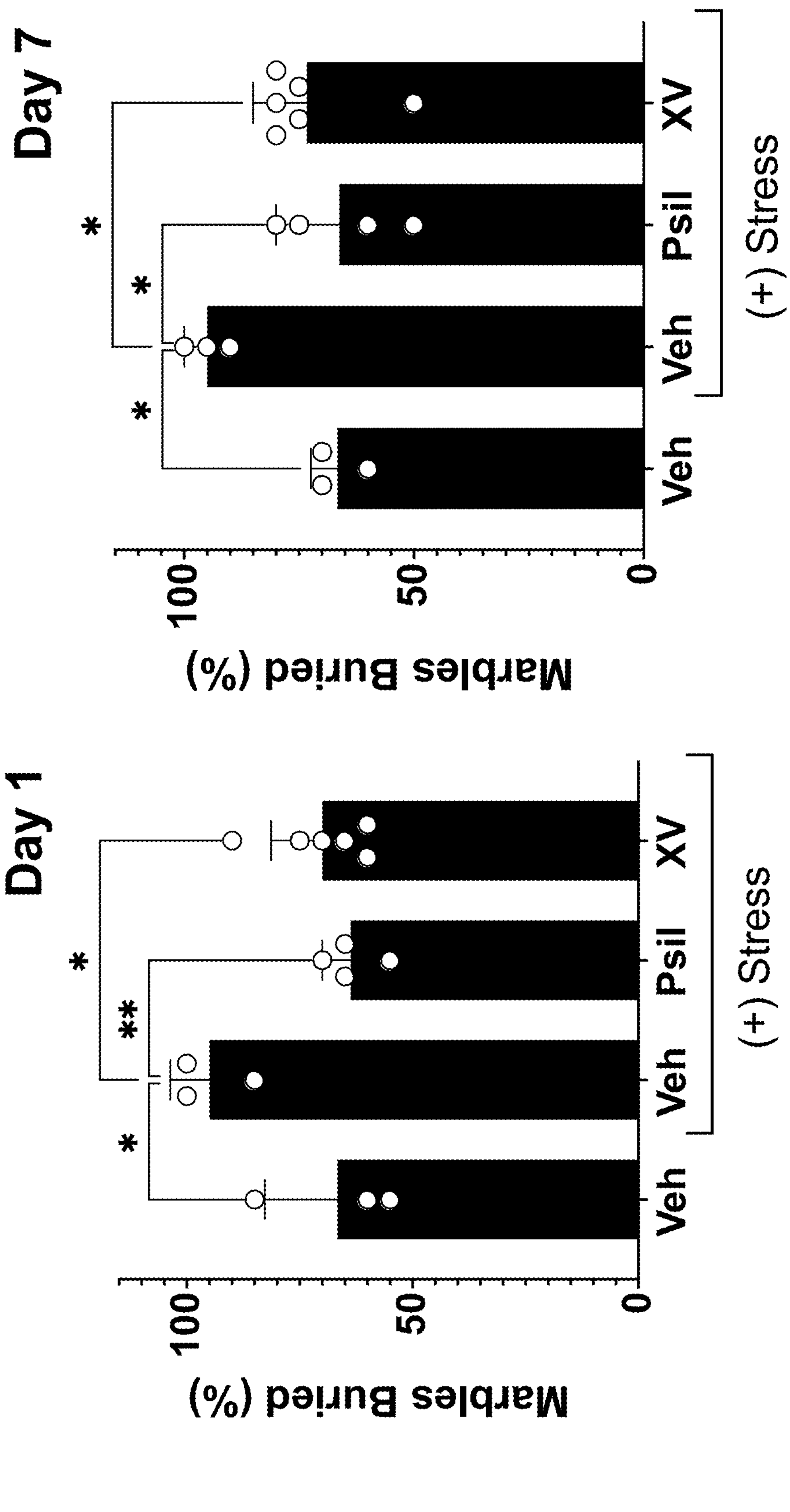
FIG. 39 depicts graphs representing certain experimental results, notably graphs obtained in the performance of experimental assays, notably a mice marble burying assay, to evaluate the pharmaceutical efficacy of an example compound having chemical formula (XV), wherein C57BL/6-Elite mice (n=4/group) were dosed i.p. with vehicle (1% DMSO in ethanol:PEG400:water [10:15:75]) or drug at 3 mg/kg for psilocin or 10 mg/kg for compound (XV), wherein analysis by one-way ANOVA compared mice cohorts, wherein the mean of each test cohort was compared with the mean of the control cohort (Vehicle+Stress) using Dunnett's multiple comparison procedure, wherein results are reported with an a threshold of 0.05 (Cl 95%), with adjusted p-values indicated as follows: * p=0.05-0.01; ** p=0.01-0.001, wherein evaluations were conducted one day (bar graph labeled "Day 1") or seven days (bar graph labeled "Day 7") post-drug administration, wherein abbreviations are as follows: Veh=vehicle; Psil=psilocin; XV=Compound (XV), and wherein white dots represent individual mice.

It is well-established that mice exposed to stress bury more marbles than non-stressed mice (Levone et al., 2021, Neuropharmacol. 201:108843). This outcome was demonstrated in mice administered vehicle, where stressed mice buried significantly more marbles than non-stressed mice (FIG. 39; Day 1 p=0.0093, Day 7 p=0.0227). This anxiety-linked behavior was rescued by psilocin administration, thus affirming anxiolytic potential for the positive control. Similarly, anxiety-linked behavior was alleviated by administering compound (XV). To illustrate, significantly less marbles were buried by stressed mice dosed with compound (XV) compared to counterparts dosed with vehicle. This result held true both 1 day and 7 days post-treatment (p=0.0080 and 0.0485, respectively). In summary, these results reveal anti-anxiety potential for compound (XV).

Mouse Sucrose Preference (SP) Assay to Assess Antidepressant Potential.

Reduced intake of pleasurable substances, e.g., of sucrose water, is a validated behavioral measure of anhedonic/depressive-like state in rodents (Moreau et al., 1992, Eur. Neurpsychopharmocol. 2:43-49; Liu et al., 2018, Nature Protocols 13:1686-1698). Hence, positive outcomes in the Sucrose Preference (SP) assay may be interpreted as an indication of therapeutic (antidepressant) potential in the treatment of a suite of psychiatric disorders. In the SP assay, cohorts of mice are pre-stressed, leading to a depressed state.

The ability of drugs to rescue this state are evaluated. Psilocin, whether administered pure or in prodrug form (psilocybin), has established antidepressant properties (Sekssaoui et al., 2024, Neuropsychopharmacology doi: 10.1038/s41386-024-01794-6) and thus served as a positive control in this assay.

Mice.

All animal protocols were approved by the University of Calgary Animal Care and Use Committee. $C_{57}$BL/6-Elite mixed sex mice were obtained from Charles River Laboratories (Toronto, Canada) at 8-9 weeks old. Mice were maintained on a 12:12 h light/dark schedule (lights on at 07:00 hours) with ad libitum access to food and water and group-housed until 2 days prior to the start of the mild chronic stress paradigm, then mice were single-housed. All subjects were randomly assigned to different experimental conditions used in this study and analysis was completed by an investigator blinded to experimental group. Before any behavioral manipulation, mice were handled for 5-10 min each day for at least three successive days and habituated to the experimental room 1 h before all testing.

Mild Chronic Stress Paradigm.

Prior to behavioral testing, mice were exposed to vehicle (1% ethanol) or corticosterone (25 ug/mL in 1% ethanol) in their drinking water for 7 days (refreshed once). For the final 5 days, mice were also exposed to restraint stress using 50 mL conical tubes (Eppendorf) for 30 mins/day in their home cage.

Drug Administration.

24 hrs after the 7-day stress paradigm, mice were weighed and drugs were administered via i.p. injection. Mice were treated with vehicle (1% DMSO in excipient consisting of filter sterilized ethanol:PEG400:water [10:15:75]) or drug (dissolved in DMSO to 100 mM and diluted in excipient to 3 mg/kg for psilocin or 10 mg/kg for compound (XV)) and remained in their home cage. As psilocin is hallucinogenic at 3 mg/kg, this dose was selected for the study. Conversely, the hallucinogenic potential of compound (XV) is negligible at 3 mg/kg and thus a higher amount (10 mg/kg) was selected for this initial study. 24 hrs after drug administration, mice underwent sucrose preference tests to evaluate anhedonia behavior.

Sucrose Preference.

Mice were introduced to 1% sucrose solution in their drinking water for 24 hrs for 2 days prior to initial sucrose preference testing to reduce impact of novelty. During the sucrose preference test, mice remained in their home cage and were provided with two identical drinking bottles containing either tap water or 2% sucrose for 24 hrs. Bottles positions were switched once during the experiment to reduce potential side biases. The consumption in water, sucrose solution, and total intake of liquids was measured by weighing each bottle before and after the 24-hr experiment. The preference for sucrose was calculated as a percentage of the consumed sucrose solution from the total intake of both water and sucrose solutions.

Statistical Analysis.

One-Way ANOVA was used to compare mice cohorts. Additionally, the mean of each test cohort was compared with the mean of the control cohort (Vehicle+Stress) using Dunnett's multiple comparison procedure. Results are reported with an $\alpha$ threshold of 0.05 (Cl 95%), with adjusted p-values indicated as follows: * p=0.05-0.01; ** p=0.01-0.001.

Results.

Figure 40:
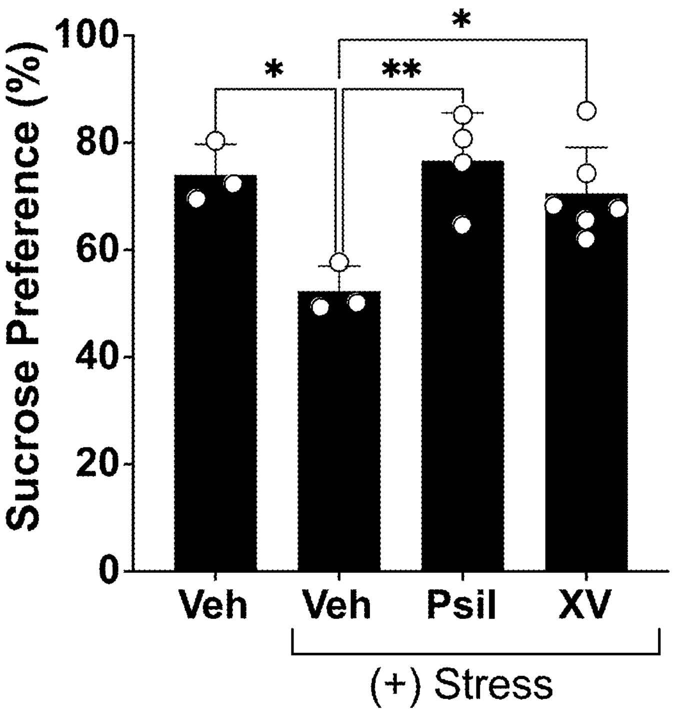
FIG. 40 depicts a graph representing certain experimental results, notably a bar graph obtained in the performance of an experimental assay, notably a mice sucrose preference assay, to evaluate the pharmaceutical efficacy of an example compound having chemical formula (XV), wherein C57BL/6-Elite mice (n=4/group) were dosed i.p. with vehicle (1% DMSO in ethanol:PEG400:water [10:15:75]) or compound at 3 mg/kg for psilocin or 10 mg/kg for Compound (XV), wherein analysis by one-way ANOVA compared mice cohorts, wherein the mean of each test cohort was compared with the mean of the control cohort (Vehicle+Stress) using Dunnett's multiple comparison procedure, wherein results are reported with an α threshold of 0.05 (Cl 95%), with adjusted p-values indicated as follows: * p=0.05-0.01; ** p=0.01-0.001, wherein abbreviations are as follows: Veh=vehicle; Psil=psilocin; XV=Compound (XV), and wherein white dots represent individual mice.

As anticipated, stressed mice with no drug (Vehicle+Stress) consumed less sucrose in the preference test, revealing a measurable depressive state (FIG. 40). Sucrose preference behaviour was significantly elevated (p=0.0055) in mice one day after psilocin administration, compared to stressed mice without drug. This result was anticipated, as psilocin (in prodrug form, psilocybin) is known to rescue depressive-like symptoms in stressed mice (Sekssaoui et al., 2024, Neuropsychopharmacology doi: 10.1038/s41386-024-01794-6) and thus served as a positive control for this assay. A similar stress-coping effect was observed in mice one day after compound (XV) dosing. In this case, significant preference for sucrose was observed compared to no drug control after one day (p=0.0265). These results show that, similar to the positive control psilocin, compound (XV) reduces depression-linked behaviour in stressed mice one day after drug administration.

Mouse Plasma Pharmacokinetics (PK) Survey.

The purpose of the study was to gain insight into the pharmacokinetic (PK) behaviour of drugs in rodents. In some contexts, drug exposure and other PK parameters may be linked to the onset and/or degree of drug efficacy. Toward the goal of assessing PK behaviour, objectives included the collection of plasma from male mice at various times after (1) a single 'low' IP (intraperitoneal) dose (4 mg/kg), and (2) a single 'high' IP dose (10 mg/kg) of drug for pharmacokinetic monitoring. The experiment was designed to enable the determination of key parameters (e.g., $C_{max}$, AUC) and was conducted in partnership with Inotiv (Boulder, Colorado; www.inotiv.com; Studies 3533-2302132 and 3533-2302538).

Animals.

The study which took part in two phases (No. 3533-2302132 and 3533-2302538) was conducted by CRO Inotiv (Boulder, CO) and was performed in accordance with the test facility standard operation procedures (SOPs), the World Health Organization Quality Practices in Basic Biomedical Research guidelines, and in compliance with all US state and federal regulations, including USDA Animal Welfare Act 9 CFR Parts 1-3. Federal Register 39129, Jul. 22, 1993. All mice were male, belonging to stain C57BL6 (supplier Envigo). Upon arrival at the facility, the mice were 6 weeks old and were acclimated 7 days prior to injection with food and water ad libitum (3 animals/cage).

Treatment.

Three cohorts of mice were included (n=6 per cohort): (1) control (vehicle treatment), (2) 4 mg/kg compound (XV), and (3) 10 mg/kg compound (XV). On day 0 of the study, animals were randomized into cohorts based on body weight. Dosing (i.p. dose route) was performed on Day 1. Sampling of plasma was performed under anesthesia (inhaled isoflurane) on 3 of 6 animals per cohort at 6 time points (15 min 30 min, 1 h, 2 h, 4 h, and 6 h post-dose) followed by sacrifice at 8 h post-dose, ex-sanguination and final plasma collection. Whole blood (100 μL) was collected for plasma preparation using $K_2$EDTA on ice (centrifugation within 5 min of collection), for a final plasma volume of 50 μL. Samples were stored at −80° C. until analysis. Notably, one part of one cohort (n=3) was dosed on a separate date from the others (n=3, 10 mg/kg; Study 3533-2302538) but all other experimental aspects were held equivalent.

Analysis.

Bioanalytical analysis of plasma was carried out using standard LC-MS/MS procedures. Prior to analysis of plasma, drug-specific quantification metrics (e.g., standard curve, LOD, Rt) were pre-established using authentic standard (>95%). Calculated concentrations (ng/mL) of analyte were used to determine PK parameters ($C_{max}$, AUC) within the limits of detection (LOD).

Results.

Figure 41:
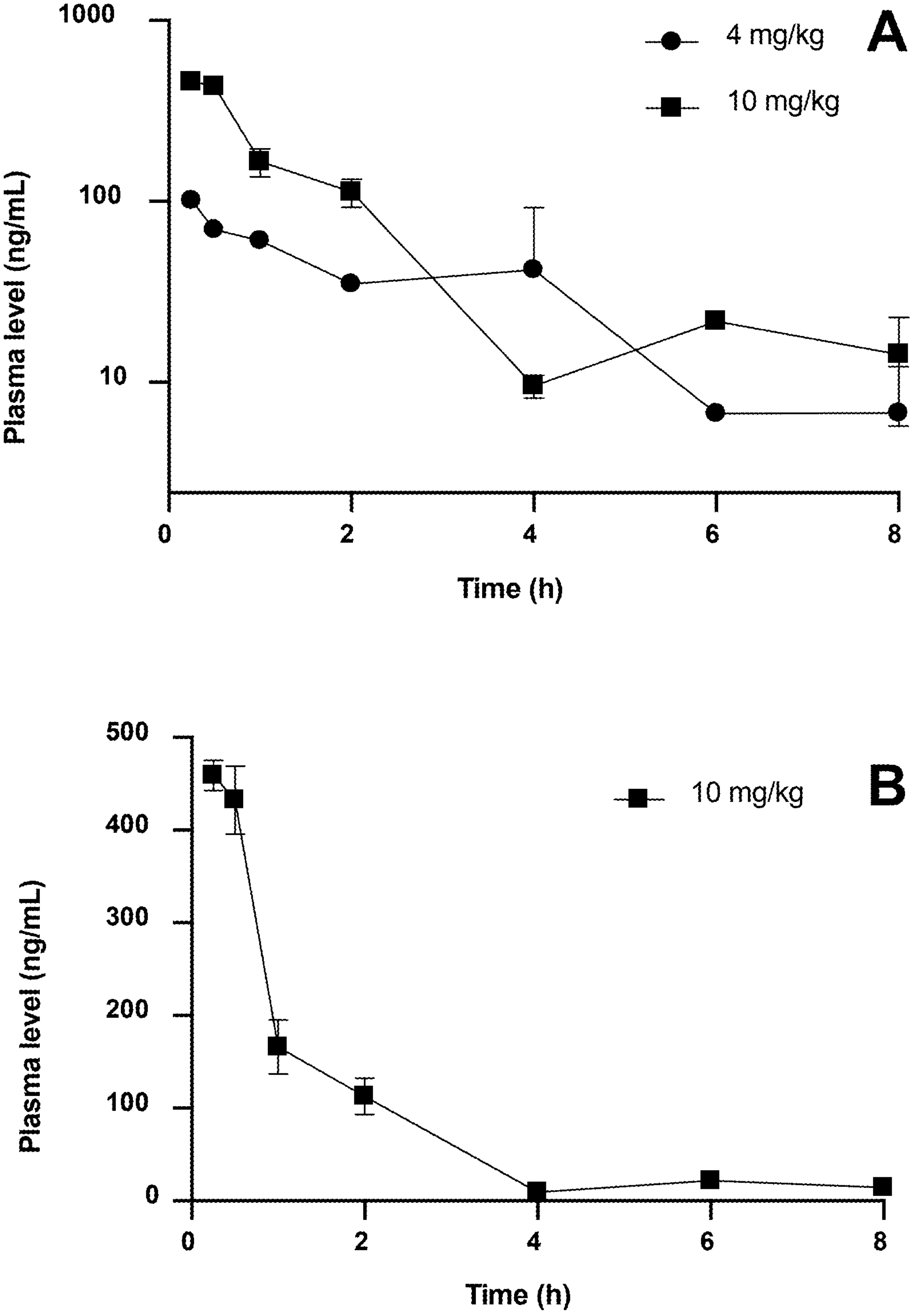
FIG. 41 depicts graphs representing certain experimental results, notably graphs obtained in the performance of an experimental assay to evaluate the pharmaceutical efficacy of an example compound having chemical formula (XV), notably a mouse pharmacokinetics (PK) assay after i.p. (intraperitoneal) dosing in healthy male mice, wherein two cohorts were part of the study, administered either 4 mg/kg or 10 mg/kg doses (n=6 per cohort), wherein one part of one cohort (n=3) was dosed on a separate date from the others (n=3, 10 mg/kg; Study 3533-2302538) but all other experimental aspects were held equivalent, wherein results are shown for both dosages, with y-axis viewed in $log_{10}$ format (graph labeled (A)), and results are shown for 10 mg/kg only, with y-axis values viewed linearly (graph labeled (B)).

PK behavior is illustrated in FIG. 41 and calculated parameters for Compound (XV) and other drugs are listed in Table 5. Compound (XV) was still detectable in most mice eight hours post-administration. Reports of directly administering psilocin—an arguably comparable drug to compound (XV)—for pharmacokinetic study are rare, although data regarding intravenous (and oral) psilocybin administration for purposes of psilocin monitoring reveal that psilocin persists well beyond 8 hours in plasma (Raithatha et al., 2023, J. Med. Chem. 67:1024-1043). While not a direct comparison, these data point to the possibility that compound (XV) may metabolize slowly like psilocin.

TABLE 5

Pharmacokinetic (PK) parameters for Compound (XV) and other drugs at two different doses.

| Molecule | Dose | $C_{max}$ ng/ml | $AUC_{t0\text{-}tlast}$ hr*ng/mL |
|---|---|---|---|
| (XV) | 4 mg/kg | 101.2 ± 4.9 | 240.6 ± 71.6 |
| | 10 mg/kg | 459.0 ± 16.4 | 589.7 ± 30.9 |
| (XII) | 4 mg/kg | 92.8 ± 17.2 | 39.7 ± 3.0 |
| | 10 mg/kg | 302.3 ± 33.7 | 145.4 ± 5.3 |
| (XVII) | 4 mg/kg | 62.1 ± 3.9 | 27.2 ± 1.6 |
| | 10 mg/kg | 384.3 ± 14.2 | 164.3 ± 7.2 |
| (XVIII) | 4 mg/kg | 8.8 ± 1.2 | 19.6 ± 0.7 |
| | 10 mg/kg | 87.5 ± 8.5 | 76.4 ± 11.5 |

Figure 15A:
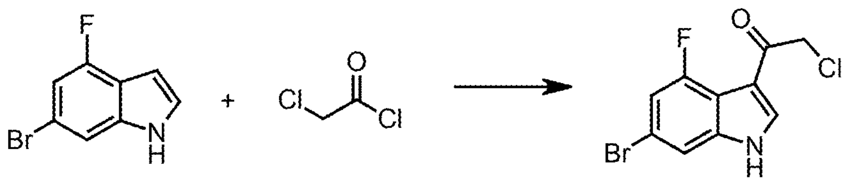
FIGS. 15A, 15B, 15C, and 15D depict further example reactions in an example chemical synthesis pathway for the synthesis of a certain example compound according to the present disclosure.

Example 12—Synthesis and Analysis of a Twelfth N-Heterocycle Substituted Tryptamine Derivative Referring to FIG. 15A, to a stirring suspension of aluminum chloride (3.01 g, 22.3 mmol) in 17 mL DCM was added chloroacetyl chloride (6.04 mL, 74.4 mmol), this was stirred together for 5 minutes, during which time the aluminum chloride appeared to dissolve. Added to this mixture, in a dropwise manner over 15 minutes was a solution of 6-Bromo-4-fluoro-1H-indole (4.15 g, 18.6 mmol) in 20 mL DCM. This was monitored by LCMS (254 nm) over a period of 3 hours at which point the reaction was cooled to 0° C. and quenched with a careful addition of 40 mL saturated sodium bicarbonate solution and a precipitate immediately formed. This was quickly collected by filtration, washed with water and DCM. It was determined by LCMS that the resulting solid was mainly intermediate Y (5.01 g, 93%) with a minor amount of the indole dimer. This material was used in the next step without further purification. LRMS-HESI: calculated for $C_{10}H_7BrClFNO$ (M+H)$^+$ 289.94 m/z, observed 289.97 m/z. (FIG. 15A, see: further also chemical reaction (d) in FIG. 3B).

Figure 15B:
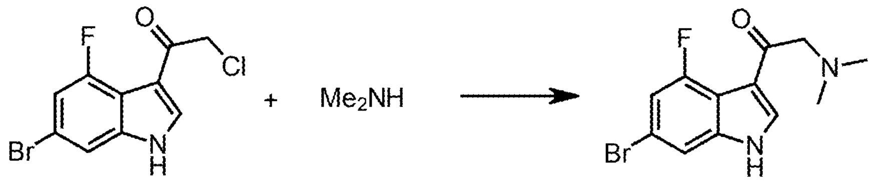

Referring next to FIG. 15B, in a reaction vial, a solution of crude intermediate Y (1.00 g, 3.44 mmol), potassium carbonate (1.43 g, 10.3 mmol), and potassium bromide (1.23 g, 10.3 mmol) in 70 mL of DMF was allowed to stir under nitrogen at room temperature for 10 minutes. Added to this was 2 M dimethylamine (16.0 mL, 32.0 mmol) and the reaction mixture was heated to 50° C. for 3 hrs. After cooling to room temperature, the reaction mixture was poured into a separatory funnel containing water (200 mL) and ethyl acetate (50 mL) and the aqueous phase was extracted with ethyl acetate (5×100 mL). The combined organic extracts were washed with water (5×100 mL), brine (50 mL), dried over anhydrous magnesium sulphate and concentrated under reduced pressure. The resulting solid was purified by FC (24 g silica, 0% to 20% MeOH in DCM) to provide intermediate Z (254 mg, 25%) as a light yellow solid. LRMS-HESI: calculated for $C_{12}H_{13}BrFN_2O$ (M+H)$^+$ 299.02 m/z, observed 299.00 m/z. (FIG. 15B, see: further also chemical reaction (l) in FIG. 3B).

Figure 15C:
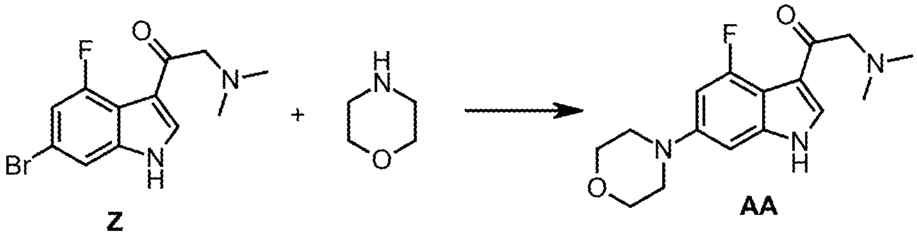

Referring next to FIG. 15C, in a pressure rated reaction vial was combined intermediate Z (45.0 mg, 150 μmol), DavePHOS (24.5 mg, 61.1 μmol), and $Pd_2(dba)_3$ (24.1 mg, 25.6 μmol) and the mixture was purged with nitrogen for 30 minutes. The vial contents were dissolved in dry dioxane (180 μL), followed by addition of morpholine (80.0 μL, 906 μmol) and 1 M LiHMDS in THE (551 μL, 551 μmol). The reaction mixture was heated to 80° C. for 20 hrs. At this point the reaction was stopped, the crude material was isolated and purification was carried out by FC (4 g silica, 0% to 20% MeOH in DCM) to provide intermediate AA (19 mg, 41%) as a colourless solid. LRMS-HESI: calculated for $C_{16}H_{20}FN_3O_2$ (M+H)$^+$ 306.16 m/z, observed 306.17 m/z. (FIG. 15C, see: further also chemical reaction (m) in FIG. 3B).

Figure 15D:
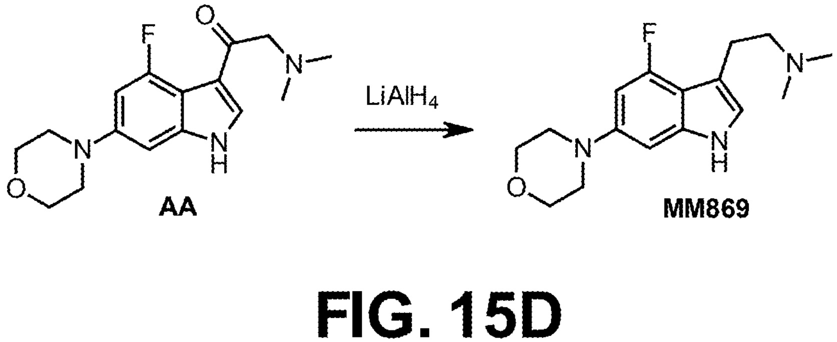

Referring next to FIG. 15D, a flame-dried flask, under nitrogen atmosphere, was charged with 2 M lithium aluminum hydride in THE (156 μL, 311 μmol) and cooled to 0° C. To the reaction vessel was added a solution of intermediate AA (19.0 mg, 62.2 μmol) in dry THE (415 μL) and dry dioxane (200 μL). The temperature of the mixture was brought to 60° C. for 2.5 hrs. After this time the mixture was cooled to room temperature and the reaction mixture was worked up according to the Fieser method. The resulting solid was purified by FC (4 g silica, 0% to 30% MeOH in DCM) to provide MM869 (2.2 mg, 12%) as a white solid. LRMS-HESI: calculated for $C_{16}H_{23}FN_{30}$ (M+H)$^+$ 292.18 m/z, observed 292.21 m/z. $^1H$ NMR (400 MHz, $CDCl_3$) δ 7.88 (s, 1H), 6.86-6.83 (m, 1H), 6.58 (d, J=1.9 Hz, 1H), 6.50 (dd, J=13.6, 1.9 Hz, 1H), 3.90-3.86 (m, 4H), 3.15-3.10 (m, 4H), 3.00-2.94 (m, 2H), 2.66-2.61 (m, 2H), 2.34 (d, J=1.9 Hz, 6H). (FIG. 15D, see: further also chemical reaction (n) in FIG. 3B).

It is noted that MM869 corresponds with chemical compound (XVI):

(XVI)

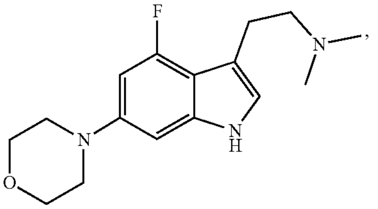

set forth herein.

5-HT Receptor Radioligand Competition Assay.

Competition assays at the $5\text{-}HT_{2A}$ receptor were performed as described in Example 11, except compound with formula (XVI) was used in place of compound with formula (XV). Resulting $K_i$ data for controls and test compounds in $5\text{-}HT_{2A}$ receptor binding assays, including data acquired for compound with formula (XVI), are summarized in Table 2. Compound with formula (XVI) (designated 'XVI' in Table 2) exhibited a $K_i$ value of 6.2 μM at the $5\text{-}HT_{2A}$ receptor. This $K_i$ value was less than those of negative controls (i.e., $K_i$<1000 μM) and hence suggested binding by compound with formula (XVI) at this receptor.

Mouse Head Twitch Response (HTR) Assay to Assess Hallucinogenic Potential.

Head Twitch Response (HTR) assays were conducted as described in Example 11, except that compound with formula (XVI) was used in place of compound with formula (XV). FIG. 38A shows HTR assay results for all drugs administered at 3 mg/kg (preliminary screening). Results show high hallucinogenic potential (mean HTR≥10) for positive controls (hatched bars, psilocin, DMT, 5-MeO-DMT). In contrast, low/no hallucinogenic potential (mean HTR≤5) is observed for negative controls (white bars, 5-Br-DMT, TBG, 6-F-DET). Mean HTR between 10 and 5 signifies reduced hallucinogenic potential relative to positive controls. Compound (XVI) has a mean HTR of 6.75, suggesting reduced hallucinogenic potential relative to positive controls.

Figure 16A:
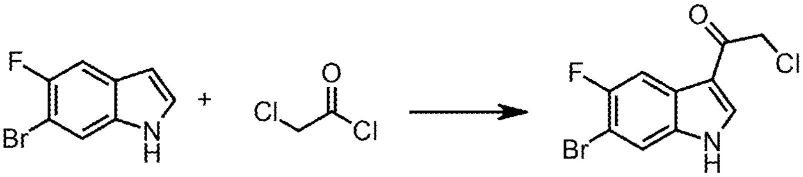
FIGS. 16A, 16B, 16C, and 16D depict further example reactions in an example chemical synthesis pathway for the synthesis of a certain example compound according to the present disclosure.

Example 13—Synthesis and Analysis of a Thirteenth N-Heterocycle Substituted Tryptamine Derivative Referring to FIG. 16A, to a stirring suspension of aluminum chloride (751 mg, 5.58 mmol) in 4.7 mL DCM was added chloroacetyl chloride (1.51 mL, 18.6 mmol), this was stirred together for 5 minutes, during which time the aluminum chloride appeared to dissolve. Added to this mixture, in a dropwise manner over 15 minutes, was a solution of 6-bromo-5-fluoroindole (1.04 g, 4.65 mmol) in 4.7 mL DCM. This was monitored by LCMS (254 nm) over a period of 1.5 hours. At this point the reaction was cooled to 0° C. and quenched with a careful addition of 9 mL saturated sodium bicarbonate solution and a precipitate immediately formed. This was collected by filtration, washed with water and DCM. After drying, the collected solid, intermediate AB (720 mg, 53%) was used in the next step without further purification. LRMS-HESI: calculated for $C_{10}H_7BrClFNO$ $(M+H)^+$ 289.94 m/z, observed 289.93 m/z. (FIG. 16A, see: further also chemical reaction (d) in FIG. 3B).

Figure 16B:
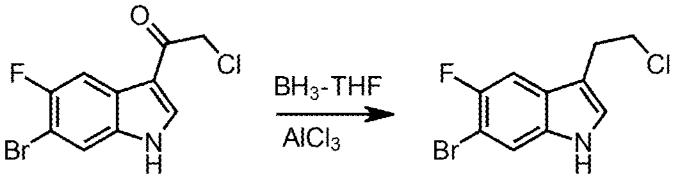

Referring next to FIG. 16B, to a suspension of aluminum chloride (334 mg, 2.48 mmol) and intermediate AB (720 mg, 2.48 mmol) in dry DCM (7.20 mL) at 0° C. was added 1 M borane-THF complex in THE (4.96 mL, 4.96 mmol). Once the addition was complete and the initial vigorous bubbling had subsided, the temperature was increased to room temperature and stirring was continued. After 100 minutes, LCMS determined that there was no longer any starting material present and the reaction was cooled back down to 0° C. prior to careful quenching with 8 mL of dilute HCl solution (2 mL of 1 M HCl diluted to 8 mL with water). This mixture was poured into a separatory funnel and the organic layer was separated from the aqueous layer. The aqueous phase was extracted with DCM (2×15 mL). All organic layers were combined, washed with water, brine, dried ($MgSO_4$), filtered and concentrated to leave intermediate AC (572 mg, 83%) as a crude yellow solid that was used in the subsequent step without purification. LRMS-HESI: calculated for $C_{10}H_9BrClFN$ $(M+H)^+$ 275.96 m/z, observed 276.00 m/z. (FIG. 16B, see: further also chemical reaction (e) in FIG. 3B).

Figure 16C:
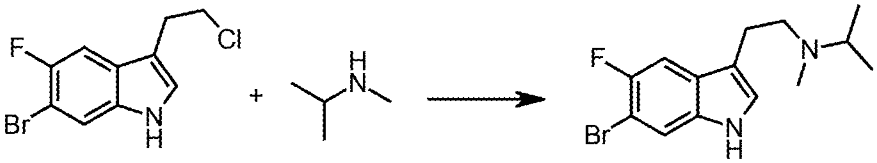

Referring next to FIG. 16C, the ethyl chloride, intermediate AC (300 mg, 1.08 mmol), was dissolved in DMF (15.8 mL). Added to this was n-isopropylmethylamine (583 µL, 5.42 mmol) and then potassium carbonate (450 mg, 3.25 mmol) and potassium bromide (387 mg, 3.25 mmol). The mixture was heated to 40° C. and left to stir at this temperature overnight. At this point the mixture contained predominantly the desired product as determined by LCMS. The mixture was poured into a separatory funnel containing 50 mL water and 50 mL ethyl acetate. The aqueous layer was extracted with ethyl acetate (3×40 mL), all organic layers were combined, washed with water (4×40 mL), brine (2×40 mL), dried ($MgSO_4$) filtered and concentrated to leave a brown oil. This was purified by column chromatography (12 g, DCM to DCM:MeOH 9:1), to provide intermediate AD (124 mg, 36%) as a light brown solid. LRMS-HESI: calculated for $C_{14}H_{19}BrFN_2$ $(M+H)^+$ 313.07 m/z, observed 313.13 m/z. (FIG. 16C, see: further also chemical reaction (f) in FIG. 3B).

Figure 16D:
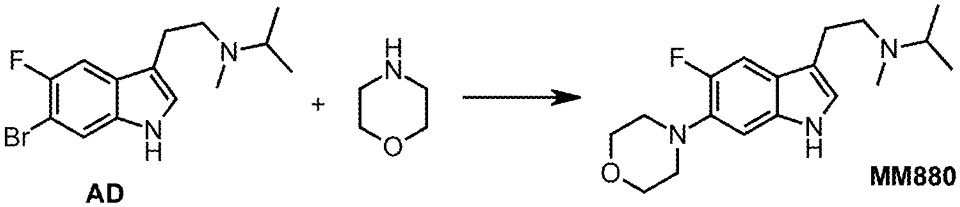

Referring next to FIG. 16D, in an oven-dried vial under nitrogen atmosphere was dissolved intermediate AD (55.0 mg, 176 µmol), $Pd_2(dba)_3$ (16.6 mg, 17.6 µmol), and DavePHOS (16.6 mg, 42.1 µmol) in dry THE (360 µL). To this stirring solution was added 1 M LiHMDS in THE (390 µL, 390 µmol) and morpholine (100 µL, 1.13 mmol). The reaction mixture was heated to 60° C. overnight. After 18 hours, IPC was run via LCMS and the reaction was determined to be complete. The mixture was cooled to room temperature and poured into a separatory funnel containing DCM (15 mL) and water (15 mL). The aqueous layer was extracted with DCM (2×15 mL), all organic layers were combined, washed with brine, dried ($MgSO_4$), filtered and concentrated to leave a brown oil. This was purified by FC (4 g silica, DCM to DCM:MeOH 9:1) to obtain MM880 (24.0 mg, 43%) as a brown oil. LRMS-HESI: calculated for $C_{18}H_{27}FN_3O$ $(M+H)^+$ 320.21 m/z, observed 320.21 m/z. $^1H$ NMR (400 MHz, $CDCl_3$) δ 8.03 (s, 1H), 7.23 (d, J=12.6 Hz, 1H), 6.99 (m, 1H), 6.92 (d, J=7.1 Hz, 1H), 3.92-3.89 (m, 4H), 3.08-2.99 (m, 5H), 2.95-2.91 (m, 2H), 2.78-2.74 (m, 2H), 2.39 (s, 3H), 1.10 (d, J=6.6 Hz, 6H). (FIG. 16D, see: further also chemical reaction (g) in FIG. 3B).

It is noted that MM880 corresponds with chemical compound (XVII):

(XVII)

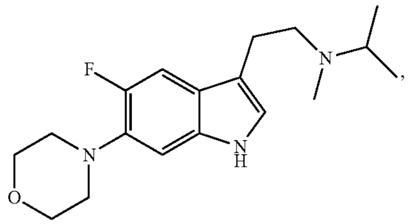

set forth herein.

5-HT Receptor Radioligand Competition Assay.

Competition assays at the $5\text{-HT}_{2A}$ receptor were performed as described in Example 11, except compound with formula (XVII) was used in place of compound with formula (XV). Resulting $K_i$ data for controls and test compounds in $5\text{-HT}_{2A}$ receptor binding assays, including data acquired for compound with formula (XVII), are summarized in Table 2. Compound with formula (XVII) (designated 'XVII' in Table 2) exhibited a $K_i$ value of 8.3 µM at the $5\text{-HT}_{2A}$ receptor. This $K_i$ value was less than those of negative controls (i.e., $K_i$<1000 µM) and hence suggested binding by compound with formula (XVII) at this receptor.

Neuroplastogenicity Assays.

Assays to reveal potential of drugs to enhance neurite outgrowth in human model (NT2) neurons were conducted as described in Example 11, except that compound with formula (XVII) was used in place of compound with formula (XV). Results of visual inspection are summarized in Table 4, where (1) (+) designates strong evidence of enhanced neurite outgrowth in drug-treated NT2 cells compared to vehicle-treated cells, and (2) (−) designates weak or no evidence of enhanced neurite outgrowth in drug-treated NT2 cells compared to vehicle-treated cells. Similar to the effects imparted by positive controls and compound with formula (XV) (FIG. 37A), human model (NT2) neurons incubated with 1 μM or 10 μM compound (XVII) grew larger in size and displayed greater overall neurite outgrowth compared with vehicle-treated (0.1% DMSO) human model neurons. These observations are summarized as a (+) designation in Table 4.

Mouse Head Twitch Response (HTR) Assay to Assess Hallucinogenic Potential.

Head Twitch Response (HTR) assays were conducted as described in Example 11, except that compound with formula (XVII) was used in place of compound with formula (XV). FIG. 38A shows HTR assay results for all drugs administered at 3 mg/kg (preliminary screening). Results show high hallucinogenic potential (mean HTR≥10) for positive controls (hatched bars; psilocin, DMT, 5-MeO-DMT). In contrast, low/no hallucinogenic potential (mean HTR≤5) is observed for negative controls (white bars; 5-Br-DMT, TBG, 6-F-DET). Mean HTR between 10 and 5 signifies reduced hallucinogenic potential relative to positive controls. Compound (XVII) has a mean HTR of 22.25, suggesting very high hallucinogenic potential greater than even the positive controls. FIG. 38B shows HTR assay results for selected drugs administered at increasing doses (0.5-10 mg/kg). Results reveal that HTR for compound (XVII) increases to ~40 HTR at maximum dose (10 mg/kg). These results suggest increasing hallucinogenic potential as dosage increases.

Mouse Plasma Pharmacokinetics (PK) Survey.

A pharmacokinetics (PK) survey was performed as described in Example 11, except that compound with formula (XVII) was used in place of compound with formula (XV). Calculated parameters for compound with formula (XVII) and other drugs are listed in Table 5. Systemic exposure ($AUC_{t0\text{-}tlast}$) was determined to be 24.2±1.6 hr*ng/mL for cohorts administered 4 mg/kg Compound (XVII), whereas those administered 10 mg/kg exhibited a mean exposure of 164.3±7.2 hr*ng/mL. Further, $C_{max}$ was determined to be 62.1±3.9 ng/mL and 384.3±14.2 ng/mL for cohorts administered 4 and 10 mg/kg Compound (XVII), respectively.

Figure 17A:
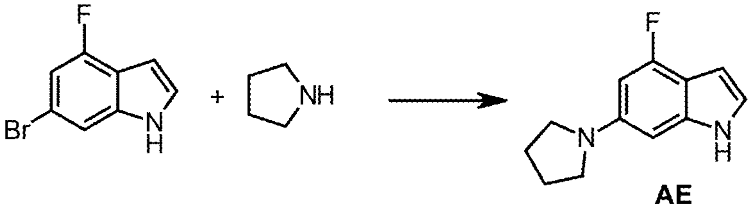
FIGS. 17A, 17B, 17C, and 17D depict further example reactions in an example chemical synthesis pathway for the synthesis of a certain example compound according to the present disclosure.

Example 14—Synthesis and Analysis of a Fourteenth N-Heterocycle Substituted Tryptamine Derivative Referring to FIG. 17A, in a pressure rated reaction vial was combined 6-bromo-4-fluoro-1H-indole (500 mg, 2.34 mmol), DavePHOS (113 mg, 280 μmol), and $Pd_2(dba)_3$ (110 mg, 117 μmol), under nitrogen atmosphere. Added to this was dry dioxane (2.34 mL), followed by the addition of pyrrolidine (433 μL, 5.14 mmol) and 1 M LiHMDS in THE (5.14 mL, 5.14 mmol). The reaction mixture was heated to 80° C. for 22 hrs. After this time, the mixture was cooled to room temperature, filtered over Celite to remove catalyst, and poured into a separatory funnel containing DCM (15 mL) and water (15 mL). The aqueous layer was extracted with DCM (2×15 mL), all organic layers were combined, washed with brine, dried ($MgSO_4$), filtered and concentrated to leave a brown oil that solidified under vacuum. This was adsorbed to silica and purified by FC (12 g silica, 0% to 100% DCM in hexanes) to provide intermediate AE (150 mg, 31%) as a white powder. LRMS-HESI: calculated for $C_{12}H_{14}FN_2$ $(M+H)^+$ 205.11 m/z, observed 205.13 m/z. (FIG. 17A, see: further also chemical reaction (a) in FIG. 3B).

Figure 17B:
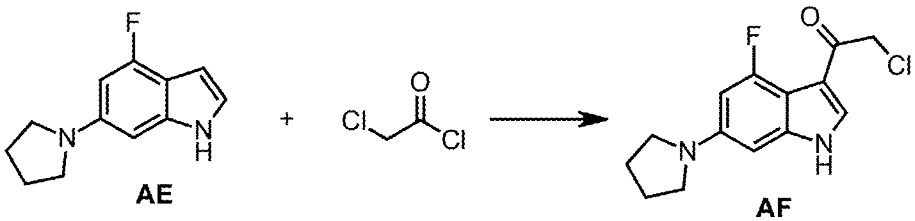

Referring next to FIG. 17B, to a stirring solution of aluminum chloride (195 mg, 1.44 mmol) in dry DCM (2.83 mL), under nitrogen atmosphere, was added chloroacetyl chloride (119 μL, 1.46 mmol) in dry DCM (2.83 mL). After 30 minutes, a solution of intermediate AE (130 mg, 636 μmol) in dry DCM (2.83 mL) was added dropwise, and the resulting mixture stirred for 24 h. The precipitated product was scraped off the side of the reaction vial, and the resulting mixture quenched by pouring over ice-water (200 mL), which once melted was transferred to a separatory funnel and extracted with ethyl acetate (3×50 mL). The combined organic extracts were washed with saturated sodium bicarbonate, brine and then dried over anhydrous magnesium sulphate. Concentration of the resulting solution resulted in isolation of crude intermediate AF (170 mg, 95%) which was used in the next step without further purification. LRMS-HESI: calculated for $C_{14}H_{15}ClFN_2O$ $(M+H)^+$ 281.09 m/z, observed 205.13 m/z. (FIG. 17B, see: further also chemical reaction (o) in FIG. 3B).

Figure 17C:
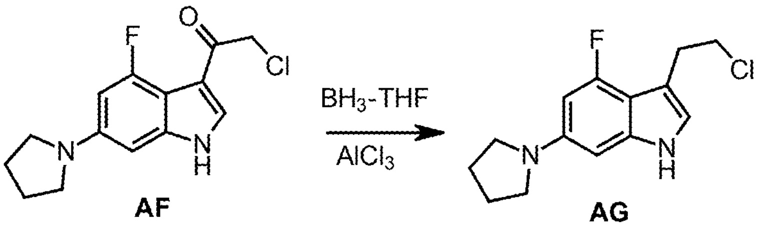

Referring next to FIG. 17C, to a suspension of aluminum chloride (242 mg, 1.82 mmol) in dry DCM (6.06 mL) at 0° C. under nitrogen atmosphere was added 1 M borane-THF in THE (3.63 mL, 3.63 mmol), and the resulting solution was stirred for 10 minutes. Added to this was a solution of intermediate AF (170 mg, 606 μmol) in dry DCM (6.06 mL) and the resulting mixture stirred at 0° C. for 3 hrs. The reaction mixture, at 0° C., was quenched through addition of water (9 mL) and 1 M HCl (1 mL). The biphasic mixture was poured into a separatory funnel containing water (50 mL) and ethyl acetate (30 mL), and the aqueous phase was extracted (3×30 mL ethyl acetate). The combined organic extracts were washed with brine (30 mL), dried over anhydrous magnesium sulphate, and concentrated under reduced pressure to yield intermediate AG (120 mg, 74%) as an amber oil. This was used in the next step with no further purification. LRMS-HESI: calculated for $C_{14}H_{17}ClFN_2$ $(M+H)^+$ 267.11 m/z, observed 267.14 m/z. (FIG. 17C, see: further also chemical reaction (p) in FIG. 3B).

Figure 17D:
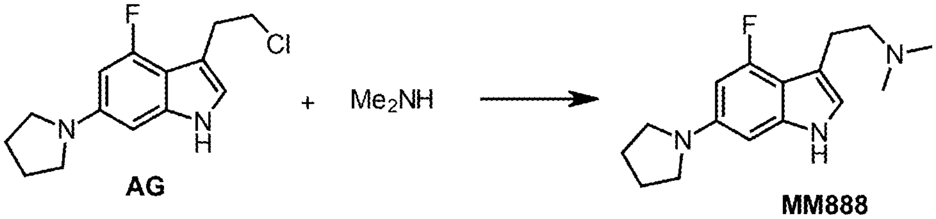

Referring next to FIG. 17D, to a solution of crude intermediate AG (120 mg, 450 μmol) in dry DMF (9.00 mL), under nitrogen atmosphere, was added 2 M dimethylamine in THE (2.09 mL, 4.18 mmol) along with potassium carbonate (187 mg, 1.35 mmol) and potassium carbonate (161 mg, 1.35 mmol). The reaction mixture heated to 50° C. for 22 hrs. After cooling to room temperature, the reaction mixture was poured into a separatory funnel containing water (200 mL) and ethyl acetate (50 mL) and the aqueous phase was extracted with ethyl acetate (5×100 mL). The combined organic extracts were washed with water (5×100 mL), brine (50 mL), dried over anhydrous magnesium sulphate and concentrated under reduced pressure. The resulting crude mixture was purified by FC (12 g silica, 0% to 30% MeOH in DCM) to provide MM888 (18.5 mg, 15%) as a light brown solid. LRMS-HESI: calculated for $C_{16}H_{23}FN_3$ $(M+H)^+$ 276.19 m/z, observed 320.21 m/z. $^1H$ NMR (400 MHz, $CDCl_3$) δ 7.71 (s, 1H), 6.73 (dt, J=2.0, 0.9 Hz, 1H), 6.26-6.18 (m, 2H), 3.33-3.24 (m, 4H), 3.01-2.93 (m, 2H), 2.69-2.62 (m, 2H), 2.36 (s, 6H), 2.07-2.00 (m, 4H).

(FIG. 17D, see: further also chemical reaction (q) in FIG. 3B).

It is noted that MM888 corresponds with chemical compound (XVIII):

(XVIII)

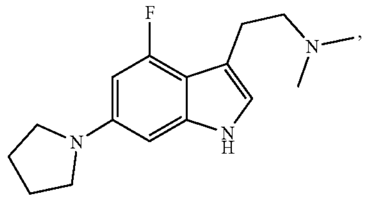

set forth herein.

5-HT Receptor Radioligand Competition Assays.

Competition assays at the 5-$HT_{1A}$ receptor were performed as described in Example 11, except compound with formula (XVIII) was used in place of compound with formula (XV). Resulting $K_i$ data for controls and test compounds in 5-$HT_{1A}$ receptor binding assays, including data acquired for compound with formula (XVIII), are summarized in Table 1. Compound with formula (XVIII) (designated 'XVIII' in Table 1) exhibited a $K_i$ value of 18.1 μM at the 5-$HT_{1A}$ receptor. This $K_i$ value was less than those of negative controls (i.e., $K_i$<1000 μM) and hence suggested binding by compound with formula (XVIII) at this receptor. Competition assays at the 5-$HT_{2A}$ receptor were performed as described in Example 11, except compound with formula (XVIII) was used in place of compound with formula (XV). Resulting $K_i$ data for controls and test compounds in 5-$HT_{2A}$ receptor binding assays, including data acquired for compound with formula (XVIII), are summarized in Table 2. Compound with formula (XVIII) (designated 'XVIII' in Table 2) exhibited a $K_i$ value of 6.13 μM at the 5-$HT_{2A}$ receptor. This $K_i$ value was less than those of negative controls (i.e., $K_i$<1000 μM) and hence suggested binding by compound with formula (XVIII) at this receptor.

5-HT Transporter (SERT) Radioligand Competition Assay.

Binding assays at SERT were performed as described in Example 11, except compound with formula (XVIII) was used in place of compound with formula (XV). Resulting $K_i$ data for controls and test compounds in SERT binding assays, including data acquired for compound with formula (XVIII), are summarized in Table 3. Compound with formula (XVIII) (designated 'XVIII' in Table 3) exhibited a $K_i$ value of 39.2 μM at SERT. This $K_i$ value was less than those of negative controls (i.e., $K_i$<1000 μM) and hence suggested binding by compound with formula (XVIII) at this transporter.

Neuroplastogenicity Assays.

Assays to reveal potential of drugs to enhance neurite outgrowth in human model (NT2) neurons were conducted as described in Example 11, except that compound with formula (XVIII) was used in place of compound with formula (XV). Results of visual inspection are summarized in Table 4, where (1) (+) designates strong evidence of enhanced neurite outgrowth in drug-treated NT2 cells compared to vehicle-treated cells, and (2) (−) designates weak or no evidence of enhanced neurite outgrowth in drug-treated NT2 cells compared to vehicle-treated cells. Similar to the effects imparted by positive controls and compound with formula (XV) (FIG. 37A), human model (NT2) neurons incubated with 1 μM or 10 μM compound (XVIII) grew larger in size and displayed greater overall neurite outgrowth compared with vehicle-treated (0.1% DMSO) human model neurons. These observations are summarized as a (+) designation in Table 4.

Mouse Head Twitch Response (HTR) Assay to Assess Hallucinogenic Potential.

Head Twitch Response (HTR) assays were conducted as described in Example 11, except that compound with formula (XVIII) was used in place of compound with formula (XV). FIG. 38A shows HTR assay results for all drugs administered at 3 mg/kg (preliminary screening). Results show high hallucinogenic potential (mean HTR≥10) for positive controls (hatched bars; psilocin, DMT, 5-MeO-DMT). In contrast, low/no hallucinogenic potential (mean HTR≤5) is observed for negative controls (white bars; 5-Br-DMT, TBG, 6-F-DET). Mean HTR between 10 and 5 signifies reduced hallucinogenic potential relative to positive controls. Compound (XVIII) has a mean HTR of 5.25, suggesting reduced hallucinogenic potential relative to positive controls. FIG. 38B shows HTR assay results for selected drugs administered at increasing doses (0.5-10 mg/kg). Results reveal that HTR for compound (XVIII) steadily increases to >20 HTR at maximum (10 mg/kg) dose. This result suggests hallucinogenic potential as dosage increases to 10 mg/kg.

Mouse Plasma Pharmacokinetics (PK) Survey.

A pharmacokinetics (PK) survey was performed as described in Example 11, except that compound with formula (XVIII) was used in place of compound with formula (XV). Calculated parameters for compound with formula (XVIII) and other drugs are listed in Table 5. Systemic exposure ($AUC_{t0\text{-}tlast}$) was determined to be 19.6±0.7 hr*ng/mL for cohorts administered 4 mg/kg Compound (XVIII), whereas those administered 10 mg/kg exhibited a mean exposure of 76.4±11.5 hr*ng/mL. Further, $C_{max}$ was determined to be 8.8±1.2 ng/mL and 87.5±8.5 ng/mL for cohorts administered 4 and 10 mg/kg Compound (XVIII), respectively.

Figure 18:
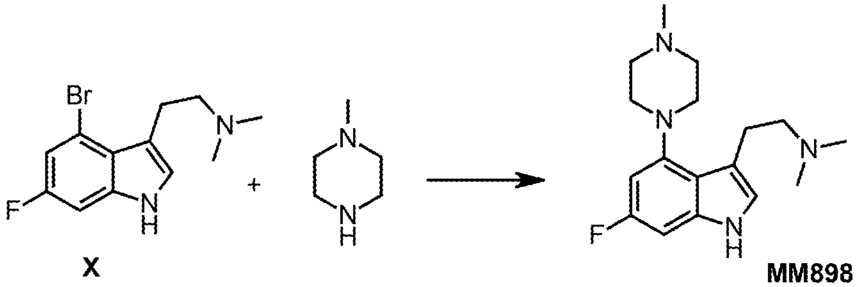
FIG. 18 depicts a further example reaction in another example chemical synthesis pathway for the synthesis of another example compound according to the present disclosure.

Example 15—Synthesis and Analysis of a Fifteenth N-Heterocycle Substituted Tryptamine Derivative Referring to FIG. 18, in a dry vial under nitrogen atmosphere was dissolved intermediate X (50.0 mg, 175 μmol), prepared as described in Example 11, $Pd_2(dba)_3$ (16.6 mg, 17.5 μmol), and DavePhos (16.6 mg, 42.1 μmol) in THE (390 μL). To this stirring solution was added 1 M LiHMDS in THE (386 μL, 386 μmol) and 1-methylpiperazine (99 μL, 1.0 mmol). The mixture was degassed for a few minutes and was stirred at 60° C. for 17 hrs. The mixture was cooled to room temperature and poured into a separatory funnel containing DCM and water. The aqueous layer was extracted with DCM (×3), all organic layers were combined, washed with brine, dried ($Na_2SO_4$), filtered and concentrated. The crude residue was purified by FC (4 g silica, 0% to 25% MeOH in DCM) to provide MM898 (20 mg, 37%) as an orange oil. LRMS-HESI: calculated for $C_{17}H_{26}FN_4$ $(M+H)^+$ 305.21 m/z, observed 305.72 m/z. $^1H$ NMR (400 MHz, $CDCl_3$) δ 8.24 (s, 1H), 6.92-6.90 (m, 1H), 6.70 (dd, J=8.9, 0.6 Hz, 1H), 6.55 (dd, J=11.6, 2.2 Hz, 1H), 3.20-2.93 (m, 6H), 2.81-2.53 (m, 6H), 2.38 (s, 3H), 2.34 (s, 6H). (FIG. 18, see: further also chemical reaction (g) in FIG. 3B).

It is noted that MM898 corresponds with chemical compound (XIX):

(XIX)

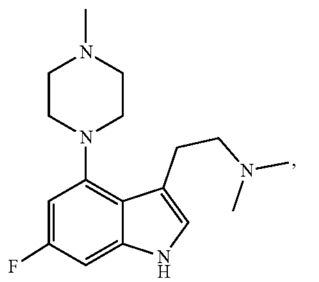

set forth herein.

Mouse Head Twitch Response (HTR) Assay to Assess Hallucinogenic Potential.

Head Twitch Response (HTR) assays were conducted as described in Example 11, except that compound with formula (XIX) was used in place of compound with formula (XV). FIG. 38A shows HTR assay results for all drugs administered at 3 mg/kg (preliminary screening). Results show high hallucinogenic potential (mean HTR≥10) for positive controls (hatched bars; psilocin, DMT, 5-MeO-DMT). In contrast, low/no hallucinogenic potential (mean HTR≤5) is observed for negative controls (white bars; 5-Br-DMT, TBG, 6-F-DET). Mean HTR between 10 and 5 signifies reduced hallucinogenic potential relative to positive controls. Compound (XIX) has a mean HTR of 11.5, suggesting high hallucinogenic potential similar to the positive controls.

Figure 19A:
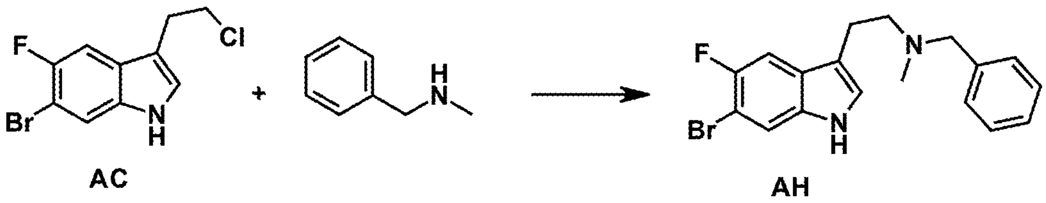
FIGS. 19A and 19B depict further example reactions in another example chemical synthesis pathway for the synthesis of another example compound according to the present disclosure.

Example 16—Synthesis and Analysis of a Sixteenth N-Heterocycle Substituted Tryptamine Derivative Referring to FIG. 19A, the ethyl chloride, intermediate AC (550 mg, 1.99 mmol), prepared as described in Example 13, was dissolved in DMF (28.9 mL). Added to this was N-benzylmethylamine (1.34 mL, 10.0 mmol) and then potassium carbonate (825 mg, 5.97 mmol) and potassium bromide (710 mg, 5.97 mmol). The mixture was heated to 40° C. and left to stir at this temperature overnight. After 20 hrs the mixture contained predominantly the desired product as determined by LCMS. The mixture was poured into a separatory funnel containing 50 mL water and 50 mL ethyl acetate. The aqueous layer was extracted with ethyl acetate (3×40 mL), all organic layers were combined, washed with water (4×40 mL), brine (2×40 mL), dried ($MgSO_4$) filtered and concentrated to leave a brown oil. This was purified by column chromatography (12 g silica, DCM to DCM:MeOH 9:1), to provide intermediate AH (357 mg, 50%) as a brown solid. LRMS-HESI: calculated for $C_{18}H_{19}BrFN_2$ $(M+H)^+$ 361.07 m/z, observed 361.14 m/z. (FIG. 19A, see: further also chemical reaction (f) in FIG. 3B).

Figure 19B:
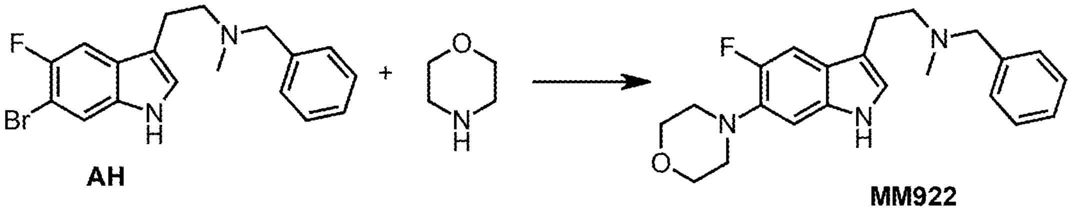

Referring next to FIG. 19B, in an oven-dried vial, under nitrogen atmosphere, was dissolved intermediate AH (80.0 mg, 221 μmol), $Pd_2(dba)_3$ (20.9 mg, 22.1 μmol), and DavePHOS (20.9 mg, 53.1 μmol) in dry THE (457 μL). To this stirring solution was added 1 M LiHMDS in THE (492 μL, 492 μmol) and morpholine (65.0 μL, 735 μmol). The reaction mixture was heated to 60° C. overnight. After 18 hours, IPC was run via LCMS and the reaction was determined to be complete. The mixture was cooled to room temperature and poured into a separatory funnel containing DCM (15 mL) and water (15 mL). The aqueous layer was extracted with DCM (2×15 mL), all organic layers were combined, washed with brine, dried ($MgSO_4$), filtered and concentrated to leave a brown oil. This was purified by FC (4 g silica, DCM to DCM:MeOH 9:1) to obtain MM922 (36.8 mg, 45%) as a brown oil. LRMS-HESI: calculated for $C_{22}H_{27}FN_{30}$ $(M+H)^+$ 368.21 m/z, observed 368.20 m/z. $^1H$ NMR (400 MHz, $CDCl_3$) δ 7.96 (s, 1H), 7.35-7.30 (m, 4H), 7.28-7.24 (m, 1H), 7.16 (d, J=12.7 Hz, 1H), 6.95 (m, 1H), 6.89 (d, J=7.1 Hz, 1H), 3.92-3.90 (m, 4H), 3.61 (s, 2H), 3.07-3.05 (m, 4H), 2.94-2.90 (m, 2H), 2.75-2.71 (m, 2H), 2.34 (s, 3H). (FIG. 19B, see: further also chemical reaction (g) in FIG. 3B).

It is noted that MM922 corresponds with chemical compound (XX):

(XX)

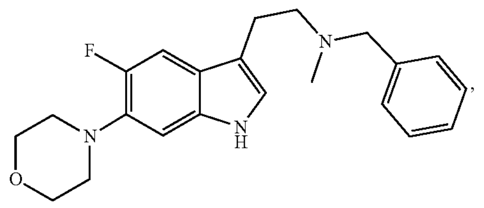

set forth herein.

5-HT Receptor Radioligand Competition Assay.

Competition assays at the $5\text{-}HT_{2A}$ receptor were performed as described in Example 11, except compound with formula (XX) was used in place of compound with formula (XV). Resulting $K_i$ data for controls and test compounds in $5\text{-}HT_{2A}$ receptor binding assays, including data acquired for compound with formula (XX), are summarized in Table 2. Compound with formula (XX) (designated 'XX' in Table 2) exhibited a $K_i$ value of 25.6 μM at the $5\text{-}HT_{2A}$ receptor. This $K_i$ value was less than those of negative controls (i.e., $K_i$<1000 μM) and hence suggested binding by compound with formula (XX) at this receptor.

Neuroplastogenicity Assays.

Assays to reveal potential of drugs to enhance neurite outgrowth in human model (NT2) neurons were conducted as described in Example 11, except that compound with formula (XX) was used in place of compound with formula (XV). Results of visual inspection are summarized in Table 4, where (1) (+) designates strong evidence of enhanced neurite outgrowth in drug-treated NT2 cells compared to vehicle-treated cells, and (2) (−) designates weak or no evidence of enhanced neurite outgrowth in drug-treated NT2 cells compared to vehicle-treated cells. Similar to the effects imparted by positive controls and compound with formula (XV) (FIG. 37A), human model (NT2) neurons incubated with 1 μM or 10 μM compound (XX) grew larger in size and displayed greater overall neurite outgrowth compared with vehicle-treated (0.1% DMSO) human model neurons. These observations are summarized as a (+) designation in Table 4.

Mouse Head Twitch Response (HTR) Assay to Assess Hallucinogenic Potential.

Head Twitch Response (HTR) assays were conducted as described in Example 11, except that compound with formula (XX) was used in place of compound with formula (XV). FIG. 38A shows HTR assay results for all drugs administered at 3 mg/kg (preliminary screening). Results show high hallucinogenic potential (mean HTR≥10) for positive controls (hatched bars, psilocin, DMT, 5-MeO-DMT). In contrast, low/no hallucinogenic potential (mean HTR≤5) is observed for negative controls (white bars, 5-Br-DMT, TBG, 6-F-DET). Mean HTR between 10 and 5 signifies reduced hallucinogenic potential relative to positive controls. Compound (XX) has a mean HTR of 7.25, suggesting reduced hallucinogenic potential relative to positive controls.

Figure 20A:
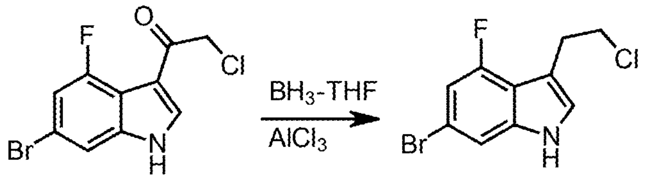
FIGS. 20A, 20B, and 20C depict further example reactions in an example chemical synthesis pathway for the synthesis of a certain example compound according to the present disclosure.

Example 17—Synthesis and Analysis of a Seventeenth N-Heterocycle Substituted Tryptamine Derivative Referring to FIG. 20A, to a suspension of aluminum chloride (2.30 g, 17.1 mmol) and intermediate Y (4.96 g, 17.1 mmol), prepared as in Example 12, in DCM (50 mL), at 0° C. was added 1 M borane-THF complex in THE (34.1 mL, 34.1 mmol). Once the addition was complete and the initial vigorous bubbling had subsided, the temperature was increased to room temperature and stirring was continued. After 100 minutes, LCMS determined that there was no longer any starting material present and the reaction was cooled back down to 0° C. prior to careful quenching with 50 mL of dilute HCl solution (12 mL of 1 M HCl diluted to 50 mL with water). This mixture was poured into a separatory funnel and the organic layer was separated from the aqueous layer. The aqueous phase was extracted with DCM (3×20 mL). All organic layers were combined, washed with water, washed with brine, dried ($MgSO_4$), filtered and concentrated to leave intermediate AI (4.70 g, 100%) as viscous oil. This was used in the next step without further purification. (FIG. 20A, see: further also chemical reaction (e) in FIG. 3B).

Figure 20B:
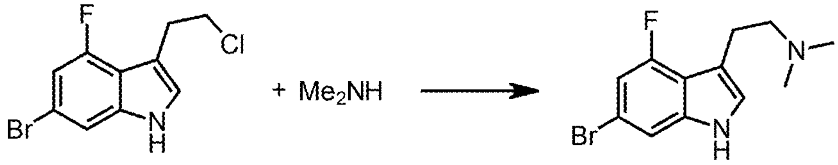

Referring next to FIG. 20B, the ethyl chloride intermediate AI (785 mg, 2.84 mmol) was dissolved in DMF (41.2 mL). Added to this was 2 M dimethylamine in THE (7.14 mL, 14.3 mmol) and then potassium carbonate (1.18 g, 8.52 mmol) and potassium bromide (1.01 g, 8.52 mmol). The mixture was heated to 40° C. and left to stir at this temperature overnight. After 20 hrs the mixture contained predominantly the desired product as determined by LCMS. The mixture was poured into a separatory funnel containing 50 mL water and 50 mL ethyl acetate. The aqueous layer was extracted with ethyl acetate (3×40 mL), all organic layers were combined, washed with water (4×40 mL), brine (2×40 mL), dried ($MgSO_4$) filtered and concentrated to leave a red solid. The material was purified by column chromatography (12 g silica, 0% to 20% MeOH in DCM) to leave intermediate AJ (542 mg, 65%) as a white solid. LRMS-HESI: calculated for $C_{12}H_{15}BrFN_2$ $(M+H)^+$ 285.04 m/z, observed 285.05 m/z. (FIG. 20B, see: further also chemical reaction (f) in FIG. 3B).

Figure 20C:
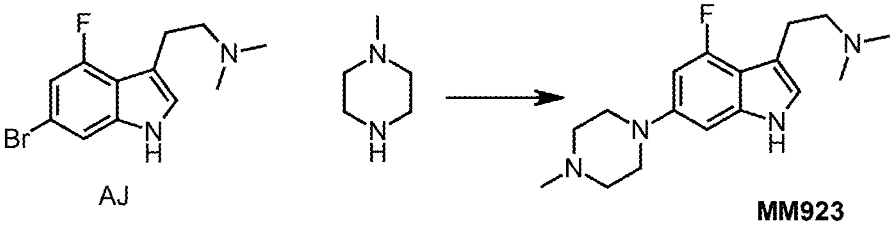

Referring next to FIG. 20C, in a dry vial under nitrogen atmosphere was dissolved intermediate AJ (75.0 mg, 263 μmol), Pd2(dba)3 (24.8 mg, 26.3 μmol), and DavePhos (24.8 mg, 63.1 μmol) in THE (584 μL). To this stirring solution was added 1 M LiHMDS in THE (579 μL, 579 μmol) and 1-methylpiperazine (175 μL, 1.58 mmol). The temperature was increased to 60° C. and stirring was continued for 18 hrs. LCMS at 90 minutes suggested that the reaction was complete, however, the mixture was left to stir overnight. In the morning the mixture was cooled to room temperature and poured into a separatory funnel containing DCM and water. The aqueous layer was extracted with DCM (×3), all organic layers were combined, washed with brine, dried ($MgSO_4$), filtered and concentrated. The crude residue was purified by FC on silica gel (4 g silica, DCM:MeOH 100:0 to 70:30) to provide MM923 (36.6 mg, 46%) as a light brown solid. LRMS-HESI: calculated for $C_{17}H_{26}FN_4$ $(M+H)^+$305.21 m/z, observed 305.23 m/z. $^1H$ NMR (400 MHz, $CDCl_3$) δ 8.26 (s, 1H), 6.80-6.79 (m, 1H), 6.55 (d, J=1.8 Hz, 1H), 6.50 (dd, J=13.8, 1.8 Hz, 1H), 3.16-3.14 (m, 4H), 2.98-2.94 (m, 2H), 2.65-2.57 (m, 6H), 2.36 (s, 3H), 2.33 (s, 6H). (FIG. 20C, see: further also chemical reaction (g) in FIG. 3B).

It is noted that MM923 corresponds with chemical compound (XXI):

(XXI)

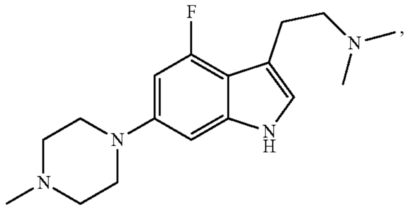

set forth herein.

Mouse Head Twitch Response (HTR) Assay to Assess Hallucinogenic Potential.

Head Twitch Response (HTR) assays were conducted as described in Example 11, except that compound with formula (XXI) was used in place of compound with formula (XV). FIG. 38A shows HTR assay results for all drugs administered at 3 mg/kg (preliminary screening). Results show high hallucinogenic potential (mean HTR≥10) for positive controls (hatched bars; psilocin, DMT, 5-MeO-DMT). In contrast, low/no hallucinogenic potential (mean HTR≤5) is observed for negative controls (white bars; 5-Br-DMT, TBG, 6-F-DET). Mean HTR between 10 and 5 signifies reduced hallucinogenic potential relative to positive controls. Compound (XXI) has a mean HTR of 9.25, suggesting marginally reduced hallucinogenic potential compared to the positive controls.

Figure 21A:
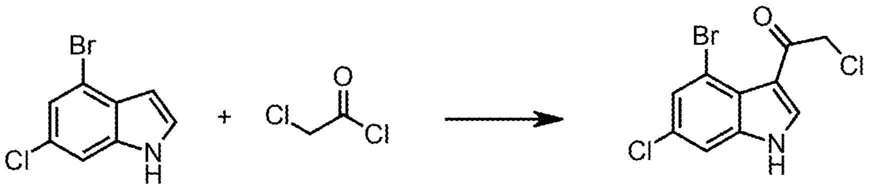
FIGS. 21A, 21B, 21C, and 21D depict further example reactions in an example chemical synthesis pathway for the synthesis of a certain example compound according to the present disclosure.

Example 18—Synthesis and Analysis of an Eighteenth N-Heterocycle Substituted Tryptamine Derivative Referring to FIG. 21A, to a stirring solution of aluminum chloride (1.31 g, 9.76 mmol) in DCM (21.7 mL) under nitrogen atmosphere was added chloroacetyl chloride (0.79 mL, 12.6 mmol) in DCM (28.1 mL) and stirred for 30 min. At this juncture, a solution of 4-bromo-6-chloro-1H-indole (1.50 g, 9.76 mmol) in DCM (56.1 mL) was added dropwise via addition funnel, and the resulting mixture stirred for 20 hrs. The reaction mixture was quenched by pouring over ice-water (200 mL), agitating thoroughly, filtering the resulting precipitate (sintered glass), and washing with saturated sodium bicarbonate and water. After drying, intermediate AK (845 mg, 42%) was collected as a beige solid. This material was used in the next step without further purification. LRMS-HESI: calculated for $C_{10}H_7BrCl_2NO$ $(M+H)^+$ 305.91 m/z, observed 305.95 m/z. (FIG. 21A, see: further also chemical reaction (d) in FIG. 3B).

Figure 21B:
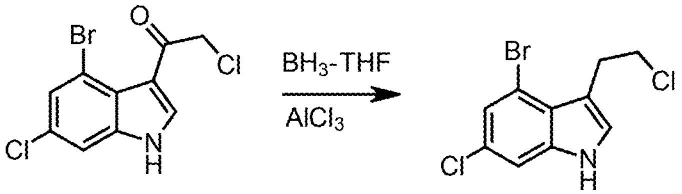

Referring next to FIG. 21B, to a suspension of aluminum chloride (1.10 g, 8.26 mmol) in dry DCM (24.0 mL) at 0° C., under nitrogen atmosphere, was added 1 M borane-THF complex in THE (16.5 mL, 16.5 mmol), and the resulting solution was stirred for 10 minutes. A suspension of intermediate AK (845 mg, 2.75 mmol) in dry DCM (16.0 mL) was added, and the resulting mixture was stirred at 0° C. for 3 hrs. The reaction mixture, at 0° C., was quenched through addition of water (20 mL) and 1 M HCl (20 mL). The biphasic mixture was poured into a separatory funnel containing water and DCM. The layers were separated and the aqueous phase was extracted with DCM (×3). The combined organic layers were washed with brine, dried over anhydrous sodium sulfate, and concentrated under reduced pressure to yield intermediate AL (798 mg, 99%) as a yellow solid which was used in the next step without further purification. (FIG. 21B, see: further also chemical reaction (e) in FIG. 3B).

Figure 21C:
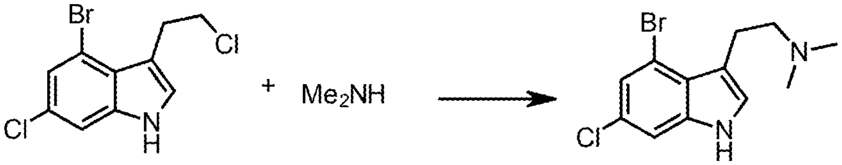

Referring next to FIG. 21C, to a solution of intermediate AL (798 mg, 2.72 mmol) in dry ACN (14.2 mL) were added potassium bromide (972 mg, 8.17 mmol) and potassium carbonate (753 mg, 5.45 mmol) followed by 2 M dimethylamine in THE (12.3 mL, 24.5 mmol). The resulting mixture was stirred at 70° C. for 18 hrs. The solids were filtered and washed with DCM, the solvent was removed under reduced pressure, and the remaining residue was purified by FC (25 g silica, 0% to 20% MeOH in DCM) to provide intermediate AM (450 mg, 55%) as a beige solid. LRMS-HESI: calculated for $C_{12}H_{15}BrClN_2$ $(M+H)^+$301.01 m/z, observed 300.99 m/z. (FIG. 21C, see: further also chemical reaction (f) in FIG. 3B).

Figure 21D:
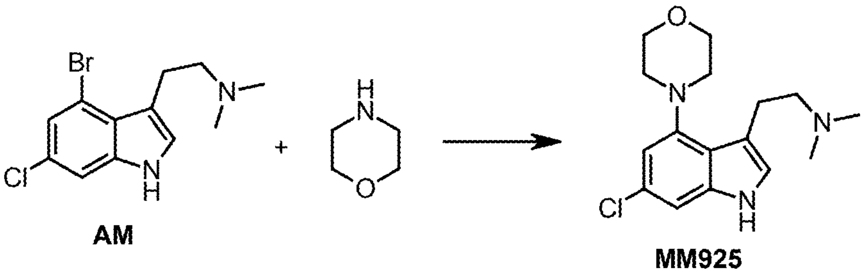

Referring next to FIG. 21D, in a dry vial under nitrogen atmosphere was dissolved intermediate AM (50.0 mg, 166 μmol), $Pd_2(dba)_3$ (15.6 mg, 16.6 μmol), and DavePHOS (15.7 mg, 39.8 μmol) in THE (368 μL). To this stirring solution was added 1 M LiHMDS (365 μL, 365 μmol) and morpholine (87.9 μL, 995 μmol). The reaction mixture was heated to 60° C. for 22 hrs. The mixture was cooled to room temperature and poured into a separatory funnel containing DCM and water. The aqueous layer was extracted with DCM (×3), all organic layers were combined, washed with brine, dried ($Na_2SO_4$), filtered and concentrated. The crude residue was purified by FC (12 g silica, 0% to 20% MeOH in DCM) to provide MM925 (31.2 mg, 61%) as a yellow solid. LRMS-HESI: calculated for $C_{16}H_{23}ClN_3O$ $(M+H)^+$ 308.15 m/z, observed 308.14 m/z. $^1H$ NMR (400 MHz, $CDCl_3$) δ 8.40 (s, 1H), 6.97 (t, J=1.9 Hz, 1H), 6.94-6.92 (m, 1H), 6.71 (d, J=1.7 Hz, 1H), 3.95-3.90 (m, 4H), 3.70-3.67 (m, 2H), 3.09-3.06 (m, 2H), 2.89-2.86 (m, 2H), 2.68 (dd, J=8.6, 6.8 Hz, 2H), 2.34 (s, 6H). (FIG. 21D, see: further also chemical reaction (g) in FIG. 3B).

It is noted that MM925 corresponds with chemical compound (XXII)

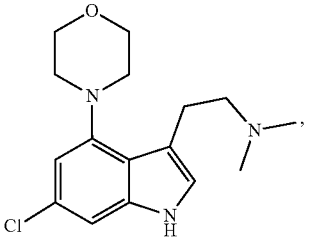

set forth herein.

Mouse Head Twitch Response (HTR) Assay to Assess Hallucinogenic Potential.

Head Twitch Response (HTR) assays were conducted as described in Example 11, except that compound with formula (XXII) was used in place of compound with formula (XV). FIG. 38A shows HTR assay results for all drugs administered at 3 mg/kg (preliminary screening). Results show high hallucinogenic potential (mean HTR≥10) for positive controls (hatched bars; psilocin, DMT, 5-MeO-DMT). In contrast, low/no hallucinogenic potential (mean HTR≤5) is observed for negative controls (white bars; 5-Br-DMT, TBG, 6-F-DET). Mean HTR between 10 and 5 signifies reduced hallucinogenic potential relative to positive controls. Compound (XXII) has a mean HTR of 6.5, suggesting reduced hallucinogenic potential compared to the positive controls.

Figure 22:
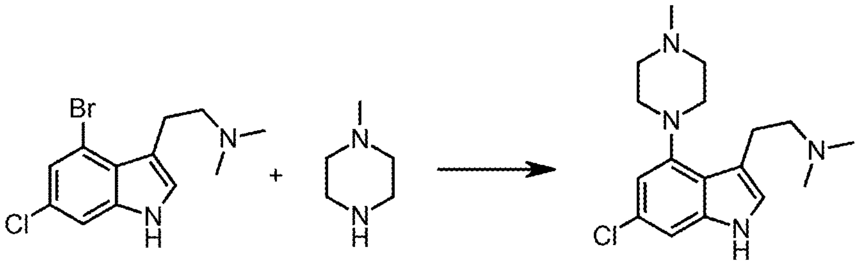
FIG. 22 depicts a further example reaction in another example chemical synthesis pathway for the synthesis of another example compound according to the present disclosure.

Example 19—Synthesis and Analysis of a Nineteenth N-Heterocycle Substituted Tryptamine Derivative Referring to FIG. 22, in a dry vial under nitrogen atmosphere was dissolved intermediate AM (50.0 mg, 166 μmol), prepared as described in Example 18, $Pd_2(dba)_3$ (15.6 mg, 16.6 μmol), and DavePhos (15.7 mg, 39.8 μmol) in THE (368 μL). To this stirring solution was added 1 M LiHMDS in THE (365 μL, 365 μmol) and 1-methylpiperazine (110 μL, 995 μmol). The mixture was degassed for a few minutes and was stirred at 60° C. for 22 hrs. At this point LCMS demonstrated that the reaction had stalled at 50% desired product and 50% starting material along with other byproducts. The mixture was cooled to room temperature and poured into a separatory funnel containing DCM and water. The aqueous layer was extracted with DCM (×3), all organic layers were combined, washed with brine, dried ($Na_2SO_4$), filtered and concentrated. Purification was carried out using two FC columns (column 1 conditions: solid loading—12 g—Solvent A/Solvent B 0:100 to 30:70, product eluting at 20% A—Solvent A: 10% NH4OH/MeOH—Solvent B: DCM) (column 2 conditions: solid loading—4 g—Solvent A/Solvent B 0:100 to 30:70, product did NOT elute—Solvent A: MeOH—Solvent B: DCM—solvent A was switched to 10% NH4OH/MeOH and the column was washed with 30% A). This purification resulted in isolation of MM973 (9.5 mg, 18%) as an orange/brown oil. LRMS-HESI: calculated for $C_{17}H_{26}ClN_4$ $(M+H)^+$ 321.18 m/z, observed 321.24 m/z. $^1H$ NMR (400 MHz, $CDCl_3$) δ 8.39 (s, 1H), 6.96-6.94 (m, 1H), 6.93-6.90 (m, 1H), 6.70 (d, J=1.7 Hz, 1H), 3.20-2.95 (m, 6H), 2.82-2.52 (m, 6H), 2.38 (s, 3H), 2.34 (s, 6H). (FIG. 22, see: further also chemical reaction (g) in FIG. 3B).

It is noted that MM973 corresponds with chemical compound (XXIII):

(XXIII)

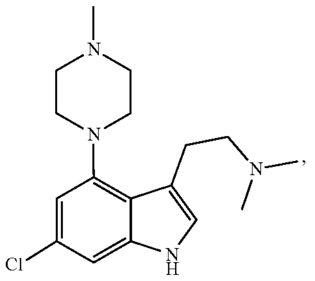

set forth herein.

5-HT Receptor Radioligand Competition Assay.

Competition assays at the $5\text{-}HT_{2A}$ receptor were performed as described in Example 11, except compound with formula (XXIII) was used in place of compound with formula (XV). Resulting $K_i$ data for controls and test compounds in $5\text{-}HT_{2A}$ receptor binding assays, including data acquired for compound with formula (XXIII), are summarized in Table 2. Compound with formula (XXIII) (designated 'XXIII' in Table 2) exhibited a $K_i$ value of 12.5 μM at the 5-$HT_{2A}$ receptor. This $K_i$ value was less than those of negative controls (i.e., $K_i$<1000 μM) and hence suggested binding by compound with formula (XXIII) at this receptor.

Neuroplastogenicity Assays.

Assays to reveal potential of drugs to enhance neurite outgrowth in human model (NT2) neurons were conducted as described in Example 11, except that compound with formula (XXIII) was used in place of compound with formula (XV). Results of visual inspection are summarized in Table 4, where (1) (+) designates strong evidence of enhanced neurite outgrowth in drug-treated NT2 cells compared to vehicle-treated cells, and (2) (−) designates weak or no evidence of enhanced neurite outgrowth in drug-treated NT2 cells compared to vehicle-treated cells. Similar to the effects imparted by positive controls and compound with formula (XV) (FIG. 37A), human model (NT2) neurons incubated with 1 μM or 10 μM compound (XXIII) grew larger in size and displayed greater overall neurite outgrowth compared with vehicle-treated (0.1% DMSO) human model neurons. These observations are summarized as a (+) designation in Table 4.

Mouse Head Twitch Response (HTR) Assay to Assess Hallucinogenic Potential.

Head Twitch Response (HTR) assays were conducted as described in Example 11, except that compound with formula (XXIII) was used in place of compound with formula (XV). FIG. 38A shows HTR assay results for all drugs administered at 3 mg/kg (preliminary screening). Results show high hallucinogenic potential (mean HTR≥10) for positive controls (hatched bars; psilocin, DMT, 5-MeO-DMT). In contrast, low/no hallucinogenic potential (mean HTR≤5) is observed for negative controls (white bars; 5-Br-DMT, TBG, 6-F-DET). Mean HTR between 10 and 5 signifies reduced hallucinogenic potential relative to positive controls. Compound (XXIII) has a mean HTR of 7.25, suggesting reduced hallucinogenic potential relative to positive controls.

Figure 23A:
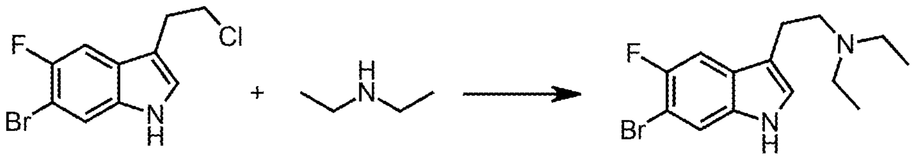
FIGS. 23A and 23B depict further example reactions in another example chemical synthesis pathway for the synthesis of another example compound according to the present disclosure.

Example 20—Synthesis and Analysis of a Twentieth N-Heterocycle Substituted Tryptamine Derivative Referring to FIG. 23A, the ethyl chloride, intermediate AC (300 mg, 1.08 mmol), prepared as described in Example 13, was dissolved in DMF (15.8 mL). Added to this was diethylamine (564 μL, 5.42 mmol) and then potassium carbonate (450 mg, 3.25 mmol) and potassium bromide (387 mg, 3.25 mmol). The mixture was heated to 40° C. and left to stir at this temperature overnight. After 22 hrs the mixture contained predominantly the desired product as determined by LCMS. The mixture was poured into a separatory funnel containing 50 mL water and 50 mL ethyl acetate. The aqueous layer was extracted with ethyl acetate (3×40 mL), all organic layers were combined, washed with water (4×40 mL), brine (2×40 mL), dried ($MgSO_4$) filtered and concentrated to leave a brown oil. This was purified by column chromatography (12 g silica, DCM to DCM:MeOH 9:1) to provide intermediate AN (135 mg, 40%) as a light brown solid. LRMS-HESI: calculated for $C_{14}H_{19}BrFN_2$ $(M+H)^+$ 313.07 m/z, observed 313.10 m/z. (FIG. 23A, see: further also chemical reaction (f) in FIG. 3B).

Figure 23B:
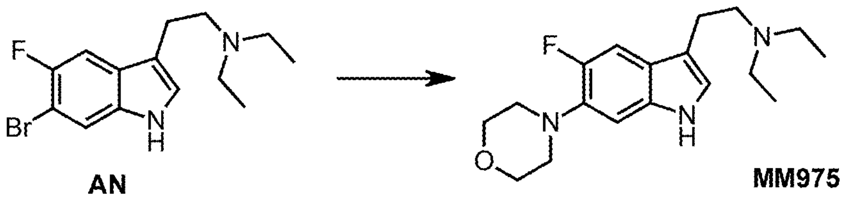

Referring next to FIG. 23B, in an oven-dried vial under nitrogen atmosphere was dissolved intermediate AN (61.0 mg, 195 μmol), $Pd_2(dba)_3$ (18.4 mg, 19.5 μmol), and DavePHOS (18.4 mg, 46.7 μmol) in dry THE (404 μL). To this stirring solution was added 1 M LiHMDS in THE (428 μL, 428 μmol) and morpholine (101 μL, 1.14 mmol). The reaction mixture was heated to 60° C. overnight. After 18 hours, IPC was run via LCMS and the reaction was determined to be complete. The mixture was cooled to room temperature and poured into a separatory funnel containing DCM (15 mL) and water (15 mL). The aqueous layer was extracted with DCM (2×15 mL), all organic layers were combined, washed with brine, dried ($MgSO_4$), filtered and concentrated to leave a brown solid. Purification was carried out by column chromatography (4 g silica, DCM:MeOH 100:0 to 80:20) to provide MM975 (17.0 mg, 27%), as light brown oil. LRMS-HESI: calculated for $C_{18}H_{27}FN_{30}$ $(M+H)^+$ 320.21 m/z, observed 320.25 m/z. $^1H$ NMR (400 MHz, $CDCl_3$) δ 8.40 (s, 1H), 7.20 (d, J=12.5 Hz, 1H), 7.00 (d, J=2.2 Hz, 1H), 6.94 (d, J=7.1 Hz, 1H), 3.91-3.88 (m, 4H), 3.06-2.93 (m, 8H), 2.90 (q, J=7.2 Hz, 4H), 1.25 (t, J=7.2 Hz, 6H). (FIG. 23B, see: further also chemical reaction (g) in FIG. 3B).

It is noted that MM975 corresponds with chemical compound (XXIV):

(XXIV)

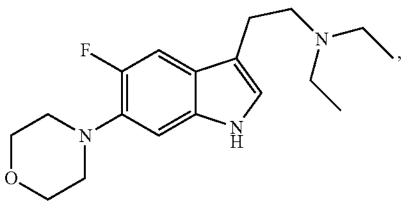

set forth herein.

Figure 24A:
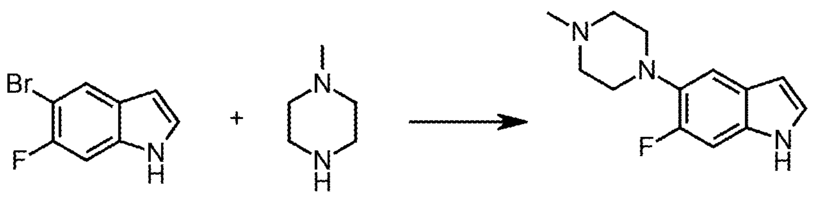
FIGS. 24A, 24B, and 24C depict further example reactions in an example chemical synthesis pathway for the synthesis of a certain example compound according to the present disclosure.

Example 21—Synthesis and Analysis of a Twenty-First N-Heterocycle Substituted Tryptamine Derivative Referring to FIG. 24A, in an oven-dried vial, under nitrogen atmosphere was combined 5-bromo-6-fluoro-1H-indole (300 mg, 1.40 mmol), $Pd_2(dba)_3$ (132 mg, 140 μmol), and DavePHOS (135 mg, 336 μmol). To the reaction vial was added dry dioxane (1.40 mL), 1-methylpiperazine (626 μL, 5.61 mmol) and 1 M LiHMDS in THE (3.08 mL, 3.08 mmol). The reaction mixture was heated to 70° C. for 20 hrs. After cooling to room temperature, the reaction mixture was diluted with DCM and poured into a separatory funnel containing water (20 mL) and extracted with DCM (3×20 mL). The combined organic extracts were washed with brine, dried over anhydrous magnesium sulphate, and concentrated under reduced pressure. The resulting crude material was purified by FC (4 g silica, 0% to 100% EtOAC in hexanes then 0% to 10% MeOH in EtOAc) to provide intermediate AO (60 mg, 18%) as a yellow oil. LRMS-HESI: calculated for $C_{13}H_{17}FN_3$ $(M+H)^+$ 234.14 m/z, observed 234.15 m/z. (FIG. 24A, see: further also chemical reaction (a) in FIG. 3B).

Figure 24B:
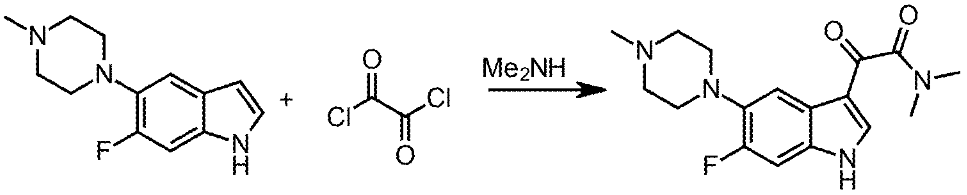

Referring next to FIG. 24B, to a solution of oxalyl chloride (55.0 μL, 643 μmol) in dry THE (1.25 mL) at 0° C. under nitrogen atmosphere was added a solution of intermediate AO (60.0 mg, 257 μmol) in dry THE (1.25 mL) in a dropwise minor. The reaction mixture was allowed to warm to room temperature and stirring continued for 3 hrs, at which time further oxalyl chloride (110 μL, 1.29 mmol) was added and the reaction mixture heated to 50° C. for 18 hrs as starting material remained visible precipitate suggests formation of SM-HCl. Following cooling to 0° C., 2 M dimethylamine in THE (1.93 mL, 3.86 mmol) was added in dropwise manner, and the reaction mixture allowed to stir for a further 1 hr. Little conversion had occurred, thus further 2 M dimethylamine in THE (4.50 mL, 9.00 mmol) was added and the reaction stirred at room temperature for 1 hr. After pouring the reaction mixture into a separatory funnel containing water (40 mL) and ethyl acetate (30 mL), the aqueous phase was extracted with ethyl acetate (3×30 mL). The combined organic extracts were washed with brine (40 mL), dried over anhydrous magnesium sulphate, and concentrated under reduced pressure. The resulting crude material was purified by FC (4 g silica, 0% to 10% MeOH in DCM) to provide intermediate AP (30 mg, 35%) as an amber oil. LRMS-HESI: calculated for $C_{17}H_{21}FN_4O_2$ $(M+H)^+$ 333.17 m/z, observed 333.24 m/z. $^1H$ NMR (400 MHz, $CDCl_3$) δ 9.90 (s, 1H), 7.91 (d, J=8.4 Hz, 1H), 7.76 (s, 1H), 7.07 (d, J=11.9 Hz, 1H), 3.19 (s, 4H), 3.09 (d, J=12.3 Hz, 6H), 2.71 (s, 4H), 2.42 (s, 3H). (FIG. 24B, see: further also chemical reaction (b) in FIG. 3B).

Figure 24C:
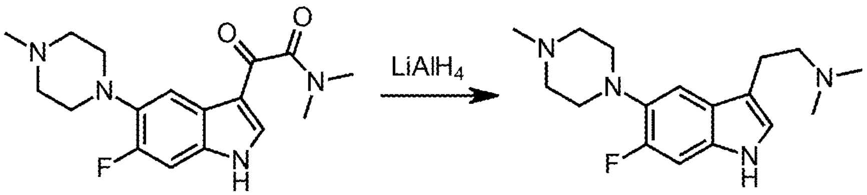

Referring next to FIG. 24C, in an oven-dried pressure rated vial, under nitrogen atmosphere, intermediate AP (30.0 mg, 90.3 μmol) was dissolved in dry THE (903 μL) and cooled to 0° C. To the stirring solution was added 2 M lithium aluminum hydride in THE (226 μL, 451 μmol) in THF. The reaction mixture was heated to reflux for 20 hrs. The reaction was worked up according to the Fieser method, and the filtrate concentrated under reduced pressure to yield a light yellow oil. The crude mixture was purified by FC (4 g silica, 0% to 10% [methanol+10% NH4OH] in DCM) to provide MM982 (14 mg, 51%) as a light yellow oil. LRMS-HESI: calculated for $C_{17}H_{26}FN_4$ $(M+H)^+$305.21 m/z, observed 292.19 m/z. $^1H$ NMR (400 MHz, $CDCl_3$) δ 8.25 (s, 1H), 7.16 (d, J=8.2 Hz, 1H), 7.04 (d, J=12.4 Hz, 1H), 6.96 (dt, J=2.2, 0.9 Hz, 1H), 3.14 (s, 4H), 2.97-2.89 (m, 2H), 2.75-2.60 (m, 6H), 2.40 (s, 3H), 2.38 (s, 6H). (FIG. 24C, see: further also chemical reaction (c) in FIG. 3B).

It is noted that MM982 corresponds with chemical compound (XXV):

(XXV)

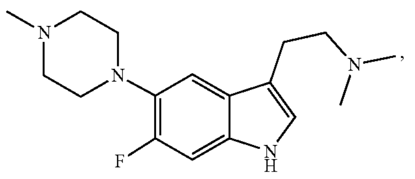

set forth herein.

Neuroplastogenicity Assays.

Assays to reveal potential of drugs to enhance neurite outgrowth in human model (NT2) neurons were conducted as described in Example 11, except that compound with formula (XXV) was used in place of compound with formula (XV). Results of visual inspection are summarized in Table 4, where (1) (+) designates strong evidence of enhanced neurite outgrowth in drug-treated NT2 cells compared to vehicle-treated cells, and (2) (−) designates weak or no evidence of enhanced neurite outgrowth in drug-treated NT2 cells compared to vehicle-treated cells. Contrary to the effects imparted by positive controls and compound with formula (XV) (FIG. 37A), human model (NT2) neurons incubated with 1 μM or 10 μM compound (XXV) did not grow larger in size and did not display greater overall neurite outgrowth compared with vehicle-treated (0.1% DMSO) human model neurons. These observations are summarized as a (−) designation in Table 4.

Mouse Head Twitch Response (HTR) Assay to Assess Hallucinogenic Potential.

Head Twitch Response (HTR) assays were conducted as described in Example 11, except that compound with formula (XXV) was used in place of compound with formula (XV). FIG. 38A shows HTR assay results for all drugs administered at 3 mg/kg (preliminary screening). Results show high hallucinogenic potential (mean HTR≥10) for positive controls (hatched bars; psilocin, DMT, 5-MeO-DMT). In contrast, low/no hallucinogenic potential (mean HTR≤5) is observed for negative controls (white bars; 5-Br-DMT, TBG, 6-F-DET). Mean HTR between 10 and 5 signifies reduced hallucinogenic potential relative to positive controls. Compound (XXV) has a mean HTR of 8.5, suggesting reduced hallucinogenic potential relative to positive controls.

Figure 25A:
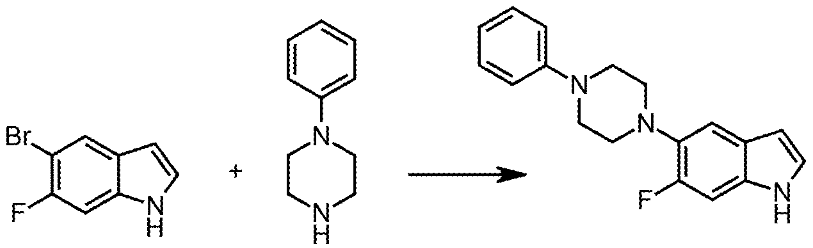
FIGS. 25A, 25B, and 25C depict further example reactions in an example chemical synthesis pathway for the synthesis of a certain example compound according to the present disclosure.

Example 22—Synthesis and Analysis of a Twenty-Second N-Heterocycle Substituted Tryptamine Derivative Referring to FIG. 25A, in an oven-dried vial, under nitrogen atmosphere was combined 5-bromo-6-fluoro-1H-indole (300 mg, 1.40 mmol), $Pd_2(dba)_3$ (132 mg, 140 μmol), and DavePHOS (135 mg, 336 μmol). To the reaction vial was added dry dioxane (1.40 mL), 1-phenylpiperazine (883 μL, 5.61 mmol) and 1 M LiHMDS in THE (3.08 mL, 3.08 mmol). The reaction mixture was heated to 70° C. for 20 hrs. After cooling to room temperature, the reaction mixture was diluted with DCM and poured into a separatory funnel containing water (20 mL) and extracted with DCM (3×20 mL). The combined organic extracts were washed with brine, dried over anhydrous magnesium sulphate, and concentrated under reduced pressure. The resulting crude material was purified by FC (4 g silica, 0% to 100% EtOAC in hexanes) to provide intermediate AQ (110 mg, 27%) as a yellow solid. LRMS-HESI: calculated for $C_{18}H_{19}FN_3$ $(M+H)^+$ 296.16 m/z, observed 296.14 m/z. (FIG. 25A, see: further also chemical reaction (a) in FIG. 3B).

Figure 25B:
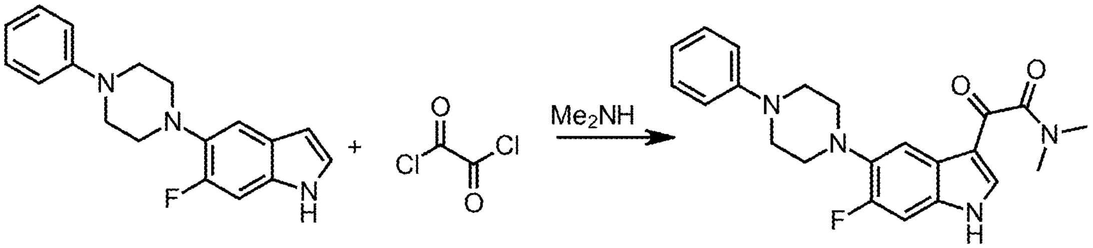

Referring next to FIG. 25B, to a solution of oxalyl chloride (145 μL, 1.69 mmol) in dry THE (1.7 mL) at 0° C. under nitrogen atmosphere was added a solution of intermediate AQ (100 mg, 339 μmol) in dry THE (1.7 mL) dropwise. The reaction mixture was then heated to 50° C. for 3 hrs. Upon cooling to 0° C., dimethylamine (2 M in THF, 5.08 mL, 10.2 mmol) was added dropwise, and the reaction mixture allowed to stir for a further 18 hrs at room temperature. After pouring the reaction mixture into a separatory funnel containing water (40 mL) and ethyl acetate (30 mL), the aqueous phase was extracted with ethyl acetate (3×30 mL). The combined organic extracts were washed with brine (40 mL), dried over anhydrous magnesium sulphate, and concentrated under reduced pressure. The resulting crude mixture was purified by FC (4 g silica, 40% to 100% EtOAc in hexanes) to provide intermediate AR (130 mg, 97%) as a white solid. LRMS-HESI: calculated for $C_{22}H_{24}FN_4O$ $(M+H)^+$ 395.19 m/z, observed 395.26 m/z. (FIG. 25B, see: further also chemical reaction (b) in FIG. 3B).

Figure 25C:
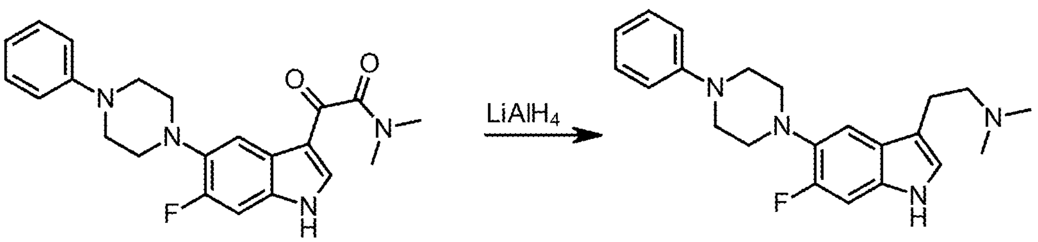

Referring next to FIG. 25C, in an oven-dried, pressure rated vial under nitrogen atmosphere, intermediate AR (150 mg, 380 μmol) was dissolved in dry THE (3.80 mL) and cooled to 0° C. To the stirring solution was added 2 M lithium aluminum hydride in THE (1.14 mL, 2.28 mmol). The reaction mixture was heated to reflux for 20 hrs. The reaction was worked up according to the Fieser method, and the filtrate concentrated under reduced pressure to yield a colourless oil. The crude mixture was purified by FC (4 g silica, 0% to 8% MeOH in DCM) provide MM983 (56.4 mg, 40%) as a white solid. LRMS-HESI: calculated for $C_{22}H_{28}FN_4$ $(M+H)^+$ 367.30 m/z, observed 367.26 m/z. $^1H$ NMR (400 MHz, $CDCl_3$) δ 8.67 (d, J=2.3 Hz, 1H), 7.38-7.31 (m, 2H), 7.21 (d, J=8.2 Hz, 1H), 7.08-7.00 (m, 3H), 6.98-6.89 (m, 2H), 3.48-3.38 (m, 4H), 3.32-3.22 (m, 4H), 2.98 (dd, J=9.2, 6.8 Hz, 2H), 2.77-2.67 (m, 2H), 2.42 (s, 6H). (FIG. 25C, see: further also chemical reaction (c) in FIG. 3B).

It is noted that MM983 corresponds with chemical compound (XXVI):

(XXVI)

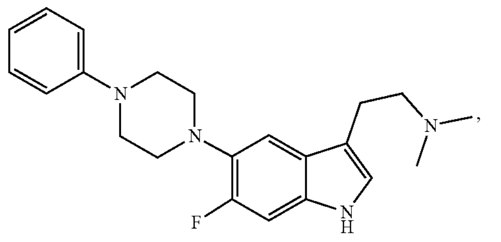

set forth herein.

Mouse Head Twitch Response (HTR) Assay to Assess Hallucinogenic Potential.

Head Twitch Response (HTR) assays were conducted as described in Example 11, except that compound with formula (XXVI) was used in place of compound with formula (XV). FIG. 38A shows HTR assay results for all drugs administered at 3 mg/kg (preliminary screening). Results show high hallucinogenic potential (mean HTR≥10) for positive controls (hatched bars; psilocin, DMT, 5-MeO-DMT). In contrast, low/no hallucinogenic potential (mean HTR≤5) is observed for negative controls (white bars; 5-Br-DMT, TBG, 6-F-DET). Mean HTR between 10 and 5 signifies reduced hallucinogenic potential relative to positive controls. Compound (XXVI) has a mean HTR of 8.25, suggesting reduced hallucinogenic potential compared to the positive controls.

Figure 26A:
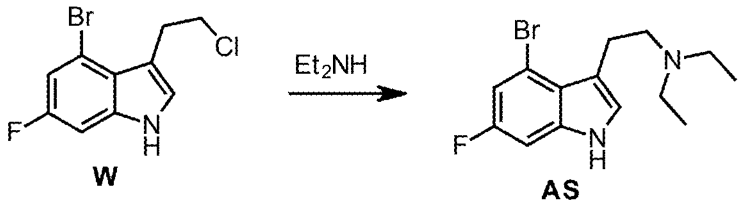
FIGS. 26A and 26B depict further example reactions in another example chemical synthesis pathway for the synthesis of another example compound according to the present disclosure.

Example 23—Synthesis and Analysis of a Twenty-Third N-Heterocycle Substituted Tryptamine Derivative Referring to FIG. 26A, to a solution of intermediate W (265 mg, 958 μmol), prepared as described in Example 11, in dry DMF (19.2 mL) was added diethylamine (897 μL, 8.62 mmol), followed by potassium bromide (342 mg, 2.87 mmol) and potassium carbonate (265 mg, 1.92 mmol). The resulting mixture was stirred at 60° C. for 3 hrs. After cooling to room temperature, the reaction mixture was poured into a separatory funnel containing water (200 mL) and ethyl acetate (50 mL) and the aqueous phase was extracted with ethyl acetate (5×100 mL). The combined organic extracts were washed with water (5×100 mL), brine (50 mL), dried over anhydrous magnesium sulphate and concentrated under reduced pressure. The resulting crude material was purified by FC (12 g silica, 0% to 20% MeOH in DCM) to provide intermediate AS (160 mg, 53%) as a light brown solid. LRMS-HESI: calculated for $C_{14}H_{19}BrFN_2$ $(M+H)^+$ 313.07 m/z, observed 313.12 m/z. (FIG. 26A, see: further also chemical reaction (f) in FIG. 3B).

Figure 26B:
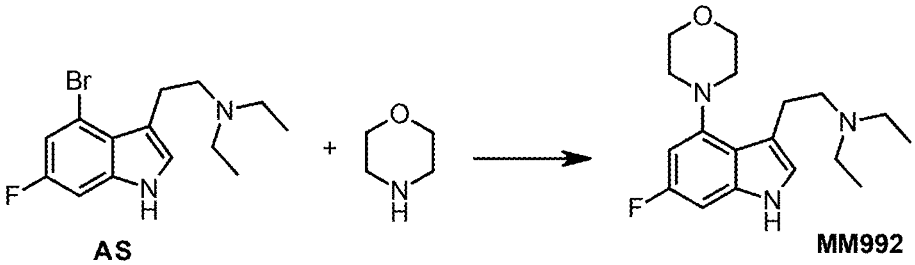

Referring next to FIG. 26B, in an oven-dried vial under nitrogen atmosphere was dissolved intermediate AS (155 mg, 495 μmol), $Pd_2(dba)_3$ (46.7 mg, 49.5 μmol), and DavePHOS (46.7 mg, 119 μmol) in dry THE (1.03 mL). To this stirring solution was added 1 M LiHMDS in THE (1.09 mL, 1.09 mmol) and morpholine (257 μL, 2.90 mmol). The reaction mixture was heated to 60° C. for 1.5 hours. At which point IPC was run via LCMS and the reaction was determined to be complete. The mixture was cooled to room temperature and poured into a separatory funnel containing ethyl acetate (15 mL) and water (15 mL). The aqueous layer was extracted with ethyl acetate (2×15 mL), all organic layers were combined, washed with brine, dried ($MgSO_4$), filtered and concentrated to leave a brown solid. The brown solid was purified by FC (4 g silica, 0% to 20% MeOH in DCM) to provide MM992 (57 mg, 36%) as an amber oil. LRMS-HESI: calculated for $C_{18}H_{27}FN_3O$ $(M+H)^+$ 320.21 m/z, observed 320.25 m/z. $^1H$ NMR (400 MHz, $CDCl_3$) δ 8.53 (s, 1H), 6.94 (dq, J=2.4, 1.2 Hz, 1H), 6.79-6.68 (m, 1H), 6.56 (dd, J=11.6, 2.2 Hz, 1H), 3.94 (t, J=4.5 Hz, 4H), 3.16-3.00 (m, 6H), 2.95-2.82 (m, 2H), 2.71 (q, J=7.2 Hz, 4H), 1.11 (t, J=7.1 Hz, 6H). (FIG. 26B, see: further also chemical reaction (g) in FIG. 3B).

It is noted that MM992 corresponds with chemical compound (XXVII):

(XXVII)

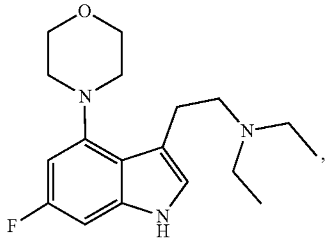

set forth herein.

5-HT Receptor Radioligand Competition Assay.

Competition assays at the 5-$HT_{2A}$ receptor were performed as described in Example 11, except compound with formula (XXVII) was used in place of compound with formula (XV). Resulting $K_i$ data for controls and test compounds in 5-$HT_{2A}$ receptor binding assays, including data acquired for compound with formula V, are summarized in Table 2. Compound with formula (XXVII) (designated 'XXVII' in Table 2) exhibited a $K_i$ value of 5.4 μM at the 5-$HT_{2A}$ receptor. This $K_i$ value was less than those of negative controls (i.e., $K_i$<1000 μM) and hence suggested binding by compound with formula (XXVII) at this receptor.

Neuroplastogenicity Assays.

Assays to reveal potential of drugs to enhance neurite outgrowth in human model (NT2) neurons were conducted as described in Example 11, except that compound with formula (XXVII) was used in place of compound with formula (XV). Results of visual inspection are summarized in Table 4, where (1) (+) designates strong evidence of enhanced neurite outgrowth in drug-treated NT2 cells compared to vehicle-treated cells, and (2) (−) designates weak or no evidence of enhanced neurite outgrowth in drug-treated NT2 cells compared to vehicle-treated cells. Contrary to the effects imparted by positive controls and compound with formula (XV) (FIG. 37A), human model (NT2) neurons incubated with 1 μM or 10 μM compound (XXVII) did not grow larger in size and did not display greater overall neurite outgrowth compared with vehicle-treated (0.1% DMSO) human model neurons. These observations are summarized as a (−) designation in Table 4.

Mouse Head Twitch Response (HTR) Assay to Assess Hallucinogenic Potential.

Head Twitch Response (HTR) assays were conducted as described in Example 11, except that compound with formula (XXVII) was used in place of compound with formula (XV). FIG. 38A shows HTR assay results for all drugs administered at 3 mg/kg (preliminary screening). Results show high hallucinogenic potential (mean HTR≥10) for positive controls (hatched bars; psilocin, DMT, 5-MeO-DMT). In contrast, low/no hallucinogenic potential (mean HTR≤5) is observed for negative controls (white bars; 5-Br-DMT, TBG, 6-F-DET). Mean HTR between 10 and 5 signifies reduced hallucinogenic potential relative to positive controls. Compound (XXVII) has a mean HTR of 8.0, suggesting reduced hallucinogenic potential relative to positive controls.

Figure 27A:
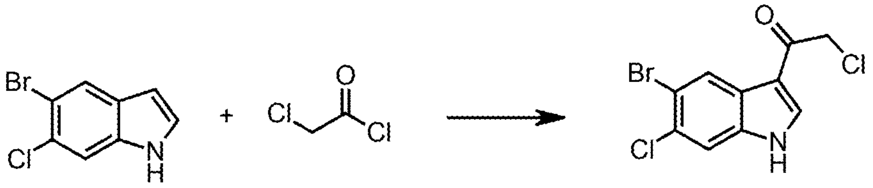
FIGS. 27A, 27B, 27C, and 27D depict further example reactions in an example chemical synthesis pathway for the synthesis of a certain example compound according to the present disclosure.

Example 24—Synthesis and Analysis of a Twenty-Fourth N-Heterocycle Substituted Tryptamine Derivative Referring to FIG. 27A, to a stirring solution of aluminum chloride (1.70 g, 12.6 mmol) in DCM (28.1 mL) under nitrogen atmosphere was added chloroacetyl chloride (1.03 mL, 12.6 mmol) in DCM (28.1 mL) and stirred for 30 min. At this juncture, a solution of 5-bromo-6-chloro-1H-indole (2.00 g, 8.42 mmol) in DCM (56.1 mL) was added dropwise via addition funnel, and the resulting mixture stirred for 20 hrs. The reaction mixture was quenched by pouring over ice-water (200 mL), agitating thoroughly, filtering the resulting precipitate (sintered glass), and washing with saturated sodium bicarbonate and water. After drying, intermediate AT (1.85 g, 72%) was collected as a beige solid. This material was used in the next step without further purification. LRMS-HESI: calculated for $C_{10}H_7BrCl_2NO$ $(M+H)^+$ 305.91 m/z, observed 305.88 m/z. (FIG. 27A, see: further also chemical reaction (d) in FIG. 3B).

Figure 27B:
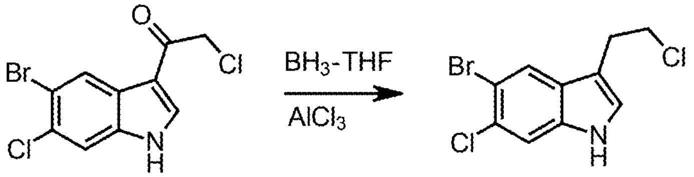

Referring next to FIG. 27B, to a suspension of aluminum chloride (1.30 g, 9.77 mmol) in dry DCM (24.0 mL) at 0° C., under nitrogen atmosphere was added 1 M borane-THF in THF (19.5 mL, 19.5 mmol), and the resulting solution was stirred for 10 minutes. A suspension of intermediate AT (1.00 g, 3.26 mmol) in dry DCM (19.0 mL) was added, and the resulting mixture was stirred at 0° C. for 3 hrs. The reaction mixture, at 0° C., was quenched through addition of water (20 mL) and 1 M HCl (20 mL). The biphasic mixture was poured into a separatory funnel containing water and DCM. The layers were separated and the aqueous phase was extracted with DCM (×3). The combined organic layers were washed with brine, dried over anhydrous sodium sulfate, and concentrated under reduced pressure to yield intermediate AU (560 mg, 59%) which was used in the next step without further purification. LRMS-HESI: calculated for $C_{10}H_9BrCl_2N$ $(M+H)^+$ 291.93 m/z, observed 291.95 m/z. (FIG. 27B, see: further also chemical reaction (e) in FIG. 3B).

Figure 27C:
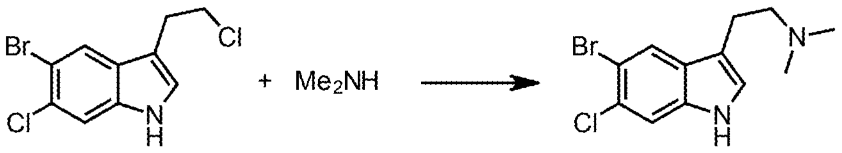

Referring next to FIG. 27C, to a solution of intermediate AU (560 mg, 1.91 mmol) in dry ACN (9.97 mL) were added potassium bromide (682 mg, 5.73 mmol) and potassium carbonate (528 mg, 3.82 mmol) followed by 2 M dimethylamine in THF (8.60 mL, 17.2 mmol). The resulting mixture was stirred at 70° C. for 19 hrs. The solids were filtered and washed with DCM, the solvent was removed under reduced pressure, and the remaining residue was absorbed to silica and purified by FC (12 g silica, 0% to 20% MeOH in DCM) to provide intermediate AV (250 mg, 43%) as a white solid. LRMS-HESI: calculated for $C_{12}H_{15}BrClN_2$ $(M+H)^+$ 301.01 m/z, observed 301.02 m/z. (FIG. 27C, see: further also chemical reaction (f) in FIG. 3B).

Figure 27D:
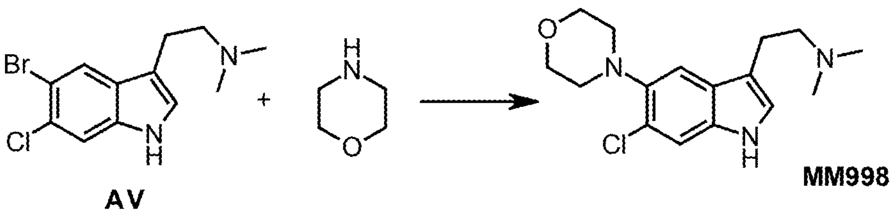

Referring next to FIG. 27D, in an oven-dried vial under nitrogen atmosphere was combined intermediate AV (75.0 mg, 249 μmol), $Pd_2(dba)_3$ (23.5 mg, 24.9 μmol) and DavePHOS (24.0 mg, 59.7 μmol) and the dry contents purged with nitrogen for 30 minutes. To the reaction vial was added dry dioxane (249 μL) followed by morpholine (132 μL, 1.49 mmol) and 1 M LiHMDS in THF (547 μL, 547 μmol). The reaction mixture was heated to 60° C. for 1 hr. After cooling to room temperature, the reaction mixture was diluted with DCM and poured into a separatory funnel containing water (20 mL) and extracted with DCM (3×20 mL). The combined organic extracts were washed with brine, dried over anhydrous magnesium sulphate, and concentrated under reduced pressure. The resulting crude solid was purified by FC (4 g silica, 0% to 10% MeOH in DCM) to provide MM998 (9.5 mg, 12%) as a colourless oil. LRMS-HESI: calculated for $C_{16}H_{23}ClN_3O$ $(M+H)^+$ 308.15 m/z, observed 308.18 m/z. $^1H$ NMR (400 MHz, $CDCl_3$) δ 8.26 (s, 1H), 7.42 (s, 1H), 7.27 (s, 1H), 7.02 (dt, J=2.3, 1.0 Hz, 1H), 3.96-3.89 (m, 4H), 3.11-3.04 (m, 4H), 3.00 (dd, J=9.3, 6.6 Hz, 2H), 2.76 (dd, J=9.2, 6.8 Hz, 2H), 2.46 (s, 6H). (FIG. 27D, see: further also chemical reaction (g) in FIG. 3B).

It is noted that MM998 corresponds with chemical compound (XXVIII):

(XXVIII)

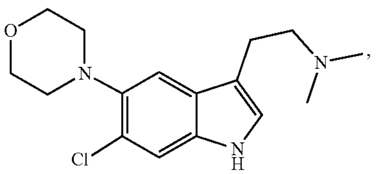

set forth herein.

Figure 28A:
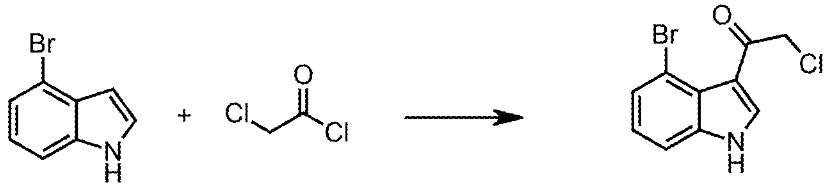
FIGS. 28A, 28B, 28C, and 28D depict further example reactions in an example chemical synthesis pathway for the synthesis of a certain example compound according to the present disclosure.

Example 25—Synthesis and Analysis of a Twenty-Fifth N-Heterocycle Substituted Tryptamine Derivative Referring to FIG. 28A, to a stirring solution of aluminum chloride (2.06 g, 15.3 mmol) in DCM (34.0 mL) under nitrogen atmosphere and at 0° C. was added chloroacetyl chloride (2.07 mL, 25.5 mmol) in DCM (34.0 mL), the temperature was increased to room temperature and stirring was continued for 30 min. At this juncture, a solution of 4-bromoindole (2.06 g, 10.2 mmol) in DCM (68.0 mL) was added dropwise via canula transfer at 0° C. The mixture was warmed to room temperature and left to react for 20 hrs (LCMS showed desired product). At this point ~150 mL of saturated sodium bicarbonate solution was carefully added to the mixture. Once gas evolution had stopped, the biphasic mixture, containing a white ppt was filtered through a Buchner funnel. LCMS analysis of the resulting solids, aqueous layer and DCM established that the desired product was overwhelmingly located in the DCM. Added to this was silica gel and the reaction mixture was loaded onto dry silica during concentration. This was immediately purified by column chromatography (24 g silica, hexanes:ethyl acetate gradient from 20% EA to 80% EA). After purification, intermediate AW (1.10 g, 40%) was obtained as a slightly yellow solid. LRMS-HESI: calculated for $C_{10}H_8BrClNO$ $(M+H)^+$ 271.95 m/z, observed 271.99 m/z. (FIG. 28A, see: further also chemical reaction (d) in FIG. 3B).

Figure 28B:
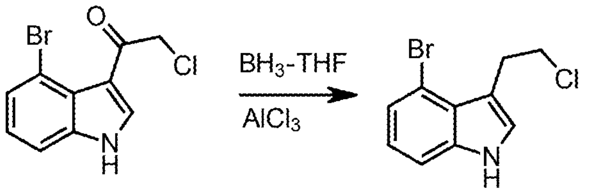

Referring next to FIG. 28B, to a suspension of aluminum chloride (1.63 g, 12.1 mmol) in dry DCM (45 mL) at 0° C. under nitrogen atmosphere was added 1 M borane-THF complex in THE (24.2 mL, 24.2 mmol), and the resulting solution was stirred for 10 minutes. A solution of intermediate AW (1.10 g, 4.04 mmol) in dry DCM (35 mL) was added, and the resulting mixture was stirred at 0° C. for 2 hrs. The reaction mixture, at 0° C., was quenched through addition of water (50 mL) and 1 M HCl (25 mL). The biphasic mixture was poured into a separatory funnel, and the aqueous phase was extracted (3×30 mL DCM). The combined organic extracts were washed with brine (30 mL), dried over anhydrous magnesium sulphate, and concentrated under reduced pressure to provide intermediate AX (952 mg, 91%), as a brown oil. This was used in the next step without further purification. LRMS-HESI: calculated for $C_{10}H_{10}BrClN$ $(M+H)^+$ 257.97 m/z, observed 258.02 m/z. (FIG. 28B, see: further also chemical reaction (e) in FIG. 3B).

Figure 28C:
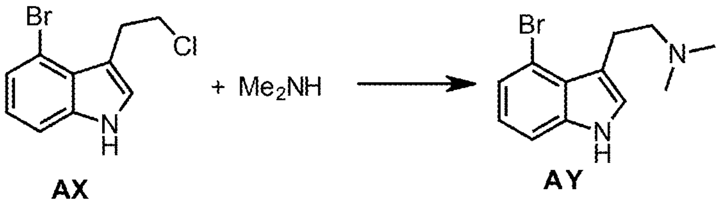

Referring next to FIG. 28C, the ethyl chloride, intermediate AX (473 mg, 1.83 mmol) was dissolved in DMF (26.6 mL). Added to this was 2 M dimethylamine in THE (4.60 mL, 9.20 mmol) followed by potassium carbonate (759 mg, 5.49 mmol) and potassium bromide (653 mg, 5.49 mmol). The mixture was heated to 40° C. and left to stir at this temperature overnight. After 18 hrs the mixture contained predominantly the desired product as determined by LCMS. The mixture was poured into a separatory funnel containing 50 mL water and 50 mL ethyl acetate. The aqueous layer was extracted with ethyl acetate (3×40 mL), all organic layers were combined, washed with water (4×40 mL), brine (2×40 mL), dried ($MgSO_4$) filtered and concentrated to leave a red solid. The material was purified by column chromatography (12 g silica, 0% to 20% MeOH in DCM) to provide intermediate AY (236 mg, 48%) as a white solid. LRMS-HESI: calculated for $C_{12}H_{16}BrN_2$ $(M+H)^+$ 267.05 m/z, observed 267.11 m/z. (FIG. 28C, see: further also chemical reaction (f) in FIG. 3B).

Figure 28D:
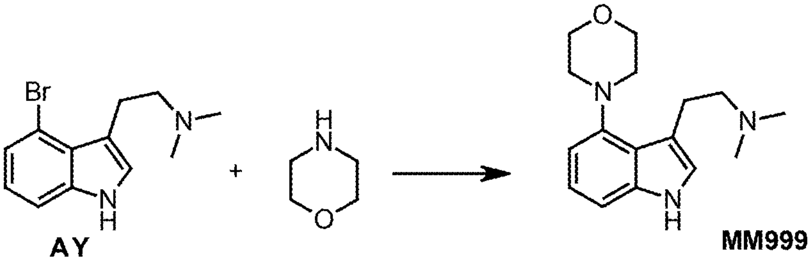

Referring next to FIG. 28D, in an oven-dried vial under nitrogen atmosphere was dissolved intermediate AY (100 mg, 374 μmol), $Pd_2(dba)_3$ (35.3 mg, 37.4 μmol), and DavePHOS (35.4 mg, 89.8 μmol) in dry THE (776 μL). To this stirring solution was added 1 M LiHMDS in THE (823 μL, 823 μmol) and morpholine (132 μL, 1.50 mmol). The reaction mixture was heated to 60° C. for 20 hrs. At which point IPC was run via LCMS and the reaction was determined to be complete. The mixture was cooled to room temperature and poured into a separatory funnel containing DCM (10 mL) and water (10 mL). The aqueous layer was extracted with DCM (2×10 mL), all organic layers were combined, washed with brine, dried ($MgSO_4$), filtered and concentrated to leave a brown solid. This was purified by FC (4 g silica, 0% to 20% MeOH in DCM) to provide MM999 (45.0 mg, 44%) as an orange waxy solid. LRMS-HESI: calculated for $C_{16}H_{24}N_3O$ $(M+H)^+$ 274.19 m/z, observed 274.22 m/z. $^1H$ NMR (400 MHz, $CDCl_3$) δ 8.13 (s, 1H), 7.12-7.11 (m, 2H), 7.01-7.00 (m, 1H), 6.81-6.77 (m, 1H), 3.95-3.93 (m, 4H), 3.18-3.14 (m, 2H), 3.08-3.06 (m, 4H), 2.77-2.73 (m, 2H), 2.39 (s, 6H). (FIG. 28D, see: further also chemical reaction (g) in FIG. 3B).

It is noted that MM999 corresponds with chemical compound (XXIX):

(XXIX)

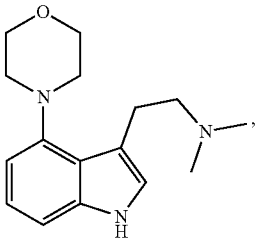

set forth herein.

Figure 29A:
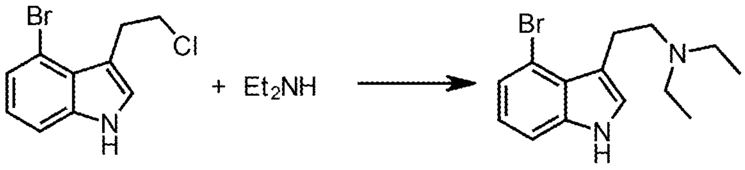
FIGS. 29A and 29B depict further example reactions in another example chemical synthesis pathway for the synthesis of another example compound according to the present disclosure.

Example 26—Synthesis and Analysis of a Twenty-Sixth N-Heterocycle Substituted Tryptamine Derivative Referring to FIG. 29A, the ethyl chloride intermediate AX (280 mg, 1.08 mmol), prepared as described in Example 25, was dissolved in DMF (15.7 mL). Added to this was diethylamine (566 μL, 5.45 mmol) and then potassium carbonate (449 mg, 3.25 mmol) and potassium bromide (387 mg, 3.25 mmol). The mixture was heated to 40° C. and left to stir at this temperature overnight. At this point the mixture contained predominantly the desired product as determined by LCMS. The mixture was poured into a separatory funnel containing 50 mL water and 50 mL ethyl acetate. The aqueous layer was extracted with ethyl acetate (3×40 mL), all organic layers were combined, washed with water (4×40 mL), brine (2×40 mL), dried ($MgSO_4$) filtered and concentrated to leave a red solid. The material was purified by column chromatography (12 g silica, 0% to 20% MeOH in DCM) to leave intermediate AZ (130 mg, 41%) as a white solid. LRMS-HESI: calculated for $C_{14}H_{20}BrN_2$ $(M+H)^+$ 295.08 m/z, observed 295.13 m/z. (FIG. 29A, see: further also chemical reaction (f) in FIG. 3B).

Figure 29B:
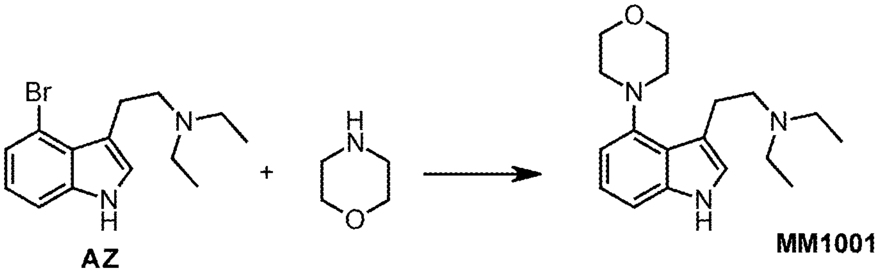

Referring next to FIG. 29B, in an oven-dried vial under nitrogen atmosphere was dissolved intermediate AZ (109 mg, 369 μmol), $Pd_2(dba)_3$ (34.9 mg, 36.9 μmol), and DavePHOS (34.9 mg, 88.6 μmol) in dry THE (766 μL). To this stirring solution was added 1 M LiHMDS in THE (812 μL, 812 μmol) and morpholine (130 μL, 1.48 mmol). The reaction mixture was heated to 60° C. for 1.5 hrs. At which point IPC was run via LCMS and the reaction was determined to be complete. The mixture was cooled to room temperature and poured into a separatory funnel containing ethyl acetate (15 mL) and water (15 mL). The aqueous layer was extracted with ethyl acetate (2×15 mL), all organic layers were combined, washed with brine, dried ($MgSO_4$), filtered and concentrated to leave a brown solid. This was adsorbed to silica and purified by FC (4 g silica, 0% to 20% MeOH in DCM) to provide MM1001 (58.0 mg, 52%) as a light brown solid. LRMS-HESI: calculated for $C_{18}H_{28}N_3O$ $(M+H)^+$ 302.22 m/z, observed 302.27 m/z. $^1H$ NMR (400 MHz, $CDCl_3$) δ 8.20 (s, 1H), 7.11-7.10 (m, 2H), 6.99 (m, 1H), 6.80-6.76 (m, 1H), 3.95-3.92 (m, 4H), 3.17-3.13 (m, 2H), 3.09-3.06 (m, 4H), 2.88-2.84 (m, 2H), 2.69 (q, J=7.2 Hz, 4H), 1.10 (t, J=7.2 Hz, 6H). (FIG. 29B, see: further also chemical reaction (g) in FIG. 3B).

It is noted that MM1001 corresponds with chemical compound (XXX):

(XXX)

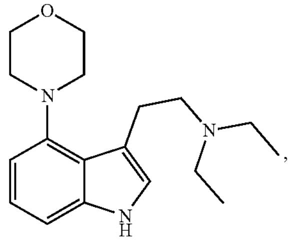

set forth herein.

Figure 30A:
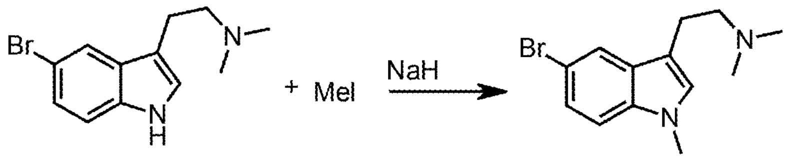
FIGS. 30A and 30B depict further example reactions in another example chemical synthesis pathway for the synthesis of another example compound according to the present disclosure.

Example 27—Synthesis and Analysis of a Twenty-Seventh N-Heterocycle Substituted Tryptamine Derivative Referring to FIG. 30A, intermediate A (700 mg, 2.62 mmol), prepared as described in Example 1, was dissolved in THF (13.1 mL) the resulting mixture was cooled to 0° C. followed by the addition of sodium hydride (60% in mineral oil, 314 mg, 7.86 mmol). The resulting mixture was warmed to room temperature over an hour. Once warm, iodomethane (233 μL, 3.72 mmol) was added and the mixture was left to react for one hour. At this point, half saturated $NaHCO_3$ and EtOAc were added to the reaction mixture and the resulting aqueous phase was extracted with EtOAc. All the organic layers were pooled, dried over $Na_2SO_4$, filtered and concentrated to provide intermediate BA (678 mg, 92%) which was used in the next step without further purification. LRMS-HESI: calculated for $C_{13}H_{18}BrN_2$ $(M+H)^+$ 281.06 m/z, observed 281.02 m/z. (FIG. 30A, see: further also chemical reaction (e) in FIG. 3A).

Figure 30B:
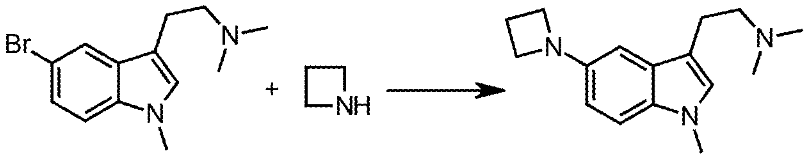

Referring next to FIG. 30B, to a solution of intermediate BA (151 mg, 537 μmol) in dry toluene (7.67 mL) was added $Pd_2(dba)_3$ (30.4 mg, 32.2 μmol). Argon was bubbled through the mixture for 10 minutes and then the atmosphere was switched to nitrogen prior to the addition of potassium tert-butoxide (123 mg, 1.07 mmol), X-PHOS (26.9 mg, 53.7 μmol), and azetidine (38.1 μL, 537 μmol). The pressure rated reaction vial was capped under nitrogen atmosphere, and the reaction mixture heated to 110° C. for 2 hrs. The reaction mixture was cooled to room temperature and filtered over a pad of celite. The resulting filtrate was partitioned between ethyl acetate (30 mL) and water (30 mL), and the aqueous phase extracted with ethyl acetate (2×30 mL). The combined organic extracts were washed with brine (30 mL), dried over anhydrous magnesium sulphate, and concentrated under reduced pressure. The resulting crude material was purified by FC (12 g silica, 0% to 20% MeOH in DCM) to provide MM895 (23.6 mg, 17%) as a single component. LRMS-HESI: calculated for $C_{16}H_{24}N_3$ $(M+H)^+$ 258.20 m/z, observed 258.23 m/z. $^1H$ NMR (400 MHz, $CDCl_3$) δ 7.17 (dd, J=8.7, 0.7 Hz, 1H), 6.83 (s, 1H), 6.65 (dd, J=2.2, 0.7 Hz, 1H), 6.55 (dd, J=8.7, 2.2 Hz, 1H), 3.90 (t, J=7.1 Hz, 4H), 3.70 (s, 3H), 2.95-2.86 (m, 2H), 2.69-2.58 (m, 2H), 2.43-2.32 (m, 8H). (FIG. 30B, see: further also chemical reaction (f) in FIG. 3A).

It is noted that MM895 corresponds with chemical compound (XXXI):

(XXXI)

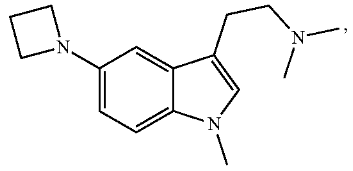

set forth herein.

Figure 31:
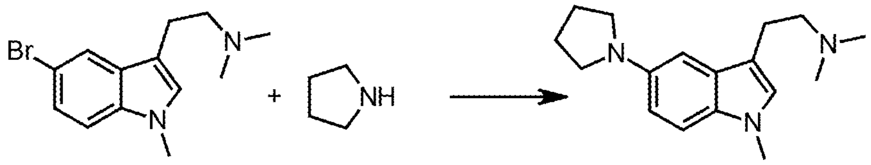
FIG. 31 depicts a further example reaction in another example chemical synthesis pathway for the synthesis of another example compound according to the present disclosure.

Example 28—Synthesis and Analysis of a Twenty-Eighth N-Heterocycle Substituted Tryptamine Derivative Referring to FIG. 31, to a solution of intermediate BA (151 mg, 537 μmol), prepared as described in Example 27, in dry toluene (7.67 mL) was added $Pd_2(dba)_3$ (30.4 mg, 32.2 μmol). Argon was bubbled through the mixture for 10 minutes and then the atmosphere was switched to nitrogen prior to the addition of potassium tert-butoxide (123 mg, 1.07 mmol), X-PHOS (26.9 mg, 53.7 μmol), and pyrrolidine (39 μL, 537 μmol). The pressure rated reaction vial was capped under nitrogen atmosphere, and the reaction mixture heated to 110° C. for 2 hrs. The reaction mixture was cooled to room temperature and filtered over a pad of celite. The resulting filtrate was partitioned between ethyl acetate (30 mL) and water (30 mL), and the aqueous phase extracted with ethyl acetate (2×30 mL). The combined organic extracts were washed with brine (30 mL), dried over anhydrous magnesium sulphate, and concentrated under reduced pressure. The resulting crude material was purified by FC (12 g silica, 0% to 20% MeOH in DCM) to provide MM896 (7.8 mg, 5.4%) as a single component. LRMS-HESI: calculated for $C_{17}H_{26}N_3$ $(M+H)^+$ 272.21 m/z, observed 272.20 m/z. $^1H$ NMR (400 MHz, $CDCl_3$) δ 7.18 (d, J=9.5 Hz, 1H), 6.82 (s, 1H), 6.75-6.70 (m, 2H), 3.70 (s, 3H), 3.38-3.31 (m, 4H), 3.01-2.93 (m, 2H), 2.74 (dd, J=9.4, 6.8 Hz, 2H), 2.44 (s, 6H), 2.08-2.02 (m, 4H). (FIG. 31, see: further also chemical reaction (f) in FIG. 3A).

It is noted that MM896 corresponds with chemical compound (XXXII):

(XXXII)

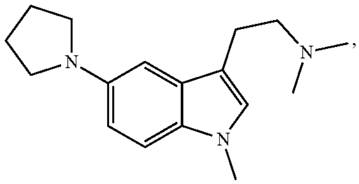

set forth herein.

Figure 32:
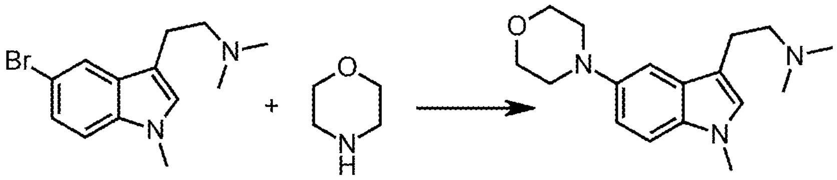
FIG. 32 depicts a further example reaction in another example chemical synthesis pathway for the synthesis of another example compound according to the present disclosure.

Example 29—Synthesis and Analysis of a Twenty-Ninth N-Heterocycle Substituted Tryptamine Derivative Referring to FIG. 32, to a solution of intermediate BA (114 mg, 405 μmol), prepared as described in Example 27, in dry toluene (5.8 mL) was added $Pd_2(dba)_3$ (23 mg, 24 μmol). Argon was bubbled through the mixture for 10 minutes and then the atmosphere was switched to nitrogen prior to the addition of potassium tert-butoxide (93 mg, 0.81 mmol), X-PHOS (20.3 mg, 40.5 μmol), and morpholine (35.8 µL, 405 µmol). The pressure rated reaction vial was capped under nitrogen atmosphere, and the reaction mixture heated to 110° C. for 2 hrs. The reaction mixture was cooled to room temperature and filtered over a pad of celite. The resulting filtrate was partitioned between ethyl acetate (30 mL) and water (30 mL), and the aqueous phase extracted with ethyl acetate (2×30 mL). The combined organic extracts were washed with brine (30 mL), dried over anhydrous magnesium sulphate, and concentrated under reduced pressure. The resulting crude material was purified by FC (12 g silica, 0% to 20% MeOH in DCM) to provide MM897 (25.5 mg, 22%) as a light brown oil. LRMS-HESI: calculated for $C_{17}H_{26}N_3O$ $(M+H)^+$ 288.21 m/z, observed 288.23 m/z. $^1H$ NMR (600 MHz, $CDCl_3$) δ 7.21 (d, J=8.8 Hz, 1H), 7.10 (d, J=2.2 Hz, 1H), 6.98 (dd, J=8.8, 2.3 Hz, 1H), 6.85 (s, 1H), 3.93-3.89 (m, 4H), 3.70 (s, 3H), 3.16-3.12 (m, 4H), 2.94-2.89 (m, 2H), 2.66-2.61 (m, 2H), 2.36 (s, 6H). (FIG. 32, see: further also chemical reaction (f) in FIG. 3A).

It is noted that MM897 corresponds with chemical compound (XXXIII):

(XXXIII)

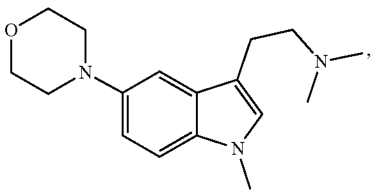

set forth herein.

The invention claimed is:

1. A chemical compound having chemical formula (I):

(I)

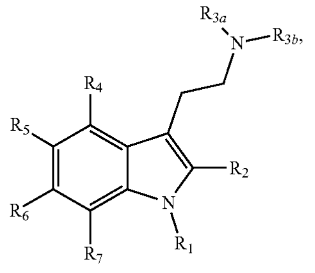

wherein one of $R_2$, $R_4$, $R_6$, and $R_7$ is an N-heterocycle substituent and one of $R_2$, $R_4$, $R_6$, and $R_7$ is a halogen atom, and wherein each of $R_2$, $R_4$, $R_6$, and $R_7$ which are not an N-heterocycle substituent or a halogen atom are a hydrogen atom, wherein $R_5$ is a halogen atom or a hydrogen atom, wherein $R_1$ is alkyl or hydrogen, and wherein $R_{3a}$ and $R_{3b}$ are each independently a hydrogen atom, an alkyl group, an aryl group, or an alkyl-aryl group, wherein the N-heterocycle substituent is an N-linked heterocyclic ring.

2. A chemical compound according to claim 1, wherein the N-heterocycle substituent is a 3-10 membered saturated N-linked heterocyclic ring.

3. A chemical compound according to claim 1, wherein the N-heterocycle substituent is a 3-10 membered saturated N-linked heterocyclic ring further having a second hetero-atom.

4. A chemical compound according to claim 1, wherein the one of $R_2$, $R_4$, $R_5$, $R_6$, and $R_7$ that is a halogen atom, is a fluorine or a chlorine atom.

5. A chemical compound according to claim 1, wherein the N-heterocycle substituent is a 3-10 membered saturated N-linked heterocyclic ring further having a second hetero-atom, wherein the second hetero-atom is an oxygen atom.

6. A chemical compound according to claim 1, wherein $R_1$ is hydrogen.

7. A chemical compound according to claim 1, wherein the N-heterocycle substituent has the chemical formula (III):

(III)

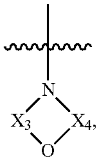

wherein in chemical formula (III) $X_3$, and $X_4$ are independently selected from a $C_1$ to $C_4$-alkylene group.

8. A chemical compound according to claim 7, wherein in formula (III) $X_3$ and $X_4$ each are methylene ($-CH_2-$).

9. A chemical compound according to claim 7, wherein in formula (III) $X_3$ is methylene ($-CH_2-$) and $X_4$ is ethylene ($-CH_2-CH_2-$).

10. A chemical compound according to claim 7, wherein in formula (III) $X_3$ and $X_4$ each are ethylene ($-CH_2-CH_2-$).

11. A chemical compound according to claim 1, wherein R4 is an N-heterocycle substituent, wherein the N-heterocycle substituent is an N-linked heterocyclic ring, R6 is a halogen atom, and R1, R2, R5, and R7 each are a hydrogen atom.

12. A chemical compound according to claim 7, wherein $R_4$ is an N-heterocycle substituent having formula (III), $R_6$ is a halogen atom, and $R_1$, $R_2$, $R_5$, and $R_7$ each are a hydrogen atom.

13. A chemical compound according to claim 7, wherein $R_4$ is an N-heterocycle substituent having formula (III), wherein $X_3$ and $X_4$ each are methylene ($-CH_2-$), $R_6$ is a halogen atom, and $R_1$, $R_2$, $R_5$, and $R_7$ each are a hydrogen atom.

14. A chemical compound according to claim 7, wherein $R_4$ is an N-heterocycle substituent having formula (III), wherein one of $X_3$ and $X_4$ is methylene ($-CH_2-$), one of $X_3$ and $X_4$ is ethylene ($-CH_2-CH_2-$), $R_6$ is a halogen atom, and $R_1$, $R_2$, $R_5$, and $R_7$ each are a hydrogen atom.

15. A chemical compound according to claim 7, wherein $R_4$ is an N-heterocycle substituent having formula (III), wherein $X_3$ and $X_4$ each are ethylene ($-CH_2-CH_2-$), $R_6$ is a halogen atom, and $R_1$, $R_2$, $R_5$, and $R_7$ each are a hydrogen atom.

16. A chemical compound according to claim 7, wherein $R_4$ is an N-heterocycle substituent having formula (III), wherein $X_3$ and $X_4$ each are ethylene ($-CH_2-CH_2-$), $R_6$ is a fluorine atom, and $R_1$, $R_2$, $R_5$, and $R_7$ each are a hydrogen atom.

17. A chemical compound according to claim 1, wherein $R_{3a}$ and $R_{3b}$ each are a hydrogen atom.

18. A chemical compound according to claim 1, wherein $R_{3a}$ and $R_{3b}$ each are a $(C_1-C_6)$-alkyl group.

19. A chemical compound according to claim 1, wherein $R_{3a}$ and $R_{3b}$ each are a methyl group ($-CH_3$).

20. A chemical compound according to claim 7, wherein $R_4$ is an N-heterocycle substituent having formula (III), wherein $X_3$ and $X_4$ each are ethylene (—$CH_2$—$CH_2$—), $R_6$ is a halogen atom, optionally a fluorine atom, $R_1$, $R_2$, $R_5$, and $R_7$ each are a hydrogen atom, and at least one of $R_{3a}$ and $R_{3b}$ is a ($C_1$-$C_6$)-alkyl group, optionally a ($C_1$-$C_3$)-alkyl group, and optionally a methyl group (—$CH_3$).

21. A chemical compound according to claim 7, wherein $R_4$ is an N-heterocycle substituent, having formula (III), wherein $X_3$ and $X_4$ each are ethylene (—$CH_2$—$CH_2$—), $R_6$ is a halogen atom, optionally a fluorine atom, $R_1$, $R_2$, $R_5$, and $R_7$ each are a hydrogen atom, and $R_{3a}$ and $R_{3b}$ each are a ($C_1$-$C_6$)-alkyl group, optionally a ($C_1$-$C_3$)-alkyl group, and optionally a methyl group (—$CH_3$).

22. A chemical compound according to claim 7, wherein $R_4$ is an N-heterocycle substituent, having formula (III), wherein $X_3$ and $X_4$ each are ethylene (—$CH_2$—$CH_2$—), $R_6$ is a halogen atom, optionally a fluorine atom, $R_1$, $R_2$, $R_5$, and $R_7$ each are a hydrogen atom, and $R_{3a}$ and $R_{3b}$ each are a hydrogen atom.

23. A chemical compound according to claim 7, wherein $R_4$ is an N-heterocycle substituent, having formula (III), wherein $X_3$ and $X_4$ each are ethylene (—$CH_2$—$CH_2$—), $R_6$ is a halogen atom, optionally a fluorine atom, $R_1$, $R_2$, $R_5$, and $R_7$ each are a hydrogen atom, and at least one of $R_{3a}$ and $R_{3b}$ is a ($C_1$-$C_6$)-alkyl-aryl group, optionally, a $CH_2$-phenyl group.

24. A chemical compound according to claim 7, wherein $R_4$ is an N-heterocycle substituent, having formula (III), wherein $X_3$ and $X_4$ each are ethylene (—$CH_2$—$CH_2$—), $R_6$ is a halogen atom, optionally a fluorine atom, $R_1$, $R_2$, $R_5$, and $R_7$ each are a hydrogen atom, at least one of $R_{3a}$ and are $R_{3b}$ is a ($C_1$-$C_6$)-alkyl-aryl group, optionally a phenyl group, and the other of $R_{3a}$ and $R_{3b}$ is a hydrogen atom.

25. A chemical compound according to claim 1, wherein the compound having formula (I) is a compound having formula (XV):

(XV)

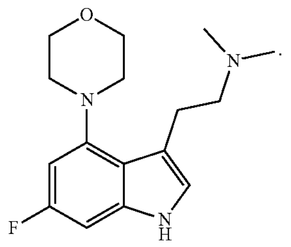

26. A pharmaceutical drug formulation comprising an effective amount of a chemical compound according to claim 1, together with a pharmaceutically acceptable excipient, diluent, or carrier.

27. A pharmaceutical drug formulation according to claim 25, wherein the compound, is formulated together with a pharmaceutically acceptable excipient, diluent, or carrier.

28. A method for treating a brain neurological disorder, the method comprising administering to a subject in need thereof a pharmaceutical formulation comprising a chemical compound according to claim 1, wherein the pharmaceutical formulation is administered in an effective amount to treat the brain neurological disorder in the subject.

29. A method for treating a brain neurological disorder, the method comprising administering to a subject in need thereof a pharmaceutical formulation comprising a chemical compound according to claim 25, wherein the pharmaceutical formulation is administered in an effective amount to treat the brain neurological disorder in the subject.

* * * * *